(12) United States Patent
Hynd et al.

(10) Patent No.: US 9,643,964 B2
(45) Date of Patent: May 9, 2017

(54) 3-(2-AMINOPYRIMIDIN-4-YL)-5-(3-HYDROXYPROPYNYL)-1H-PYRROLO[2,3-C]PYRIDINE DERIVATIVES AS NIK INHIBITORS FOR THE TREATMENT OF CANCER

(71) Applicant: Janssen Pharmaceutica NV, Beerse (BE)

(72) Inventors: George Hynd, Harlow (GB); Stephen Price, Harlow (GB); Janusz Kulagowski, Harlow (GB); Calum MacLeod, Harlow (GB); Samuel Edward Mann, Harlow (GB); Terry Aaron Panchal, Harlow (GB); Patrizia Tisselli, Harlow (GB); John Gary Montana, Harlow (GB)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/786,338

(22) PCT Filed: Apr. 24, 2014

(86) PCT No.: PCT/EP2014/058361
§ 371 (c)(1),
(2) Date: Oct. 22, 2015

(87) PCT Pub. No.: WO2014/174021
PCT Pub. Date: Oct. 30, 2014

(65) Prior Publication Data
US 2016/0075699 A1 Mar. 17, 2016

(30) Foreign Application Priority Data

Apr. 24, 2013 (EP) ..................................... 13165167
Sep. 26, 2013 (EP) ..................................... 13186116

(51) Int. Cl.
*A61K 31/506* (2006.01)
*C07D 471/04* (2006.01)

(52) U.S. Cl.
CPC .................................. *C07D 471/04* (2013.01)

(58) Field of Classification Search
CPC ............................ C07D 471/04; A61K 31/506
See application file for complete search history.

(56) References Cited

U.S. PATENT DOCUMENTS

2012/0214762 A1  8/2012  Staben et al.

FOREIGN PATENT DOCUMENTS

| WO | WO 2007/058850 A2 | 5/2007 |
|----|-------------------|--------|
| WO | WO 2007/058850 A3 | 5/2007 |
| WO | WO 2009/092431 A1 | 7/2009 |
| WO | WO 2009/158011 A1 | 12/2009 |
| WO | WO 2010/042337 A1 | 4/2010 |
| WO | WO 2010/051781 A1 | 5/2010 |
| WO | WO 2012/123522 A1 | 9/2012 |
| WO | WO 2015/044267 A1 | 4/2015 |
| WO | WO 2015/044269 A1 | 4/2015 |
| WO | WO 2016/062789 A1 | 4/2016 |
| WO | WO 2016/062790 A1 | 4/2016 |
| WO | WO 2016/062791 A1 | 4/2016 |
| WO | WO 2016/062792 A1 | 4/2016 |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
R.J. Kok, 25 Pharmaceutical Research, 2413-2415 (2008).*
Z. Ghiassi-Nejad et al. 2 Expert Review of Gastroenterology & Hepatology, 803-816 (2008).*
C.J. O'Brien, Head and Neck, 946-952 (2003).*
H. Nandeesha et al., 370 Clinica Chimica Acta, 89-93 (2006).*
S. Yamada et al., 242 The Journal of Pharmacology and Experimental Therapeutics, 326-330 (1987).*
J. Kim et al., 150 Endocrinology, 3576-3583 (2009).*
J.D. Cashman et al., 171 Journal of Surgical Research, 495-503 (2011).*
Yamamoto et al., 90 Proceedings of the National Academy of Sciences, 1814-1818 (1993).*

(Continued)

*Primary Examiner* — Alexander R Pagano

(57) ABSTRACT

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, to processes to prepare such compounds and compositions, and to the use of such compounds or pharmaceutical compositions for the prevention or treatment of diseases such as cancer, inflammatory disorders, metabolic disorders including obesity and diabetes, and autoimmune disorders.

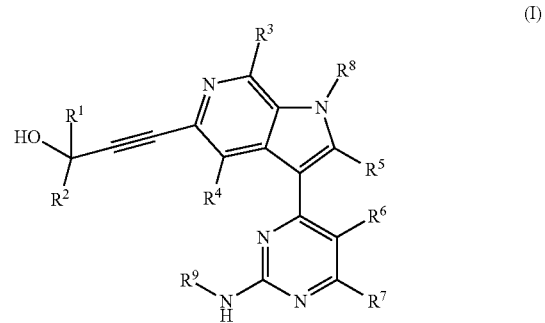

15 Claims, No Drawings

(56) References Cited

OTHER PUBLICATIONS

A. Kim et al., 2014 International Journal of Nephrology and Renovascular Disease, 361-381 (2014).*
Kinase Inhibitors, Methods in Molecular Biology 795 (B. Kuster ed., 2012).*
H. Jing et al., 37 Molecular Cells, 189-195 (2014).*
N.D. Perkins, 12 Nature Reviews Cancer, 121-132 (2012).*
C. Carbone et al., 16 Expert Opinion on Therapeutic Targets, S1-S10 (2012).*
Y. Herishanu et al., 117 Blood, 563-574 (2011) (chronic lymphocytic leukemia).*
F. Pacifico et al. 321 Molecular and Cellular Endocrinology, 29-35 (2010).*
T. Tremlay et al., 62 Metabolism Clinical and Experimental, S2-S5 (2013).*
U. McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
Allen, I.C., et al., "NLPR12 Suppresses Colon Inflammation and Tumorigenesis Through the Negative Regulation of Noncanonical NF-κB Signaling", Immunity, (2012), vol. 36, pp. 742-754.
Annunziata, C.M., et al., "Frequent Engagement of the Classical and Alternative NF-κb Pathways by Diverse Genetic Abnormalities in Multiple Myeloma", Cancer Cell, (2007), vol. 12, pp. 115-130.
Aya, K., et al., "NF-κb-Inducing Kinase Controls Lymphocyte and Osteoclast Activities in Inflammatory Arthritis", J. Clin. Invest., (2005), vol. 115, No. 7, pp. 1848-1854.
Bhattacharyya, S., et al., "Tumor Necrosis Factor α-Induced Inflammation Is Increased but Apoptosis Is Inhibited by Common Food Additive Carrageenan", J. Biol. Chem., (2011), vol. 285, No. 50, pp. 39511-39522.
Bitar, M.S., et al., "Inflammation and Apoptosis in Aortic Tissues of Aged Type II Diabetes: Amelioration With α-Lipoic Acid Through Phosphatidylinositol 3-Kinase/AkT-Dependent Mechanism", Life Sciences, (2010), vol. 86, pp. 844-853.
Choudhary, S., et al., "NF-κB-Inducing Kinase (NIK) Mediates Skeletal Muscle Insulin Resistance: Blockade by Adiponectin", Endocrinology, (2011), vol. 152, No. 10, pp. 3622-3627.
Chung, S., et al., "NF-κB Inducing Kinase, NIK Mediates Cigarette SMOKE/TNFα-Induced Histone Acetylation and Inflammation Through Differential Activation of IKKS", PLoS ONE, (2011), vol. 6, No. 8, pp. e23488.
Demchenko, Y.N. et al., "Classical and/or Alternative NF-κB Pathway Activation in Multiple Myeloma", Blood, (2010), vol. 115, No. 17, pp. 3541-3552.
Keats, J.J., et al., "Promiscuous Mutations Activate the Noncanonical NF-κB Pathway in Multiple Myeloma", Cancer Cell, (2007), vol. 12, pp. 131-144.
Nishina, T., et al., "NIK Is Involved in Constitutive Activation of the Alternative NF-κB Pathway and Proliferation of Pancreatic Cancer Cells", Biochem. Bioph. Res. Co., (2009), vol. 388, pp. 96-101.
Pham, L.V., et al., "Constitutive BR3 Receptor Signaling in Diffuse, Large B-Cell Lymphomas Stabilizes Nuclear Factor-κB-Inducing Kinase While Activating Both Canonical and Alternative Nuclear Factor-κB Pathways", Blood, (2011), vol. 117, No. 1, pp. 200-210.

Ranuncolo, S.M., et al., "Hodgkin Lymphoma Requires Stabilized NIK and Constitutive Relb Expression for Survival", Blood, (2012), vol. 120, No. 18, pp. 3756-3763.
Rosebeck, S., et al., "Cleavage of NIK by the API2-MALT1 Fusion Onoprotein Leads to Noncanonical NF-κB Activation", Science, (2011), vol. 331, pp. 468-472.
Saitoh, Y., et al., "Overexpressed NF-κB-Inducing Kinase Contributes to the Tumorigenesis of Adult T-Cell Leukemia and Hodgkin Reed-Sternberg Cells", Blood, (2008), vol. 111, No. 10, pp. 5118-5129.
Shuto, T., et al., "Activation of NF-B by Nontypeable Hemophilus Influenzae Is Mediated by Toll-Like Receptor 2-TAK1-Dependent NIK-IKKα/B-IκBα and MKK3/6-p38 Map Kinase Signaling Pathways in Epithelial Cells", PNAS, (2001), vol. 98, No. 15, pp. 8774-8779.
Thu, Y.M., et al., "NF-κB Inducing Kinase (NIK) Modulates Melanoma Tumorigenesis by Regulating Expression of Pro-Survival Factors Through the β-Catenin Pathway", Oncogene, (2012), vol. 31, No. 20, pp. 2580-2592.
Thu and Richmond, "NF-κB Inducing Kinase: A Key Regulator in the Immune System and in Cancer", Cytokine & Growth Factor Reviews, (2010), vol. 21, pp. 213-226.
Wixted, W.E., et al., "A Model to Identify Novel Targets Involved in Oxidative Stress-Induced Apoptosis in Human Lung Epithelial Cells by RNA Interference", Toxicology in Vitro, (2010), vol. 24, pp. 310-318.
Yamamoto, M., et al., "Epigenetic Alteration of the NF-κB -Inducing Kinase (NIK) Gene Is Involved in Enhanced NIK Expression in Basal-Like Breast Cancer", Cancer Science, (2010), vol. 101, No. 11, pp. 2391-2397.
Yang, C., et al., "NIK Stabilization in Osteoclasts Results in Osteoporosis and Enhanced Inflammatory Osteolysis", PLoS ONE, (2010), vol. 5, No. 11, pp. e15383.
Zhao, Y., et al., "NF-κB-Inducing Kinase Increases Renal Tubule Epithelial Inflammation Associated With Diabetes", Experimental Diabetes Research, (2011), vol. 2011, pp. 1-9.
Greene, T.W., "Protective Groups in Organic Synthesis", (1991) John Wiley & Sons, New York.
International Search Report dated Jun. 2, 2014 for PCT/EP2014/058361.
Gennaro, A.R., Remington's $18^{th}$ ed., Mack Publishing Company, (1990) see especially Part 8: Pharmaceutical preparations and their Manufacture, pp. 1435-1712.
Fustero, S., et al., "From 2000 to Mid-2010: A Fruitful Decade for the Synthesis of Pyrazoles", Chemical Reviews, (2011), vol. 111, pp. 6984-7034.
Baraldi, P.G., et al., "Pyrrolo-and Pyrazolo-[3,4-e][1,2,4]Triazolo[1,5-c]Pyrimidines as Adenosine Receptor Antagonists", Bioorganic & Medicinal Chemistry, (2012), vol. 20, pp. 1046-1059.
Merour, J.Y, et al., "Recent Advances in the Synthesis and Properties of 4-, 5-, 6- or 7-Azaindoles", Tetrahedron, (2013), vol. 69, pp. 4767-4834.
Taber, D.F., et al., "Indole Synthesis: A Review and Proposed Classification", Tetrahedron, (2011), vol. 67, pp. 7195-7210.
Elguero, J., "Comprehensive Heterocyclic Chemistry II", Chem. Rev., (1996), vol. 2011, No. 111, pp. 6984-7034, Pergamon Press: Oxford.
Greene, T.W., et al., "Greene's Protective Groups in Organic Synthesis", $4^{th}$ ed., (2007), Wiley-Interscience, Hoboken, New Jersey.

* cited by examiner

3-(2-AMINOPYRIMIDIN-4-YL)-5-(3-HYDROXYPROPYNYL)-1H-PYRROLO[2,3-C]PYRIDINE DERIVATIVES AS NIK INHIBITORS FOR THE TREATMENT OF CANCER

CROSS REFERENCE TO RELATED APPLICATIONS

This application is a national stage of PCT Application No. PCT/EP2014/058361, filed Apr. 24, 2014, which claims priority for EPO Patent Application No. 13165167.1, filed Apr. 24, 2013 and EPO Patent Application No. 13186116.3, filed Sep. 26, 2013, all of which are hereby incorporated by reference in their entirety.

FIELD OF THE INVENTION

The present invention relates to pharmaceutical agents useful for therapy and/or prophylaxis in a mammal, and in particular to inhibitors of NF-κB-inducing kinase (NIK— also known as MAP3K14) useful for treating diseases such as cancer, inflammatory disorders, metabolic disorders including obesity and diabetes, and autoimmune disorders. The invention is also directed to pharmaceutical compositions comprising such compounds, to processes to prepare such compounds and compositions, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK— also known as MAP3K14) useful for treating diseases such as cancer and inflammatory disorders. Nuclear factor-kappa B (NF-κB) is a transcription factor regulating the expression of various genes involved in the immune response, cell proliferation, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK has a role in both but has been shown to be indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226)

Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. ibid 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129).

It has been demonstrated that the API2-MALT1 fusion oncoprotein created by the recurrent translocation t(11;18)(q21;q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11;18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010. 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2011, 1-13). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable Hemophilus influenza (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al 2011). A shRNA screen was used in an in vitro model of oxidative stress induced cell death (as a model of COPD) to interrogate a human druggable genome siRNA library in order to identify genes that modulate the cellular response to stress. NIK was one of the genes identified in this screen as a potential new therapeutic target to modulate epithelial apoptosis in chronic lung diseases (Wixted et al. *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS One* 2010, 5, 1-9, e15383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune and alloresponses, like GVHD (Graft Versus Host Disease) and transplant rejection, without crippling the immune system as severely as do inhibitors of canonical NF-κB activation.

WO2010/042337 describes novel 6-azaindole aminopyrimidine derivatives having NIK inhibitory activity.

DESCRIPTION OF THE INVENTION

The present invention concerns novel compounds of Formula (I):

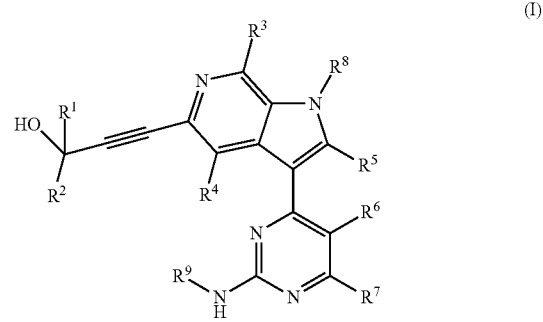

and tautomers and stereoisomeric forms thereof, wherein
$R^1$ is selected from the group of hydrogen; $C_{1-6}$alkyl; $C_{1-6}$alkyl substituted with one or more fluoro substituents; and $C_{1-6}$alkyl substituted with one substituent selected from the group of —$NR^{1a}R^{1b}$, —OH and —$OC_{1-4}$alkyl;
$R^2$ is selected from the group of hydrogen; $C_{1-6}$alkyl; $C_{1-6}$alkyl substituted with one or more fluoro substituents; $C_{1-6}$alkyl substituted with one substituent selected from the group of —$NR^{2a}R^{2b}$, —OH, —$OC_{1-4}$alkyl, $C_{3-6}$cycloalkyl, Het$^1$, Het$^2$ and phenyl; —C(=O)—$NR^{2c}R^{2d}$; $C_{3-6}$cycloalkyl; Het$^1$; Het$^2$; and phenyl; wherein
the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
$R^{1a}$, $R^{1b}$, $R^{2a}$, $R^{2b}$, $R^{2c}$ and $R^{2d}$ are each independently selected from hydrogen and $C_{1-4}$alkyl;
Het$^1$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one $C_{1-4}$alkyl;
Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
or $R^1$ and $R^2$ together with the carbon atom to which they are attached form a $C_{3-6}$cycloalkyl or a Het$^3$ group; wherein
Het$^3$ is a heterocyclyl selected from the group of piperidinyl, tetrahydropyranyl, pyrrolidinyl, tetrahydrofuranyl, azetidinyl and oxetanyl, each of which may be optionally substituted with one $C_{1-4}$alkyl;
or Het$^3$ is 2-oxo-3-pyrrolidinyl optionally substituted with one $C_{1-4}$alkyl;
$R^3$ is selected from the group of hydrogen; halo; $C_{3-6}$cycloalkyl; $C_{1-4}$alkyl; $C_{1-4}$alkyl substituted with one or more fluoro substituents; and $C_{1-4}$alkyloxy substituted with one or more fluoro substituents;
$R^4$ is selected from the group of hydrogen; halogen; $C_{1-4}$alkyl; $C_{1-4}$alkyl substituted with one or more fluoro substituents; and cyano;
$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl, $C_{3-6}$cycloalkyl, and Het$^4$; $C_{3-6}$cycloalkyl; and —C(=O)—$NR^{5c}R^{5d}$; wherein
$R^{5a}$ and $R^{5b}$ are each independently selected from the group of hydrogen and $C_{1-4}$alkyl; and $R^{5c}$ and $R^{5d}$ are each independently selected from the group of hydrogen; $C_{1-6}$alkyl optionally substituted with Het$^5$; and $C_{2-6}$alkyl substituted with one substituent selected from —$NR^{5x}R^{5y}$, —OH and —$OC_{1-4}$alkyl;
Het$^4$ is a heterocyclyl selected from the group of piperidinyl, morpholinyl, piperazinyl, tetrahydropyranyl, pyrrolidinyl, tetrahydrofuranyl, azetidinyl and oxetanyl, each of which may be optionally substituted with one $C_{1-4}$alkyl;
Het$^5$ is a heterocyclyl selected from the group of piperidinyl, morpholinyl, piperazinyl, tetrahydropyranyl, pyrrolidinyl, tetrahydrofuranyl, azetidinyl and oxetanyl, each of which may be optionally substituted with one $C_{1-4}$alkyl;
$R^{5x}$ and $R^{5y}$ are each independently selected from the group of hydrogen and $C_{1-4}$alkyl; or $R^{5c}$ and $R^{5d}$ together with the nitrogen atom to which they are attached form a Het$^6$ group; wherein Het$^6$ is a heterocyclyl selected from the group of piperidinyl, pyrrolidinyl, azetidinyl, piperazinyl and morpholinyl, each of which may be optionally substituted with one substituent selected from $C_{1-4}$alkyl; —$OC_{1-4}$alkyl; and $C_{1-4}$alkyl substituted with one —OH;
$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; $C_{1-6}$alkyl substituted with one $NH_2$; —$C_{1-6}$alkyloxy$C_{1-4}$alkyl; —$C_{1-6}$alkyl-C(=O)—$NR^{6a}R^{6b}$; —$OC_{1-6}$alkyl; —$OC_{1-6}$alkyl substituted with one or more fluoro substituents; —$OC_{1-6}$alkyl substituted with one Het$^7$ substituent; —$OC_{2-6}$alkyl substituted with one substituent selected from the group of —$NR^{6c}R^{6d}$, —OH, and —$OC_{1-4}$alkyl; and —C(=O)—$NR^{6a}R^{6b}$; wherein
$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkylN$R^{6x}R^{6y}$; or
$R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;
$R^{6x}$ is hydrogen or $C_{1-4}$alkyl and $R^{6y}$ is $C_{1-4}$alkyl; and Het$^7$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;
$R^7$ is selected from the group of hydrogen, $C_{1-4}$alkyl, cyano, —$OC_{1-4}$alkyl, —$NHC_{1-4}$alkyl, —NH—C(=O)—$C_{1-4}$alkyl and —C(=O)—$NR^{7a}R^{7b}$; wherein
$R^{7a}$ and $R^{7b}$ are each independently selected from hydrogen and $C_{1-4}$alkyl;
$R^8$ is selected from the group of hydrogen; —C(=O)—$NR^{8g}R^{8h}$; Het$^8$; $C_{1-6}$alkyl optionally substituted with Het$^9$; —C(=O)—Het$^{12}$; $C_{3-6}$cycloalkyl optionally substituted with one —$OC_{1-4}$alkyl; $C_{1-6}$alkyl substituted with one cyano; —$CH_2$—C(=O)$NR^{8a}R^{8b}$; and $C_{2-6}$alkyl substituted with one or more substituents independently selected from the group of
(i) fluoro,
(ii) —$NR^{8a}R^{8b}$,
(iii) —$NR^{8c}C(=O)R^{8d}$,
(iv) —$NR^{8c}C(=O)NR^{8a}R^{8b}$,
(v) —$NR^{8c}C(=O)OR^{8e}$,
(vi) —$NR^{8c}S(=O)_2NR^{8a}R^{8b}$,
(vii) —$NR^{8c}S(=O)_2R^{8d}$,
(viii) —$OR^{8f}$,
(ix) —$OC(=O)NR^{8a}R^{8b}$,
(x) —$C(=O)NR^{8a}R^{8b}$,
(xi) —$SR^{8e}$,
(xii) —$S(O)_2R^{8d}$, and
(xiii) —$S(O)_2NR^{8a}R^{8b}$; wherein
$R^{8a}$, $R^{8b}$, $R^{8c}$ and $R^{8f}$ are each independently selected from the group of hydrogen; $C_{1-6}$alkyl, which may be optionally substituted with one substituent selected from Het$^{10}$ and Het$^{11}$; $C_{3-6}$cycloalkyl; and $C_{2-6}$alkyl substituted with one substituent selected from —$NR^{8x}R^{8y}$, —OH, and —$OC_{1-4}$alkyl;
$R^{8d}$ is selected from the group of $C_{1-6}$alkyl, which may be optionally substituted with one substituent selected from —$NR^{8x}R^{8y}$, —OH, —$OC_{1-4}$alkyl, Het$^{10}$ and Het$^{11}$; and $C_{3-6}$cycloalkyl;
$R^{8e}$ is selected from the group of $C_{1-6}$alkyl, which may be optionally substituted with one substituent selected from Het$^{10}$ and Het$^{11}$; C$_{3-6}$cycloalkyl; and C$_{2-6}$alkyl substituted with one substituent selected from —NR$^{8x}$R$^{8y}$, —OH, and —OC$_{1-4}$alkyl;

wherein R$^{8x}$ and R$^{8y}$ are each independently selected from hydrogen and C$_{1-4}$alkyl;

R$^{8g}$ and R$^{8h}$ are each independently selected from the group of hydrogen, C$_{1-4}$alkyl and C$_{2-4}$alkyl substituted with one —OC$_{1-4}$alkyl;

and

Het$^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—C$_{1-4}$alkyl, C$_{1-4}$alkyl, C$_{3-6}$cycloalkyl, C$_{1-4}$alkyl substituted with one C$_{3-6}$cycloalkyl, C$_{1-4}$alkyl substituted with one or more fluoro substituents, and C$_{1-4}$alkyl substituted with one —OC$_{1-4}$alkyl;

Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, C$_{1-4}$alkyl, C$_{1-4}$alkyl substituted with one or more fluoro substituents, and —OC$_{1-4}$alkyl; or Het$^9$ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one C$_{1-4}$alkyl; or Het$^9$ is selected from the group of (a), (b), (c), (d), and (e)

Het$^{10}$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one C$_{1-4}$alkyl;

Het$^{11}$ is selected from the group of (a), (b), (c), (d), and (e)

Het$^{12}$ is a heterocyclyl selected from the group of 1-piperidinyl, 1-piperazinyl, 1-pyrrolidinyl and 1-azetidinyl, each of which may be optionally substituted with one substituent selected from C$_{1-4}$alkyl and —OC$_{1-4}$alkyl;

R$^9$ is hydrogen or C$_{1-4}$alkyl;

and the pharmaceutically acceptable salts and the solvates thereof.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable salt, or a solvate thereof, in combination with an additional pharmaceutical agent for use in the treatment or prevention of cancer, inflammatory disorders, autoimmune disorders, and metabolic disorders such as diabetes and obesity.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof.

The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity.

Additionally, the invention relates to a method of treating or preventing a cell proliferative disease in a warm-blooded animal which comprises administering to the said animal an effective amount of a compound of formula (I), a pharmaceutically acceptable salt, or a solvate thereof, as defined herein, or a pharmaceutical composition or combination as defined herein.

DETAILED DESCRIPTION OF THE INVENTION

The chemical names of the compounds of the present invention were generated according to the nomenclature rules agreed upon by IUPAC (International Union of Pure and Applied Chemistry) using the commercial MDL Isis AutoNom software (product version 2.5). In case of tautomeric forms, the name of the depicted form of the structure was generated. However it should be clear that the other non-depicted tautomeric form is also included within the scope of the present invention.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein represents fluoro, chloro, bromo and iodo.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term '$C_{2-6}$alkyl' as used herein as a group or part of a group represents a straight or branched chain saturated hydrocarbon radical having from 2 to 6 carbon atoms such as ethyl, n-propyl, isopropyl, n-butyl, s-butyl, t-butyl, n-pentyl, n-hexyl, 2-methylbutyl and the like.

The term '$C_{1-4}$alkoxy' or '$C_{1-4}$alkyloxy' as used herein as a group or part of a group represents a straight or branched chain saturated hydrocarbon radical having from 1 to 4 carbon atoms bonded to an oxygen atom such as methoxy, ethoxy, isopropoxy and the like. Similar, the term '$C_{1-6}$alkoxy' or '$C_{1-6}$alkyloxy' as used herein as a group or part of a group represents a straight or branched chain saturated hydrocarbon radical having from 1 to 6 carbon atoms bonded to an oxygen atom.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The term $C_{1-6}$alkyl substituted with one or more substituents as used herein as a group or part of a group refers to a $C_{1-6}$alkyl group as defined herein wherein one or more than one hydrogen atom is replaced with another group. The term therefore includes monosubstituted$C_{1-6}$alkyl and also polysubstituted$C_{1-6}$alkyl. There may be one, two, three or more hydrogen atoms replaced with a substituent, so the fully or partially substituted $C_{1-6}$alkyl may have one, two, three or more substituents. Examples of such groups wherein the substituent is for example, fluoro include fluoromethyl, difluoromethyl, trifluoromethyl, fluoroethyl, trifluoroethyl and the like.

In general, whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term optionally substituted, for example as used in optionally substituted $C_{1-6}$alkyl, means that, unless otherwise is indicated or is clear from the context, the group is unsubstituted or substituted by one or more, for example 1, 2 or 3, substituents.

In a particular embodiment, the expression "$C_{1-6}$alkyl optionally substituted with $Het^5$" is limited to "$C_{1-6}$alkyl optionally substituted with one $Het^5$". In a particular embodiment, the expression "$C_{1-6}$alkyl optionally substituted with $Het^9$" is limited to "$C_{1-6}$alkyl optionally substituted with one $Het^5$".

C(O) or C(=O) represents a carbonyl moiety.
$S(O)_2$ represents a sulfonyl moiety.

Substituents covered by the term "$Het^x$", "heterocyclyl" or "heteroaryl" may be attached to the remainder of the molecule of Formula (I) through any available ring carbon or heteroatom as appropriate, if not otherwise specified.

The skilled person will realize that the group '$C_{2-4}$alkyloxy$C_{1-4}$alkyl' which is present e.g. in the definition of $R^{6b}$, is attached to the remainder of the molecule of Formula (I) via the $C_{2-4}$alkyl: i.e. —$C_{2-4}$alkyloxy$C_{1-4}$alkyl. Similar, $C_{2-4}$alkylNR$^{6x}$R$^{6y}$ which is present e.g. in the definition of $R^{6b}$, is attached to the remainder of the molecule of Formula (I) via the $C_{2-4}$alkyl: i.e. —$C_{2-4}$alkylNR$^{6x}$R$^{6y}$.

Whenever substituents are represented by chemical structure, " - - - " represents the bond of attachment to the remainder of the molecule of Formula (I).

When any variable occurs more than one time in any constituent, each definition is independent.

When any variable occurs more than one time in any formula (e.g. formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention.

It follows that a single compound may exist in both stereoisomeric and tautomeric form.

The present invention relates in particular to compounds of Formula (I) as defined herein, and tautomers and stereoisomeric forms thereof, wherein $R^1$ is selected from the group of hydrogen; $C_{1-6}$alkyl; $C_{1-6}$alkyl substituted with one or more fluoro substituents; and $C_{1-6}$alkyl substituted with one substituent selected from the group of —$NR^{1a}R^{1b}$, —OH and —$OC_{1-4}$alkyl;

$R^2$ is selected from the group of hydrogen; $C_{1-6}$alkyl; $C_{1-6}$alkyl substituted with one or more fluoro substituents; $C_{1-6}$alkyl substituted with one substituent selected from the group of —$NR^{2a}R^{2b}$, —OH, —$OC_{1-4}$alkyl, $C_{3-6}$cycloalkyl, $Het^2$ and phenyl; —C(=O)—$NR^{2c}R^{2d}$; $C_{3-6}$cycloalkyl; $Het^2$; and phenyl; wherein
the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

$R^{1a}$, $R^{1b}$, $R^{2a}$, $R^{2b}$, $R^{2c}$ and $R^{2d}$ are each independently selected from hydrogen and $C_{1-4}$alkyl;

$Het^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is selected from the group of hydrogen; halo; $C_{3-6}$cycloalkyl; $C_{1-4}$alkyl; $C_{1-4}$alkyl substituted with one or more fluoro substituents; and $C_{1-4}$alkyloxy substituted with one or more fluoro substituents;

$R^4$ is selected from the group of hydrogen; halogen; $C_{1-4}$alkyl; $C_{1-4}$alkyl substituted with one or more fluoro substituents; and cyano;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl, $C_{3-6}$cycloalkyl, and $Het^4$; $C_{3-6}$cycloalkyl; and —C(=O)—$NR^{5c}R^{5d}$; wherein $R^{5a}$ and $R^{5b}$ are each independently selected from the group of hydrogen and $C_{1-4}$alkyl; and $R^{5c}$ and $R^{5d}$ are each independently selected from the group of hydrogen; $C_{1-6}$alkyl optionally substituted with one $Het^5$; and $C_{2-6}$alkyl substituted with one substituent selected from —$NR^{5x}R^{5y}$, —OH and —$OC_{1-4}$alkyl;

Het$^4$ is a heterocyclyl selected from the group of piperidinyl, morpholinyl, piperazinyl, tetrahydropyranyl, pyrrolidinyl, tetrahydrofuranyl, azetidinyl and oxetanyl, each of which may be optionally substituted with one $C_{1-4}$alkyl;

Het$^5$ is a heterocyclyl selected from the group of piperidinyl, morpholinyl, piperazinyl, tetrahydropyranyl, pyrrolidinyl, tetrahydrofuranyl, azetidinyl and oxetanyl, each of which may be optionally substituted with one $C_{1-4}$alkyl;

$R^{5x}$ and $R^{5y}$ are each independently selected from the group of hydrogen and $C_{1-4}$alkyl; or $R^{5c}$ and $R^{5d}$ together with the nitrogen atom to which they are attached form a Het$^6$ group; wherein Het$^6$ is a heterocyclyl selected from the group of piperidinyl, pyrrolidinyl, azetidinyl, piperazinyl and morpholinyl, each of which may be optionally substituted with one substituent selected from $C_{1-4}$alkyl; —$OC_{1-4}$alkyl; and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; $C_{1-6}$alkyl substituted with one $NH_2$; —$C_{1-6}$alkyloxy$C_{1-4}$alkyl; —$C_{1-6}$alkyl-C(=O)—$NR^{6a}R^{6b}$; —$OC_{1-6}$alkyl; —$OC_{1-6}$alkyl substituted with one or more fluoro substituents; —$OC_{1-6}$ alkyl substituted with one Het$^7$ substituent; —$OC_{2-6}$alkyl substituted with one substituent selected from the group of —$NR^{6c}R^{6d}$, —OH, and —$OC_{1-4}$alkyl; and —C(=O)—$NR^{6a}R^{6b}$ wherein $R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkyl$NR^{6x}R^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;

$R^{6x}$ is hydrogen or $C_{1-4}$alkyl and $R^{6y}$ is $C_{1-4}$alkyl; and Het$^7$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;

$R^7$ is selected from the group of hydrogen, $C_{1-4}$alkyl, cyano, —$OC_{1-4}$alkyl, —$NHC_{1-4}$alkyl, —NH—C(=O)—$C_{1-4}$alkyl and —C(=O)—$NR^{7a}R^{7b}$; wherein $R^{7a}$ and $R^{7b}$ are each independently selected from hydrogen and $C_{1-4}$alkyl;

$R^8$ is selected from the group of hydrogen; —C(=O)—$NR^{8g}R^{8h}$; Het$^8$; $C_{1-6}$alkyl optionally substituted with one Het$^9$; —C(=O)—Het$^{12}$; $C_{3-6}$cycloalkyl optionally substituted with one —$OC_{1-4}$alkyl; $C_{1-6}$alkyl substituted with one cyano; —$CH_2$—C(=O)$NR^{8a}R^{8b}$; and $C_{2-6}$alkyl substituted with one or more substituents independently selected from the group of
(i) fluoro,
(ii) —$NR^{8a}R^{8b}$,
(iii) —$NR^{8c}C(=O)R^{8d}$,
(iv) —$NR^{8c}C(=O)NR^{8a}R^{8b}$,
(v) —$NR^{8c}C(=O)OR^{8e}$,
(vi) —$NR^{8c}S(=O)_2NR^{8a}R^{8b}$,
(vii) —$NR^{8c}S(=O)_2R^{8d}$,
(viii) —$OR^{8f}$,
(ix) —$OC(=O)NR^{8a}R^{8b}$,
(x) —$C(=O)NR^{8a}R^{8b}$,
(xi) —$SR^{8e}$,
(xii) —$S(O)_2R^{8d}$, and
(xiii) —$S(O)_2NR^{8a}R^{8b}$; wherein
$R^{8a}$, $R^{8b}$, $R^{8c}$ and $R^{8f}$ are each independently selected from the group of hydrogen; $C_{1-6}$alkyl, which may be optionally substituted with one substituent selected from Het$^{10}$ and Het$^{11}$; $C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH, —$OC_{1-4}$alkyl, Het$^{10}$ and Het$^{11}$; and $C_{3-6}$cycloalkyl;

$R^{8e}$ is selected from the group of $C_{1-6}$alkyl, which may be optionally substituted with one substituent selected from Het$^{10}$ and Het$^{11}$; $C_{3-6}$cycloalkyl; and $C_{2-6}$alkyl substituted with one substituent selected from —$NR^{8x}R^{8y}$, —OH, and —$OC_{1-4}$alkyl;

wherein $R^{8x}$ and $R^{8y}$ are each independently selected from hydrogen and $C_{1-4}$alkyl;

$R^{8g}$ and $R^{8h}$ are each independently selected from the group of hydrogen, $C_{1-4}$alkyl and $C_{2-4}$alkyl substituted with one —$OC_{1-4}$alkyl;

and

Het$^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—$C_{1-4}$alkyl, $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;

Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —$OC_{1-4}$alkyl; or Het$^9$ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one $C_{1-4}$alkyl; or Het$^9$ is selected from the group of

(a)

(b)

(c)

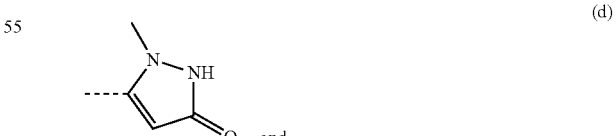
(d)
and

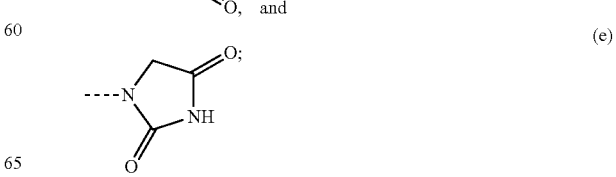
(e)

Het¹⁰ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one $C_{1-4}$alkyl;
Het¹¹ is selected from the group of

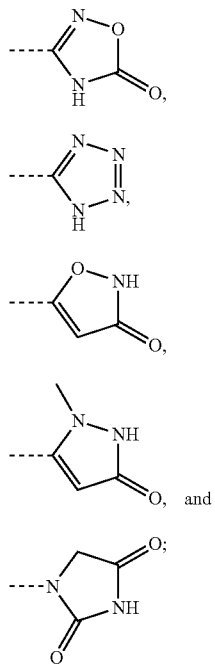

Het¹² is a heterocyclyl selected from the group of 1-piperidinyl, 1-piperazinyl, 1-pyrrolidinyl and 1-azetidinyl, each of which may be optionally substituted with one substituent selected from $C_{1-4}$alkyl and —$OC_{1-4}$alkyl;
R⁹ is hydrogen or $C_{1-4}$alkyl;
and the pharmaceutically acceptable salts and the solvates thereof.

The present invention relates in particular to compounds of Formula (I) as defined herein, and tautomers and stereoisomeric forms thereof, wherein
R¹ is selected from the group of hydrogen; $C_{1-6}$alkyl; $C_{1-6}$alkyl substituted with one or more fluoro substituents; and $C_{1-6}$alkyl substituted with one substituent selected from the group of —NR¹ᵃR¹ᵇ, —OH and —$OC_{1-4}$alkyl;
R² is selected from the group of hydrogen; $C_{1-6}$alkyl; $C_{1-6}$alkyl substituted with one or more fluoro substituents; $C_{1-6}$alkyl substituted with one substituent selected from the group of —NR²ᵃR²ᵇ, —OH, —$OC_{1-4}$alkyl, $C_{3-6}$cycloalkyl, Het² and phenyl; —C(=O)—NR²ᶜR²ᵈ; $C_{3-6}$cycloalkyl; Het²; and phenyl; wherein
the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
R¹ᵃ, R¹ᵇ, R²ᵃ, R²ᵇ, R²ᶜ and R²ᵈ are each independently selected from hydrogen and $C_{1-4}$alkyl;
Het² is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
or R¹ and R² together with the carbon atom to which they are attached form a $C_{3-6}$cycloalkyl;
R³ is selected from the group of hydrogen; halo; $C_{3-6}$cycloalkyl; $C_{1-4}$alkyl; $C_{1-4}$alkyl substituted with one or more fluoro substituents; and $C_{1-4}$alkyloxy substituted with one or more fluoro substituents;
R⁴ is hydrogen;
R⁵ is selected from the group of hydrogen; $C_{1-6}$alkyl; $C_{1-6}$alkyl substituted with one or more fluoro substituents; cyano; $C_{1-6}$alkyl substituted with one substituent selected from the group of —NR⁵ᵃR⁵ᵇ, —OH, —$OC_{1-4}$alkyl; $C_{3-6}$cycloalkyl; and —C(=O)—NR⁵ᶜR⁵ᵈ; wherein
R⁵ᵃ and R⁵ᵇ are each independently selected from the group of hydrogen and $C_{1-4}$alkyl; and R⁵ᶜ and R⁵ᵈ are each independently selected from the group of hydrogen; and $C_{2-6}$alkyl substituted with one substituent selected from —NR⁵ˣR⁵ʸ, —OH and —$OC_{1-4}$alkyl;
R⁵ˣ and R⁵ʸ are each independently selected from the group of hydrogen and $C_{1-4}$alkyl;
R⁶ is selected from the group of hydrogen; halogen; cyano; $C_{1-6}$alkyl; $C_{1-6}$alkyl substituted with one or more fluoro substituents; $C_{1-6}$alkyl substituted with one —OH; $C_{1-6}$alkyl substituted with one NH₂; —$C_{1-6}$alkyloxy$C_{1-4}$alkyl; —$OC_{1-6}$alkyl; —$OC_{1-6}$alkyl substituted with one or more fluoro substituents; and —$OC_{2-6}$alkyl substituted with one —$OC_{1-4}$alkyl;
R⁷ is selected from the group of hydrogen, $C_{1-4}$alkyl, —$OC_{1-4}$alkyl, and —$NHC_{1-4}$alkyl;
R⁸ is selected from the group of hydrogen; —C(=O)—NR⁸ᵍR⁸ʰ; Het⁸; $C_{1-6}$alkyl optionally substituted with one Het⁹; —C(=O)—Het¹²; $C_{3-6}$cycloalkyl optionally substituted with one —$OC_{1-4}$alkyl; $C_{1-6}$alkyl substituted with one cyano; —CH₂—C(=O)NR⁸ᵃR⁸ᵇ; and $C_{2-6}$alkyl substituted with one or more substituents independently selected from the group of (i), (ii), (iii), (viii), (ix), (x), and (xii); wherein
R⁸ᵃ, R⁸ᵇ, R⁸ᶜ and R⁸ᶠ are each independently selected from the group of hydrogen; $C_{1-6}$alkyl; $C_{3-6}$cycloalkyl; and $C_{2-6}$alkyl substituted with one substituent selected from —OH, and —$OC_{1-4}$alkyl;
R⁸ᵈ is $C_{1-6}$alkyl;
R⁸ᵍ and R⁸ʰ are each independently selected from the group of hydrogen, $C_{1-4}$alkyl and $C_{2-4}$alkyl substituted with one —$OC_{1-4}$alkyl;
and
Het⁸ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—$C_{1-4}$alkyl, $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;
Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —$OC_{1-4}$alkyl; or Het⁹ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one $C_{1-4}$alkyl; or Het⁹ is selected from the group of

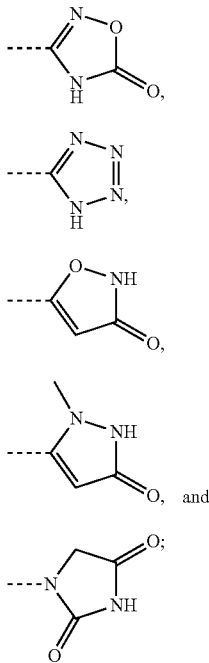

Het¹² is a heterocyclyl selected from the group of 1-piperidinyl, 1-piperazinyl, 1-pyrrolidinyl and 1-azetidinyl, each of which may be optionally substituted with one substituent selected from $C_{1-4}$alkyl and —$OC_{1-4}$alkyl;

$R^9$ is hydrogen or $C_{1-4}$alkyl;

and the pharmaceutically acceptable salts and the solvates thereof.

The present invention relates in particular to compounds of Formula (I) as defined herein, and tautomers and stereoisomeric forms thereof, wherein $R^1$ is selected from the group of hydrogen; $C_{1-6}$alkyl; $C_{1-6}$alkyl substituted with one or more fluoro substituents; and $C_{1-6}$alkyl substituted with one substituent selected from the group of —$NR^{1a}R^{1b}$, —OH and —$OC_{1-4}$alkyl;

$R^2$ is selected from the group of hydrogen; $C_{1-6}$alkyl; $C_{1-6}$alkyl substituted with one or more fluoro substituents; $C_{1-6}$alkyl substituted with one substituent selected from the group of —$NR^{2a}R^{2b}$, —OH, —$OC_{1-4}$alkyl, $C_{3-6}$cycloalkyl, Het² and phenyl; —C(=O)—$NR^{2c}R^{2d}$; $C_{3-6}$cycloalkyl; Het²; and phenyl; wherein the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

$R^{1a}$, $R^{1b}$, $R^{2a}$, $R^{2b}$, $R^{2c}$ and $R^{2d}$ are each independently selected from hydrogen and $C_{1-4}$alkyl;

Het² is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is selected from the group of hydrogen; halo; $C_{3-6}$cycloalkyl; $C_{1-4}$alkyl; $C_{1-4}$alkyl substituted with one or more fluoro substituents; and $C_{1-4}$alkyloxy substituted with one or more fluoro substituents;

$R^4$ is hydrogen;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl; $C_{3-6}$cycloalkyl; and —C(=O)—$NR^{5c}R^{5d}$; wherein $R^{5a}$ and $R^{5b}$ are each independently selected from the group of hydrogen and $C_{1-4}$alkyl; and $R^{5c}$ and $R^{5d}$ are each independently selected from the group of hydrogen; and $C_{2-6}$alkyl substituted with one substituent selected from —$NR^{5x}R^{5y}$, —OH and —$OC_{1-4}$alkyl;

$R^{5x}$ and $R^{5y}$ are each independently selected from the group of hydrogen and $C_{1-4}$alkyl;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; $C_{1-6}$alkyl substituted with one $NH_2$; —$C_{1-6}$alkyloxy$C_{1-4}$alkyl; —$OC_{1-6}$alkyl; —$OC_{1-6}$alkyl substituted with one or more fluoro substituents; and —$OC_{2-6}$alkyl substituted with one —$OC_{1-4}$alkyl;

$R^7$ is selected from the group of hydrogen, $C_{1-4}$alkyl, —$OC_{1-4}$alkyl, and —$NHC_{1-4}$alkyl;

$R^8$ is selected from the group of hydrogen; —C(=O)—$NR^{8g}R^{8h}$; Het⁸; $C_{1-6}$alkyl optionally substituted with one Het⁹; —C(=O)—Het¹²; $C_{3-6}$cycloalkyl optionally substituted with one —$OC_{1-4}$alkyl; $C_{1-6}$alkyl substituted with one cyano; —$CH_2$—C(=O)$NR^{8a}R^{8b}$; and $C_{2-6}$alkyl substituted with one or more substituents independently selected from the group of (i), (ii), (viii), (ix), (x), and (xii); wherein $R^{8a}$, $R^{8b}$, and $R^{8f}$ are each independently selected from the group of hydrogen; $C_{1-6}$alkyl; $C_{3-6}$cycloalkyl; and $C_{2-6}$alkyl substituted with one substituent selected from —OH, and —$OC_{1-4}$alkyl;

$R^{8d}$ is $C_{1-6}$alkyl;

$R^{8g}$ and $R^{8h}$ are each independently selected from the group of hydrogen, $C_{1-4}$alkyl and $C_{2-4}$alkyl substituted with one —$OC_{1-4}$alkyl;

and

Het⁸ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—$C_{1-4}$alkyl, $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;

Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —$OC_{1-4}$alkyl; or Het⁹ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one $C_{1-4}$alkyl; or Het⁹ is selected from the group of

-continued

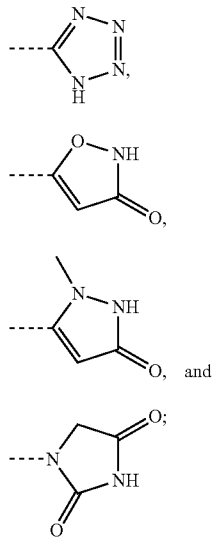

Het$^{12}$ is a heterocyclyl selected from the group of 1-piperidinyl, 1-piperazinyl, 1-pyrrolidinyl and 1-azetidinyl, each of which may be optionally substituted with one substituent selected from C$_{1-4}$alkyl and —OC$_{1-4}$alkyl;

R$^9$ is hydrogen or C$_{1-4}$alkyl;

and the pharmaceutically acceptable salts and the solvates thereof.

The present invention relates in particular to compounds of Formula (I) as defined herein, and tautomers and stereoisomeric forms thereof, wherein R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$; and C$_{3-6}$cycloalkyl;

R$^{1a}$, R$^{1b}$, R$^{2a}$, R$^{2b}$, R$^{2c}$ and R$^{2d}$ are each independently selected from hydrogen and C$_{1-4}$alkyl;

or R$^1$ and R$^2$ together with the carbon atom to which they are attached form a C$_{3-6}$cycloalkyl;

R$^3$ is selected from the group of hydrogen; halo; C$_{3-6}$cycloalkyl; C$_{1-4}$alkyl; C$_{1-4}$alkyl substituted with one or more fluoro substituents; and C$_{1-4}$alkyloxy substituted with one or more fluoro substituents;

R$^4$ is hydrogen;

R$^5$ is selected from the group of hydrogen; C$_{1-6}$alkyl; C$_{1-6}$alkyl substituted with one or more fluoro substituents; cyano; C$_{1-6}$alkyl substituted with one substituent selected from the group of —NR$^{5a}$R$^{5b}$, —OH, —OC$_{1-4}$alkyl; C$_{3-6}$cycloalkyl; and —C(=O)—NR$^{5c}$R$^{5d}$; wherein R$^{5a}$ and R$^{5b}$ are each independently selected from the group of hydrogen and C$_{1-4}$alkyl; and R$^{5c}$ and R$^{5d}$ are each independently selected from the group of hydrogen; and C$_{2-6}$alkyl substituted with one substituent selected from —NR$^{5x}$R$^{5y}$, —OH and —OC$_{1-4}$alkyl;

R$^{5x}$ and R$^{5y}$ are each independently selected from the group of hydrogen and C$_{1-4}$alkyl;

R$^6$ is selected from the group of hydrogen; halogen; cyano; C$_{1-6}$alkyl; C$_{1-6}$alkyl substituted with one or more fluoro substituents; C$_{1-6}$alkyl substituted with one —OH; C$_{1-6}$alkyl substituted with one NH$_2$; —C$_{1-6}$alkyloxyC$_{1-4}$alkyl; —OC$_{1-6}$alkyl; —OC$_{1-6}$alkyl substituted with one or more fluoro substituents; and —OC$_{2-6}$alkyl substituted with one —OC$_{1-4}$alkyl;

R$^7$ is selected from the group of hydrogen, C$_{1-4}$alkyl, —OC$_{1-4}$alkyl, and —NHC$_{1-4}$alkyl;

R$^8$ is selected from the group of hydrogen; —C(=O)—NR$^{8g}$R$^{8h}$; Het$^8$; C$_{1-6}$alkyl optionally substituted with one Het$^9$; —C(=O)—Het$^{12}$; C$_{3-6}$cycloalkyl optionally substituted with one —OC$_{1-4}$alkyl; C$_{1-6}$alkyl substituted with one cyano; —CH$_2$—C(=O)NR$^{8a}$R$^{8b}$; and C$_{2-6}$alkyl substituted with one or more substituents independently selected from the group of (i), (ii), (viii), (ix), (x), and (xii); wherein R$^{8a}$, R$^{8b}$, and R$^{8f}$ are each independently selected from the group of hydrogen; C$_{1-6}$alkyl; C$_{3-6}$cycloalkyl; and C$_{2-6}$alkyl substituted with one substituent selected from —OH, and —OC$_{1-4}$alkyl;

R$^{8d}$ is C$_{1-6}$alkyl;

R$^{8g}$ and R$^{8h}$ are each independently selected from the group of hydrogen, C$_{1-4}$alkyl and C$_{2-4}$alkyl substituted with one —OC$_{1-4}$alkyl;

and

Het$^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—C$_{1-4}$alkyl, C$_{1-4}$alkyl, C$_{3-6}$cycloalkyl, C$_{1-4}$alkyl substituted with one C$_{3-6}$cycloalkyl, C$_{1-4}$alkyl substituted with one or more fluoro substituents, and C$_{1-4}$alkyl substituted with one —OC$_{1-4}$alkyl;

Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, C$_{1-4}$alkyl, C$_{1-4}$alkyl substituted with one or more fluoro substituents, and —OC$_{1-4}$alkyl; or Het$^9$ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one C$_{1-4}$alkyl; or Het$^9$ is selected from the group of

(e) 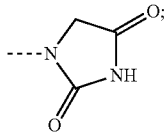

Het$^{12}$ is a heterocyclyl selected from the group of 1-piperidinyl, 1-piperazinyl, 1-pyrrolidinyl and 1-azetidinyl, each of which may be optionally substituted with one substituent selected from C$_{1-4}$alkyl and —OC$_{1-4}$alkyl;

R$^9$ is hydrogen or C$_{1-4}$alkyl;

and the pharmaceutically acceptable salts and the solvates thereof.

The present invention relates in particular to compounds of Formula (I) as defined herein, and tautomers and stereoisomeric forms thereof, wherein R$^1$ is selected from the group of hydrogen; C$_{1-6}$alkyl; and C$_{1-6}$alkyl substituted with one or more fluoro substituents;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —OC$_{1-4}$alkyl and C$_{3-6}$cycloalkyl; —C(=O)—NR$^{2c}$R$^{2d}$; C$_{3-6}$cycloalkyl; Het$^1$; Het$^2$; and phenyl;

R$^{2c}$ and R$^{2d}$ are each independently selected from C$_{1-4}$alkyl;

Het$^1$ is a heterocyclyl selected from the group of piperidinyl, azetidinyl and oxetanyl, each of which may be optionally substituted with one C$_{1-4}$alkyl;

Het$^2$ is a heteroaryl selected from the group of thiazolyl, oxazolyl, isoxazolyl and pyridinyl;

or R$^1$ and R$^2$ together with the carbon atom to which they are attached form a C$_{3-6}$cycloalkyl or a Het$^3$ group; wherein Het$^3$ is a heterocyclyl selected from the group of piperidinyl, tetrahydrofuranyl and azetidinyl, each of which may be optionally substituted with one C$_{1-4}$alkyl; or Het$^3$ is 2-oxo-3-pyrrolidinyl substituted with one C$_{1-4}$alkyl on the nitrogen atom;

R$^3$ is selected from the group of hydrogen; halo; C$_{3-6}$cycloalkyl; C$_{1-4}$alkyl; and C$_{1-4}$alkyl substituted with one or more fluoro substituents;

R$^4$ is hydrogen;

R$^5$ is selected from the group of hydrogen; C$_{1-6}$alkyl; and —C(=O)—NR$^{5c}$R$^{5d}$; wherein R$^{5c}$ and R$^{5d}$ are each independently selected from the group of hydrogen; and C$_{2-6}$alkyl substituted with one —OC$_{1-4}$alkyl;

R$^6$ is selected from the group of hydrogen; halogen; cyano; C$_{1-6}$alkyl; C$_{1-6}$alkyl substituted with one or more fluoro substituents; C$_{1-6}$alkyl substituted with one NH$_2$; —C$_{1-6}$alkyloxyC$_{1-4}$alkyl; —O—C$_{1-6}$alkyl; and —OC$_{2-6}$alkyl substituted with one —OC$_{1-4}$alkyl;

R$^7$ is selected from the group of hydrogen, and C$_{1-4}$alkyl;

R$^8$ is selected from the group of hydrogen; —C(=O)—NR$^{8g}$R$^{8h}$; Het$^8$; C$_{1-6}$alkyl optionally substituted with one Het$^9$; —C(=O)—Het$^{12}$; C$_{1-4}$alkyl substituted with one cyano; —CH$_2$—C(=O)NR$^{8a}$R$^{8b}$; and C$_{2-6}$alkyl substituted with one or more substituents independently selected from the group of (ii), (iii), (viii), (x), (xii); wherein R$^{8a}$, R$^{8b}$, R$^{8c}$, and R$^{8f}$ are each independently selected from the group of hydrogen; C$_{1-6}$alkyl; and C$_{2-6}$alkyl substituted with one substituent selected from —OH, and —OC$_{1-4}$alkyl;

R$^{8d}$ is C$_{1-6}$alkyl;

R$^{8g}$ and R$^{8h}$ are each independently selected from C$_{1-4}$alkyl; Het$^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from C$_{1-4}$alkyl, C$_{3-6}$cycloalkyl, —C(=O)—C$_{1-4}$alkyl, C$_{1-4}$alkyl substituted with one C$_{3-6}$cycloalkyl, C$_{1-4}$alkyl substituted with one or more fluoro substituents, and C$_{1-4}$alkyl substituted with one —OC$_{1-4}$alkyl;

Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl; or Het$^9$ is pyrazolyl which may be optionally substituted with one C$_{1-4}$alkyl; or Het$^9$ is

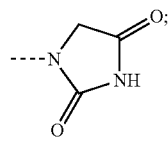

Het$^{12}$ is 1-piperazinyl which may be optionally substituted with one C$_{1-4}$alkyl substituent;

R$^9$ is hydrogen or C$_{1-4}$alkyl;

and the pharmaceutically acceptable salts and the solvates thereof.

The present invention relates in particular to compounds of Formula (I) as defined herein, and tautomers and stereoisomeric forms thereof, wherein R$^1$ is selected from the group of hydrogen; C$_{1-6}$alkyl; and C$_{1-6}$alkyl substituted with one or more fluoro substituents;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —OC$_{1-4}$alkyl and C$_{3-6}$cycloalkyl; —C(=O)—NR$^{2c}$R$^{2d}$; C$_{3-6}$cycloalkyl; Het$^2$ and phenyl; in particular R$^2$ is selected from the group of hydrogen; C$_{1-6}$alkyl; C$_{1-6}$alkyl substituted with one or more fluoro substituents; C$_{1-6}$alkyl substituted with one substituent selected from the group of —OC$_{1-4}$alkyl and C$_{3-6}$cycloalkyl; —C(=O)—NR$^{2c}$R$^{2d}$; and C$_{3-6}$cycloalkyl;

R$^{2c}$ and R$^{2d}$ are each independently selected from C$_{1-4}$alkyl;

Het$^2$ is a heteroaryl selected from the group of thiazolyl, oxazolyl, isoxazolyl and pyridinyl;

or R$^1$ and R$^2$ together with the carbon atom to which they are attached form a C$_{3-6}$cycloalkyl;

R$^3$ is selected from the group of hydrogen; halo; C$_{3-6}$cycloalkyl; C$_{1-4}$alkyl; and C$_{1-4}$alkyl substituted with one or more fluoro substituents;

R$^4$ is hydrogen;

R$^5$ is selected from the group of hydrogen; C$_{1-6}$alkyl; and —C(=O)—NR$^{5c}$R$^{5d}$; wherein R$^{5c}$ and R$^{5d}$ are each independently selected from the group of hydrogen; and C$_{2-6}$alkyl substituted with one —OC$_{1-4}$alkyl;

R$^6$ is selected from the group of hydrogen; halogen; cyano; C$_{1-6}$alkyl; C$_{1-6}$alkyl substituted with one or more fluoro substituents; C$_{1-6}$alkyl substituted with one NH$_2$; and —OC$_{2-6}$alkyl substituted with one —OC$_{1-4}$alkyl;

R$^7$ is selected from the group of hydrogen, and C$_{1-4}$alkyl;

R$^8$ is selected from the group of hydrogen; —C(=O)—NR$^{8g}$R$^{8h}$; Het$^8$; C$_{1-6}$alkyl optionally substituted with one Het$^9$; —C(=O)—Het$^{12}$; C$_{1-4}$alkyl substituted with one cyano; —CH$_2$—C(=O)NR$^{8a}$R$^{8b}$; and C$_{2-6}$alkyl substituted with one or more substituents independently selected from the group of (ii), (viii), (x), (xii); wherein $R^{8a}$, $R^{8b}$, and $R^{8f}$ are each independently selected from the group of hydrogen; $C_{1-6}$alkyl; and $C_{2-6}$alkyl substituted with one substituent selected from —OH, and —$OC_{1-4}$alkyl;
$R^{8d}$ is $C_{1-6}$alkyl;
$R^{8g}$ and $R^{8h}$ are each independently selected from $C_{1-4}$alkyl;
$Het^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, —C(═O)—$C_{1-4}$alkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;
$Het^9$ is a heterocyclyl selected from the group of morpholinyl, piperidinyl, tetrahydropyranyl, tetrahydrofuranyl, and oxetanyl, each of which may be optionally substituted with one $C_{1-4}$alkyl; or $Het^9$ is pyrazolyl which may be optionally substituted with one $C_{1-4}$alkyl; or $Het^9$ is

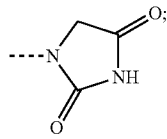

$Het^{12}$ is 1-piperazinyl which may be optionally substituted with one $C_{1-4}$alkyl substituent;
$R^9$ is hydrogen or $C_{1-4}$alkyl;
and the pharmaceutically acceptable salts and the solvates thereof.

The present invention relates in particular to compounds of Formula (I) as defined herein, and tautomers and stereoisomeric forms thereof, wherein
$R^1$ is selected from the group of $C_{1-6}$alkyl; and $C_{1-6}$alkyl substituted with one or more fluoro substituents;
$R^2$ is selected from the group of $C_{1-6}$alkyl and $C_{3-6}$cycloalkyl;
or $R^1$ and $R^2$ together with the carbon atom to which they are attached form a $C_{3-6}$cycloalkyl;
$R^3$ is selected from the group of hydrogen; $C_{3-6}$cycloalkyl; and $C_{1-4}$alkyl;
$R^4$ is hydrogen;
$R^5$ is hydrogen;
$R^6$ is selected from the group of hydrogen; halogen; $C_{1-6}$alkyl; and —$OC_{1-6}$alkyl;
$R^7$ is hydrogen;
$R^8$ is selected from the group of hydrogen; $Het^8$; $C_{1-6}$alkyl optionally substituted with one $Het^9$; and $C_{2-6}$alkyl substituted with one or more —$OR^{8f}$ substituents;
$R^{8f}$ is $C_{1-4}$alkyl;
$Het^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;
$Het^9$ is a heterocyclyl selected from the group of morpholinyl, piperidinyl, tetrahydropyranyl, tetrahydrofuranyl, and oxetanyl, each of which may be optionally substituted with one $C_{1-4}$alkyl;
$R^9$ is hydrogen;
and the pharmaceutically acceptable salts and the solvates thereof.

The present invention relates in particular to compounds of Formula (I) as defined herein, and tautomers and stereoisomeric forms thereof, wherein
$R^1$ is selected from the group of $C_{1-6}$alkyl; and $C_{1-6}$alkyl substituted with one or more fluoro substituents;
$R^2$ is selected from the group of $C_{1-6}$alkyl and $C_{3-6}$cycloalkyl;
$R^3$ is selected from the group of hydrogen; $C_{3-6}$cycloalkyl; and $C_{1-4}$alkyl;
$R^4$ is hydrogen;
$R^5$ is hydrogen;
$R^6$ is selected from the group of halogen; $C_{1-6}$alkyl; and —$OC_{1-6}$alkyl; in particular halogen;
$R^7$ is hydrogen;
$R^8$ is selected from the group of hydrogen; $Het^8$; $C_{1-6}$alkyl optionally substituted with one $Het^9$; and $C_{2-6}$alkyl substituted with one or more —$OR^{8f}$ substituents;
$R^{8f}$ is $C_{1-4}$alkyl;
$Het^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;
$Het^9$ is a heterocyclyl selected from the group of morpholinyl, piperidinyl, tetrahydropyranyl, tetrahydrofuranyl, and oxetanyl, each of which may be optionally substituted with one $C_{1-4}$alkyl;
$R^9$ is hydrogen;
and the pharmaceutically acceptable salts and the solvates thereof.

The present invention relates in particular to compounds of Formula (I) as defined herein, and tautomers and stereoisomeric forms thereof, wherein
$R^1$ is selected from the group of methyl; and methyl substituted with one fluoro substituent;
$R^2$ is selected from the group of methyl and cyclopropyl;
or $R^1$ and $R^2$ together with the carbon atom to which they are attached form a cyclopentyl;
$R^3$ is selected from the group of hydrogen; cyclopropyl; and methyl;
$R^4$ is hydrogen;
$R^5$ is hydrogen;
$R^6$ is selected from the group of hydrogen; fluoro; chloro; methyl; and methoxy;
$R^7$ is hydrogen;
$R^8$ is selected from the group of hydrogen; $Het^8$; $C_{1-6}$alkyl optionally substituted with one $Het^9$; and $C_{2-4}$alkyl substituted with one or more —$OR^{8f}$ substituents;
$R^{8f}$ is $CH_3$;
$Het^8$ is a heterocyclyl, bound through any available carbon atom, selected from the group of piperidinyl, pyrrolidinyl, azetidinyl and oxetanyl, each of which may be optionally substituted with one substituent selected from $C_{1-4}$alkyl, cyclopropyl, $C_{1-4}$alkyl substituted with 3 fluoro substituents, and $C_{1-4}$alkyl substituted with one $C_{3-6}$cycloalkyl;
$Het^9$ is a heterocyclyl selected from the group of morpholinyl, tetrahydrofuranyl, and oxetanyl, each of which may be optionally substituted with one methyl;
$R^9$ is hydrogen;
and the pharmaceutically acceptable salts and the solvates thereof.

The present invention relates in particular to compounds of Formula (I) as defined herein, and tautomers and stereoisomeric forms thereof, wherein
$R^1$ is selected from the group of methyl; and methyl substituted with one fluoro substituent;
$R^2$ is selected from the group of methyl and cyclopropyl;
$R^3$ is selected from the group of hydrogen; cyclopropyl; and methyl;
$R^4$ is hydrogen;
$R^5$ is hydrogen; $R^6$ is selected from the group of fluoro; chloro; methyl; and methoxy; in particular $R^6$ is selected from fluoro and chloro; more in particular $R_6$ is selected from fluoro;
$R^7$ is hydrogen;
$R^8$ is selected from the group of hydrogen; Het$^8$; $C_{1-6}$alkyl optionally substituted with one Het$^9$; and $C_{2-4}$alkyl substituted with one or more —OR$^{8f}$ substituents;
$R^{8f}$ is CH$_3$;
Het$^8$ is a heterocyclyl, bound through any available carbon atom, selected from the group of piperidinyl, pyrrolidinyl, azetidinyl and oxetanyl, each of which may be optionally substituted with one substituent selected from $C_{1-4}$alkyl, cyclopropyl, $C_{1-4}$alkyl substituted with 3 fluoro substituents, and $C_{1-4}$alkyl substituted with one cyclopropyl;
Het$^9$ is a heterocyclyl selected from the group of morpholinyl, tetrahydrofuranyl, and oxetanyl, each of which may be optionally substituted with one methyl;
$R^9$ is hydrogen;
and the pharmaceutically acceptable salts and the solvates thereof.

The present invention relates in particular to compounds of Formula (I) as defined herein, and tautomers and stereoisomeric forms thereof, wherein
$R^1$ is selected from the group of hydrogen; $C_{1-6}$alkyl; $C_{1-6}$alkyl substituted with one or more fluoro substituents; and $C_{1-6}$alkyl substituted with one substituent selected from the group of —NR$^{1a}$R$^{1b}$, —OH and —OC$_{1-4}$alkyl;
$R^2$ is selected from the group of hydrogen; $C_{1-6}$alkyl; $C_{1-6}$alkyl substituted with one or more fluoro substituents; $C_{1-6}$alkyl substituted with one substituent selected from the group of —NR$^{2a}$R$^{2b}$, —OH, —OC$_{1-4}$alkyl, $C_{3-6}$cycloalkyl, Het$^2$ and phenyl; $C_{3-6}$cycloalkyl; Het$^2$; and phenyl; wherein the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
$R^{1a}$, $R^{1b}$, $R^{2a}$, and $R^{2b}$ are each independently selected from hydrogen and $C_{1-4}$alkyl;
Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
or $R^1$ and $R^2$ together with the carbon atom to which they are attached form a $C_{3-6}$cycloalkyl;
$R^3$ is selected from the group of hydrogen; $C_{1-4}$alkyl; and $C_{1-4}$alkyl substituted with one or more fluoro substituents;
$R^4$ is selected from the group of hydrogen; halogen; $C_{1-4}$alkyl; $C_{1-4}$alkyl substituted with one or more fluoro substituents; and cyano;
$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —NR$^{5a}$R$^{5b}$, —OH, —OC$_{1-4}$alkyl, $C_{3-6}$cycloalkyl, and Het$^4$; $C_{3-6}$cycloalkyl; and —C(=O)—NR$^{5c}$R$^{5d}$; wherein
$R^{5a}$ and $R^{5b}$ are each independently selected from the group of hydrogen and $C_{1-4}$alkyl; and $R^{5c}$ and $R^{5d}$ are each independently selected from the group of hydrogen; $C_{1-6}$alkyl optionally substituted with Het$^5$; and $C_{2-6}$alkyl substituted with one substituent selected from —NR$^{5x}$R$^{5y}$, —OH and —OC$_{1-4}$alkyl;
Het$^4$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one $C_{1-4}$alkyl;
Het$^5$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one $C_{1-4}$alkyl;
$R^{5x}$ and $R^{5y}$ are each independently selected from the group of hydrogen and $C_{1-4}$alkyl; or
$R^{5c}$ and $R^{5d}$ together with the nitrogen atom to which they are attached form a Het$^6$ group; wherein Het$^6$ is a heterocyclyl selected from the group of piperidinyl, pyrrolidinyl, azetidinyl, piperazinyl and morpholinyl, each of which may be optionally substituted with one substituent selected from $C_{1-4}$alkyl and $C_{1-4}$alkyl substituted with one —OH;
$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-C(=O)—NR$^{6a}$R$^{6b}$; —OC$_{1-6}$ alkyl; —OC$_{1-6}$alkyl substituted with one or more fluoro substituents; —OC$_{1-6}$alkyl substituted with one Het$^7$ substituent; —OC$_{2-6}$alkyl substituted with one substituent selected from the group of —NR$^{6c}$R$^{6d}$, —OH, and —OC$_{1-4}$alkyl; and —C(=O)—NR$^{6a}$R$^{6b}$; wherein
$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkylNR$^{6x}$R$^{6y}$; or
$R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;
$R^{6x}$ is hydrogen or $C_{1-4}$alkyl and $R^{6y}$ is $C_{1-4}$alkyl; and Het$^7$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;
$R^7$ is selected from the group of hydrogen, $C_{1-4}$alkyl, cyano, —OC$_{1-4}$alkyl, —NHC$_{1-4}$alkyl, —NH—C(=O)—$C_{1-4}$alkyl and —C(=O)—NR$^{7a}$R$^{7b}$; wherein
$R^{7a}$ and $R^{7b}$ are each independently selected from hydrogen and $C_{1-4}$alkyl;
$R^8$ is selected from the group of hydrogen; Het$^8$; $C_{1-6}$alkyl optionally substituted with Het$^9$; and $C_{2-6}$alkyl substituted with one or more substituents independently selected from the group of
(i) fluoro,
(ii) —NR$^{8a}$R$^{8b}$,
(iii) —NR$^{8c}$C(=O)R$^{8d}$,
(iv) —NR$^{8c}$C(=O)NR$^{8a}$R$^{8b}$,
(v) —NR$^{8c}$C(=O)OR$^{8e}$,
(vi) —NR$^{8c}$S(=O)$_2$NR$^{8a}$R$^{8b}$,
(vii) —NR$^{8c}$S(=O)$_2$R$^{8d}$,
(viii) —OR$^{8f}$,
(ix) —OC(=O)NR$^{8a}$R$^{8b}$,
(x) —C(=O)NR$^{8a}$R$^{8b}$,
(xi) —SR$^{8e}$, (xii) —S(O)₂R⁸ᵈ, and
(xiii) —S(O)₂NR⁸ᵃR⁸ᵇ; wherein
R⁸ᵃ, R⁸ᵇ, R⁸ᶜ and R⁸ᶠ are each independently selected from the group of hydrogen; C₁₋₆alkyl, which may be optionally substituted with one substituent selected from Het¹⁰ and Het¹¹; C₃₋₆cycloalkyl; and C₂₋₆alkyl substituted with one substituent selected from —NR⁸ˣR⁸ʸ, —OH, and —OC₁₋₄alkyl;
R⁸ᵈ is selected from the group of C₁₋₆alkyl, which may be optionally substituted with one substituent selected from —NR⁸ˣR⁸ʸ, —OH, —OC₁₋₄alkyl, Het¹⁰ and Het¹¹; and C₃₋₆cycloalkyl;
R⁸ᵉ is selected from the group of C₁₋₆alkyl, which may be optionally substituted with one substituent selected from Het¹⁰ and Het¹¹; C₃₋₆cycloalkyl; and C₂₋₆alkyl substituted with one substituent selected from —NR⁸ˣR⁸ʸ, —OH, and —OC₁₋₄alkyl;
wherein R⁸ˣ and R⁸ʸ are each independently selected from hydrogen and C₁₋₄alkyl;
and
Het⁸ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one C₁₋₄alkyl;
Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one C₁₋₄alkyl;
Het¹⁰ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one C₁₋₄alkyl;
Het¹¹ is selected from the group of

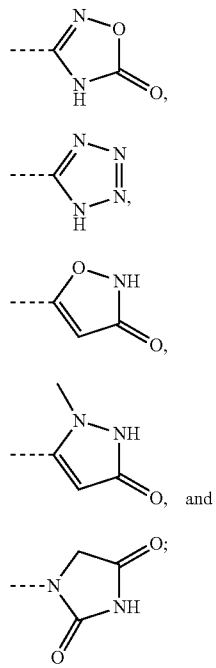

R⁹ is hydrogen or C₁₋₄alkyl;
and the pharmaceutically acceptable salts and the solvates thereof.

The present invention relates in particular to compounds of Formula (I) as defined herein, and tautomers and stereoisomeric forms thereof, wherein
R¹ is selected from the group of hydrogen; C₁₋₆alkyl; C₁₋₆alkyl substituted with one or more fluoro substituents; and C₁₋₆alkyl substituted with one substituent selected from the group of —NR¹ᵃR¹ᵇ, —OH and —OC₁₋₄alkyl;
R² is selected from the group of hydrogen; C₁₋₆alkyl; C₁₋₆alkyl substituted with one or more fluoro substituents; C₁₋₆alkyl substituted with one substituent selected from the group of —NR²ᵃR²ᵇ, —OH, —OC₁₋₄alkyl, C₃₋₆cycloalkyl, Het¹, Het² and phenyl; C₃₋₆cycloalkyl; Het¹; Het²; and phenyl; wherein
the phenyl groups are optionally substituted with one or two substituents independently selected from the group of halogen, cyano, C₁₋₄alkyl, C₁₋₄alkoxy, C₁₋₄alkyl substituted with one or more fluoro substituents, and C₁₋₄alkyloxy substituted with one or more fluoro substituents;
R¹ᵃ, R¹ᵇ, R²ᵃ, and R²ᵇ are each independently selected from hydrogen and C₁₋₄alkyl;
Het¹ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C₁₋₄alkyl;
Het² is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, C₁₋₄alkyl, C₁₋₄alkoxy, C₁₋₄alkyl substituted with one or more fluoro substituents, and C₁₋₄alkyloxy substituted with one or more fluoro substituents;
or R¹ and R² together with the carbon atom to which they are attached form a C₃₋₆cycloalkyl or a Het³ group; wherein
Het³ is a heterocyclyl selected from the group of piperidinyl, tetrahydropyranyl, pyrrolidinyl, tetrahydrofuranyl, azetidinyl and oxetanyl, each of which may be optionally substituted with one C₁₋₄alkyl;
R³ is selected from the group of hydrogen; C₁₋₄alkyl; and C₁₋₄alkyl substituted with one or more fluoro substituents;
R⁴ is selected from the group of hydrogen; halogen; C₁₋₄alkyl; C₁₋₄alkyl substituted with one or more fluoro substituents; and cyano;
R⁵ is selected from the group of hydrogen; C₁₋₆alkyl; C₁₋₆alkyl substituted with one or more fluoro substituents; cyano; C₁₋₆alkyl substituted with one substituent selected from the group of —NR⁵ᵃR⁵ᵇ, —OH, —OC₁₋₄alkyl, C₃₋₆cycloalkyl, and Het⁴; C₃₋₆cycloalkyl; and —C(=O)—NR⁵ᶜR⁵ᵈ; wherein
R⁵ᵃ and R⁵ᵇ are each independently selected from the group of hydrogen and C₁₋₄alkyl; and R⁵ᶜ and R⁵ᵈ are each independently selected from the group of hydrogen; C₁₋₆alkyl optionally substituted with Het⁵; and C₂₋₆alkyl substituted with one substituent selected from —NR⁵ˣR⁵ʸ, —OH and —OC₁₋₄alkyl;
Het⁴ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C₁₋₄alkyl;
Het⁵ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C₁₋₄alkyl;
R⁵ˣ and R⁵ʸ are each independently selected from the group of hydrogen and C₁₋₄alkyl; or
R⁵ᶜ and R⁵ᵈ together with the nitrogen atom to which they are attached form a Het⁶ group; wherein Het⁶ is a heterocyclyl selected from the group of piperidinyl, pyrrolidinyl, azetidinyl, piperazinyl and morpholinyl, each of which may be optionally substituted with one substituent selected from $C_{1-4}$alkyl and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-C(=O)—NR$^{6a}$R$^{6b}$; —OC$_{1-6}$ alkyl; —OC$_{1-6}$alkyl substituted with one or more fluoro substituents; —OC$_{1-6}$alkyl substituted with one Het$^7$ substituent; —OC$_{2-6}$alkyl substituted with one substituent selected from the group of —NR$^{6c}$R$^{6d}$, —OH, and —OC$_{1-4}$alkyl; and —C(=O)—NR$^{6a}$R$^{6b}$; wherein $R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkylNR$^{6x}$R$^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;

$R^{6x}$ is hydrogen or $C_{1-4}$alkyl and $R^{6y}$ is $C_{1-4}$alkyl; and Het$^7$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;

$R^7$ is selected from the group of hydrogen, $C_{1-4}$alkyl, cyano, —OC$_{1-4}$alkyl, —NHC$_{1-4}$alkyl, —NH—C(=O)—$C_{1-4}$alkyl and —C(=O)—NR$^{7a}$R$^{7b}$; wherein $R^{7a}$ and $R^{7b}$ are each independently selected from hydrogen and $C_{1-4}$alkyl;

$R^8$ is selected from the group of hydrogen; Het$^8$; $C_{1-6}$alkyl optionally substituted with Het$^9$; and $C_{2-6}$alkyl substituted with one or more substituents independently selected from the group of
(i) fluoro,
(ii) —NR$^{8a}$R$^{8b}$,
(iii) —NR$^{8c}$C(=O)R$^{8d}$,
(iv) —NR$^{8c}$C(=O)NR$^{8a}$R$^{8b}$,
(v) —NR$^{8c}$C(=O)OR$^{8e}$,
(vi) —NR$^{8c}$S(=O)$_2$NR$^{8a}$R$^{8b}$,
(vii) —NR$^{8c}$S(=O)$_2$R$^{8d}$,
(viii) —OR$^{8f}$,
(ix) —OC(=O)NR$^{8a}$R$^{8b}$,
(x) —C(=O)NR$^{8a}$R$^{8b}$,
(xi) —SR$^{8e}$,
(xii) —S(O)$_2$R$^{8d}$, and
(xiii) —S(O)$_2$NR$^{8a}$R$^{8b}$; wherein
$R^{8a}$, $R^{8b}$, $R^{8c}$ and $R^{8f}$ are each independently selected from the group of hydrogen; $C_{1-6}$alkyl, which may be optionally substituted with one substituent selected from Het$^{10}$ and Het$^{11}$; $C_{3-6}$cycloalkyl; and $C_{2-6}$alkyl substituted with one substituent selected from —NR$^{8x}$R$^{8y}$, —OH, and —OC$_{1-4}$alkyl;

$R^{8d}$ is selected from the group of $C_{1-6}$alkyl, which may be optionally substituted with one substituent selected from —NR$^{8x}$R$^{8y}$, —OH, —OC$_{1-4}$alkyl, Het$^{10}$ and Het$^{11}$; and $C_{3-6}$cycloalkyl;

$R^{8e}$ is selected from the group of $C_{1-6}$alkyl, which may be optionally substituted with one substituent selected from Het$^{10}$ and Het$^{11}$; $C_{3-6}$cycloalkyl; and $C_{2-6}$alkyl substituted with one substituent selected from —NR$^{8x}$R$^{8y}$, —OH, and —OC$_{1-4}$alkyl;
wherein $R^{8x}$ and $R^{8y}$ are each independently selected from hydrogen and $C_{1-4}$alkyl; and Het$^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one $C_{1-4}$alkyl;

Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one $C_{1-4}$alkyl;

Het$^{10}$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one $C_{1-4}$alkyl;

Het$^{11}$ is selected from the group of

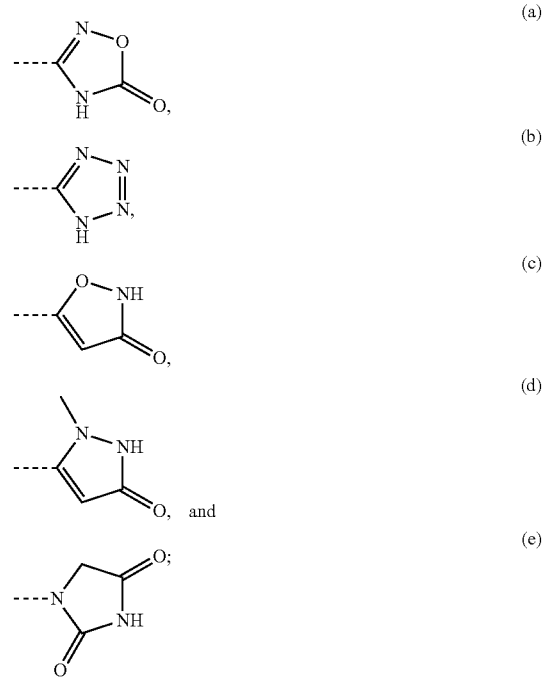

and $R^9$ is hydrogen or $C_{1-4}$alkyl;

and the pharmaceutically acceptable salts and the solvates thereof.

The present invention relates in particular to compounds of Formula (I) as defined herein, and tautomers and stereoisomeric forms thereof, wherein $R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; $C_{3-6}$cycloalkyl; and Het$^2$;

Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl or a Het$^3$ group; in particular $C_{3-6}$cycloalkyl; wherein Het³ is a heterocyclyl selected from the group of piperidinyl, tetrahydropyranyl, pyrrolidinyl, tetrahydrofuranyl, azetidinyl and oxetanyl, each of which may be optionally substituted with one $C_{1-4}$alkyl;

$R^3$ is selected from the group of hydrogen; $C_{1-4}$alkyl; and $C_{1-4}$alkyl substituted with one or more fluoro substituents;

$R^4$ is selected from the group of hydrogen; halogen; $C_{1-4}$alkyl; $C_{1-4}$alkyl substituted with one or more fluoro substituents; and cyano;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl, and Het⁴; and —C(=O)—$NR^{5c}R^{5d}$; wherein $R^{5a}$ and $R^{5b}$ are each independently selected from the group of hydrogen and $C_{1-4}$alkyl; and $R^{5c}$ and $R^{5d}$ are each independently selected from the group of hydrogen; $C_{1-6}$alkyl optionally substituted with Het⁵; and $C_{2-6}$alkyl substituted with one substituent selected from —$NR^{5x}R^{5y}$, —OH and —$OC_{1-4}$alkyl;

Het⁴ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one $C_{1-4}$alkyl;

Het⁵ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one $C_{1-4}$alkyl;

$R^{5x}$ and $R^{5y}$ are each independently selected from the group of hydrogen and $C_{1-4}$alkyl; or $R^{5c}$ and $R^{5d}$ together with the nitrogen atom to which they are attached form a Het⁶ group; wherein Het⁶ is a heterocyclyl selected from the group of piperidinyl, pyrrolidinyl, azetidinyl, piperazinyl and morpholinyl, each of which may be optionally substituted with one substituent selected from $C_{1-4}$alkyl and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-C(=O)—$NR^{6a}R^{6b}$; —$OC_{1-6}$alkyl; —$OC_{1-6}$alkyl substituted with one or more fluoro substituents; —$OC_{1-6}$alkyl substituted with one Het⁷ substituent; —$OC_{2-6}$alkyl substituted with one substituent selected from the group of —$NR^{6c}R^{6d}$, —OH, and —$OC_{1-4}$alkyl; and —C(=O)—$NR^{6a}R^{6b}$; wherein $R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkyl$NR^{6x}R^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;

$R^{6x}$ is hydrogen or $C_{1-4}$alkyl and $R^{6y}$ is $C_{1-4}$alkyl; and Het⁷ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;

$R^7$ is selected from the group of hydrogen, cyano, —$OC_{1-4}$alkyl, —$NHC_{1-4}$alkyl, —NH—C(=O)—$C_{1-4}$alkyl and —C(=O)—$NR^{7a}R^{7b}$; wherein $R^{7a}$ and $R^{7b}$ are each independently selected from hydrogen and $C_{1-4}$alkyl;

$R^8$ is selected from the group of hydrogen; Het⁸; $C_{1-6}$alkyl optionally substituted with Het⁹; and $C_{2-6}$alkyl substituted with one or more substituents independently selected from the group of (i) fluoro,
(ii) —$NR^{8a}R^{8b}$,
(iii) —$NR^{8c}C(=O)R^{8d}$,
(iv) —$NR^{8c}C(=O)NR^{8a}R^{8b}$,
(v) —$NR^{8c}C(=O)OR^{8e}$,
(vi) —$NR^{8c}S(=O)_2NR^{8a}R^{8b}$,
(vii) —$NR^{8c}S(=O)_2R^{8d}$,
(viii) —$OR^{8f}$,
(ix) —$OC(=O)NR^{8a}R^{8b}$,
(x) —$C(=O)NR^{8a}R^{8b}$,
(xi) —$SR^{8e}$,
(xii) —$S(O)_2R^{8d}$, and
(xiii) —$S(O)_2NR^{8a}R^{8b}$; wherein $R^{8a}$, $R^{8b}$, $R^{8c}$ and $R^{8f}$ are each independently selected from the group of hydrogen; $C_{1-6}$alkyl, which may be optionally substituted with one substituent selected from Het¹⁰ and Het¹¹; $C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH, —$OC_{1-4}$alkyl, Het¹⁰ and Het¹¹; and $C_{3-6}$cycloalkyl;

$R^{8e}$ is selected from the group of $C_{1-6}$alkyl, which may be optionally substituted with one substituent selected from Het¹⁰ and Het¹¹; $C_{3-6}$cycloalkyl; and $C_{2-6}$alkyl substituted with one substituent selected from —$NR^{8x}R^{8y}$, —OH, and —$OC_{1-4}$alkyl;

wherein $R^{8x}$ and $R^{8y}$ are each independently selected from hydrogen and $C_{1-4}$alkyl;

and

Het⁸ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one $C_{1-4}$alkyl;

Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one $C_{1-4}$alkyl;

Het¹⁰ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one $C_{1-4}$alkyl;

Het¹¹ is selected from the group of

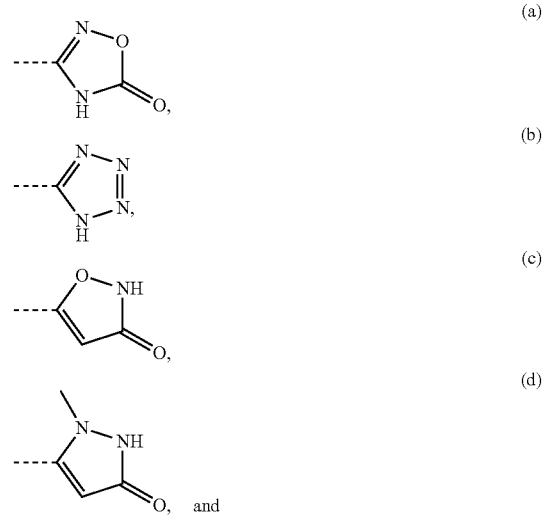

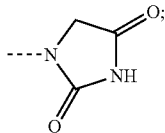

(e)

and
R$^9$ is hydrogen or C$_{1-4}$alkyl;
and the pharmaceutically acceptable salts and the solvates thereof.

The present invention relates in particular to compounds of Formula (I) as defined herein, and tautomers and stereoisomeric forms thereof, wherein
R$^1$ is selected from the group of hydrogen; C$_{1-6}$alkyl; and C$_{1-6}$alkyl substituted with one or more fluoro substituents;
R$^2$ is selected from the group of hydrogen; C$_{1-6}$alkyl; C$_{1-6}$alkyl substituted with one or more fluoro substituents; C$_{3-6}$cycloalkyl; and Het$^2$; wherein
Het$^2$ is a heteroaryl selected from the group of thienyl, thiazolyl, pyrrolyl, oxazolyl, pyrazolyl, imidazolyl, isoxazolyl, and isothiazolyl;
or R$^1$ and R$^2$ together with the carbon atom to which they are attached form a C$_{3-6}$cycloalkyl group;
R$^3$ is selected from the group of hydrogen;
R$^4$ is selected from the group of hydrogen;
R$^5$ is selected from the group of hydrogen;
R$^6$ is selected from the group of hydrogen; halogen; cyano; C$_{1-6}$alkyl; C$_{1-6}$alkyl substituted with one or more fluoro substituents; C$_{1-6}$alkyl substituted with one —OH;
R$^7$ is selected from the group of hydrogen; wherein
R$^8$ is selected from the group of hydrogen; C$_{1-6}$alkyl optionally substituted with Het$^9$; and C$_{2-6}$alkyl substituted with one or more substituents independently selected from the group of
(i) fluoro,
(ii) —NR$^{8a}$R$^{8b}$,
(iii) —NR$^{8c}$C(=O)R$^{8d}$,
(iv) —NR$^{8c}$C(=O)NR$^{8a}$R$^{8b}$,
(v) —NR$^{8c}$C(=O)OR$^{8e}$,
(vi) —NR$^{8c}$S(=O)$_2$NR$^{8a}$R$^{8b}$,
(vii) —NR$^{8c}$S(=O)$_2$R$^{8d}$,
(viii) —OR$^{8f}$,
(ix) —OC(=O)NR$^{8a}$R$^{8b}$,
(x) —C(=O)NR$^{8a}$R$^{8b}$,
(xi) —SR$^{8e}$,
(xii) —S(O)$_2$R$^{8d}$, and
(xiii) —S(O)$_2$NR$^{8a}$R$^{8b}$; wherein
R$^{8a}$, R$^{8b}$, R$^{8c}$ and R$^{8f}$ are each independently selected from the group of hydrogen; C$_{1-6}$alkyl; and C$_{2-6}$alkyl substituted with one substituent selected from —NR$^{8x}$R$^{8y}$, —OH, and —OC$_{1-4}$alkyl;
R$^{8d}$ is selected from the group of C$_{1-6}$alkyl;
R$^{8e}$ is selected from the group of C$_{1-6}$alkyl;
wherein R$^{8x}$ and R$^{8y}$ are each independently selected from hydrogen and C$_{1-4}$alkyl;
and
Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one C$_{1-4}$alkyl; and
R$^9$ is hydrogen or C$_{1-4}$alkyl;
and the pharmaceutically acceptable salts and the solvates thereof.

The present invention relates in particular to compounds of Formula (I) as defined herein, and tautomers and stereoisomeric forms thereof, wherein
R$^1$ is selected from the group of hydrogen and C$_{1-4}$alkyl;
R$^2$ is selected from the group of hydrogen; C$_{1-4}$alkyl; C$_{1-4}$alkyl substituted with one or more fluoro substituents; C$_{1-4}$alkyl substituted with one substituent selected from the group of —NR$^{2a}$R$^{2b}$, —OH, —OC$_{1-4}$alkyl, C$_{3-6}$cycloalkyl, Het$^1$, Het$^2$ and phenyl; C$_{3-6}$cycloalkyl; Het$^1$; Het$^2$; and phenyl; wherein
the phenyl group is optionally substituted with one or two substituents independently selected from the group of halogen, cyano, C$_{1-4}$alkyl, C$_{1-4}$alkoxy, C$_{1-4}$alkyl substituted with one or more fluoro substituents and C$_{1-4}$alkyloxy substituted with one or more fluoro substituents;
R$^{1a}$, R$^{1b}$, R$^{2a}$, and R$^{2b}$ are each independently selected from hydrogen and C$_{1-4}$alkyl;
Het$^1$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C$_{1-4}$alkyl;
Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, C$_{1-4}$alkyl, C$_{1-4}$alkoxy, C$_{1-4}$alkyl substituted with one or more fluoro substituents and C$_{1-4}$alkyloxy substituted with one or more fluoro substituents;
or R$^1$ and R$^2$ together with the carbon atom to which they are attached form a C$_{3-6}$cycloalkyl or a Het$^3$ group; wherein
Het$^3$ is a heterocyclyl selected from the group of piperidinyl, tetrahydropyranyl, pyrrolidinyl, tetrahydrofuranyl, azetidinyl and oxetanyl, each of which may be optionally substituted with one C$_{1-4}$alkyl;
R$^3$ is selected from the group of hydrogen; C$_{1-4}$alkyl; and C$_{1-4}$alkyl substituted with one or more fluoro substituents;
R$^4$ is selected from the group of hydrogen; halogen; C$_{1-4}$alkyl; C$_{1-4}$alkyl substituted with one or more fluoro substituents; and cyano;
R$^5$ is selected from the group of hydrogen; C$_{1-4}$alkyl; C$_{1-4}$alkyl substituted with one or more fluoro substituents; cyano; and —C(=O)—NR$^{5c}$R$^{5d}$; wherein
R$^{5c}$ is selected from the group of hydrogen and C$_{1-4}$alkyl;
R$^{5d}$ is selected from the group of C$_{1-4}$alkyl; and C$_{2-4}$alkyl substituted with one —OC$_{1-4}$alkyl;
or R$^{5c}$ and R$^{5d}$ together with the nitrogen atom to which they are attached form a Het$^6$ group; wherein Het$^6$ is a heterocyclyl selected from the group of piperidinyl, pyrrolidinyl, azetidinyl, piperazinyl and morpholinyl, each of which may be optionally substituted with one substituent selected from C$_{1-4}$alkyl and C$_{1-4}$alkyl substituted with one —OH;
R$^6$ is selected from the group of hydrogen; halogen; cyano; C$_{1-4}$alkyl; C$_{1-4}$alkyl substituted with one or more fluoro substituents; C$_{1-4}$alkyl substituted with one —OH; —C$_{1-4}$alkyloxyC$_{1-4}$alkyl; —C$_{1-4}$alkyl-C(=O)—NR$^{6a}$R$^{6b}$; —OC$_{1-4}$ alkyl; and —OC$_{2-4}$alkyl substituted with one —OH or —OC$_{1-4}$alkyl; wherein
R$^{6a}$ is selected from hydrogen and C$_{1-4}$alkyl; and
R$^{6b}$ is selected from hydrogen, C$_{1-4}$alkyl and C$_{2-4}$alkyloxyC$_{1-4}$alkyl;
R$^7$ is selected from the group of hydrogen, C$_{1-4}$alkyl, cyano, —OC$_{1-4}$alkyl, —NHC$_{1-4}$alkyl, —NH—C(=O)—C$_{1-4}$alkyl and —C(=O)—NR$^{7a}$R$^{7b}$; wherein
R$^{7a}$ and R$^{7b}$ are each independently selected from hydrogen and C$_{1-4}$alkyl;

$R^8$ is selected from the group of hydrogen; $Het^8$; $C_{1-4}$alkyl optionally substituted with $Het^9$; and $C_{2-4}$alkyl substituted with one or more substituents independently selected from the group of
(ii) —$NR^{8a}R^{8b}$,
(viii) —$OR^{8f}$, and
(x) —C(=O)$NR^{8a}R^{8b}$; wherein
$R^{8a}$, $R^{8b}$ and $R^{8f}$ are each independently selected from the group of hydrogen and $C_{1-4}$alkyl;
and
$Het^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one $C_{1-4}$alkyl;
$Het^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one $C_{1-4}$alkyl;
$R^9$ is hydrogen or $C_{1-4}$alkyl;
and the pharmaceutically acceptable salts and the solvates thereof.

The present invention relates in particular to compounds of Formula (I) as defined herein, and tautomers and stereoisomeric forms thereof, wherein
$R^1$ is selected from the group of hydrogen and $C_{1-4}$alkyl;
$R^2$ is selected from the group of hydrogen; $C_{1-4}$alkyl; $C_{1-4}$alkyl substituted with one or more fluoro substituents; $C_{1-4}$alkyl substituted with one substituent selected from the group of —$NR^{2a}R^{2b}$, —OH, —$OC_{1-4}$alkyl, $C_{3-6}$cycloalkyl, $Het^2$ and phenyl; $C_{3-6}$cycloalkyl; $Het^2$; and phenyl; wherein the phenyl group is optionally substituted with one or two substituents independently selected from the group of halogen, cyano, $C_{1-4}$alkyl, $C_{1-4}$alkoxy, $C_{1-4}$alkyl substituted with one or more fluoro substituents and $C_{1-4}$alkyloxy substituted with one or more fluoro substituents;
$R^{1a}$, $R^{1b}$, $R^{2a}$, and $R^{2b}$ are each independently selected from hydrogen and $C_{1-4}$alkyl;
$Het^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents and $C_{1-4}$alkyloxy substituted with one or more fluoro substituents;
or $R^1$ and $R^2$ together with the carbon atom to which they are attached form a $C_{3-6}$cycloalkyl;
$R^3$ is selected from the group of hydrogen; $C_{1-4}$alkyl; and $C_{1-4}$alkyl substituted with one or more fluoro substituents;
$R^4$ is selected from the group of hydrogen; halogen; $C_{1-4}$alkyl; $C_{1-4}$alkyl substituted with one or more fluoro substituents; and cyano;
$R^5$ is selected from the group of hydrogen; $C_{1-4}$alkyl; $C_{1-4}$alkyl substituted with one or more fluoro substituents; cyano; and —C(=O)—$NR^{5c}R^{5d}$; wherein
$R^{5c}$ is selected from the group of hydrogen and $C_{1-4}$alkyl;
$R^{5d}$ is selected from the group of $C_{1-4}$alkyl; and $C_{2-4}$alkyl substituted with one —$OC_{1-4}$alkyl;
or $R^{5c}$ and $R^{5d}$ together with the nitrogen atom to which they are attached form a $Het^6$ group; wherein $Het^6$ is a heterocyclyl selected from the group of piperidinyl, pyrrolidinyl, azetidinyl, piperazinyl and morpholinyl, each of which may be optionally substituted with one substituent selected from $C_{1-4}$alkyl and $C_{1-4}$alkyl substituted with one —OH;
$R^6$ is selected from the group of hydrogen; halogen; cyano; $C_{1-4}$alkyl; $C_{1-4}$alkyl substituted with one or more fluoro substituents; $C_{1-4}$alkyl substituted with one —OH; —$C_{1-4}$alkyloxy$C_{1-4}$alkyl; —$C_{1-4}$alkyl-C(=O)—$NR^{6a}R^{6b}$; —$OC_{1-4}$alkyl; and —$OC_{2-4}$alkyl substituted with one —OH or —$OC_{1-4}$alkyl; wherein
$R^{6a}$ is selected from hydrogen and $C_{1-4}$alkyl; and
$R^{6b}$ is selected from hydrogen, $C_{1-4}$alkyl and $C_{2-4}$alkyloxy$C_{1-4}$alkyl;
$R^7$ is selected from the group of hydrogen, $C_{1-4}$alkyl, cyano, —$OC_{1-4}$alkyl, —$NHC_{1-4}$alkyl, —NH—C(=O)—$C_{1-4}$alkyl and —C(=O)—$NR^{7a}R^{7b}$; wherein
$R^{7a}$ and $R^{7b}$ are each independently selected from hydrogen and $C_{1-4}$alkyl;
$R^8$ is selected from the group of hydrogen; $Het^8$; $C_{1-4}$alkyl optionally substituted with $Het^9$; and $C_{2-4}$alkyl substituted with one or more substituents independently selected from the group of
(ii) —$NR^{8a}R^{8b}$,
(viii) —$OR^{8f}$, and
(x) —C(=O)$NR^{8a}R^{8b}$; wherein
$R^{8a}$, $R^{8b}$ and $R^{8f}$ are each independently selected from the group of hydrogen and $C_{1-4}$alkyl;
and
$Het^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one $C_{1-4}$alkyl;
$Het^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one $C_{1-4}$alkyl;
$R^9$ is hydrogen or $C_{1-4}$alkyl;
and the pharmaceutically acceptable salts and the solvates thereof.

The present invention relates in particular to compounds of Formula (I) as defined herein, and tautomers and stereoisomeric forms thereof, wherein
$R^1$ is selected from the group of hydrogen and $C_{1-4}$alkyl;
$R^2$ is selected from the group of hydrogen; $C_{1-4}$alkyl; $C_{1-4}$alkyl substituted with one or more fluoro substituents; $C_{3-6}$cycloalkyl; and $Het^2$; wherein
the phenyl group is optionally substituted with one or two substituents independently selected from the group of halogen, cyano, $C_{1-4}$alkyl, $C_{1-4}$alkoxy, $C_{1-4}$alkyl substituted with one or more fluoro substituents and $C_{1-4}$alkyloxy substituted with one or more fluoro substituents;
$R^{1a}$, $R^{1b}$, $R^{2a}$, and $R^{2b}$ are each independently selected from hydrogen and $C_{1-4}$alkyl;
$Het^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents and $C_{1-4}$alkyloxy substituted with one or more fluoro substituents;
or $R^1$ and $R^2$ together with the carbon atom to which they are attached form a $C_{3-6}$cycloalkyl or a $Het^3$ group; in particular $C_{3-6}$cycloalkyl; wherein
$Het^3$ is a heterocyclyl selected from the group of piperidinyl, tetrahydropyranyl, pyrrolidinyl, tetrahydrofuranyl, azetidinyl and oxetanyl, each of which may be optionally substituted with one $C_{1-4}$alkyl;
$R^3$ is selected from the group of hydrogen; $C_{1-4}$alkyl; and $C_{1-4}$alkyl substituted with one or more fluoro substituents;

$R^4$ is selected from the group of hydrogen; halogen; $C_{1-4}$alkyl; $C_{1-4}$alkyl substituted with one or more fluoro substituents; and cyano;
$R^5$ is selected from the group of hydrogen; $C_{1-4}$alkyl; $C_{1-4}$alkyl substituted with one or more fluoro substituents; cyano; and —C(=O)—NR$^{5c}$R$^{5d}$; wherein
$R^{5c}$ is selected from the group of hydrogen and $C_{1-4}$alkyl;
$R^{5d}$ is selected from the group of $C_{1-4}$alkyl; and $C_{2-4}$alkyl substituted with one —OC$_{1-4}$alkyl;
or $R^{5c}$ and $R^{5d}$ together with the nitrogen atom to which they are attached form a Het$^6$ group; wherein Het$^6$ is a heterocyclyl selected from the group of piperidinyl, pyrrolidinyl, azetidinyl, piperazinyl and morpholinyl, each of which may be optionally substituted with one substituent selected from $C_{1-4}$alkyl and $C_{1-4}$alkyl substituted with one —OH;
$R^6$ is selected from the group of hydrogen; halogen; cyano; $C_{1-4}$alkyl; $C_{1-4}$alkyl substituted with one or more fluoro substituents; $C_{1-4}$alkyl substituted with one —OH; —C$_{1-4}$alkyloxyC$_{1-4}$alkyl; —C$_{1-4}$alkyl-C(=O)—NR$^{6a}$R$^{6b}$; —OC$_{1-4}$ alkyl; and —OC$_{2-4}$alkyl substituted with one —OH or —OC$_{1-4}$alkyl; wherein
$R^{6a}$ is selected from hydrogen and $C_{1-4}$alkyl; and
$R^{6b}$ is selected from hydrogen, $C_{1-4}$alkyl and $C_{2-4}$alkyloxyC$_{1-4}$alkyl;
$R^7$ is selected from the group of hydrogen, cyano, —OC$_{1-4}$alkyl, —NHC$_{1-4}$alkyl, —NH—C(=O)—C$_{1-4}$alkyl and —C(=O)—NR$^{7a}$R$^{7b}$; wherein
$R^{7a}$ and $R^{7b}$ are each independently selected from hydrogen and $C_{1-4}$alkyl;
$R^8$ is selected from the group of hydrogen; Het$^8$; $C_{1-4}$alkyl optionally substituted with Het$^9$; and $C_{2-4}$alkyl substituted with one or more substituents independently selected from the group of
(ii) —NR$^{8a}$R$^{8b}$,
(viii) —OR$^{8f}$, and
(x) —C(=O)NR$^{8a}$R$^{8b}$; wherein
$R^{8a}$, $R^{8b}$ and $R^{8f}$ are each independently selected from the group of hydrogen and $C_{1-4}$alkyl;
and
Het$^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one $C_{1-4}$alkyl;
Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one $C_{1-4}$alkyl;
$R^9$ is hydrogen or $C_{1-4}$alkyl;
and the pharmaceutically acceptable salts and the solvates thereof.

In an embodiment, the present invention relates to those compounds of formula (I) and the pharmaceutically acceptable addition salts, and the solvates thereof, or any subgroup thereof as mentioned in any of the other embodiments, wherein
$R^6$ is selected from the group of hydrogen; halogen; cyano; $C_{1-4}$alkyl; $C_{1-4}$alkyl substituted with one or more fluoro substituents; $C_{1-4}$alkyl substituted with one —OH; —C$_{1-4}$alkyloxyC$_{1-4}$alkyl; —C$_{1-4}$alkyl-C(=O)—NR$^{6a}$R$^{6b}$; —OC$_{1-4}$ alkyl; and —OC$_{2-4}$alkyl substituted with one —OH or —OC$_{1-4}$alkyl; wherein
$R^{6a}$ is selected from hydrogen and $C_{1-4}$alkyl; and
$R^{6b}$ is selected from hydrogen, $C_{1-4}$alkyl and $C_{2-4}$alkyloxyC$_{1-4}$alkyl;
$R^7$ is hydrogen; or
$R^6$ is hydrogen; and $R^7$ is selected from the group of hydrogen, $C_{1-4}$alkyl, cyano, —OC$_{1-4}$alkyl, —NHC$_{1-4}$alkyl, —NH—C(=O)—C$_{1-4}$alkyl and —C(=O)—NR$^{7a}$R$^{7b}$; wherein
$R^{7a}$ and $R^{7b}$ are each independently selected from hydrogen and $C_{1-4}$alkyl;
and the pharmaceutically acceptable salts and the solvates thereof.

In an additional embodiment, the present invention relates to compounds of Formula (I) as defined herein, and tautomers and stereoisomeric forms thereof, wherein
$R^1$ is selected from the group of hydrogen and $C_{1-4}$alkyl;
$R^2$ is selected from the group of hydrogen, $C_{1-4}$alkyl, and Het$^2$; wherein
Het$^2$ is a heteroaryl selected from the group of thiazolyl, pyrazolyl, and imidazolyl;
or $R^1$ and $R^2$ together with the carbon atom to which they are attached form a $C_{3-6}$cycloalkyl group;
$R^3$ is hydrogen;
$R^4$ is hydrogen;
$R^5$ is hydrogen;
$R^6$ is selected from the group of hydrogen and halogen;
$R^7$ is hydrogen;
$R^8$ is selected from the group of hydrogen; $C_{1-4}$alkyl optionally substituted with Het$^9$; and $C_{2-4}$alkyl substituted with a substituent selected from the group of
(ii) —NR$^{8a}$R$^{8b}$, and
(viii) —OR$^{8f}$; wherein
$R^{8a}$, $R^{8b}$ and $R^{8f}$ are each independently selected from the group of hydrogen and $C_{1-4}$alkyl;
Het$^9$ is a heterocyclyl selected from the group of morpholinyl, piperidinyl, tetrahydropyranyl, pyrrolidinyl, tetrahydrofuranyl, azetidinyl and oxetanyl, each of which may be optionally substituted with one $C_{1-4}$alkyl; and
$R^9$ is hydrogen or $C_{1-4}$alkyl;
and the pharmaceutically acceptable salts and the solvates thereof.

In an additional embodiment, the present invention relates to compounds of Formula (I) as defined herein, and tautomers and stereoisomeric forms thereof, wherein
$R^1$ is selected from the group of hydrogen and $C_{1-4}$alkyl;
$R^2$ is selected from the group of hydrogen, $C_{1-4}$alkyl, and Het$^2$; wherein
Het$^2$ is thiazolyl;
or $R^1$ and $R^2$ together with the carbon atom to which they are attached form a $C_{3-6}$cycloalkyl group;
$R^3$ is hydrogen;
$R^4$ is hydrogen;
$R^5$ is hydrogen;
$R^6$ is selected from the group of hydrogen and halogen;
$R^7$ is hydrogen;
$R^8$ is selected from the group of hydrogen; $C_{1-4}$alkyl optionally substituted with Het$^9$; and $C_{2-4}$alkyl substituted with a substituent selected from the group of
(ii) —NR$^{8a}$R$^{8b}$, and
(viii) —OR$^{8f}$; wherein
$R^{8a}$, $R^{8b}$ and $R^{8f}$ are each independently selected from the group of hydrogen and $C_{1-4}$alkyl;
Het$^9$ is a heterocyclyl selected from the group of morpholinyl, tetrahydrofuranyl, and oxetanyl; and
$R^9$ is hydrogen or $C_{1-4}$alkyl;
and the pharmaceutically acceptable salts and the solvates thereof.

In an additional embodiment, the present invention relates to compounds of Formula (I) as defined herein, and tautomers and stereoisomeric forms thereof, wherein
$R^1$ is $C_{1-4}$alkyl;
$R^2$ is $C_{1-4}$alkyl;

or $R^1$ and $R^2$ together with the carbon atom to which they are attached form a $C_{3-6}$cycloalkyl group;
$R^3$ is hydrogen;
$R^4$ is hydrogen;
$R^5$ is hydrogen;
$R^6$ is selected from the group of hydrogen and halogen; in particular hydrogen and chloro; more in particular chloro;
$R^7$ is hydrogen;
$R^8$ is selected from the group of hydrogen; $C_{1-4}$alkyl; and $C_{2-4}$alkyl substituted with one —$OR^{8f}$ substituent; wherein $R^{8f}$ is selected from the group of hydrogen and $C_{1-4}$alkyl;
$R^9$ is hydrogen;
and the pharmaceutically acceptable salts and the solvates thereof.

Another embodiment of the present invention relates to those compounds of formula (I) and the pharmaceutically acceptable addition salts, and the solvates thereof, or any subgroup thereof as mentioned in any of the other embodiments wherein one or more of the following restrictions apply:

a) $R^1$ is selected from the group of $C_{1-6}$alkyl; and $C_{1-6}$alkyl substituted with one or more fluoro substituents;
$R^2$ is selected from the group of $C_{1-6}$alkyl and $C_{3-6}$cycloalkyl;
or $R^1$ and $R^2$ together with the carbon atom to which they are attached form a $C_{3-6}$cycloalkyl;
in particular $R^1$ is selected from the group of $C_{1-6}$alkyl; and $C_{1-6}$alkyl substituted with one or more fluoro substituents; $R^2$ is selected from the group of $C_{1-6}$alkyl and $C_{3-6}$cycloalkyl;
b) $R^3$ is selected from the group of hydrogen; $C_{3-6}$cycloalkyl; and $C_{1-4}$alkyl;
c) $R^4$ is hydrogen;
d) $R^5$ is hydrogen;
e) $R^6$ is selected from the group of hydrogen; halogen; $C_{1-6}$alkyl; and —$OC_{1-6}$alkyl; in particular $R^6$ is selected from the group of halogen; $C_{1-6}$alkyl; and —$OC_{1-6}$alkyl; more in particular $R^6$ is halogen; even more in particular $R^6$ is fluoro;
f) $R^7$ is hydrogen;
g) $R^8$ is selected from the group of hydrogen; $Het^8$; $C_{1-6}$alkyl optionally substituted with one $Het^9$; and $C_{2-6}$alkyl substituted with one or more —$OR^{8f}$ substituents;
h) $R^{8f}$ is $C_{1-4}$alkyl;
i) $Het^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl;
j) $Het^9$ is a heterocyclyl selected from the group of morpholinyl, piperidinyl, tetrahydropyranyl, tetrahydrofuranyl, and oxetanyl, each of which may be optionally substituted with one $C_{1-4}$alkyl;
k) $R^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein $R^2$ is selected from the group of hydrogen, methyl and thiazolyl.

In an embodiment, the present invention relates to those compounds of formula (I) and the pharmaceutically acceptable addition salts, and the solvates thereof, or any subgroup thereof as mentioned in any of the other embodiments, wherein $R^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein $R^2$ is selected from the group of $C_{1-4}$alkyl and thiazolyl; in particular methyl and thiazolyl; more in particular thiazolyl.

In an embodiment, the present invention relates to those compounds of formula (I) and the pharmaceutically acceptable addition salts, and the solvates thereof, or any subgroup thereof as mentioned in any of the other embodiments, wherein $R^2$ is methyl.

In an embodiment, the present invention relates to those compounds of formula (I) and the pharmaceutically acceptable addition salts, and the solvates thereof, or any subgroup thereof as mentioned in any of the other embodiments, wherein $R^1$ is selected from the group of hydrogen; $C_{1-4}$alkyl; $C_{1-4}$alkyl substituted with one or more fluoro substituents; $R^2$ is selected from the group of hydrogen; $C_{1-4}$alkyl; $C_{1-4}$alkyl substituted with one or more fluoro substituents; $C_{3-6}$cycloalkyl and $Het^2$.

In an embodiment, the present invention relates to those compounds of formula (I) and the pharmaceutically acceptable addition salts, and the solvates thereof, or any subgroup thereof as mentioned in any of the other embodiments, wherein $R^2$ is selected from the group of hydrogen; $C_{1-6}$alkyl; $C_{1-6}$alkyl substituted with one or more fluoro substituents.

In an embodiment, the present invention relates to those compounds of formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl and $Het^2$.

In an embodiment, the present invention relates to those compounds of formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl and $Het^2$; or $R^1$ and $R^2$ together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein $R^1$ is $C_{1-4}$alkyl; $R^2$ is $C_{1-4}$alkyl; or $R^1$ and $R^2$ together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein $R^1$ is selected from the group of $C_{1-4}$alkyl and $C_{1-4}$alkyl substituted with one or more fluoro substituents; $R^2$ is selected from the group of $C_{1-4}$alkyl; $C_{1-4}$alkyl substituted with one or more fluoro substituents; $C_{3-6}$cycloalkyl and $Het^2$;
or $R^1$ and $R^2$ together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl and Het$^2$; or R$^1$ and R$^2$ together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein R$^3$ is hydrogen; R$^4$ is hydrogen; R$^5$ is hydrogen; R$^7$ is hydrogen.

In an embodiment, the present invention relates to those compounds of formula (I) and the pharmaceutically acceptable addition salts, and the solvates thereof, or any subgroup thereof as mentioned in any of the other embodiments, wherein Het$^2$ is thiazolyl optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents; and
Het$^9$ is selected from the group of morpholinyl, tetrahydrofuranyl and oxetanyl, each of which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het$^2$ is thiazolyl; and
Het$^9$ is selected from the group of morpholinyl, tetrahydrofuranyl and oxetanyl.

In an embodiment, the present invention relates to those compounds of formula (I) and the pharmaceutically acceptable addition salts, and the solvates thereof, or any subgroup thereof as mentioned in any of the other embodiments, wherein R$^1$ and R$^2$ together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein R$^6$ is hydrogen, halogen or $C_{1-4}$alkyl; in particular hydrogen or halogen; more in particular hydrogen or chloro.

In an embodiment, the present invention relates to those compounds of formula (I) and the pharmaceutically acceptable addition salts, and the solvates thereof, or any subgroup thereof as mentioned in any of the other embodiments, wherein R$^6$ is hydrogen, halogen, $C_{1-4}$alkyl or —O$C_{1-6}$alkyl.

In an embodiment, the present invention relates to those compounds of formula (I) and the pharmaceutically acceptable addition salts, and the solvates thereof, or any subgroup thereof as mentioned in any of the other embodiments, wherein
R$^1$ is $C_{1-4}$alkyl; in particular methyl;
R$^2$ is $C_{1-4}$alkyl; in particular methyl;
R$^3$ is hydrogen;
R$^4$ is hydrogen;
R$^5$ is hydrogen;
R$^6$ is hydrogen or halogen;
R$^7$ is hydrogen;
R$^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein
R$^1$ is $C_{1-4}$alkyl; in particular methyl;
R$^2$ is $C_{1-4}$alkyl; in particular methyl;
or R$^1$ and R$^2$ together with the carbon atom to which they are attached form a $C_{3-6}$cycloalkyl.

R$^3$ is hydrogen;
R$^4$ is hydrogen;
R$^5$ is hydrogen;
R$^6$ is hydrogen or halogen; in particular hydrogen or chloro;
R$^7$ is hydrogen;
R$^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein R$^6$ is chloro.

In an embodiment, the present invention relates to those compounds of formula (I) and the pharmaceutically acceptable addition salts, and the solvates thereof, or any subgroup thereof as mentioned in any of the other embodiments, wherein R$^6$ is fluoro.

In an embodiment, the present invention relates to those compounds of formula (I) and the pharmaceutically acceptable addition salts, and the solvates thereof, or any subgroup thereof as mentioned in any of the other embodiments, wherein
R$^1$ is $C_{1-4}$alkyl;
R$^2$ is $C_{1-4}$alkyl;
or R$^1$ and R$^2$ together with the carbon atom to which they are attached form a $C_{3-6}$cycloalkyl;
R$^6$ is chloro.

In an embodiment, the present invention relates to those compounds of formula (I) and the pharmaceutically acceptable addition salts, and the solvates thereof, or any subgroup thereof as mentioned in any of the other embodiments, wherein
R$^1$ is $C_{1-4}$alkyl;
R$^2$ is $C_{1-4}$alkyl;
or R$^1$ and R$^2$ together with the carbon atom to which they are attached form a $C_{3-6}$cycloalkyl;
R$^6$ is chloro, fluoro, methyl, or methoxy; in particular R$^6$ is chloro, fluoro, or methyl; more in particular R$^6$ is chloro or fluoro; even more in particular R$^6$ is fluoro.

In an embodiment, the present invention relates to those compounds of formula (I) and the pharmaceutically acceptable addition salts, and the solvates thereof, or any subgroup thereof as mentioned in any of the other embodiments, wherein
R$^1$ is $C_{1-4}$alkyl;
R$^2$ is selected from the group of $C_{1-4}$alkyl and $C_{3-6}$cycloalkyl;
or R$^1$ and R$^2$ together with the carbon atom to which they are attached form a $C_{3-6}$cycloalkyl;
R$^6$ is chloro, fluoro, methyl, or methoxy; in particular R$^6$ is chloro, fluoro, or methyl; more in particular R$^6$ is chloro or fluoro; even more in particular R$^6$ is fluoro.

In an embodiment, the present invention relates to those compounds of formula (I) and the pharmaceutically acceptable addition salts, and the solvates thereof, or any subgroup thereof as mentioned in any of the other embodiments, wherein
R$^1$ is $C_{1-4}$alkyl;
R$^2$ is selected from the group of $C_{1-4}$alkyl and $C_{3-6}$cycloalkyl;
R$^6$ is chloro, fluoro, methyl, or methoxy; in particular R$^6$ is chloro, fluoro, or methyl; more in particular R$^6$ is chloro or fluoro; even more in particular R$^6$ is fluoro.

In an embodiment, the present invention relates to those compounds of formula (I) and the pharmaceutically acceptable addition salts, and the solvates thereof, or any subgroup thereof as mentioned in any of the other embodiments, wherein $R^1$ is $C_{1-4}$alkyl; in particular $R^1$ is methyl;
$R^2$ is $C_{3-6}$cycloalkyl; in particular $R^2$ is cyclopropyl;
or $R^1$ and $R^2$ together with the carbon atom to which they are attached form a $C_{3-6}$cycloalkyl;
$R^6$ is chloro, fluoro, methyl or methoxy; in particular $R^6$ is chloro, fluoro, or methyl; more in particular $R^6$ is chloro or fluoro; even more in particular $R^6$ is fluoro.

In an embodiment, the present invention relates to those compounds of formula (I) and the pharmaceutically acceptable addition salts, and the solvates thereof, or any subgroup thereof as mentioned in any of the other embodiments, wherein
$R^1$ is $C_{1-4}$alkyl; in particular $R^1$ is methyl;
$R^2$ is $C_{3-6}$cycloalkyl; in particular $R^2$ is cyclopropyl;
$R^6$ is chloro, fluoro, methyl, or methoxy; in particular $R^6$ is chloro, fluoro, or methyl; more in particular $R^6$ is chloro or fluoro; even more in particular $R^6$ is fluoro.

In an embodiment, the present invention relates to those compounds of formula (I) and the pharmaceutically acceptable addition salts, and the solvates thereof, or any subgroup thereof as mentioned in any of the other embodiments, wherein
$R^1$ is selected from the group of $C_{1-6}$alkyl; and $C_{1-6}$alkyl substituted with one or more fluoro substituents;
$R^2$ is selected from the group of $C_{1-6}$alkyl and $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein $R^8$ is other than hydrogen.

In an embodiment, the present invention relates to those compounds of formula (I) and the pharmaceutically acceptable addition salts, and the solvates thereof, or any subgroup thereof as mentioned in any of the other embodiments, wherein $R^1$ and $R^2$ are other than hydrogen.

In an embodiment, the present invention relates to those compounds of formula (I) and the pharmaceutically acceptable addition salts, and the solvates thereof, or any subgroup thereof as mentioned in any of the other embodiments, wherein $R^1$ and $R^2$ are not taken together.

In an embodiment, the present invention relates to those compounds of formula (I) and the pharmaceutically acceptable addition salts, and the solvates thereof, or any subgroup thereof as mentioned in any of the other embodiments, wherein $R^1$ and $R^2$ are taken together.

In an embodiment, the present invention relates to those compounds of formula (I) and the pharmaceutically acceptable addition salts, and the solvates thereof, or any subgroup thereof as mentioned in any of the other embodiments, wherein when $R^1$ and $R^2$ are taken together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein $R^6$ is selected from the group of hydrogen; halogen; $C_{1-6}$alkyl; and —$OC_{1-6}$alkyl.

In an embodiment, the present invention relates to those compounds of formula (I) and the pharmaceutically acceptable addition salts, and the solvates thereof, or any subgroup thereof as mentioned in any of the other embodiments, wherein $R^6$ is selected from the group of halogen; $C_{1-6}$alkyl; and —$OC_{1-6}$alkyl.

In an embodiment, the present invention relates to those compounds of formula (I) and the pharmaceutically acceptable addition salts, and the solvates thereof, or any subgroup thereof as mentioned in any of the other embodiments, wherein $R^6$ is selected from the group of halogen and $C_{1-6}$alkyl; in particular $R^6$ is halogen.

In an embodiment, the present invention relates to those compounds of formula (I) and the pharmaceutically acceptable addition salts, and the solvates thereof, or any subgroup thereof as mentioned in any of the other embodiments, wherein $R^6$ is chloro, fluoro, methyl, or methoxy; in particular $R^6$ is chloro, fluoro, or methyl; more in particular $R^6$ is chloro or fluoro; even more in particular $R^6$ is fluoro.

In an embodiment, the present invention relates to those compounds of formula (I) and the pharmaceutically acceptable addition salts, and the solvates thereof, or any subgroup thereof as mentioned in any of the other embodiments, wherein $R^6$ is chloro, fluoro, methyl, or methoxy; and wherein $R^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein $R^{8f}$ is $C_{1-6}$alkyl; in particular $C_{1-4}$alkyl; more in particular methyl.

In an embodiment, the present invention relates to those compounds of formula (I) and the pharmaceutically acceptable addition salts, and the solvates thereof, or any subgroup thereof as mentioned in any of the other embodiments, wherein
$R^1$ is selected from the group of hydrogen; $C_{1-6}$alkyl; $C_{1-6}$alkyl substituted with one or more fluoro substituents; and $C_{1-6}$alkyl substituted with one substituent selected from the group of —$NR^{1a}R^{1b}$, —OH and —$OC_{1-4}$alkyl;
$R^2$ is selected from the group of hydrogen; $C_{1-6}$alkyl; $C_{1-6}$alkyl substituted with one or more fluoro substituents; $C_{1-6}$alkyl substituted with one substituent selected from the group of —$NR^{2a}R^{2b}$, —OH, —$OC_{1-4}$alkyl, and $C_{3-6}$cycloalkyl; —C(=O)—$NR^{2c}R^{2d}$; and $C_{3-6}$cycloalkyl;
or $R^1$ and $R^2$ together with the carbon atom to which they are attached form a $C_{3-6}$cycloalkyl;
$R^3$ is selected from the group of hydrogen; halo; $C_{3-6}$cycloalkyl; and $C_{1-4}$alkyl;
$R^8$ is other than —C(=O)—$NR^{8g}R^{8h}$; —C(=O)—$Het^{12}$; —$CH_2$—C(=O)$NR^{8a}R^{8b}$; and $C_{2-6}$alkyl substituted with one or more —C(=O)$NR^{8a}R^{8b}$ substituents; in particular $R^8$ is other than —C(=O)—$NR^{8g}R^{8h}$; —$CH_2$—C(=O)$NR^{8a}R^{8b}$; and $C_{2-6}$alkyl substituted with one or more —C(=O)$NR^{8a}R^{8b}$ substituents.

In an embodiment, the present invention relates to those compounds of formula (I) and the pharmaceutically acceptable addition salts, and the solvates thereof, or any subgroup thereof as mentioned in any of the other embodiments, wherein
$R^1$ is selected from the group of hydrogen; $C_{1-6}$alkyl; $C_{1-6}$alkyl substituted with one or more fluoro substituents; and $C_{1-6}$alkyl substituted with one substituent selected from the group of —$NR^{1a}R^{1b}$, —OH and —$OC_{1-4}$alkyl;
$R^2$ is selected from the group of hydrogen; $C_{1-6}$alkyl; $C_{1-6}$alkyl substituted with one or more fluoro substituents; $C_{1-6}$alkyl substituted with one substituent selected from the group of —$NR^{2a}R^{2b}$, —OH, —$OC_{1-4}$alkyl, and $C_{3-6}$cycloalkyl; —C(=O)—$NR^{2c}R^{2d}$; and $C_{3-6}$cycloalkyl;
or $R^1$ and $R^2$ together with the carbon atom to which they are attached form a $C_{3-6}$cycloalkyl;
$R^3$ is selected from the group of hydrogen; halo; $C_{3-6}$cycloalkyl; and $C_{1-4}$alkyl;
$R^8$ is selected from the group of hydrogen; —C(=O)—$NR^{8g}R^{8h}$; $Het^8$; $C_{1-6}$alkyl optionally substituted with one $Het^9$; —C(=O)—$Het^{12}$; $C_{3-6}$cycloalkyl optionally substituted with one —OC$_{1-4}$alkyl; C$_{1-6}$alkyl substituted with one cyano; and C$_{2-6}$alkyl substituted with one or more substituents independently selected from the group of (i), (ii), (viii), (ix), and (xii); in particular R$^8$ is selected from the group of hydrogen; Het$^8$; C$_{1-6}$alkyl optionally substituted with one Het$^9$; C$_{3-6}$cycloalkyl optionally substituted with one —OC$_{1-4}$ alkyl; C$_{1-6}$alkyl substituted with one cyano; and C$_{2-6}$alkyl substituted with one or more substituents independently selected from the group of (i), (ii), and (viii); more in particular R$^8$ is selected from the group of hydrogen; Het$^8$; C$_{1-6}$alkyl optionally substituted with one Het$^9$; C$_{1-6}$alkyl substituted with one cyano; and C$_{2-6}$alkyl substituted with one or more —OR$^{8f}$ substituents.

In an embodiment, the present invention relates to those compounds of formula (I) and the pharmaceutically acceptable addition salts, and the solvates thereof, or any subgroup thereof as mentioned in any of the other embodiments, wherein R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$; and C$_{3-6}$cycloalkyl;

or R$^1$ and R$^2$ together with the carbon atom to which they are attached form a C$_{3-6}$cycloalkyl;

R$^3$ is selected from the group of hydrogen; halo; C$_{3-6}$cycloalkyl; and C$_{1-4}$alkyl;

R$^6$ is other than hydrogen; in particular R$^6$ is halogen.

In an embodiment, the present invention relates to those compounds of formula (I) and the pharmaceutically acceptable addition salts, and the solvates thereof, or any subgroup thereof as mentioned in any of the other embodiments, wherein R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$ and C$_{3-6}$cycloalkyl;

or R$^1$ and R$^2$ together with the carbon atom to which they are attached form a C$_{3-6}$cycloalkyl;

R$^3$ is selected from the group of hydrogen; halo; C$_{3-6}$cycloalkyl; and C$_{1-4}$alkyl;

R$^8$ is other than —C(=O)—NR$^{8g}$R$^{8h}$; —CH$_2$—C(=O)NR$^{8a}$R$^{8b}$; and C$_{2-6}$alkyl substituted with one or more —C(=O)NR$^{8a}$R$^{8b}$ substituents;

Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl; or Het$^9$ is pyrazolyl which may be optionally substituted with one C$_{1-4}$alkyl; in particular Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$; and C$_{3-6}$cycloalkyl;

or R$^1$ and R$^2$ together with the carbon atom to which they are attached form a C$_{3-6}$cycloalkyl;

R$^3$ is selected from the group of hydrogen; halo; C$_{3-6}$cycloalkyl; and C$_{1-4}$alkyl;

R$^8$ is other than —C(=O)—NR$^{8g}$R$^{8h}$; —C(=O)—Het$^{12}$; —CH$_2$—C(=O)NR$^{8a}$R$^{8b}$; and C$_{2-6}$alkyl substituted with one or more —C(=O)NR$^{8a}$R$^{8b}$ substituents;

Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl; or Het$^9$ is pyrazolyl which may be optionally substituted with one C$_{1-4}$alkyl; in particular Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents;

R$^8$ is other than —C(=O)—NR$^{8g}$R$^{8h}$; —C(=O)—Het$^{12}$; —CH$_2$—C(=O)NR$^{8a}$R$^{8b}$; and C$_{2-6}$alkyl substituted with one or more —C(=O)NR$^{8a}$R$^{8b}$ substituents;

$C_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$; and C$_{3-6}$cycloalkyl;
or R$^1$ and R$^2$ together with the carbon atom to which they are attached form a C$_{3-6}$cycloalkyl;
R$^3$ is selected from the group of hydrogen; halo; C$_{3-6}$cycloalkyl; and C$_{1-4}$alkyl;
R$^7$ is hydrogen;
R$^8$ is other than —C(=O)—NR$^{8g}$R$^{8h}$; —C(=O)—Het$^{12}$; —CH$_2$—C(=O)NR$^{8a}$R$^{8b}$; and C$_{2-6}$alkyl substituted with one or more —C(=O)NR$^{8a}$R$^{8b}$ substituents;
Het$^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from C$_{1-4}$alkyl, C$_{3-6}$cycloalkyl, C$_{1-4}$alkyl substituted with one C$_{3-6}$cycloalkyl, C$_{1-4}$alkyl substituted with one or more fluoro substituents, and C$_{1-4}$alkyl substituted with one —OC$_{1-4}$alkyl;
Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl; or Het$^9$ is pyrazolyl which may be optionally substituted with one C$_{1-4}$alkyl; in particular Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl;
R$^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein
R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;
R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$; and C$_{3-6}$cycloalkyl;
or R$^1$ and R$^2$ together with the carbon atom to which they are attached form a C$_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein
R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;
R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, and C$_{3-6}$cycloalkyl; —C(=O)—NR$^{2c}$R$^{2d}$; and C$_{3-6}$cycloalkyl;
or R$^1$ and R$^2$ together with the carbon atom to which they are attached form a C$_{3-6}$cycloalkyl;
R$^6$ is selected from the group of halogen; C$_{1-6}$alkyl; and —OC$_{1-6}$alkyl;
R$^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein R$^3$ is selected from the group of hydrogen; halo; C$_{3-6}$cycloalkyl; C$_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R$^8$ is other than —C(=O)—NR$^{8g}$R$^{8h}$; —CH$_2$—C(=O)NR$^{8a}$R$^{8b}$; and
C$_{2-6}$alkyl substituted with one or more —C(=O)NR$^{8a}$R$^{8b}$ substituents.

In an embodiment, the present invention relates to those compounds of formula (I) and the pharmaceutically acceptable addition salts, and the solvates thereof, or any subgroup thereof as mentioned in any of the other embodiments, wherein R$^8$ is other than —C(=O)—NR$^{8g}$R$^{8h}$; —C(=O)—Het$^{12}$; —CH$_2$—C(=O)NR$^{8a}$R$^{8b}$; and C$_{2-6}$alkyl substituted with one or more —C(=O)NR$^{8a}$R$^{8b}$ substituents.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of hydrogen; Het$^8$; C$_{1-6}$alkyl optionally substituted with one Het$^9$; and C$_{2-6}$alkyl substituted with one or more —OR$^{8f}$ substituents;
R$^{8f}$ is C$_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of hydrogen; Het$^8$; C$_{1-6}$alkyl optionally substituted with one Het$^9$; and C$_{2-6}$alkyl substituted with one or more —OR$^{8f}$ substituents;
R$^{8f}$ is C$_{1-4}$alkyl; R$^9$ is hydrogen.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of hydrogen; Het$^8$; C$_{1-6}$alkyl optionally substituted with one Het$^9$; and C$_{2-6}$alkyl substituted with one or more —OR$^{8f}$ substituents;
R$^{8f}$ is C$_{1-4}$alkyl; R$^9$ is hydrogen; R$^6$ is other than hydrogen.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of Het$^8$; C$_{1-6}$alkyl optionally substituted with one Het$^9$; and C$_{2-6}$alkyl substituted with one or more —OR$^{8f}$ substituents;
R$^{8f}$ is C$_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of Het$^8$; C$_{1-6}$alkyl optionally substituted with one Het$^9$; and C$_{2-6}$alkyl substituted with one or more —OR$^{8f}$ substituents;
R$^{8f}$ is C$_{1-4}$alkyl; R$^9$ is hydrogen; R$^6$ is other than hydrogen.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of hydrogen; C$_{1-6}$alkyl optionally substituted with Het$^9$; and C$_{2-6}$alkyl substituted with one or more substituents independently selected from the group of
(ii) —NR$^{8a}$R$^{8b}$,
(viii) —OR$^{8f}$.

In an embodiment, the present invention relates to those compounds of formula (I) and the pharmaceutically acceptable addition salts, and the solvates thereof, or any subgroup thereof as mentioned in any of the other embodiments, wherein
R$^2$ is selected from the group of hydrogen and C$_{1-6}$alkyl;
R$^8$ is selected from the group of hydrogen; C$_{1-6}$alkyl; and C$_{2-6}$alkyl substituted with one or more substituents independently selected from the group of
(ii) —NR$^{8a}$R$^{8b}$,
(viii) —OR$^{8f}$.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of hydrogen; C$_{1-6}$alkyl optionally substituted with Het$^9$; and C$_{2-6}$alkyl substituted with one or more substituents independently selected from the group of
(ii) —NR$^{8a}$R$^{8b}$,
(viii) —OR$^{8f}$,
R$^{8a}$, R$^{8b}$ and R$^{8f}$ are each independently selected from the group of hydrogen and C$_{1-4}$alkyl;
Het$^9$ is a heterocyclyl selected from the group of morpholinyl, tetrahydrofuranyl and oxetanyl.

In an embodiment, the present invention relates to those compounds of formula (I) and the pharmaceutically acceptable addition salts, and the solvates thereof, or any subgroup thereof as mentioned in any of the other embodiments, wherein R$^8$ is selected from the group of hydrogen; —C(=O)—NR$^{8g}$R$^{8h}$; Het$^8$; C$_{1-6}$alkyl optionally substituted with one Het$^9$; —C(=O)—Het$^{12}$; C$_{3-6}$cycloalkyl optionally substituted with one —OC$_{1-4}$alkyl; C$_{1-6}$alkyl substituted with one cyano; —CH$_2$—C(=O)NR$^{8a}$R$^{8b}$; and C$_{2-6}$alkyl substituted with one or more substituents independently selected from the group of (i), (ii), (viii), (ix), (x), and (xii).

In an embodiment, the present invention relates to those compounds of formula (I) and the pharmaceutically acceptable addition salts, and the solvates thereof, or any subgroup thereof as mentioned in any of the other embodiments, wherein R$^8$ is selected from hydrogen, CH$_3$, —CH(CH$_3$)$_2$,

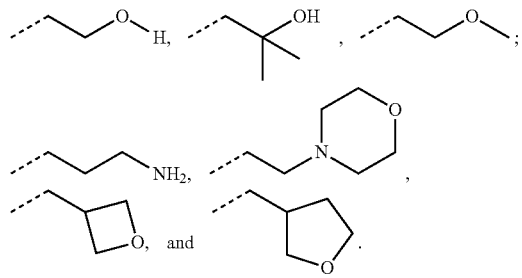

More in particular, R$^8$ is selected from

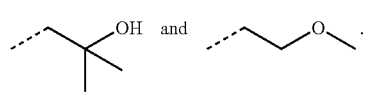

In an embodiment, the present invention relates to those compounds of formula (I) and the pharmaceutically acceptable addition salts, and the solvates thereof, or any subgroup thereof as mentioned in any of the other embodiments, wherein R$^8$ is selected from hydrogen, —CH(CH$_3$)$_2$,

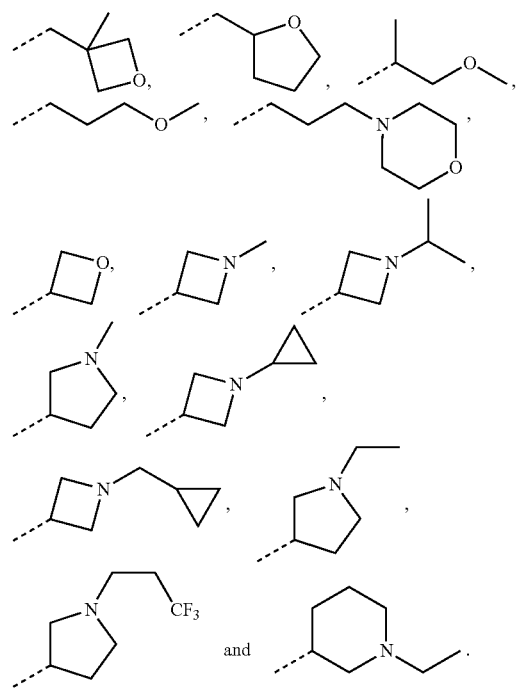

In an embodiment, the present invention relates to those compounds of formula (I) and the pharmaceutically acceptable addition salts, and the solvates thereof, or any subgroup thereof as mentioned in any of the other embodiments, wherein R$^8$ is selected from —CH(CH$_3$)$_2$,

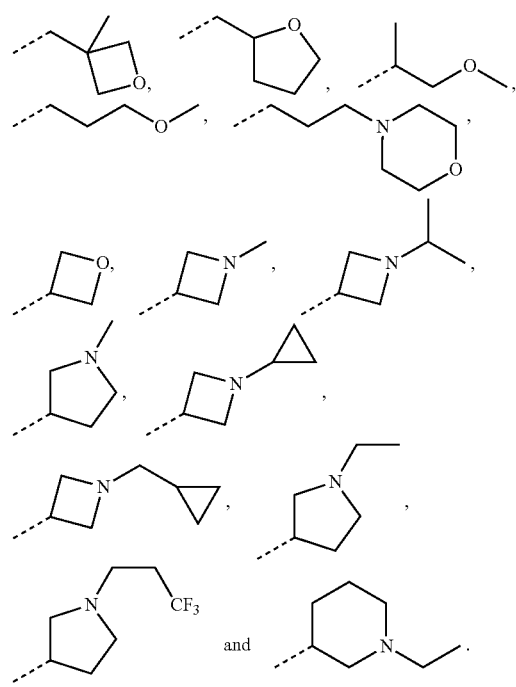

In an embodiment, the present invention relates to those compounds of formula (I) and the pharmaceutically acceptable addition salts, and the solvates thereof, or any subgroup thereof as mentioned in any of the other embodiments, wherein $R^8$ is selected from $CH_3$, $-CH(CH_3)_2$,

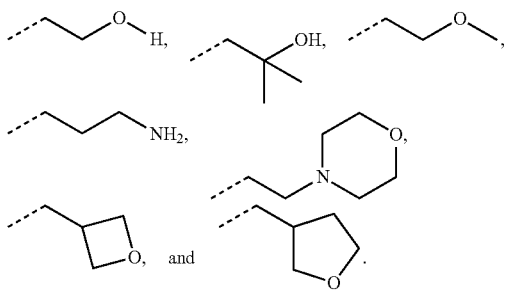

In an additional embodiment, the present invention relates to compounds of Formula (I) as defined herein, and tautomers and stereoisomeric forms thereof, wherein
$R^1$ is $C_{1-4}$alkyl;
$R^2$ is $C_{1-4}$alkyl;
or $R^1$ and $R^2$ together with the carbon atom to which they are attached form a $C_{3-6}$cycloalkyl group;
$R^3$ is hydrogen;
$R^4$ is hydrogen;
$R^5$ is hydrogen;
$R^6$ is selected from the group of hydrogen and halogen; in particular hydrogen and chloro; more in particular chloro;
$R^7$ is hydrogen;
$R^8$ is selected from the group of from hydrogen, $-CH(CH_3)_2$,

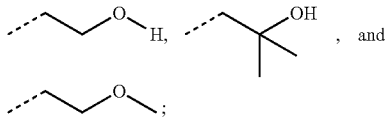

$R^9$ is hydrogen;
and the pharmaceutically acceptable salts and the solvates thereof.

In an embodiment, the present invention relates to those compounds of formula (I) and the pharmaceutically acceptable addition salts, and the solvates thereof, or any subgroup thereof as mentioned in any of the other embodiments, wherein
$R^1$ is selected from the group of hydrogen; $C_{1-6}$alkyl; $C_{1-6}$alkyl substituted with one or more fluoro substituents; and $C_{1-6}$alkyl substituted with one substituent selected from the group of $-NR^{1a}R^{1b}$, $-OH$ and $-OC_{1-4}$alkyl;
$R^2$ is selected from the group of hydrogen; $C_{1-6}$alkyl; $C_{1-6}$alkyl substituted with one or more fluoro substituents; $C_{1-6}$alkyl substituted with one substituent selected from the group of $-NR^{2a}R^{2b}$, $-OH$, $-OC_{1-4}$alkyl, $C_{3-6}$cycloalkyl, $Het^2$ and phenyl;
$C_{3-6}$cycloalkyl; $Het^2$; and phenyl; wherein the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
or $R^1$ and $R^2$ together with the carbon atom to which they are attached form a $C_{3-6}$cycloalkyl.

In an embodiment, the present invention relates to those compounds of formula (I) and the pharmaceutically acceptable addition salts, and the solvates thereof, or any subgroup thereof as mentioned in any of the other embodiments, wherein
$R^1$ is selected from the group of hydrogen; $C_{1-6}$alkyl; $C_{1-6}$alkyl substituted with one or more fluoro substituents; and $C_{1-6}$alkyl substituted with one substituent selected from the group of $-NR^{1a}R^{1b}$, $-OH$ and $-OC_{1-4}$alkyl;
$R^2$ is selected from the group of hydrogen; $C_{1-6}$alkyl; $C_{1-6}$alkyl substituted with one or more fluoro substituents; $C_{1-6}$alkyl substituted with one substituent selected from the group of $-NR^{2a}R^{2b}$, $-OH$, $-OC_{1-4}$alkyl, $C_{3-6}$cycloalkyl, $Het^2$ and phenyl; $-C(=O)-NR^{2c}R^{2d}$; $C_{3-6}$cycloalkyl; $Het^2$; and phenyl; wherein the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents; or $R^1$ and $R^2$ together with the carbon atom to which they are attached form a $C_{3-6}$cycloalkyl or a $Het^3$ group; wherein $Het^3$ is 2-oxo-3-pyrrolidinyl optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein
$R^8$ is selected from the group of hydrogen; $-C(=O)-NR^{8g}R^{8h}$; $Het^8$; $C_{1-6}$alkyl optionally substituted with one $Het^9$; $-C(=O)-Het^{12}$; $C_{3-6}$cycloalkyl optionally substituted with one $-OC_{1-4}$alkyl; and $C_{2-6}$alkyl substituted with one or more substituents independently selected from the group of (i), (ii), (iii), (iv), (v), (vi), (vii), (viii), (ix), (x), (xi), (xii), and (xiii).

In an embodiment, the present invention relates to those compounds of formula (I) and the pharmaceutically acceptable addition salts, and the solvates thereof, or any subgroup thereof as mentioned in any of the other embodiments, wherein $Het^9$ is a heterocyclyl selected from the group of morpholinyl, piperidinyl, tetrahydrofuranyl, and oxetanyl, each of which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein $Het^9$ is a heterocyclyl selected from the group of morpholinyl, piperidinyl, tetrahydropyranyl, tetrahydrofuranyl, and oxetanyl, each of which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein $Het^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, $C_{1-4}$alkyl substituted with one $C_{3-6}$cycloalkyl, and $C_{1-4}$alkyl substituted with one $-OC_{1-4}$alkyl; provided that when $Het^8$ is oxetanyl, then $R^3$ is other than hydrogen.

In an embodiment, the present invention relates to those compounds of formula (I) and the pharmaceutically acceptable addition salts, and the solvates thereof, or any subgroup thereof as mentioned in any of the other embodiments, wherein Het⁸ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl; provided that when Het⁸ is oxetanyl, then R³ is other than hydrogen.

In an embodiment, the present invention relates to those compounds of formula (I) and the pharmaceutically acceptable addition salts, and the solvates thereof, or any subgroup thereof as mentioned in any of the other embodiments, wherein when Het⁸ is a heterocyclyl containing a N-atom, then said heterocyclyl is attached to the remainder of the molecule via a carbon atom, and is substituted on the N-atom.

In an embodiment, the present invention relates to those compounds of formula (I) and the pharmaceutically acceptable addition salts, and the solvates thereof, or any subgroup thereof as mentioned in any of the other embodiments, wherein when Het⁹ is a heterocyclyl containing a N-atom, then said heterocyclyl is attached to the remainder of the molecule via a carbon atom, and is substituted on the N-atom.

In an embodiment, the present invention relates to those compounds of formula (I) and the pharmaceutically acceptable addition salts, and the solvates thereof, or any subgroup thereof as mentioned in any of the other embodiments, wherein Het⁸ is a heterocyclyl, bound through any available carbon atom, selected from the group of piperidinyl, pyrrolidinyl, tetrahydrofuranyl, and azetidinyl, each of which may be optionally substituted with one substituent selected from $C_{1-4}$alkyl, $C_{3-6}$cycloalkyl, $C_{1-4}$alkyl substituted with one $C_{3-6}$cycloalkyl, and $C_{1-4}$alkyl substituted with one —$OC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁸ is a heterocyclyl, bound through any available carbon atom, selected from the group of piperidinyl, pyrrolidinyl, tetrahydrofuranyl, and azetidinyl, each of which may be optionally substituted with one substituent selected from $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁸ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —$OC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —$OC_{1-4}$alkyl; or Het⁹ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —$OC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁹ is a heterocyclyl selected from the group of morpholinyl, piperidinyl, tetrahydropyranyl, tetrahydrofuranyl, and oxetanyl, each of which may be optionally substituted with one $C_{1-4}$alkyl; or Het⁹ is pyrazolyl which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁹ is a heterocyclyl selected from the group of morpholinyl, piperidinyl, tetrahydropyranyl, tetrahydrofuranyl, and oxetanyl, each of which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het¹ is a heterocyclyl selected from the group of piperidinyl, tetrahydropyranyl, pyrrolidinyl, tetrahydrofuranyl, azetidinyl and oxetanyl, each of which may be optionally substituted with one $C_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R⁴ is hydrogen or halogen.

In an embodiment, the present invention relates to those compounds of formula (I) and the pharmaceutically acceptable addition salts, and the solvates thereof, or any subgroup thereof as mentioned in any of the other embodiments, wherein $R^{8g}$ and $R^{8h}$ are each independently selected from the group of hydrogen, $C_{1-4}$alkyl and $C_{2-4}$alkyl substituted with one —$OC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein Het⁶ is a heterocyclyl selected from the group of piperidinyl, pyrrolidinyl, azetidinyl, piperazinyl and morpholinyl, each of which may be optionally substituted with one substituent selected from $C_{1-4}$alkyl; and —$OC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein R⁷ is selected from the group of hydrogen, $C_{1-4}$alkyl, —$OC_{1-4}$alkyl, and —$NHC_{1-4}$alkyl.

In an embodiment, the present invention relates to those compounds of formula (I) and the pharmaceutically acceptable addition salts, and the solvates thereof, or any subgroup thereof as mentioned in any of the other embodiments, wherein $R^{8a}$, $R^{8b}$, $R^{8c}$ and $R^{8f}$ are each independently selected from the group of hydrogen; $C_{1-6}$alkyl; $C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH and —$OC_{1-4}$alkyl; and $C_{3-6}$cycloalkyl;

$R^{8e}$ is selected from the group of $C_{1-6}$alkyl, which may be optionally substituted with one substituent selected from $C_{3-6}$cycloalkyl; and $C_{2-6}$alkyl substituted with one substituent selected from —$NR^{8x}R^{8y}$, —OH, and —$OC_{1-4}$alkyl.

All possible combinations of the above-indicated embodiments are considered to be embraced within the scope of this invention.

In an embodiment the compound of Formula (I) is selected from the group consisting of any of the exemplified compounds, tautomers and stereoisomeric forms thereof, and the free bases, the pharmaceutically acceptable addition salts, and the solvates thereof.

Specific compounds according to the invention include:

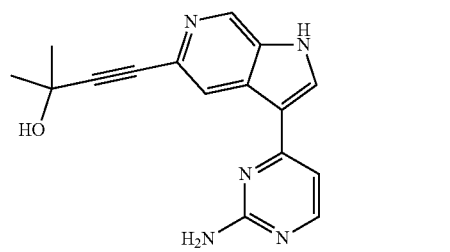

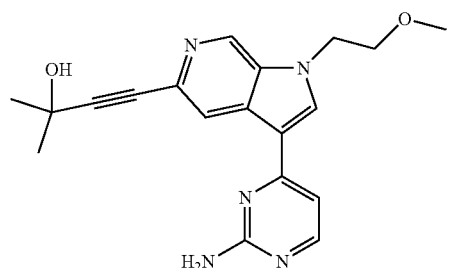

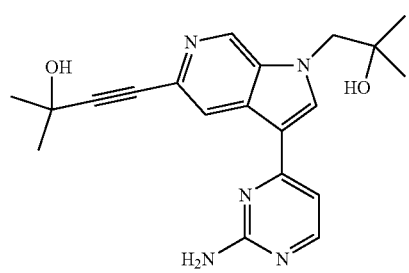

-continued

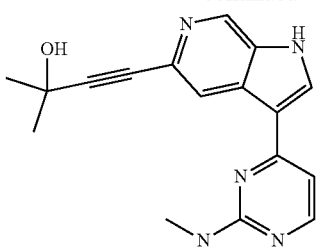

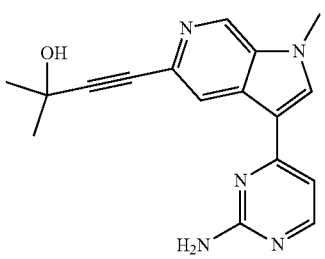

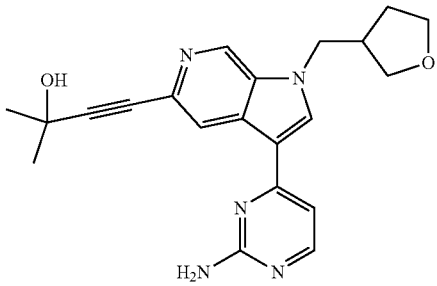

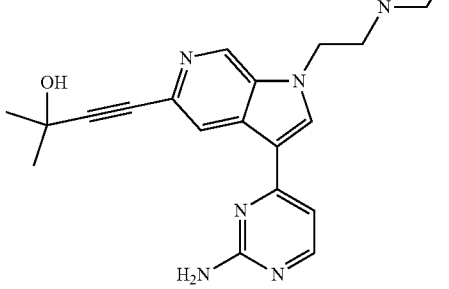

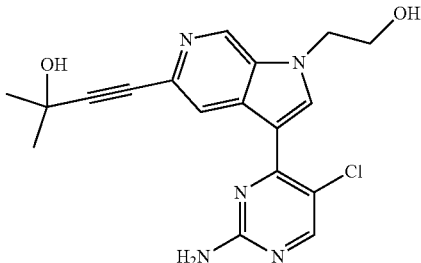

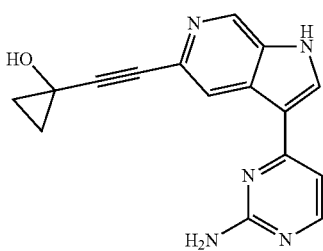

57
-continued
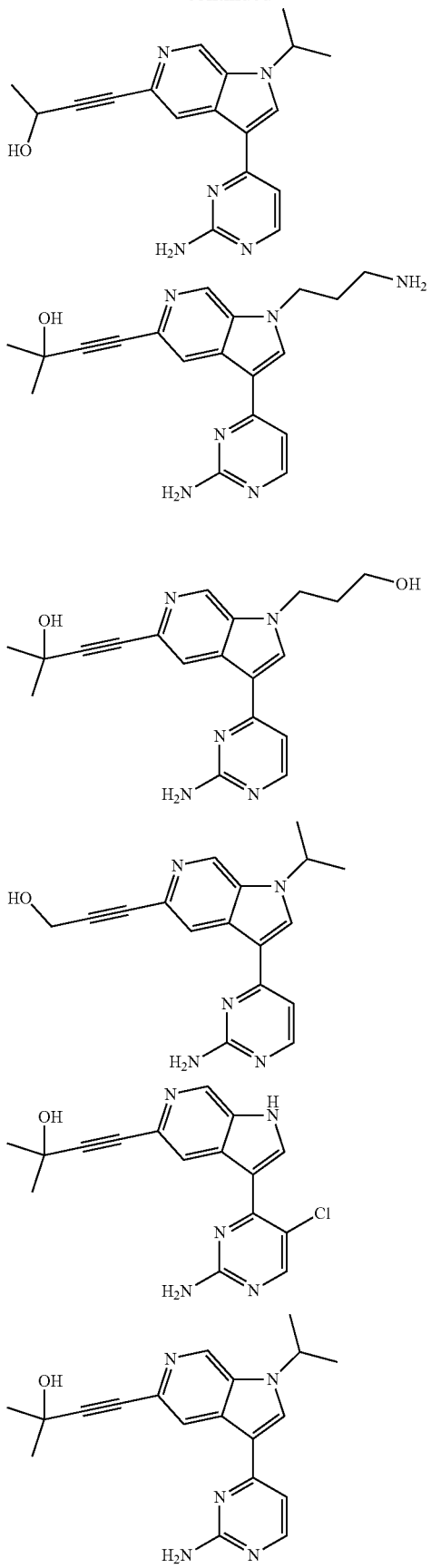
58
-continued
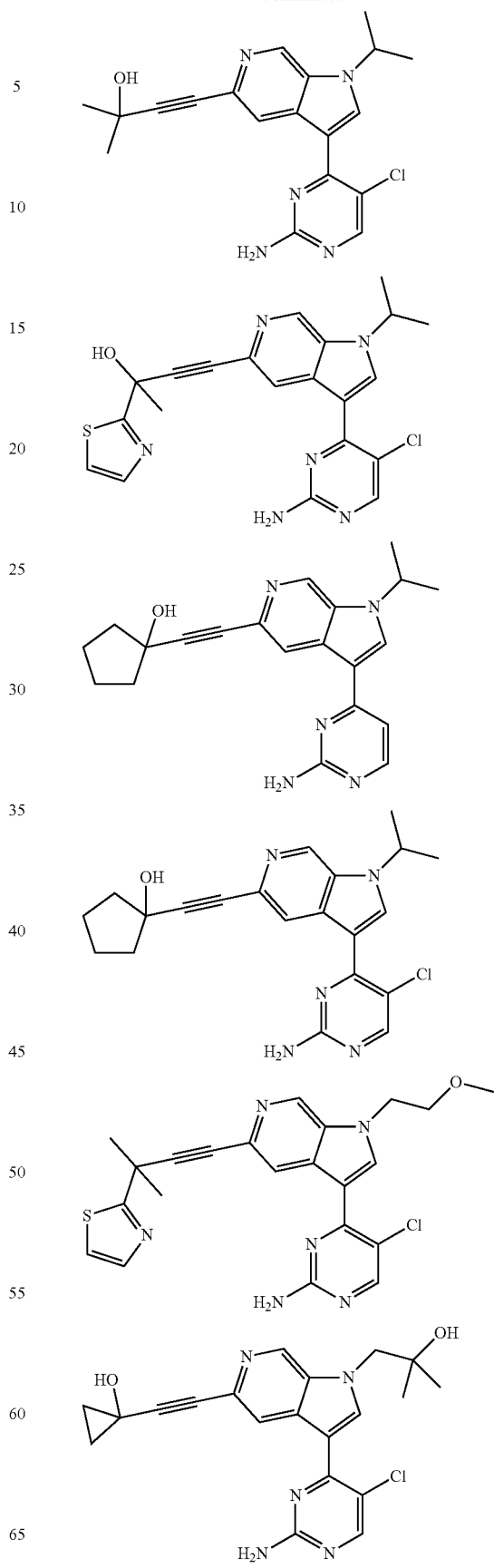

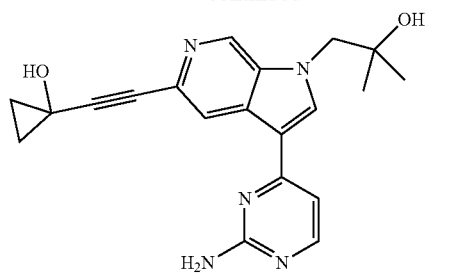
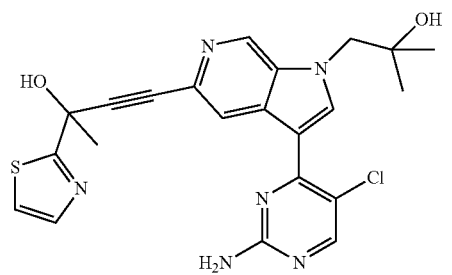
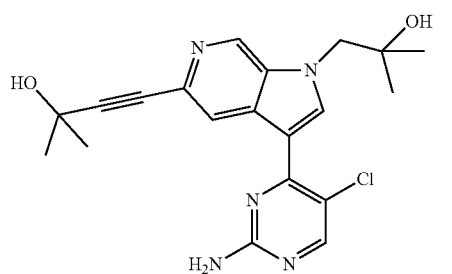
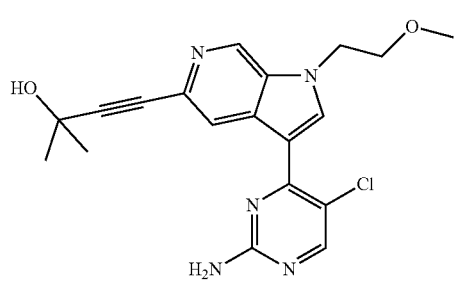
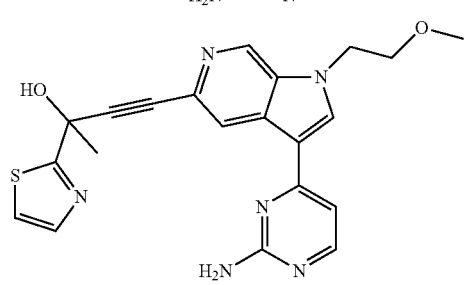
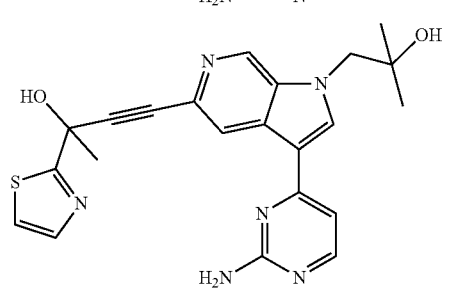
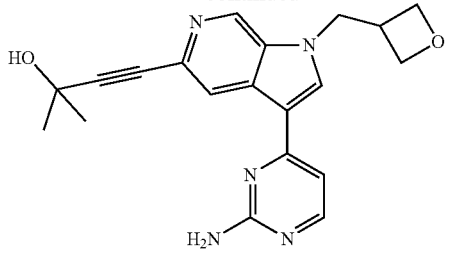
and the pharmaceutically acceptable salts and solvates forms of such compounds.
Specific compounds according to the invention include:
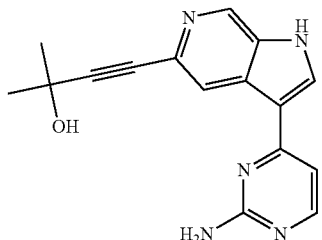
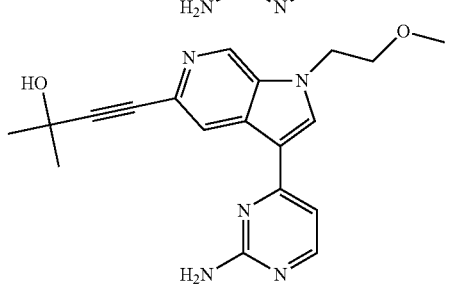
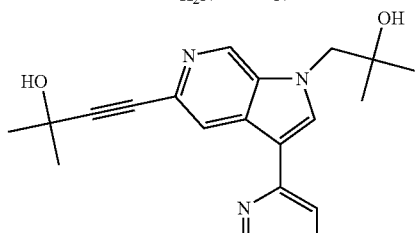
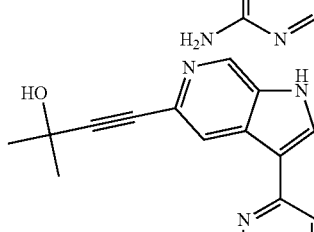
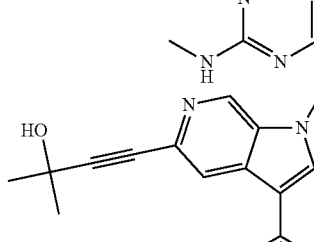

-continued
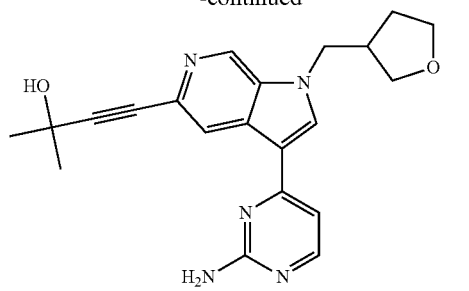
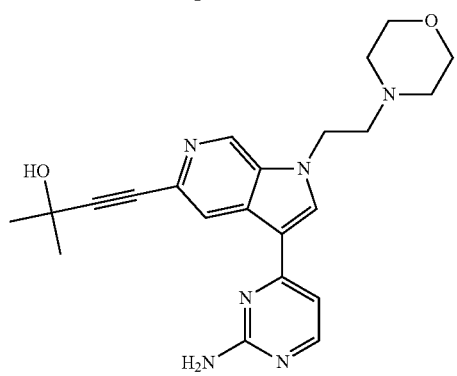
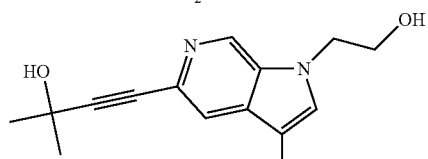
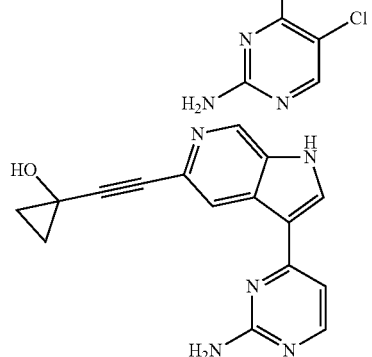
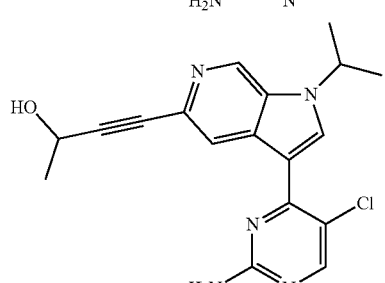
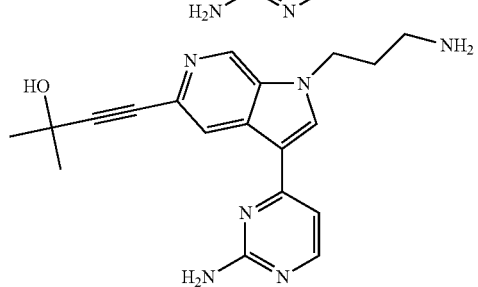
-continued
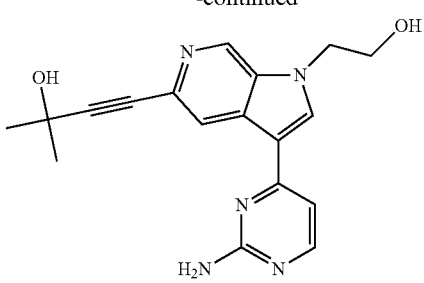
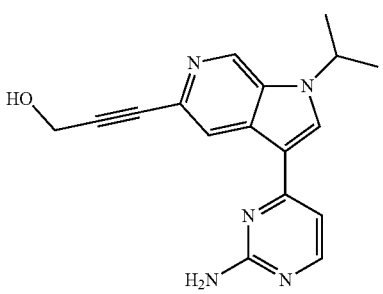
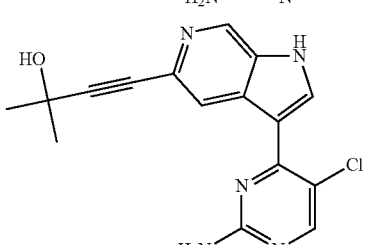
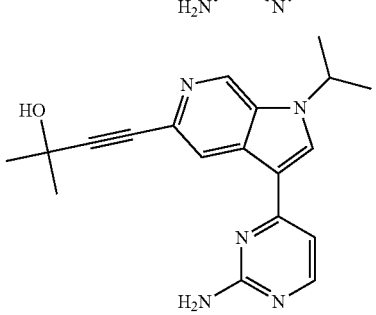
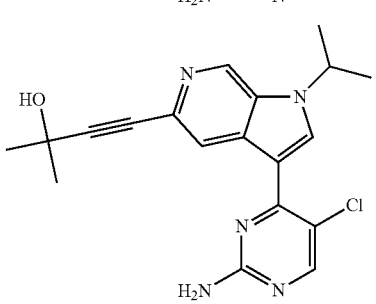
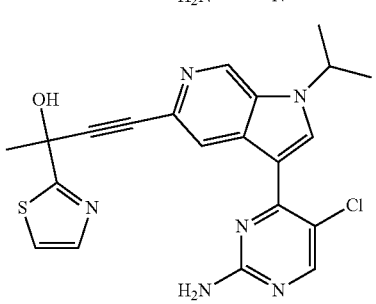

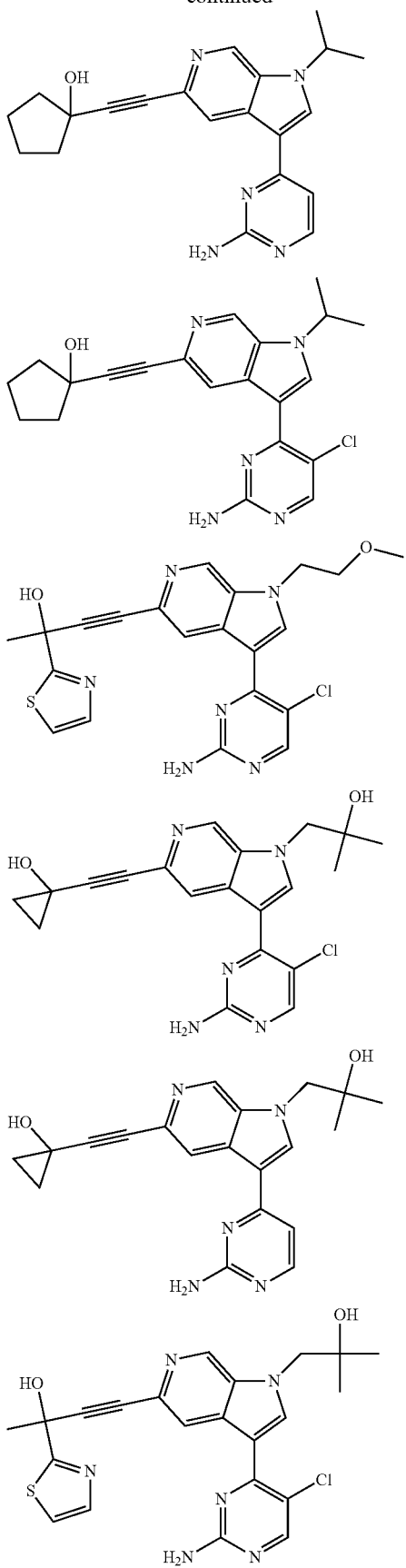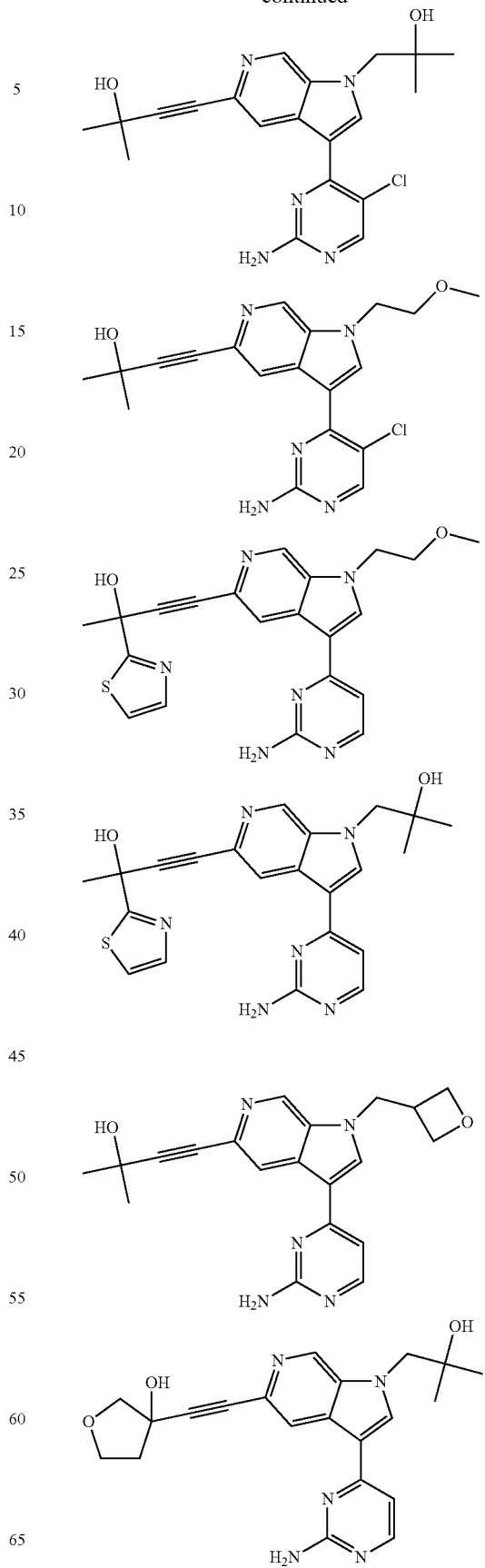

65
-continued
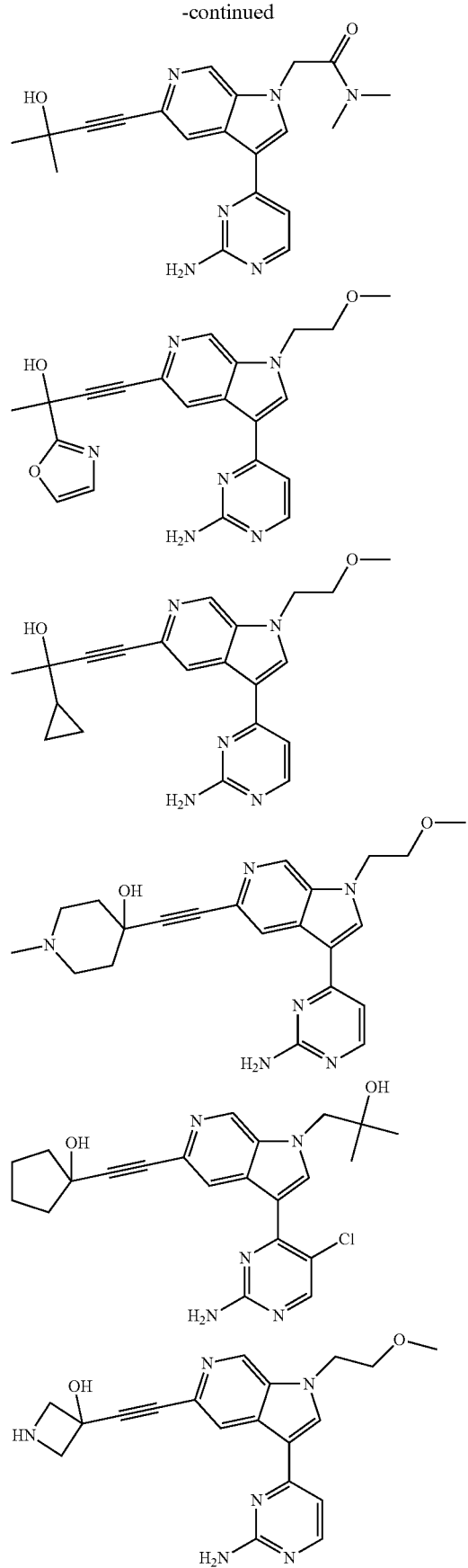
66
-continued
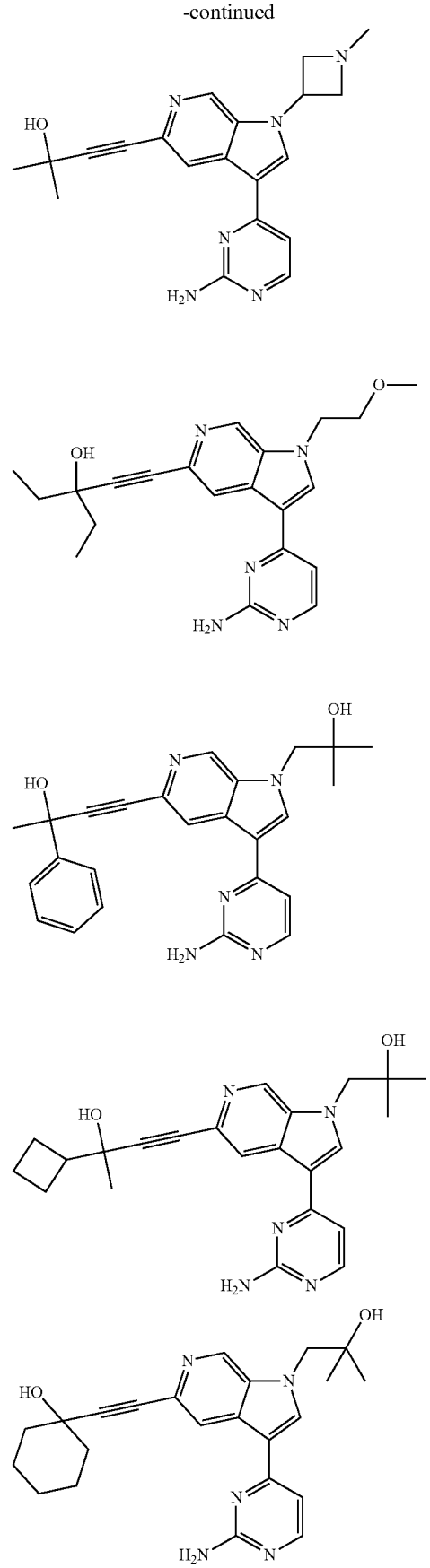

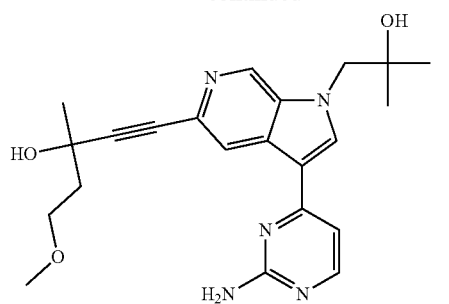
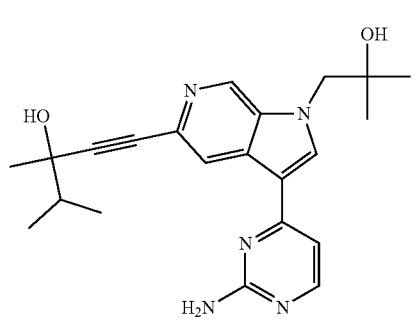
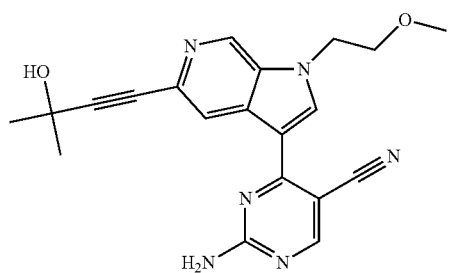
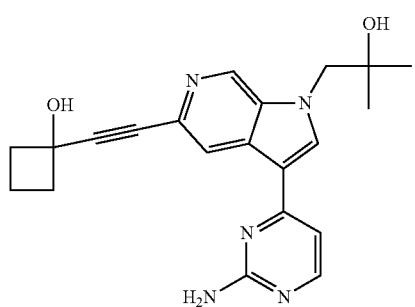
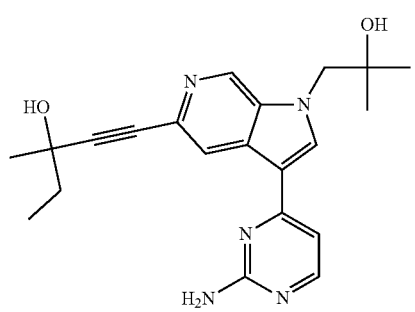
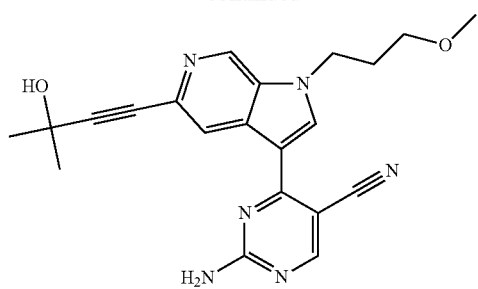
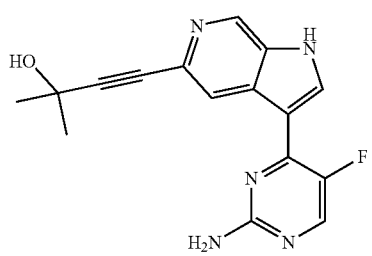
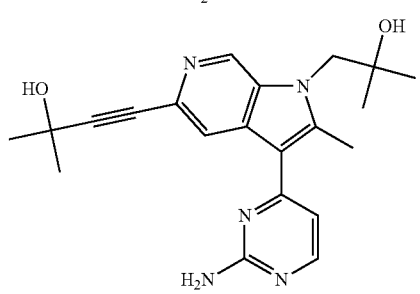
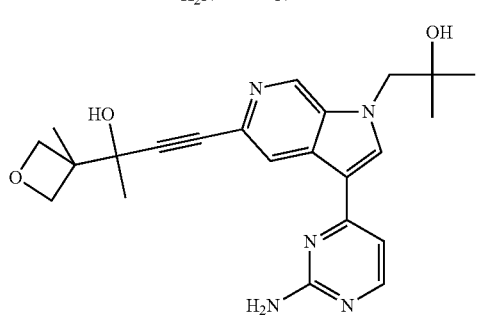
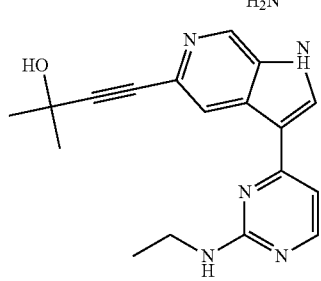
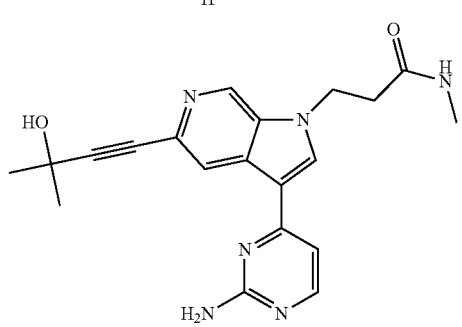

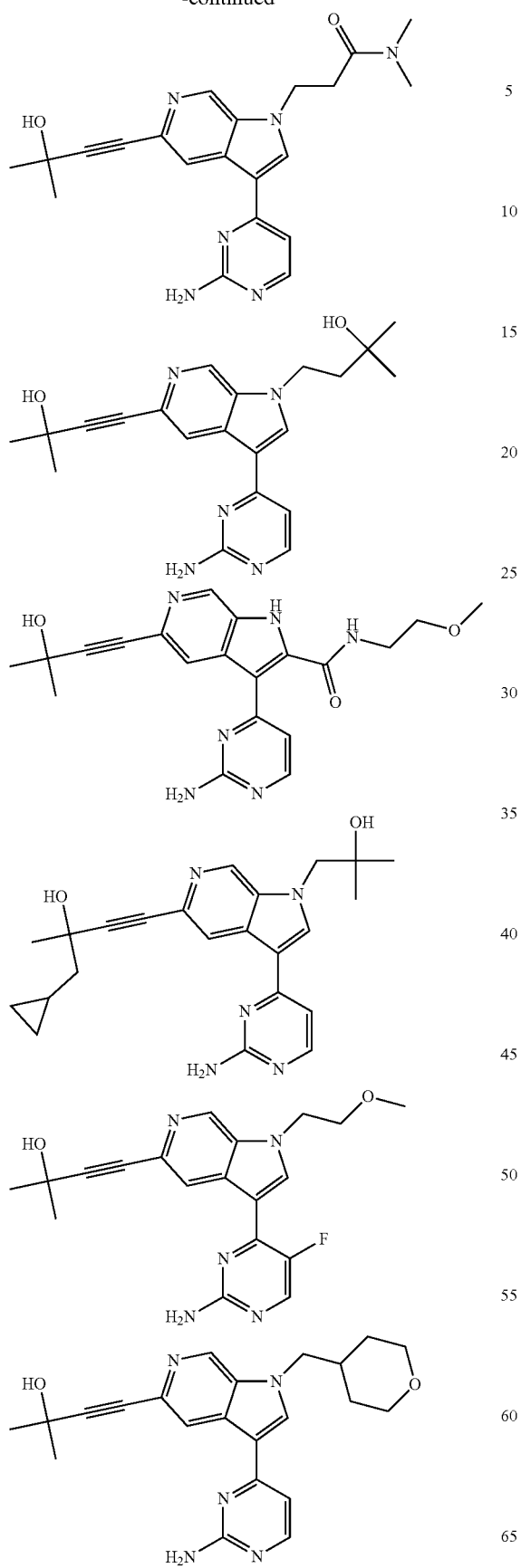
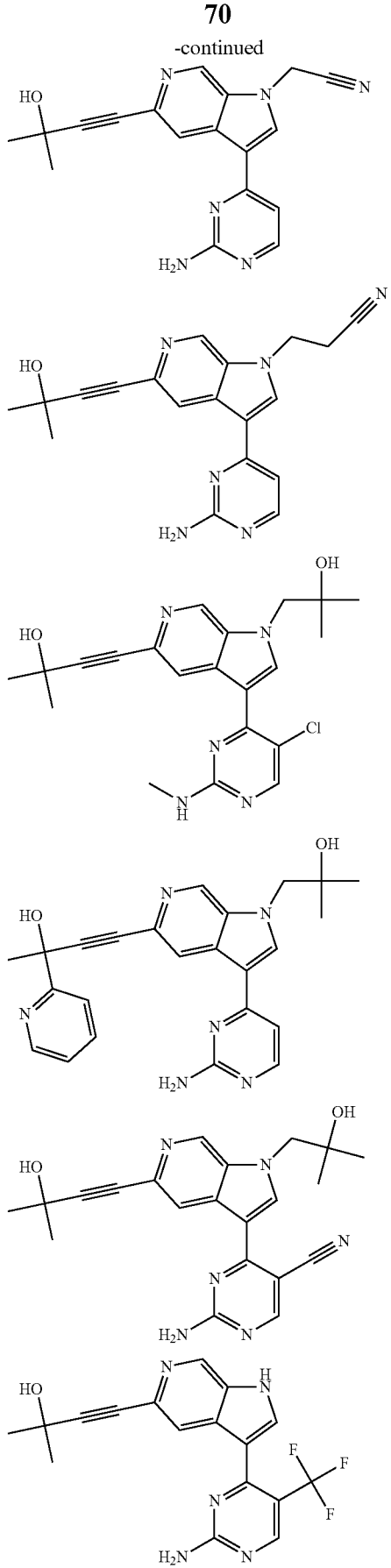

71
-continued
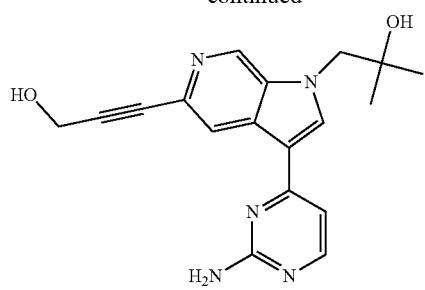
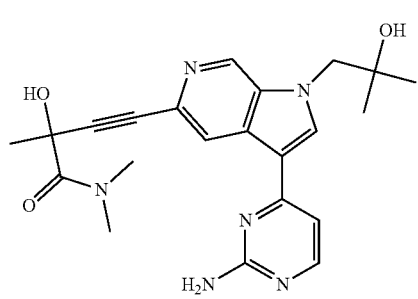
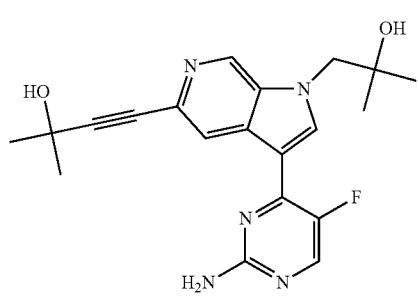
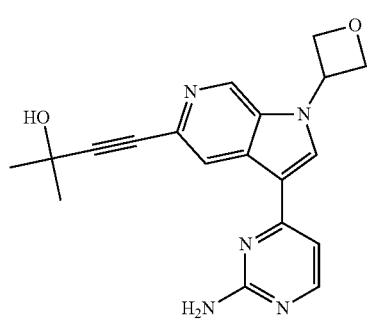
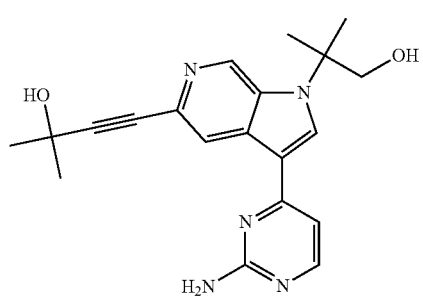
72
-continued
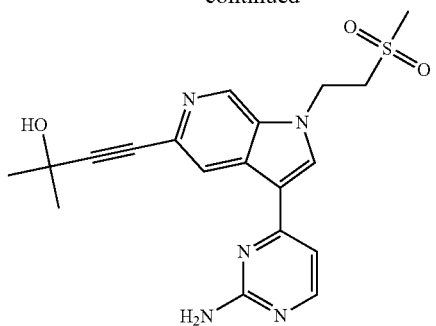
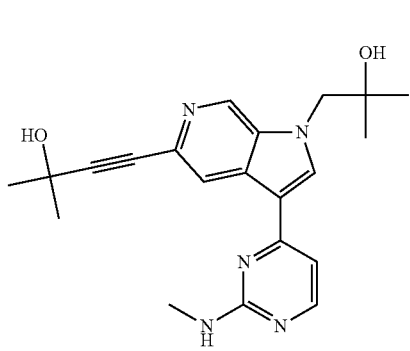
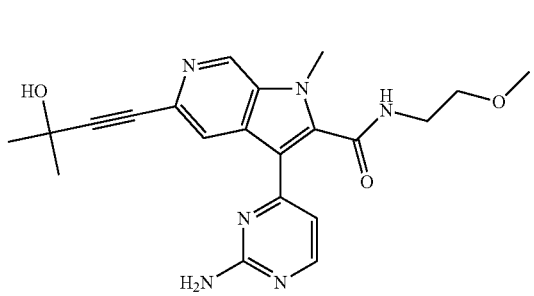
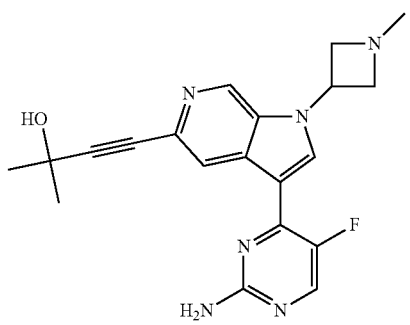
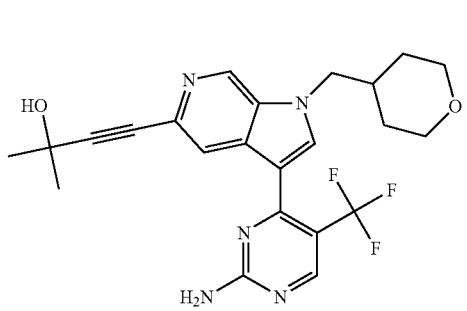

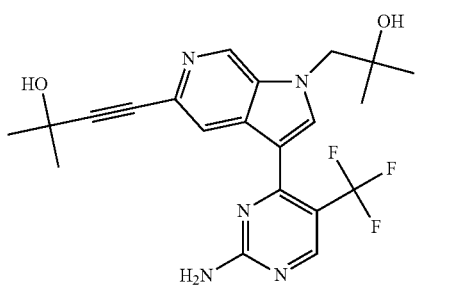
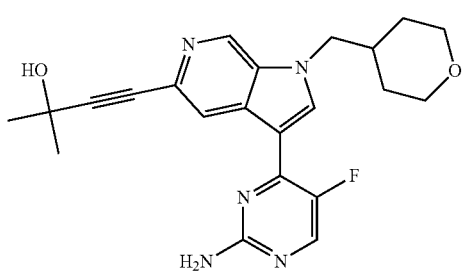
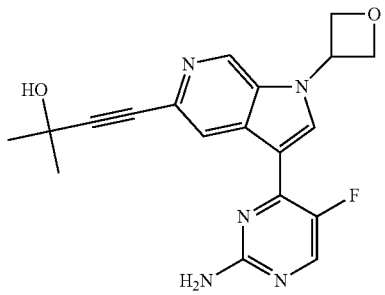
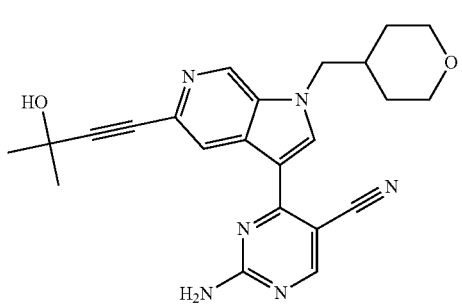
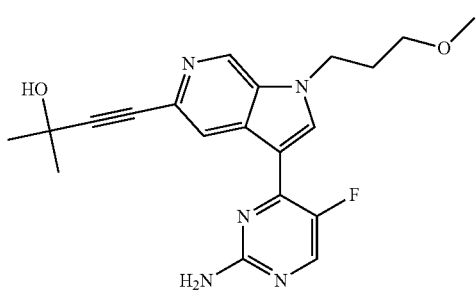
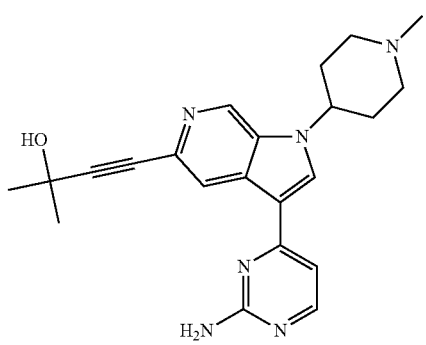
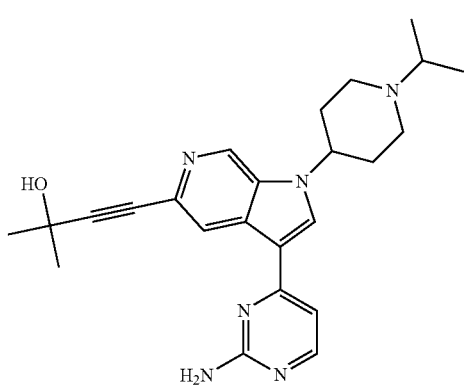
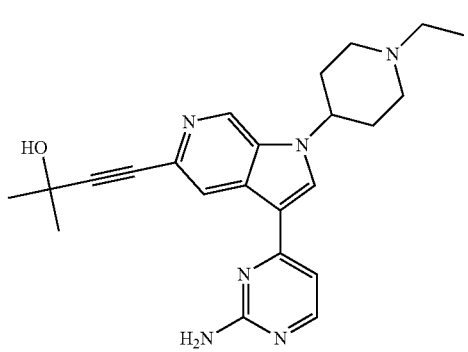
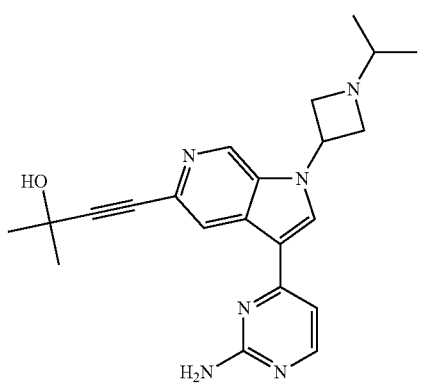

75
-continued
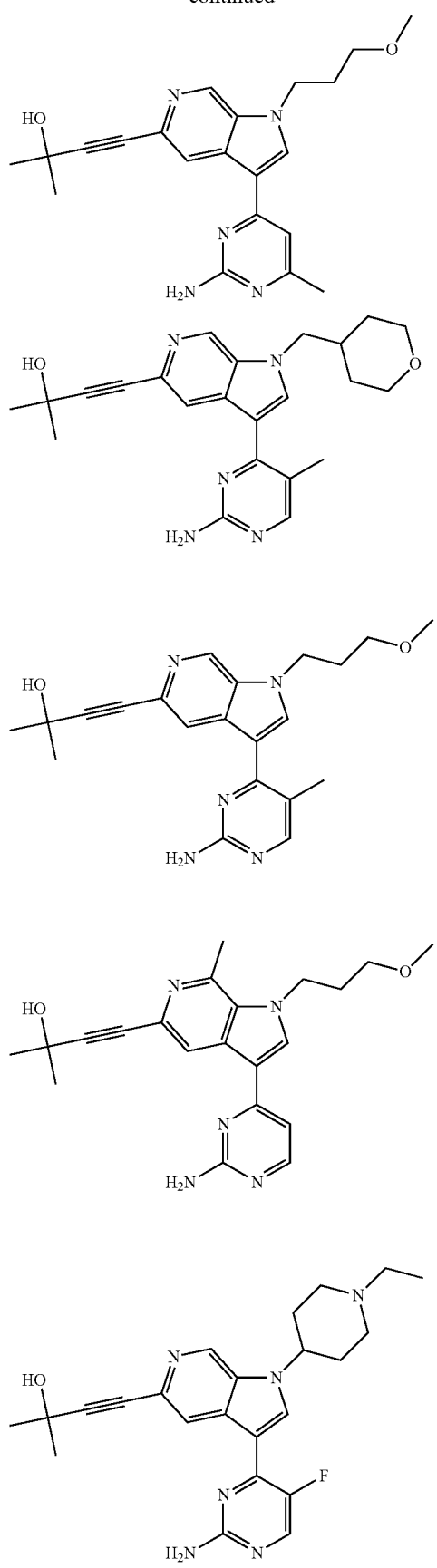
76
-continued
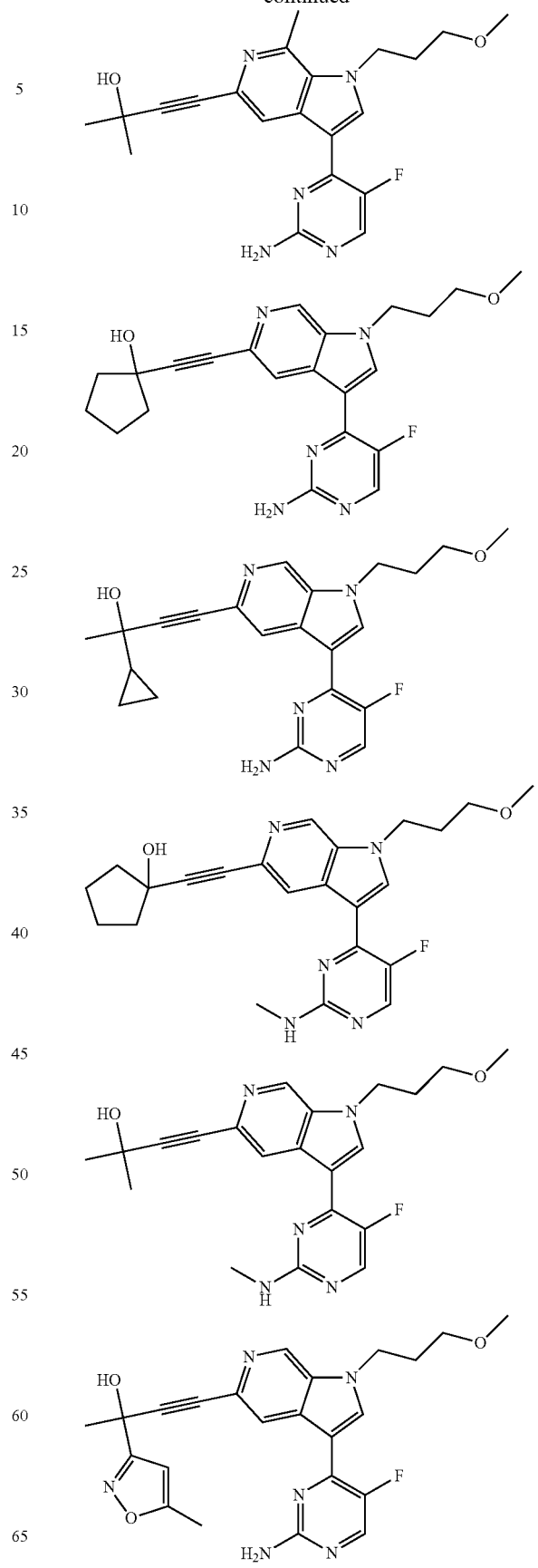

77
-continued
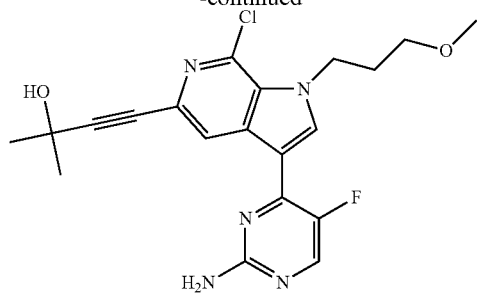
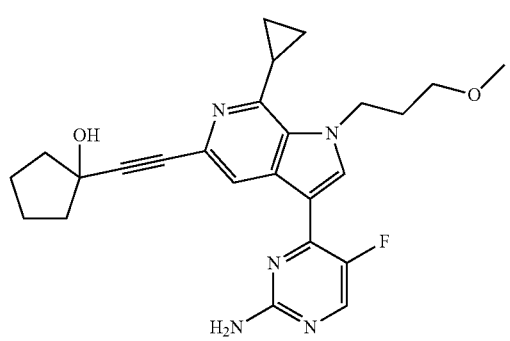
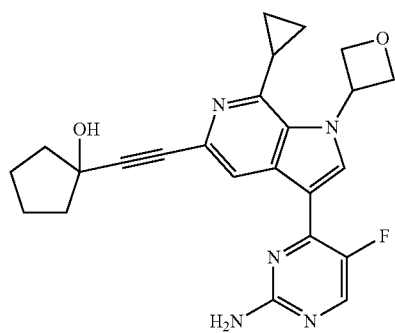
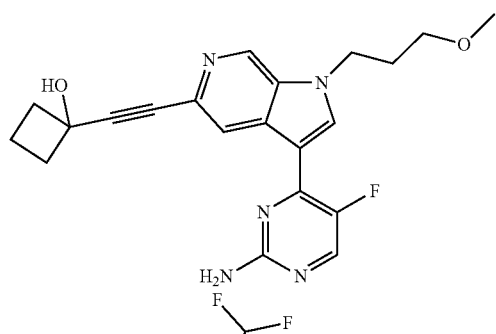
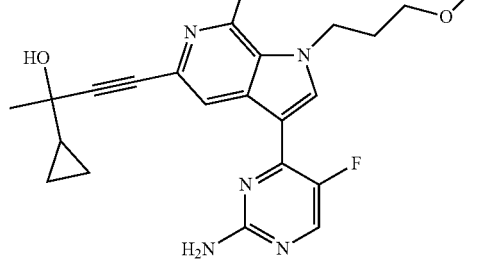
78
-continued
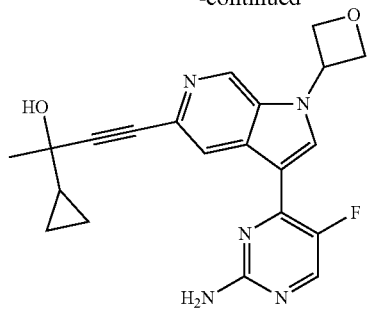
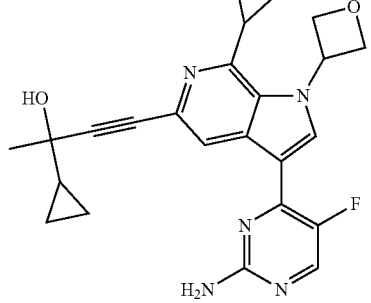
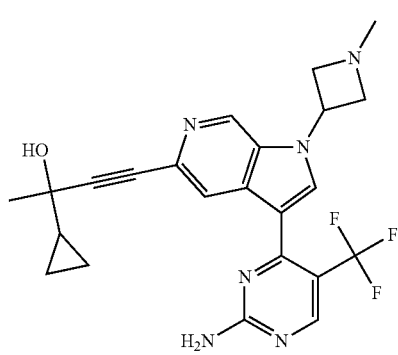
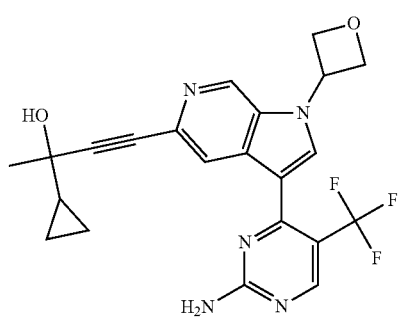
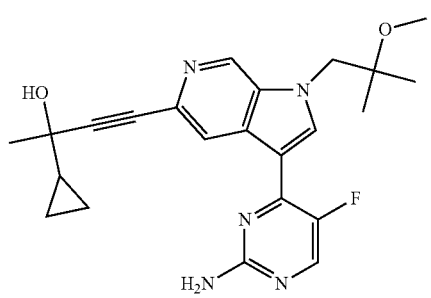

-continued
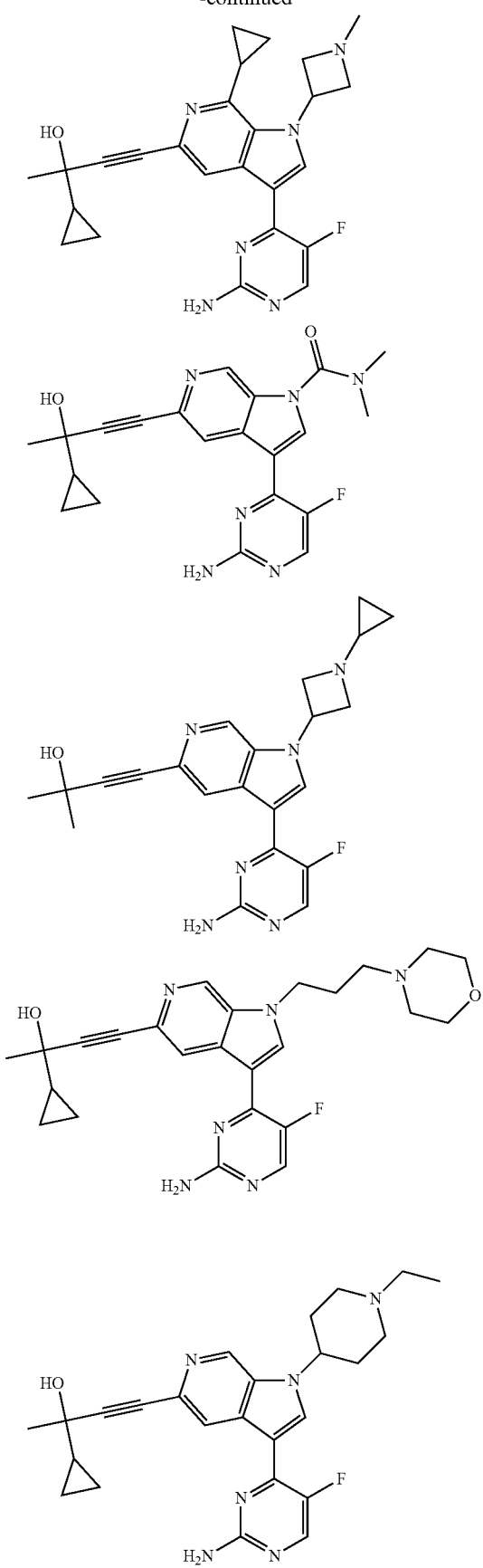
-continued
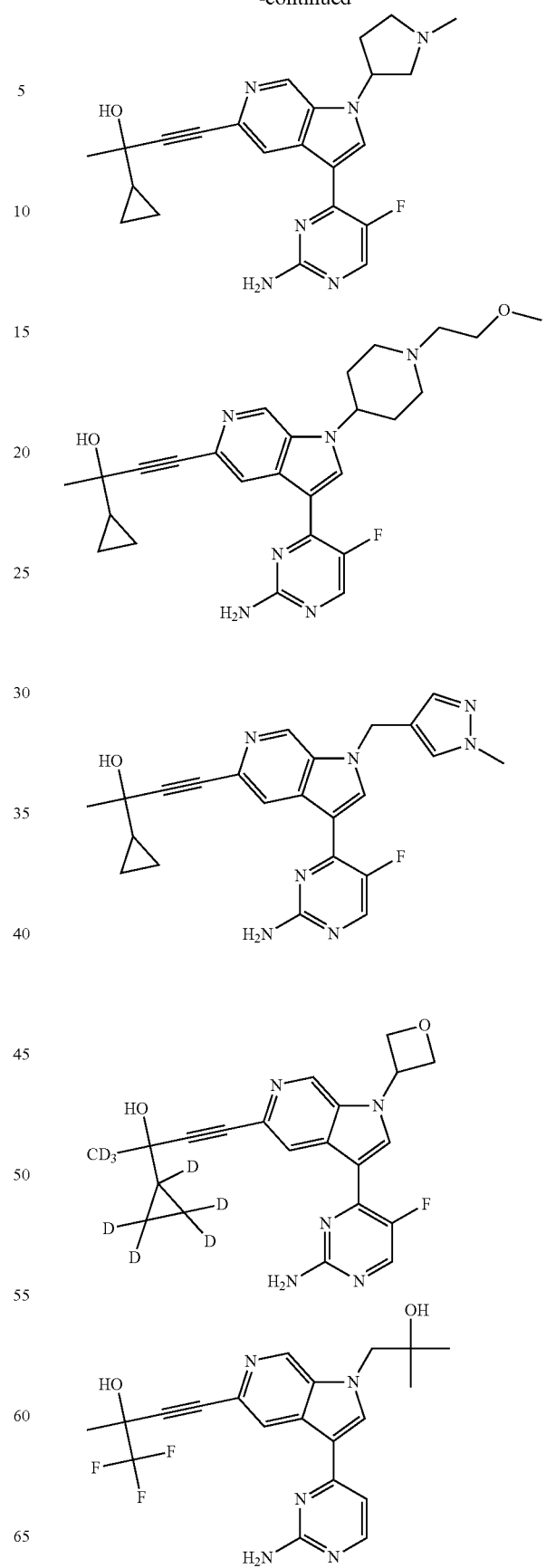

81
-continued
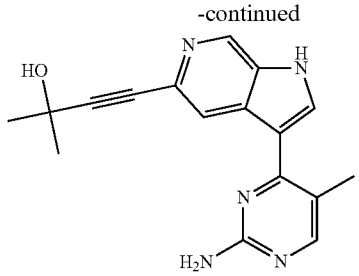
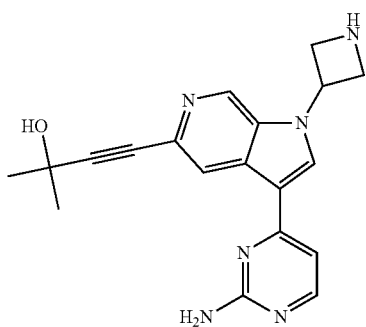
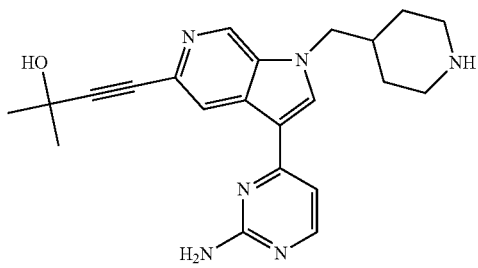
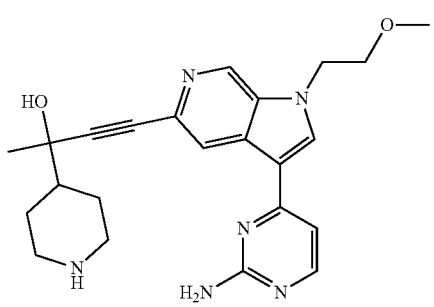
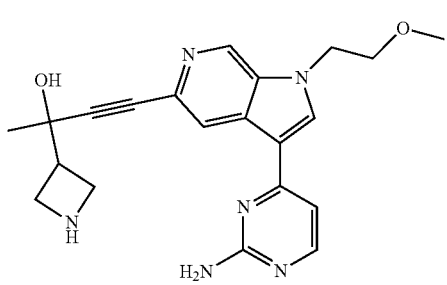
82
-continued
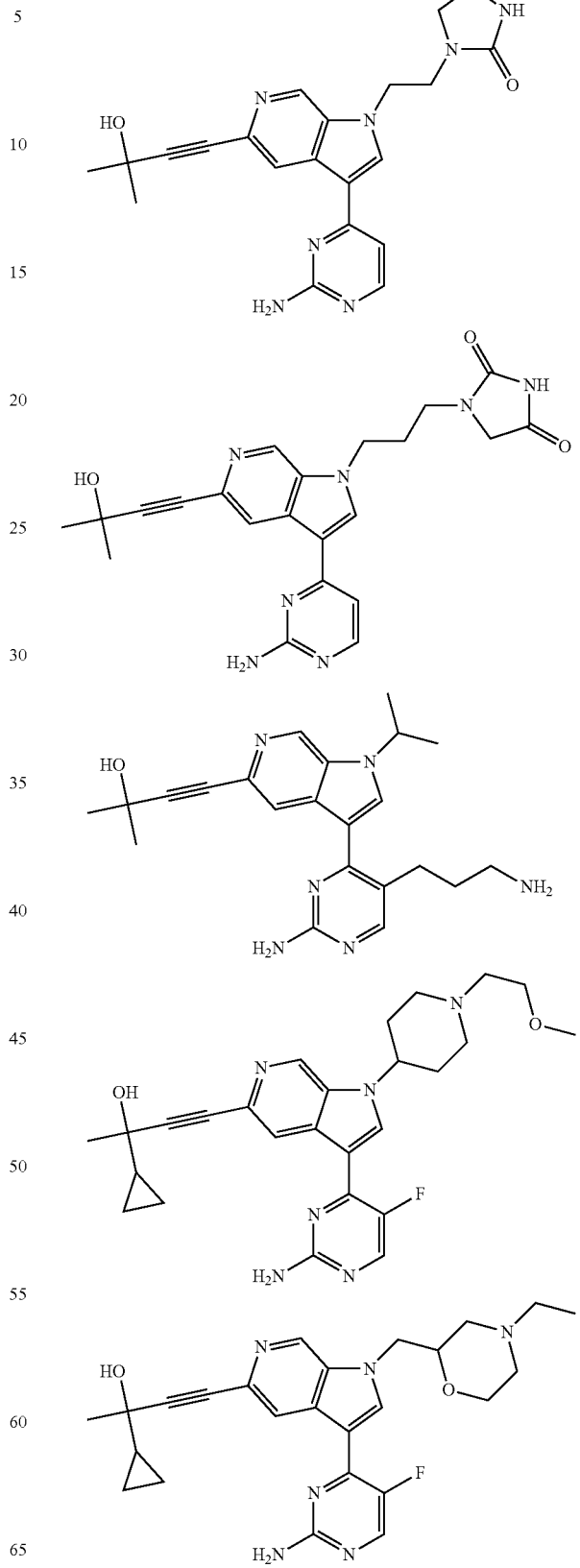

83
-continued
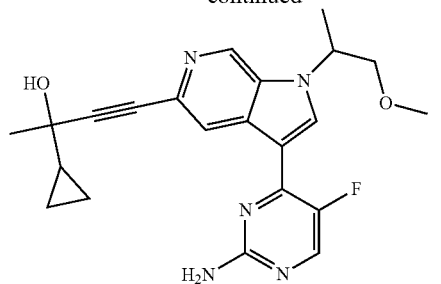
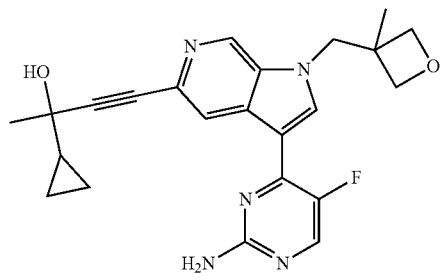
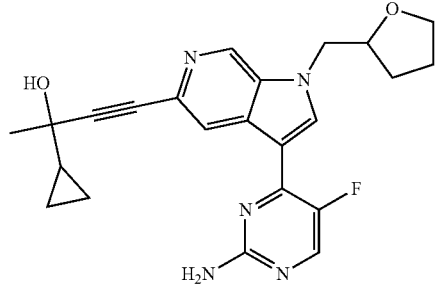
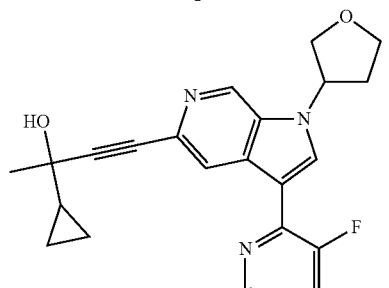
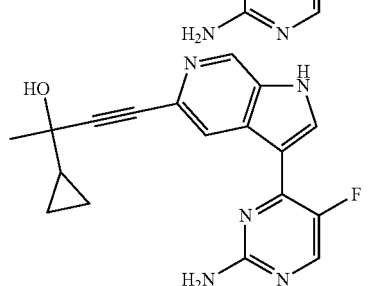
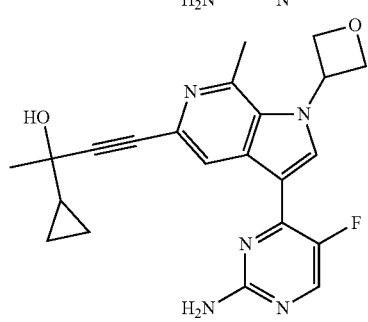
84
-continued
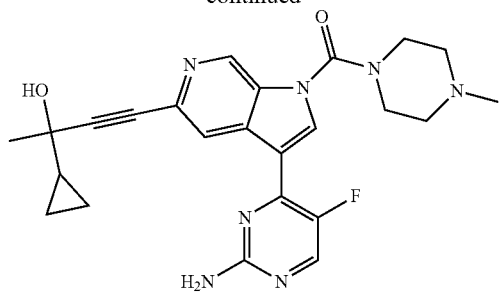
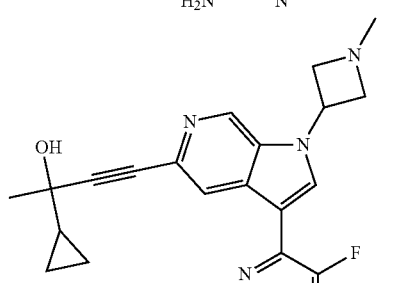
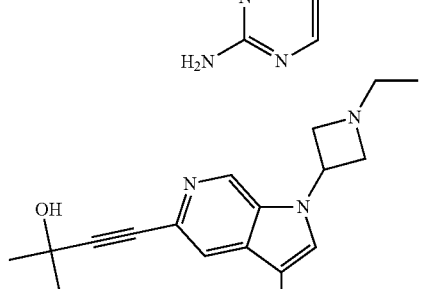
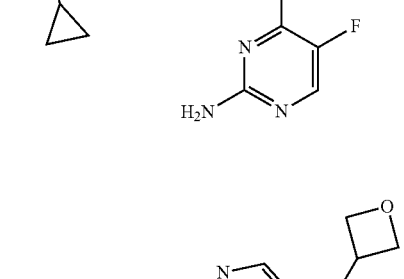
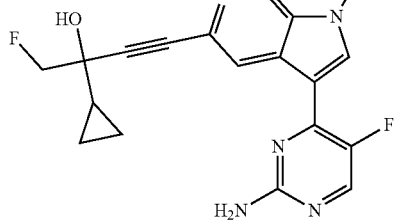
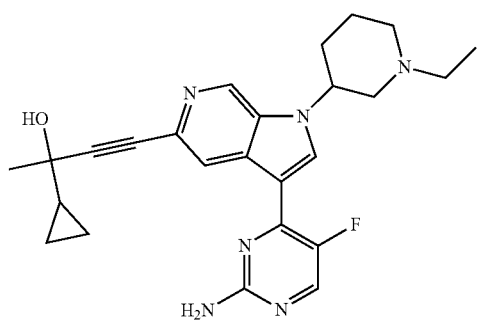

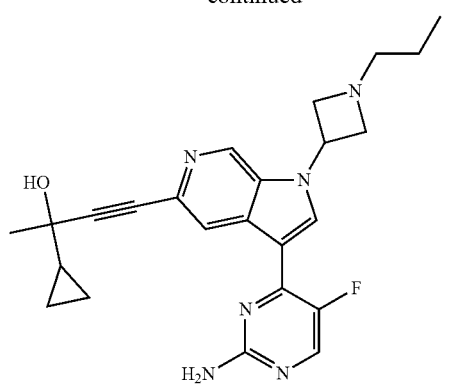
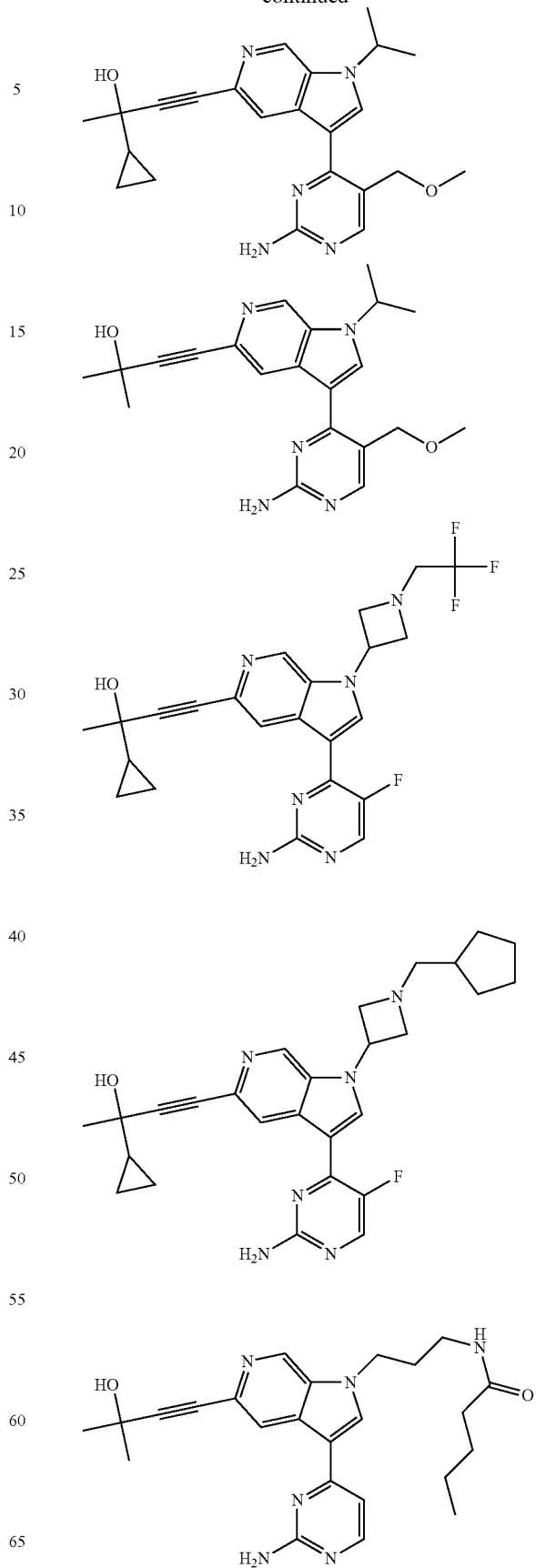

87
-continued
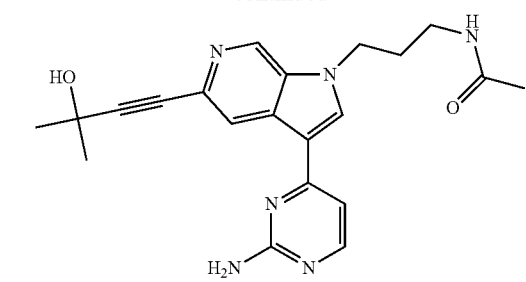
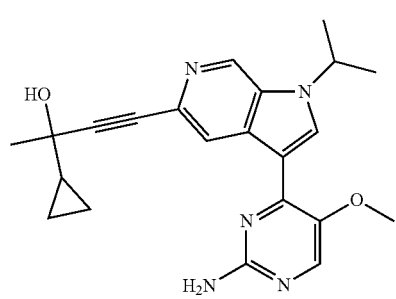
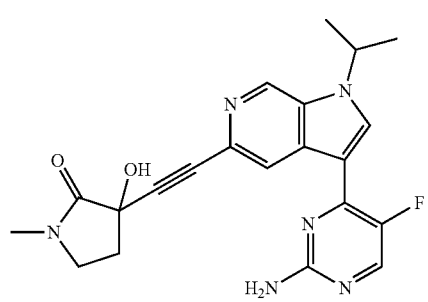
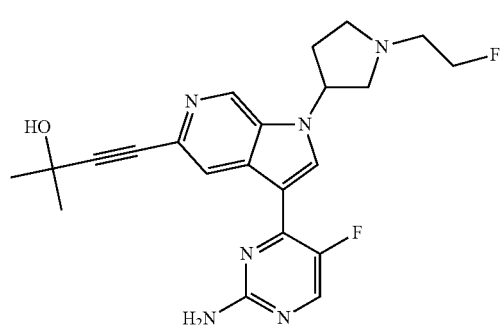
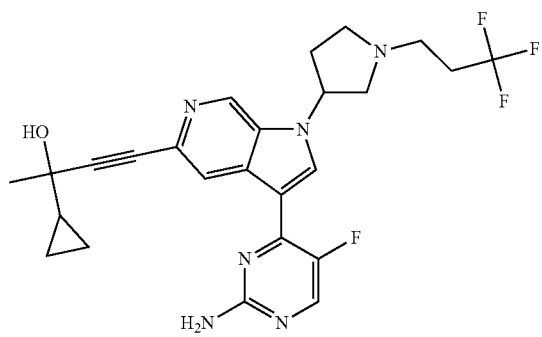
88
-continued
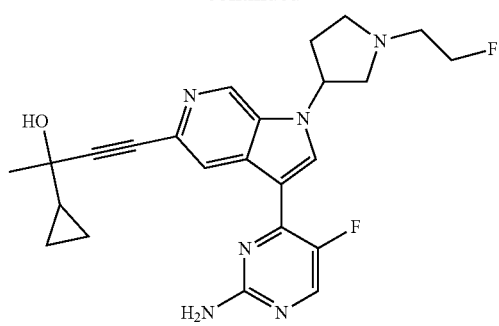
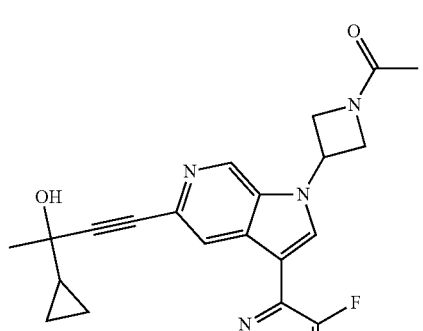
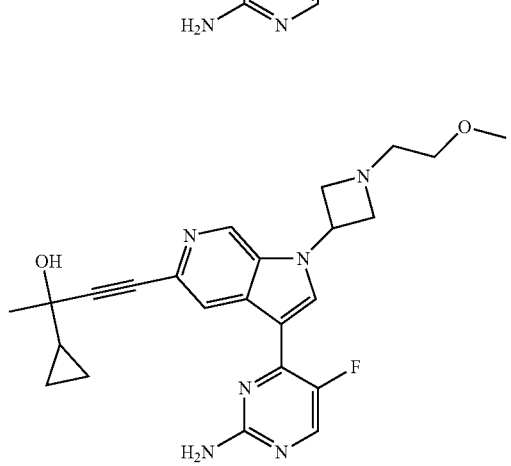
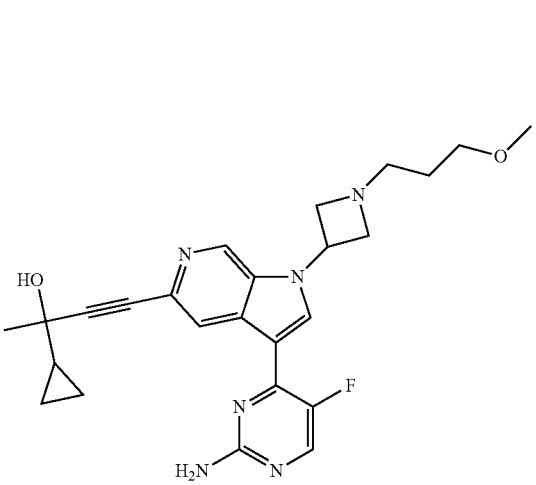

89
-continued
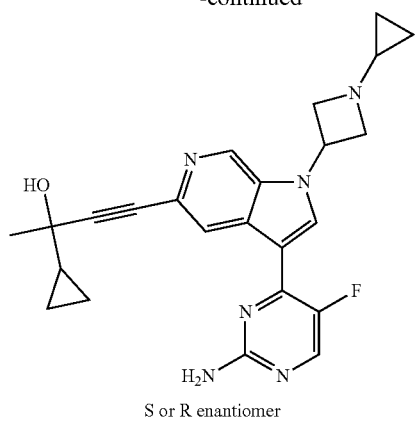
S or R enantiomer
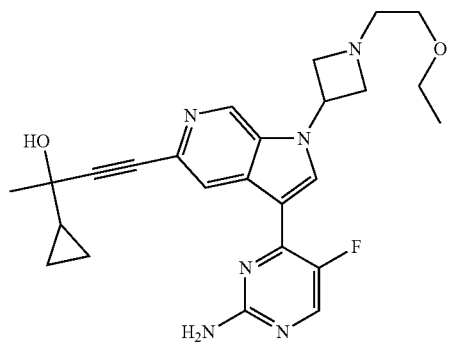
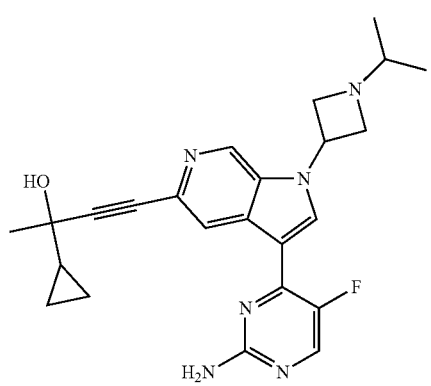
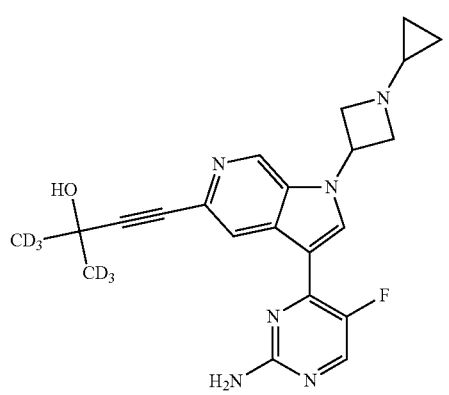
90
-continued
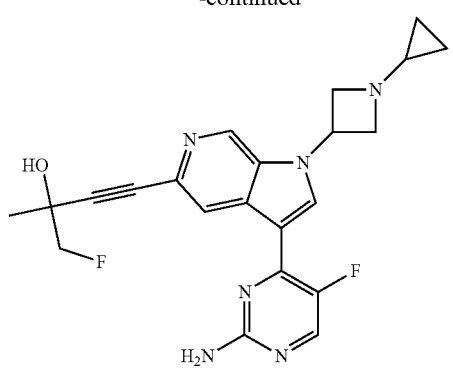
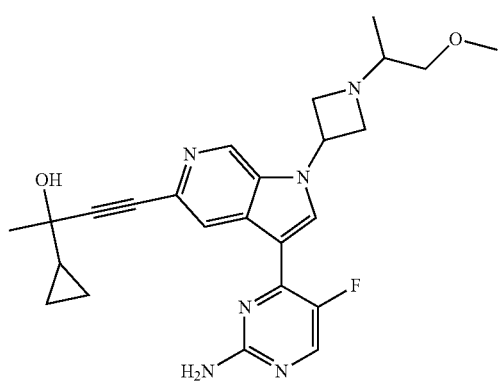
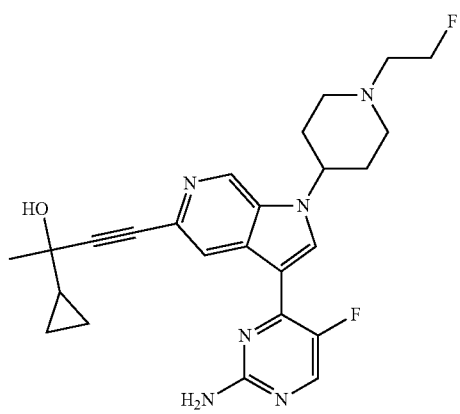
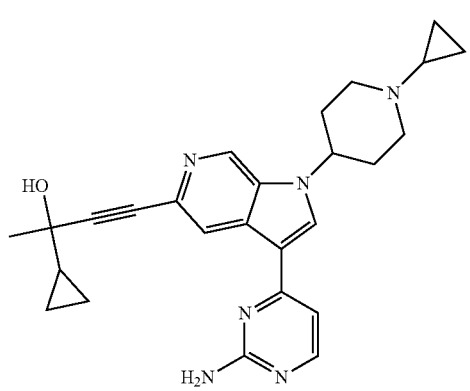

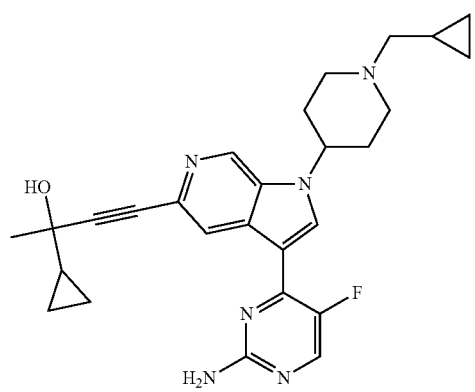
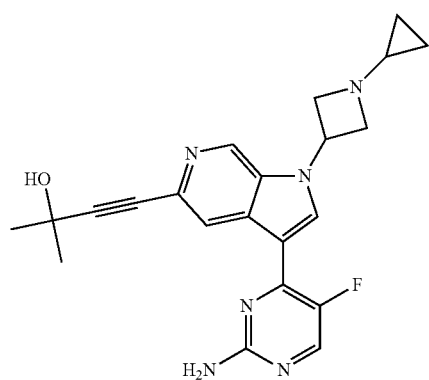
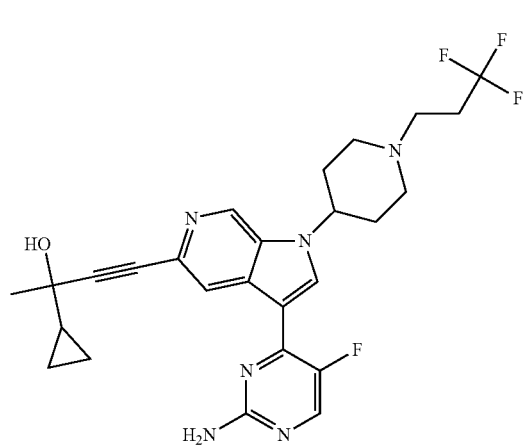
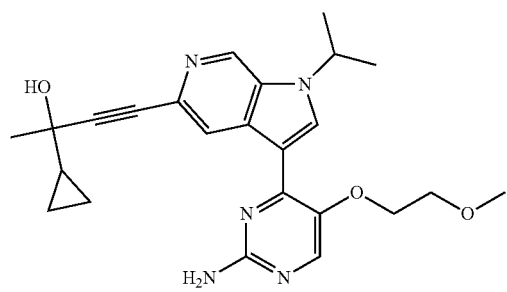
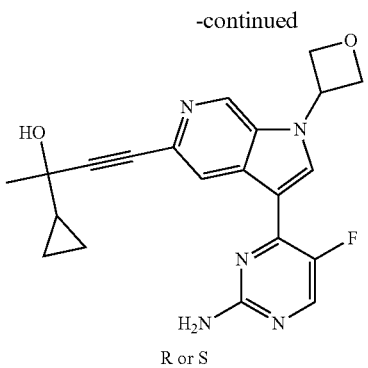
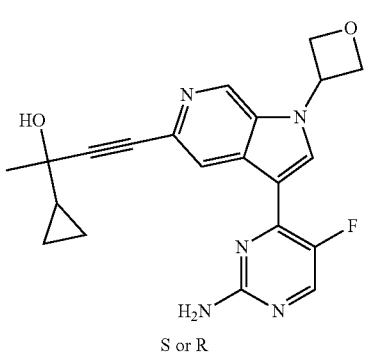
R or S
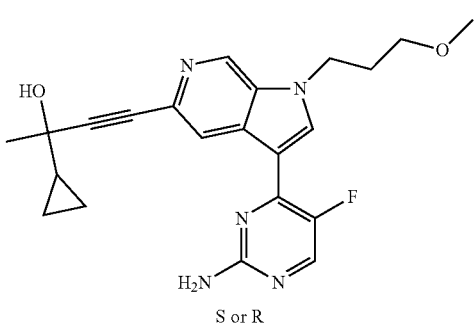
S or R
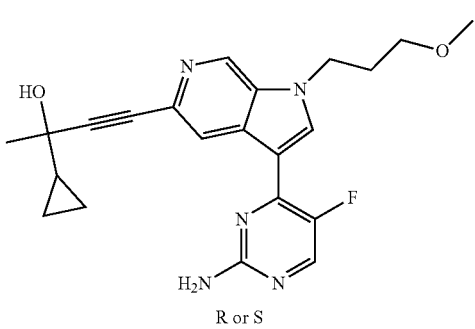
S or R
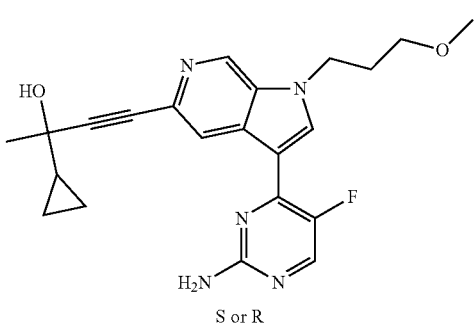
R or S
tautomers and stereoisomeric forms thereof,
and the pharmaceutically acceptable salts and the solvates thereof.
More specific compounds according to the invention include:

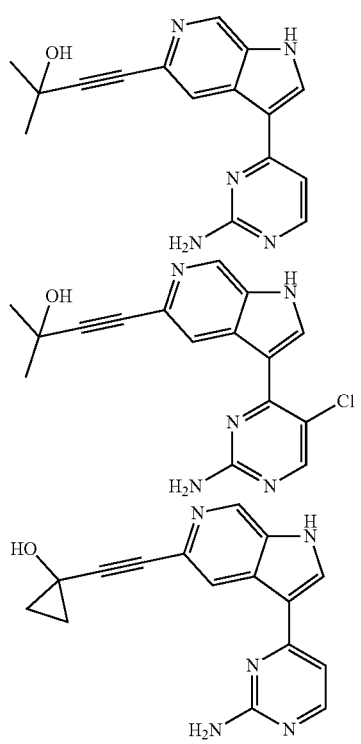
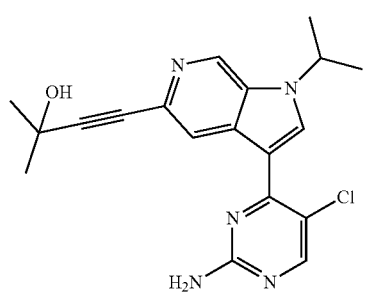
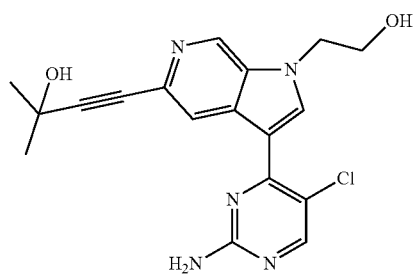
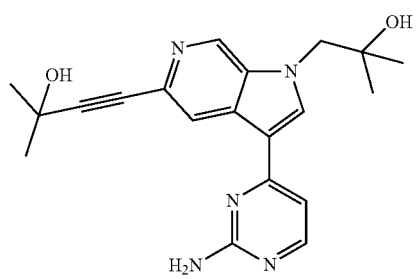
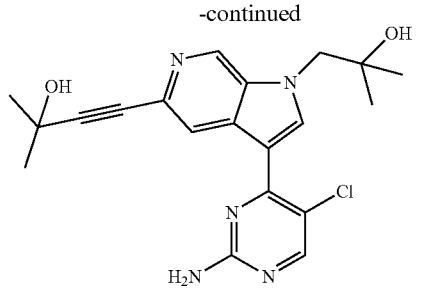
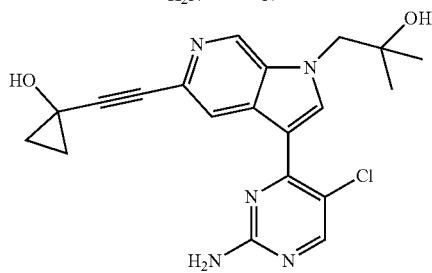
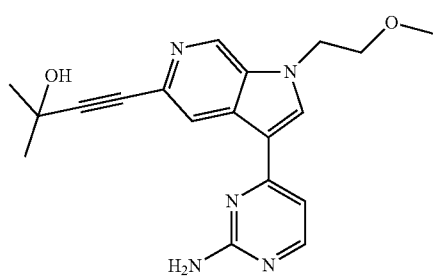
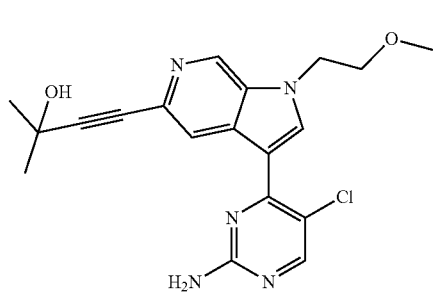
tautomers thereof,
and the pharmaceutically acceptable salts and the solvates thereof.
More specific compounds according to the invention include:
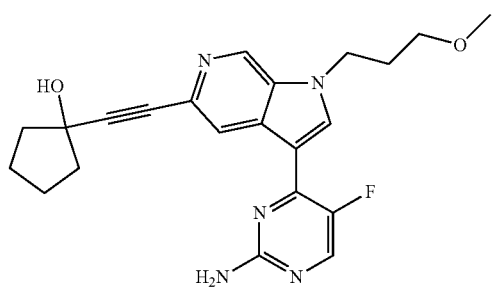

-continued
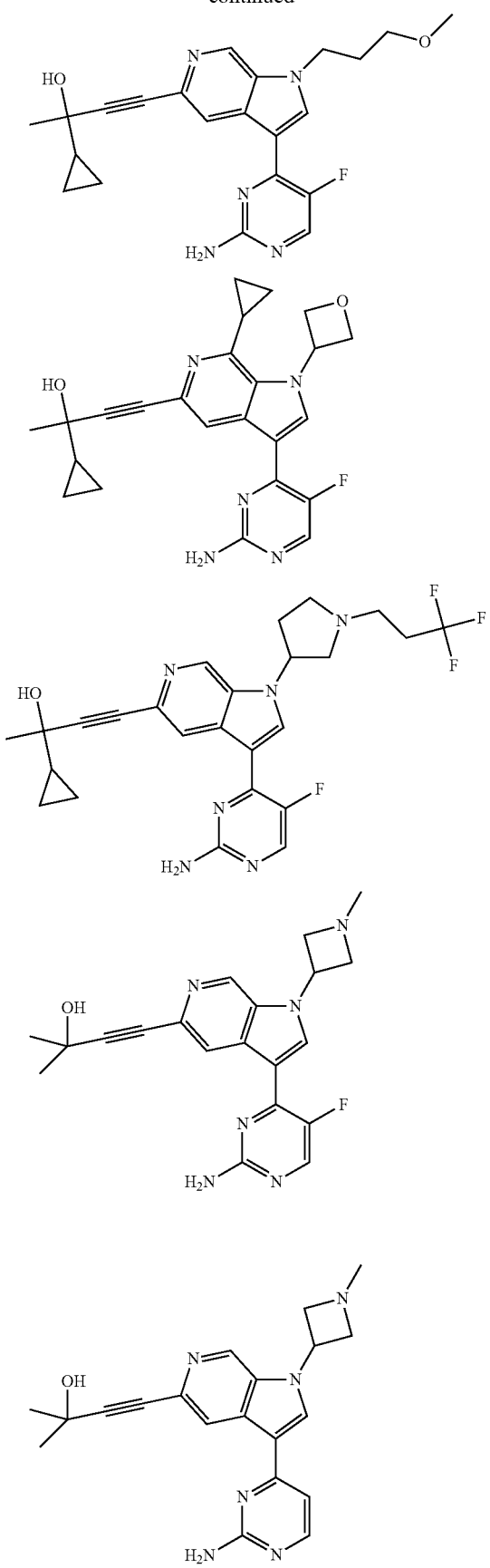
-continued
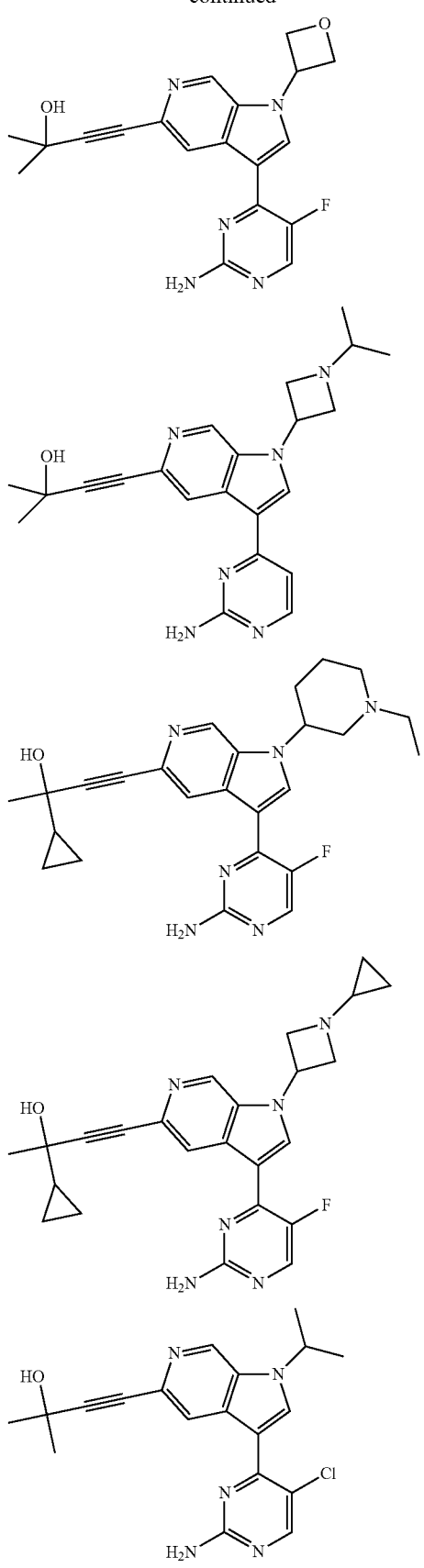

-continued
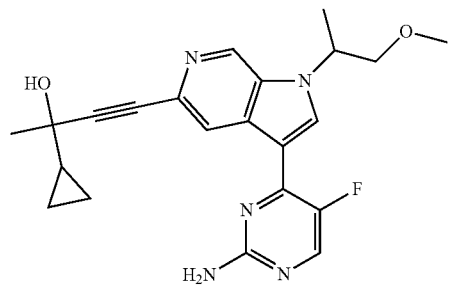
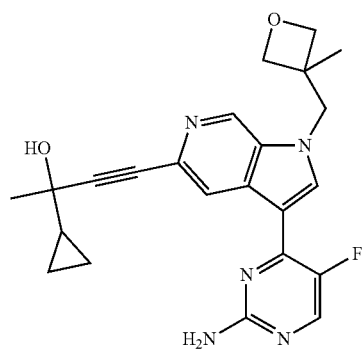
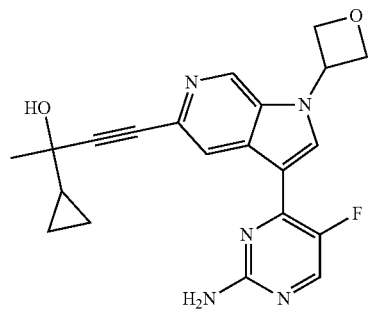
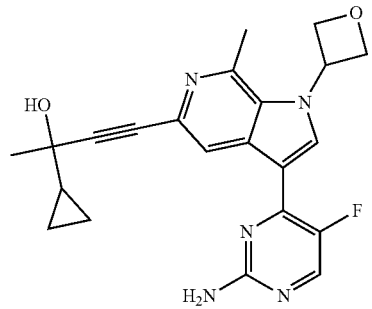
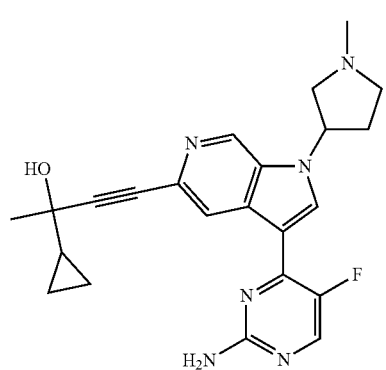
-continued
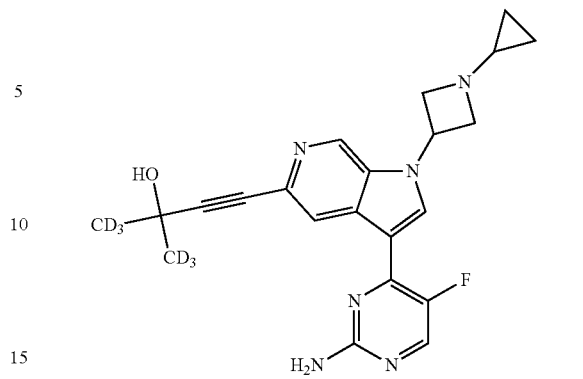
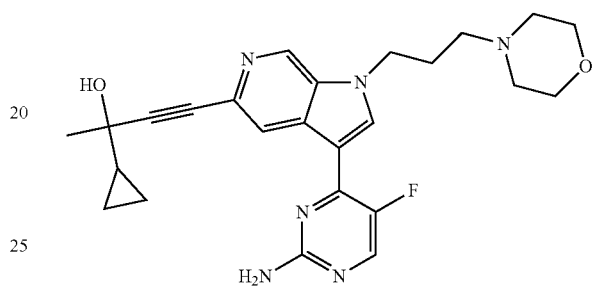
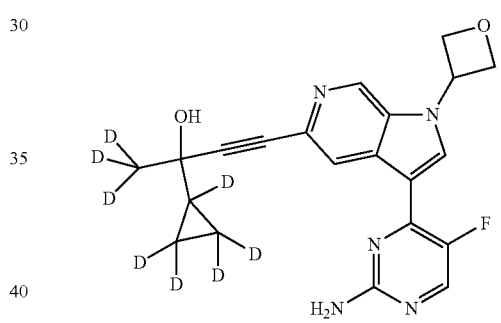
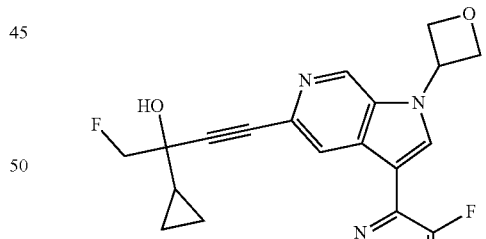
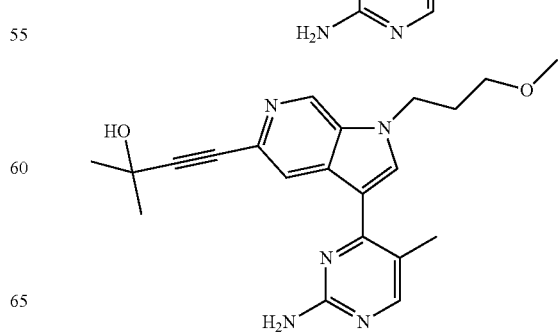

-continued

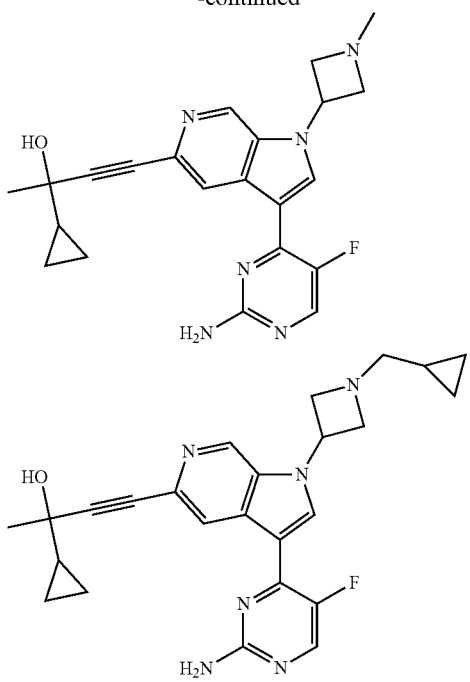

-continued

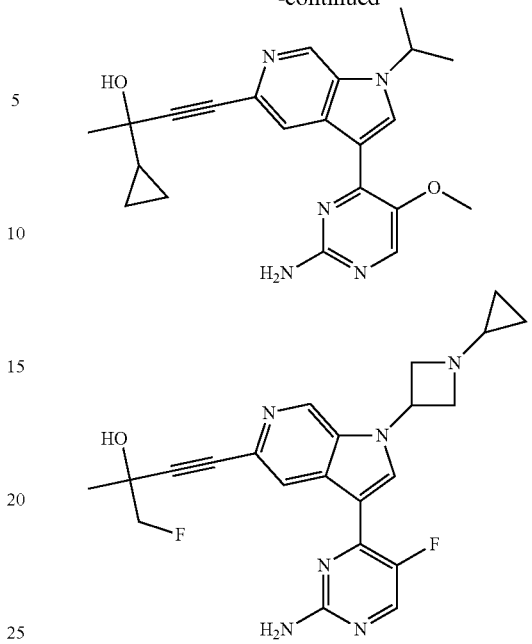

tautomers and stereoisomeric forms thereof, and the pharmaceutically acceptable salts and the solvates thereof.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Conversely, said salt forms can be converted into the free base form by treatment with an appropriate base.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid.

Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Conversely, said salt forms can be converted into the free acid forms by treatment with an appropriate acid.

The term solvate comprises the solvent addition forms as well as the salts thereof, which the compounds of formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2$H, $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^2$H, $^3$H, $^{11}$C and $^{18}$F. More preferably, the radioactive isotope is $^2$H. In particular, deuterated compounds are intended to be included within the scope of the present invention Methods of Synthesis Compounds of Formula (I) can be prepared by methods known to those who are skilled in the art. The following schemes are only meant to represent examples of the invention and are in no way meant to be a limit of the invention.

The symbol 'Δ' means that the reaction step typically may be performed under heating.

Herein, the term 'Ac' means acetyl, 'Me' means methyl, 'DIPEA' means diisopropylethylamine, 'DCM' means dichloromethane, 'DMF' means N,N-dimethylformamide, 'DMF.DMA' means N,N-dimethylformamide dimethyl acetal, 'HATU' means 1-[bis(dimethylamino)methylene]-1H-[1,2,3]triazolo[4,5-b]pyridin-1-ium 3-oxide hexafluorophosphate, 'NMP' means N-methyl-2-pyrrolidone, 'TsCl' means tosyl chloride, 'DMAP' means 4-dimethylaminopyridine, 'NIS' means N-iodosuccinimide, 'NCS' means N-chlorosuccinimide, 'AcOH' means acetic acid, 'Et$_3$N' means trietylamine, 'Pd(PPh$_3$)$_4$' means tetrakis(triphenylphosphine)palladium, 'PhN(SO$_2$CF$_3$)$_2$' means N-phenyl-bis(trifluoromethanesulfonimide), 'Boc' means example tert-butyl carbonate, '[Ir(OMe)cod]$_2$' means (1,5-cyclooctadiene)(methoxy) iridium(I) dimer, 'TFA' means trifluoroacetic acid.

Scheme 1

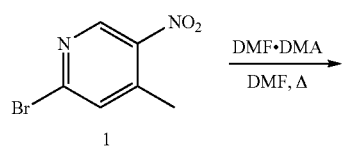

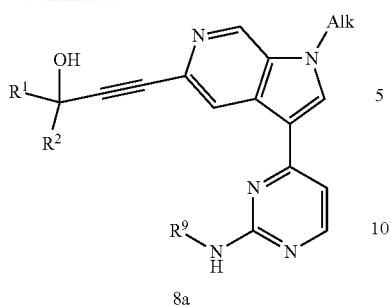

8a

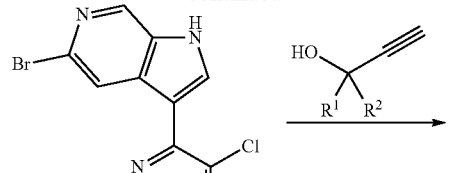

9

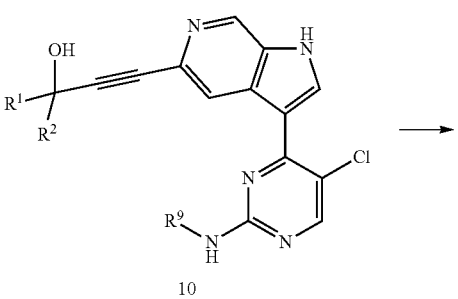

10

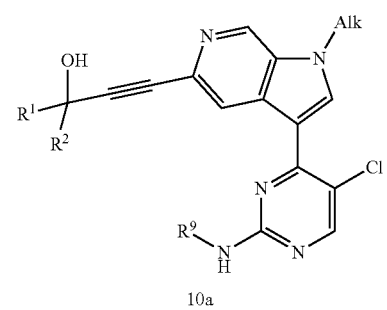

10a

Scheme 1 illustrates methods of preparing compounds of Formula (I), wherein $R^3$-$R^7$ are hydrogen and $R^8$ is hydrogen or $C_{1-6}$alkyl, hereby represented by formulae 8 and 8a, respectively, and wherein $R^1$, $R^2$ and $R^9$ are as defined in Formula (I) and Alk represents $C_{1-6}$alkyl. Methylpyridine 1 can be treated with N,N-dimethylformamide dimethyl acetal to give vinylamine 2. Reduction and cyclisation of vinylamine 2 can be achieved using iron in acetic acid to yield azaindole 3. Treatment of azaindole 3 with aluminum chloride/acyl chloride gives ketone 4 which, in turn, can be reacted with tosyl chloride (TsCl) to yield N-substituted azaindole 5. Heating intermediate 5 with tert-butoxybis (dimethylamino)methane gives aminopropenone 6 which, when reacted with a suitable guanidine in the presence of a base such as sodium methoxide in a protic solvent, such as n-butanol, with heating, yields aminopyrimidines 7. The aryl bromide group in aminopyrimidine 7 can be reacted with alkynes under palladium-catalyzed Sonogashira coupling conditions, using for example Pd(PPh$_3$)$_4$, CuI and a base such as triethylamine in acetonitrile, with heating, to furnish final products such as 8. Final compound 8 can be further N-alkylated under appropriate conditions, such as using a $C_{1-6}$alkylhalide, such us a $C_{1-6}$alkyl iodide in the presence of a suitable base in an appropriate solvent, to furnish final products such as 8a. Final compound 8 can also be N-alkylated with an optionally substituted $C_{1-6}$alkylhalide or an optionally substituted $C_{2-6}$alkylhalide, under the conditions used for carrying out the N-alkylation of compounds 8 to final compound 8a, to yield final compounds wherein $R^8$ is an optionally substituted $C_{1-6}$alkyl or $C_{2-6}$alkyl.

Scheme 2

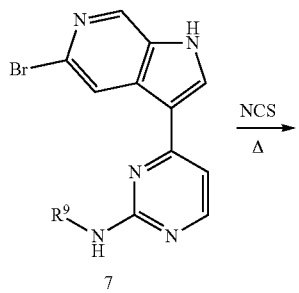

7

Scheme 2 illustrates methods of preparing compounds of Formula (I), wherein $R^3$-$R^5$ and $R^7$ are hydrogen, $R^6$ is chloro, and $R^8$ is hydrogen or $C_{1-6}$alkyl, hereby represented by formula 10 or 10a, respectively, wherein $R^1$, $R^2$ and $R^9$ are as defined in Formula (I) and Alk represents $C_{1-6}$alkyl. Aminopyrimidines 7 can be treated with N-chlorosuccinimide under appropriate conditions, such as for example in acetonitrile under heating, to yield chloropyrimidines 9. The aryl bromide moiety in 9 can be reacted with alkynes under palladium-catalyzed Sonogashira coupling conditions, using for example Pd(PPh$_3$)$_4$, CuI and a base such as triethylamine in acetonitrile, with heating, to furnish final products such as 10. Final compounds 10 can be further N-alkylated under appropriate conditions, such as using a $C_{1-6}$alkylhalide, such as a $C_{1-6}$alkyl iodide in the presence of a suitable base in an appropriate solvent, to furnish final products such as 10a. Aminopyrimidines 7 can also be treated with N-bromosuccinimide and N-iodosuccinimide, under the conditions used for carrying out the chlorination of aminopyrimidines 7 to chloropyrimidines 9, to yield the corresponding bromopyrimidine and iodopyrimidine intermediates. The bromopyrimidine and iodopyrimidine intermediates can be converted to final compounds of formula 10 and 10a, wherein chloro has been replaced with bromo or iodo, in the same way as described for compounds 10 and 10a from chloropyrimidines 9.

Scheme 3

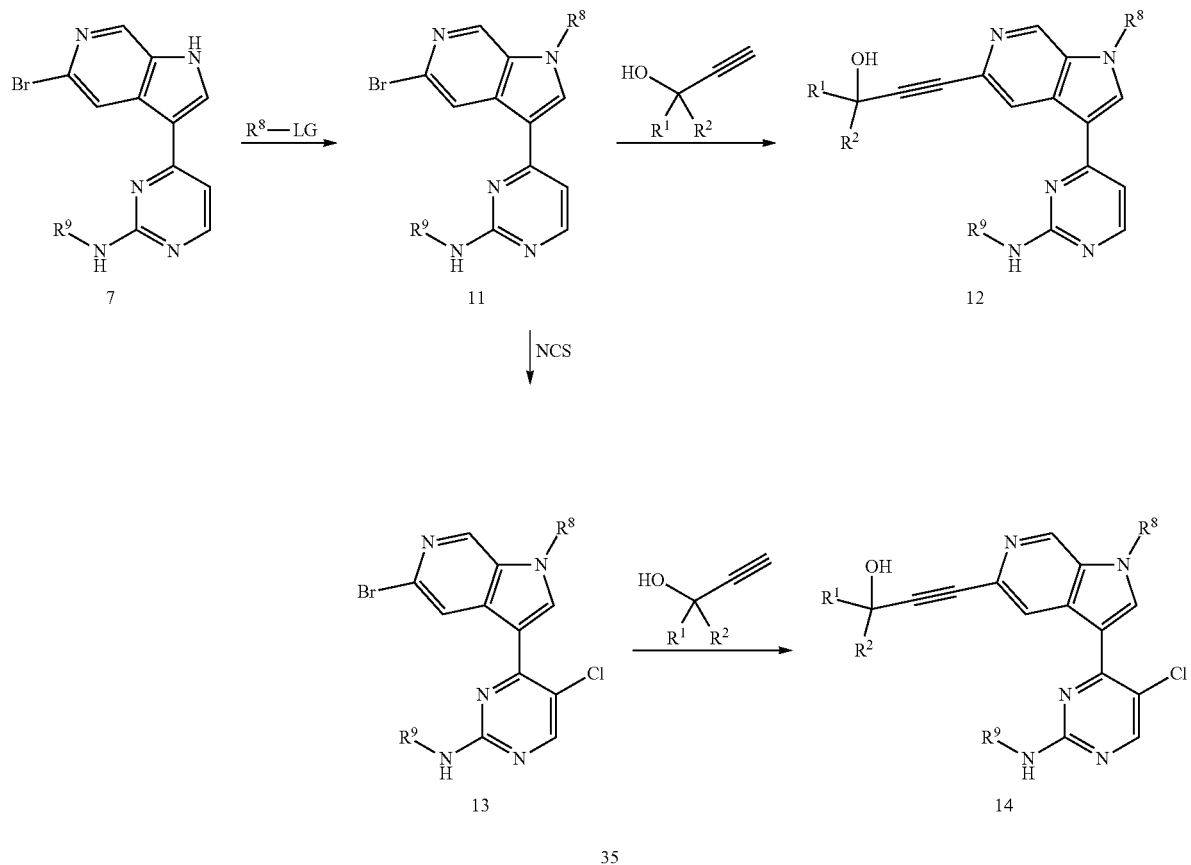

Scheme 3 illustrates methods of preparing compounds of Formula (I) wherein $R^3$-$R^5$ and $R^7$ are hydrogen, and $R^6$ is hydrogen, hereby represented by formula 12, or $R^6$ is chloro, hereby represented by formula 14, wherein $R^1$, $R^2$, $R^8$ and $R^9$ are as defined in Formula (I). Treatment of azaindole 7 with a suitable alkylating agent under basic conditions, such as $R^8$-LG, wherein LG is a leaving group, such as chloro, bromo or iodo, using for instance, cesium carbonate in DMF under heating, yields N-substituted azaindoles 11. The aryl bromide function in N-substituted azaindole 11 can then be reacted with alkynes under palladium-catalyzed Sonogashira conditions, using for example Pd(PPh$_3$)$_4$, CuI and a base such as triethylamine in acetonitrile, with heating, to furnish final products such as 12. Alternatively, the aminopyrimidine moiety in N-substituted azaindole 11 can be treated with N-chlorosuccinimide to yield chloropyrimidines 13. As above, the aryl bromide moiety in 13 can be reacted with alkynes under palladium-catalyzed Sonogashira conditions, using for example Pd(PPh$_3$)$_4$, CuI and a base such as triethylamine in acetonitrile, with heating, to furnish final products such as 14. N-Substituted azaindoles 11 can also be treated with N-bromosuccinimide and N-iodosuccinimide, under the conditions used for carrying out the chlorination of azaindoles 11 to chloropyrimidines 13, to yield the corresponding bromopyrimidine and iodopyrimidine intermediates. The bromopyrimidine and iodopyrimidine intermediates can be converted to final compounds of formula 14, wherein chloro has been replaced with bromo or iodo, in the same way as described for compounds 14 from chloropyrimidines 13.

Scheme 4

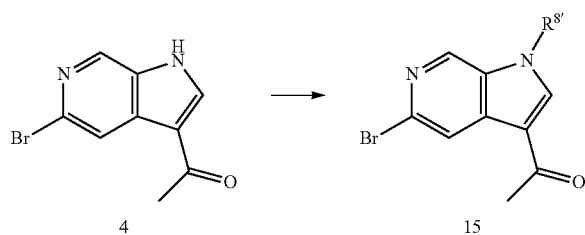

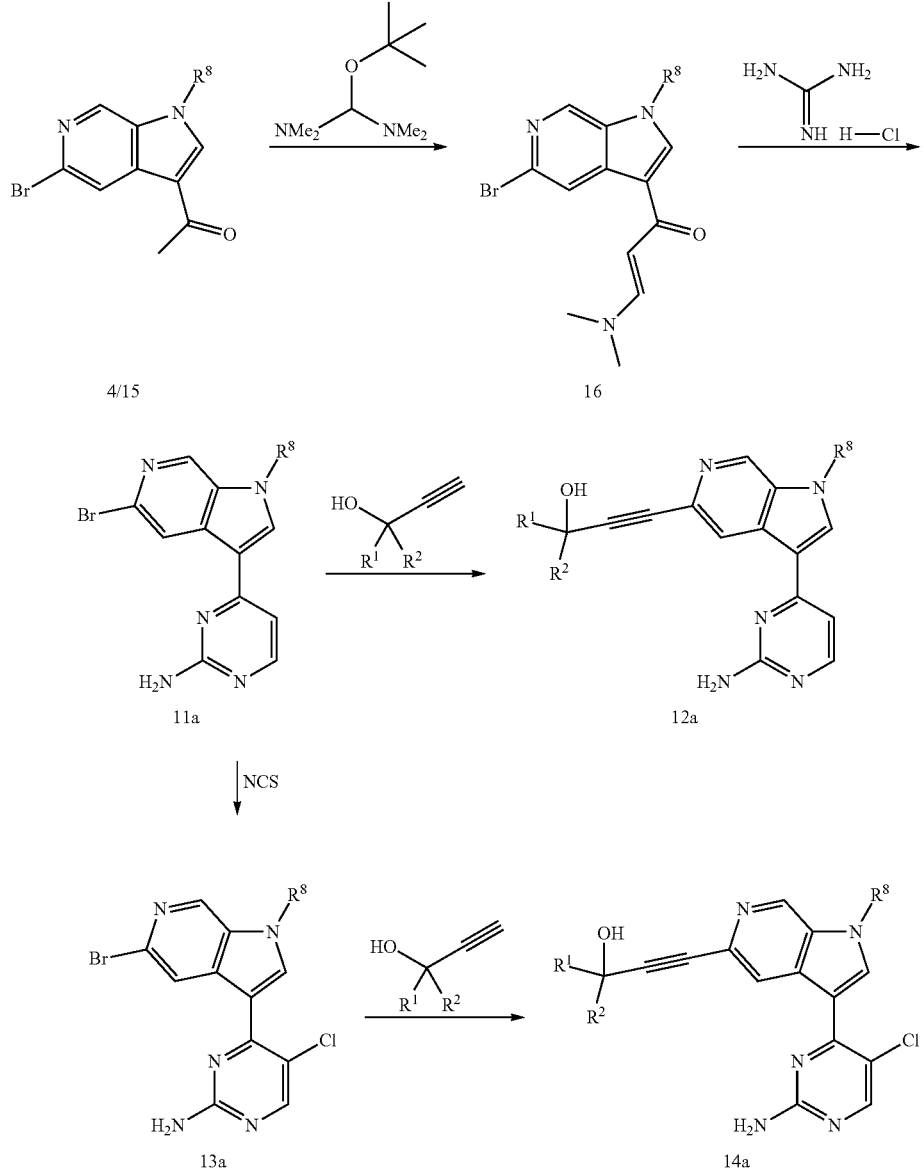

Scheme 4 illustrates methods of preparing compounds of Formula (I), wherein $R^3$-$R^5$, $R^7$ and $R^9$ are hydrogen, and $R^6$ is hydrogen, hereby referred to as compound of formula 12a or $R^6$ is chloro, hereby referred to as compound of formula 14a, wherein $R^1$, $R^2$ and $R^8$ are as defined in Formula (I). Azaindole ketone 4 can be reacted with an appropriate alkylating agent such as LG-$R^{8'}$ under suitable conditions, wherein LG is a suitable leaving group, for example, mesylate, triflate or halo, such as chloro, bromo, or iodo, and wherein $R^{8'}$ is $R^8$ as defined in Formula (I), except hydrogen, to yield N-substituted azaindoles 15. Alternatively, azaindole ketone 4 can be reacted with a reagent such as Alk$^1$-OH under Mitsunobu type conditions, wherein Alk$^1$ represents an optionally substituted $C_{1-6}$alkyl or an optionally substituted $C_{2-6}$alkyl as in $R^8$ in Formula (I), to yield N-substituted azaindoles 15. Heating intermediate 4 or 15 with tert-butoxybis(dimethylamino)methane gives the corresponding aminopropenone 16 which, when reacted with guanidine, yields the corresponding aminopyrimidine 11a. The aryl bromide moiety in 11a can be reacted with alkynes under palladium-catalyzed Sonogashira coupling conditions, using for example Pd(PPh$_3$)$_4$, CuI and a base such as triethylamine in acetonitrile, with heating, to furnish final products such as 12a. Alternatively, the aminopyrimidine moiety in 11a can be treated with N-chlorosuccinimide to yield the corresponding chloropyrimidine in 13a. As above, the aryl bromide moiety in 13a can be reacted with alkynes under palladium-catalyzed Sonogashira coupling conditions, to furnish final products such as 14a. Aminopyrimidines 11a can also be treated with N-bromosuccinimide and N-iodosuccinimide, under the conditions used for carrying out the chlorination of Aminopyrimidines 11a to chloropyrimidines 13a, to yield the corresponding bromopyrimidine and iodopyrimidine intermediates. The bromopyrimidine and iodopyrimidine intermediates can be converted to final compounds of formula 14a, wherein chloro has been replaced with bromo or iodo, in the same way as described for compounds 14a from chloropyrimidines 13a.

Scheme 5

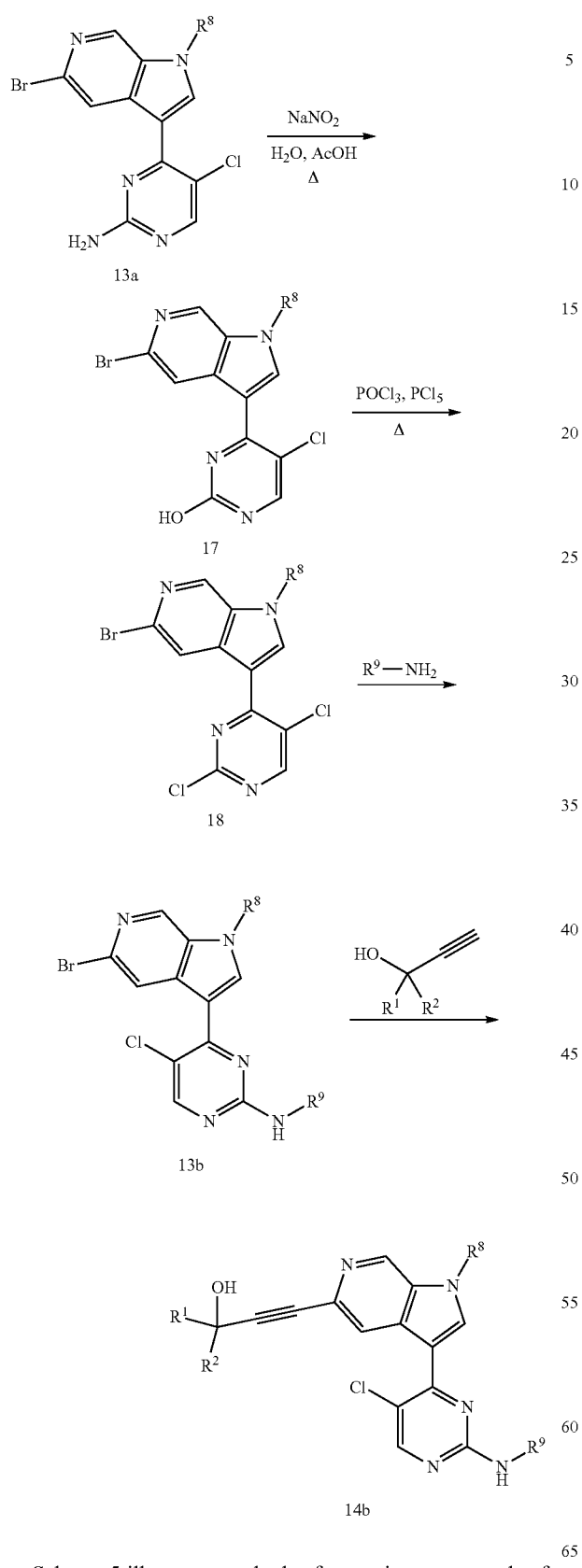

and $R^1$, $R^2$, $R^8$ and $R^9$ are as defined in Formula (I), hereby referred to as compound of formula 14b. Treatment of the aminopyrimidine moiety in 13a with sodium nitrite in acetic acid yields hydroxypyrimidine 17, which when treated with phosphorous oxychloride/phosphorus pentachloride, gives dichloropyrimidine 18. Dichloropyrimidine 18 can be reacted with appropriate amines under acid or base-catalysis, such as for instance N,N-diisopropylethylamine in N-methyl-2-pyrrolidone (NMP), or p-toluenesulfonic acid in dioxane under heating, to yield aminopyrimidines 13b. As above, the aryl bromide moiety in 13b can be reacted with alkynes under palladium-catalyzed Sonogashira coupling conditions, to furnish final products such as 14b.

Scheme 6

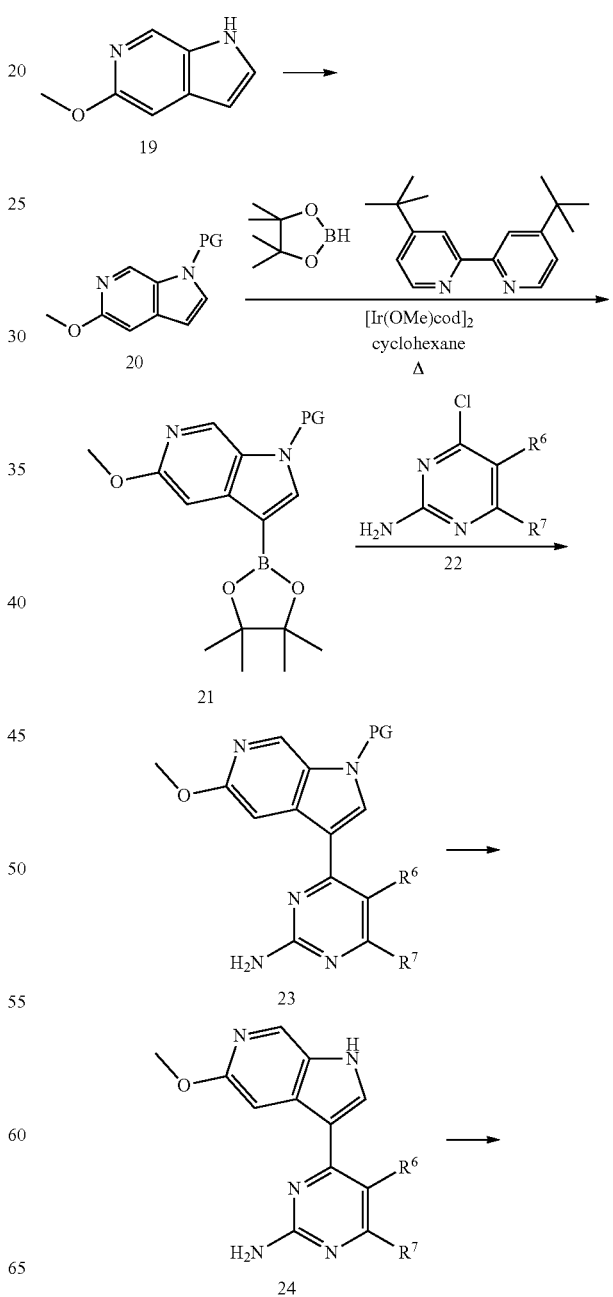

Scheme 5 illustrates methods of preparing compounds of Formula (I) wherein $R^3$-$R^5$ and $R^7$ are hydrogen, $R^6$ is chloro -continued

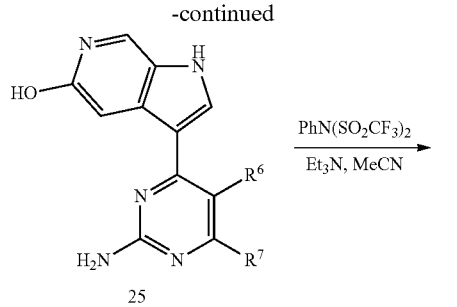
25

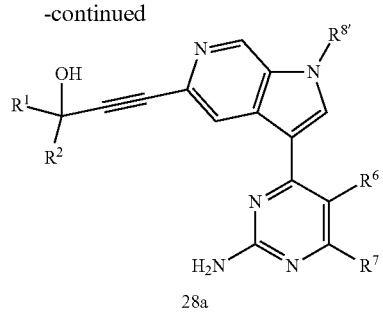
28a

Scheme 6 illustrates methods of preparing compounds of Formula (I) wherein $R^3$-$R^5$, and $R^9$ are hydrogen, and $R^1$, $R^2$, $R^6$ and $R^7$ are as defined in Formula (I), and $R^8$ are hydrogen or $R^{8'}$, hereby referred to as compounds of formula 28 or 28a, respectively, wherein $R^{8'}$ is $R^8$ as defined in Formula (I), except hydrogen. Protection of azaindole 19 by treatment for instance, with di-tert-butyl dicarbonate, yields azaindole 20, wherein PG is a suitable protecting group, such as a carbamate type, for example tert-butyl carbonate (Boc). The iridium-catalyzed C—H borylation of 20 (e.g. wherein [Ir(OMe)cod]$_2$ means (1,5-cyclooctadiene) (methoxy) iridium(I) dimer) yields boronate 21. Reaction of 21 with heteroaryl chlorides 22 under palladium-catalyzed conditions yields 23 which, after deprotection under suitable conditions, for instance by treatment with trifluoroacetic acid (TFA) when the protecting group is Boc, yields intermediates 24. Methyl ethers 24 can be converted to the corresponding hydroxyl intermediates 25 upon treatment with for example, aqueous hydrobromic acid in acetic acid under heating. The resulting hydroxyl functionality in 25 can then be reacted to form an appropriate leaving group, followed by Sonogashira coupling, with or without sequential protection/deprotection steps at the NH functionality of the azaindole. Advantageously, when 25 is treated with N-phenyl-bis(trifluoromethanesulfonimide), it can give bistriflates 26, which in turn can be reacted with alkynes under palladium-catalyzed Sonogashira conditions, to give alkynes 27. Finally, intermediates 27 can be treated with lithium hydroxide to furnish final products 28. Final products 28 can be further N-alkylated by treatment with an appropriate alkylating agent such as LG-$R^{8'}$ under suitable conditions, wherein LG is a suitable leaving group, for example, mesylate, triflate or halo, such as chloro, bromo, or iodo, to yield N-substituted azaindoles 28a. Alternatively, final products 28 can be reacted with a reagent such as Alk$^1$-OH under Mitsunobu type conditions, wherein Alk$^1$ represents an optionally substituted $C_{1-6}$alkyl or an optionally substituted $C_{2-6}$alkyl as in $R^8$ in Formula (I), to yield N-substituted azaindoles 28a.

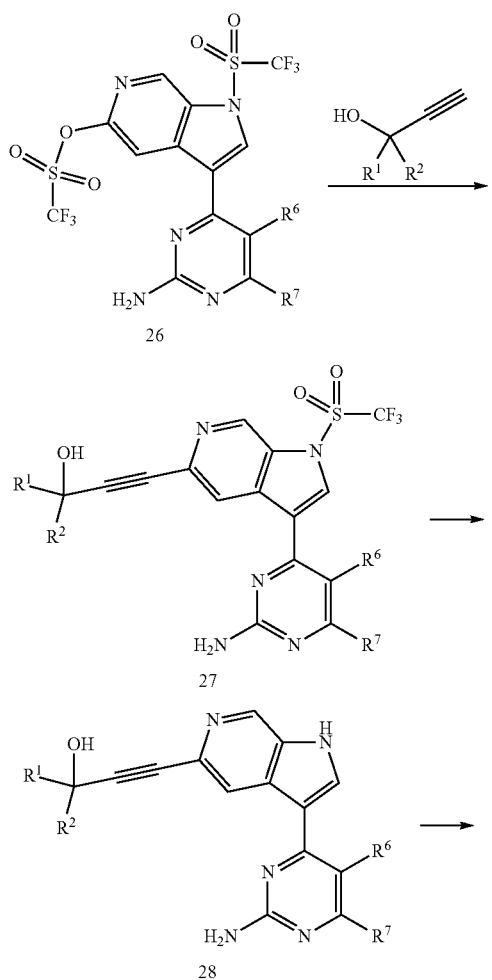

Scheme 7

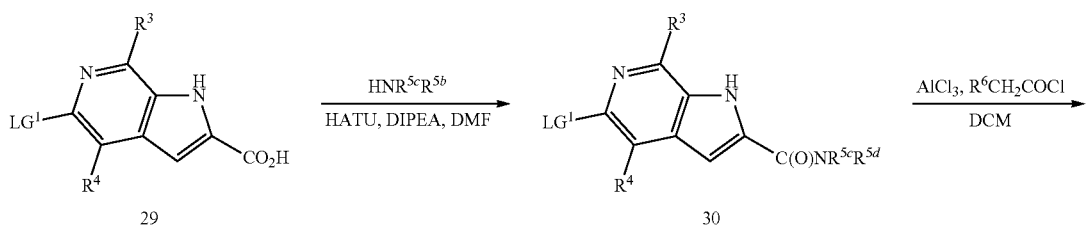

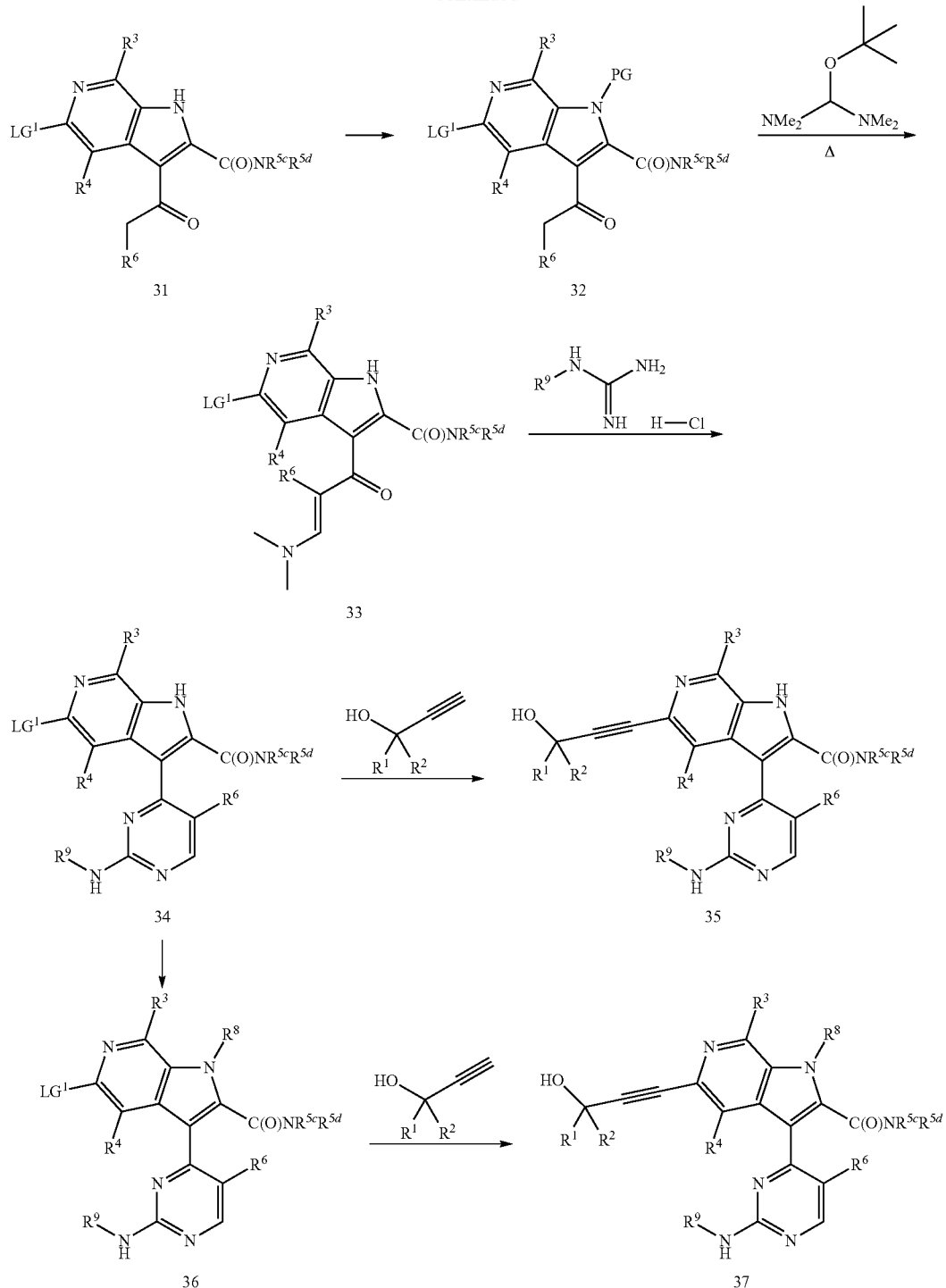

Scheme 7 illustrates methods of preparing compounds of Formula (I), wherein $R^1$-$R^4$, $R^{5c}$, $R^{5d}$, $R^6$ and $R^9$ are as defined in Formula (I), $R^7$ is hydrogen and $R^8$ is hydrogen, hereby represented by formula 35, or $R^8$ is as defined in Formula (I), hereby represented by formula 37. Azaindole 29, wherein $LG^1$ is a leaving group such as a suitable halide, can be reacted with an amine under standard coupling conditions, such as 1-[bis(dimethylamino)methylene]-1H-[1,2,3]triazolo[4,5-b]pyridin-1-ium 3-oxide hexafluorophosphate (HATU) in N,N-dimethylformamide (DMF) to give amide 30. Treatment of 30 with aluminium chloride and an acid chloride gives ketone 31, which can in turn be protected with a suitable group, such as tosyl for instance to give N-substituted azaindole 32. Heating intermediate 32 with tert-butoxybis(dimethylamino)methane gives aminopropenone 33 which, when reacted with a suitable guanidine in the presence of a base such as sodium methoxide in a protic solvent, such as n-butanol, with heating, yields aminopyrimidine 34. The aryl-LG$^1$ group in compound 34 can be reacted with alkynes under palladium-catalyzed Sonogashira coupling conditions, using for example Pd(PPh$_3$)$_4$, CuI and a base such as triethylamine in acetonitrile, with heating, to furnish final products such as 35. Alternatively, intermediate 34 can be further functionalised by treatment with a suitable electrophile under appropriate conditions, such as a C$_{1-6}$alkyl iodide in the presence of a suitable base in an appropriate solvent, to furnish 36. As above, the aryl-LG$^1$ moiety in 36 can be reacted with alkynes under palladium-catalyzed Sonogashira conditions, using for example tetrakis(triphenylphosphine)palladium (Pd(PPh$_3$)$_4$), CuI and a base such as triethylamine in acetonitrile, with heating, to furnish final products such as 37.

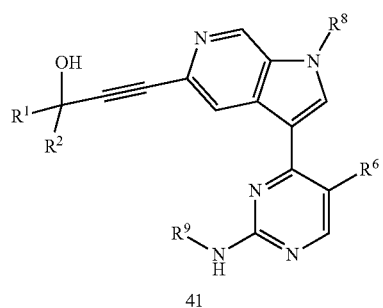

41

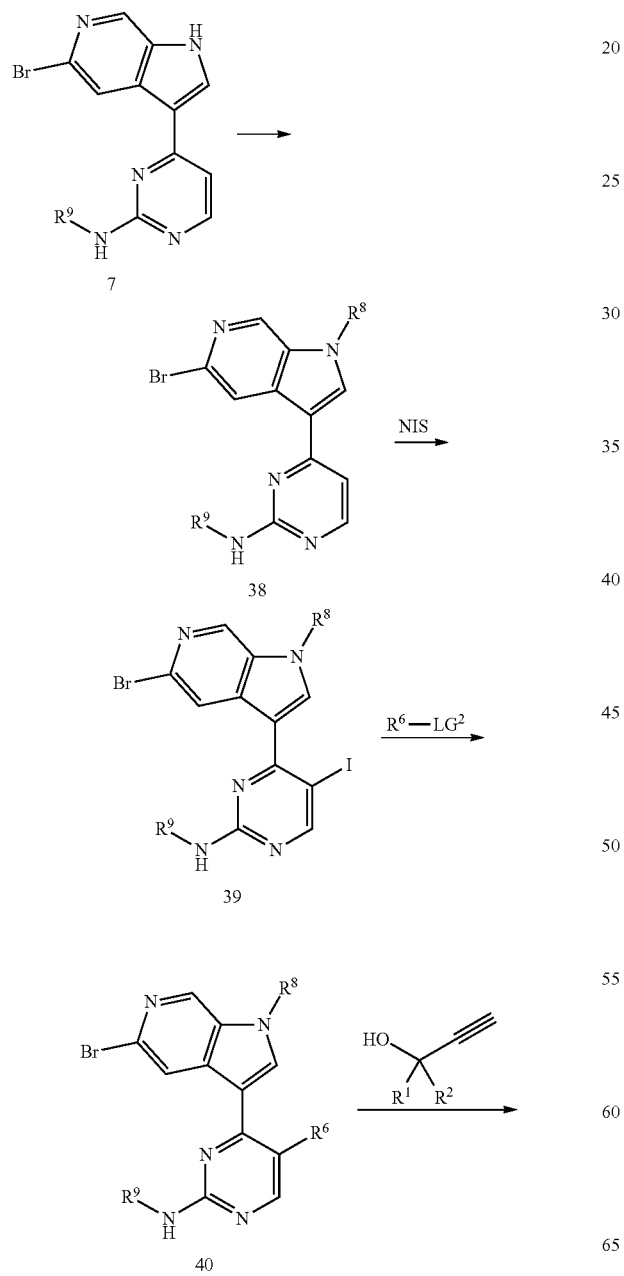

Scheme 8 illustrates methods of preparing compounds of Formula (I), wherein R$^3$-R$^5$ and R$^7$ are hydrogen and R$^1$, R$^2$, R$^6$, R$^8$ and R$^9$ are as defined in Formula (I), hereby represented by formula 41. Aminopyrimidines 7 can be N-functionalised with a suitable electrophile under appropriate conditions, such as using a C$_{1-6}$alkyl halide in the presence of a suitable base in an appropriate solvent, to furnish 38. Compound 38 can be treated with N-iodosuccinimide under appropriate conditions, such as in acetonitrile under heating, to yield iodopyrimidine 39. Compound 39 can be further functionalised by reacting with a suitable coupling partner R$^6$-LG$^2$, wherein LG$^2$ is a suitable leaving group, under appropriate conditions, such as using copper cyanide under palladium catalysis where R$^6$ is nitrile, to give substituted pyrimidine 40. The aryl bromide moiety in 40 can be reacted with alkynes under palladium-catalyzed Sonogashira coupling conditions, using for example Pd(PPh$_3$)$_4$, CuI and a base such as triethylamine in acetonitrile, with heating, to furnish final products such as 41.

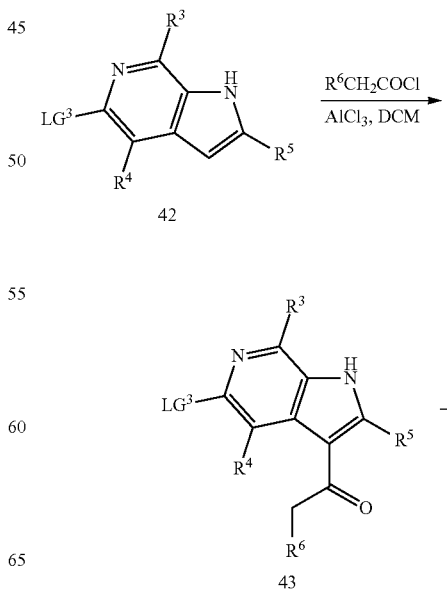

117
-continued

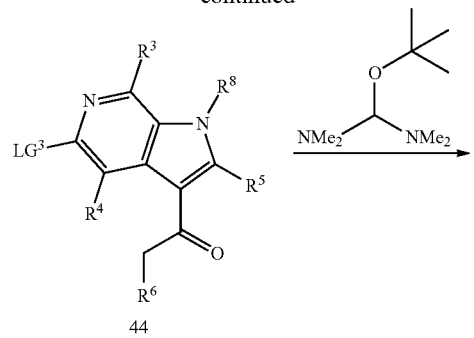

44

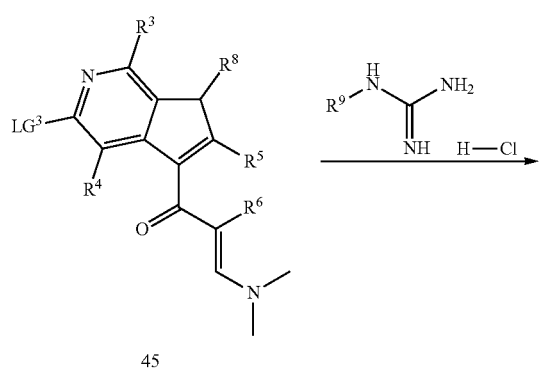

45

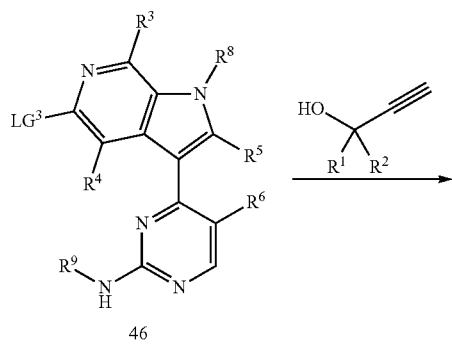

46

118
-continued

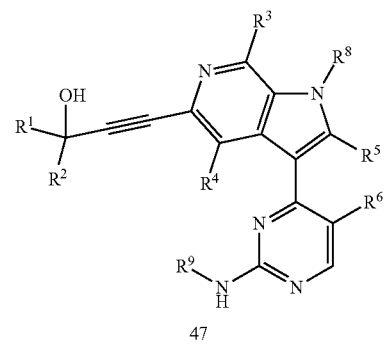

47

Scheme 9 illustrates methods of preparing compounds of Formula (I), wherein $R^7$ is hydrogen, $R^1$-$R^5$, $R^8$ and $R^9$ are as defined in Formula (I) and $R^6$ is selected from the group of hydrogen; cyano; $C_{1-6}$alkyl; $C_{1-6}$alkyl substituted with one or more fluoro substituents; $C_{1-6}$alkyl substituted with one —OH; $C_{1-6}$alkyl substituted with one $NH_2$; —$C_{1-6}$alkyloxy$C_{1-4}$alkyl; —$C_{1-6}$alkyl-C(=O)—$NR^{6a}R^{6b}$; and —C(=O)—$NR^{6a}R^{6b}$ as defined in Formula (I), hereby represented by compounds of formula 47. Treatment of azaindole 42, wherein $LG^3$ is a leaving group such as a suitable halide, with aluminum chloride and an acid chloride gives ketone 43, which, in turn, can be further N-functionalised by reaction with a suitable electrophile under appropriate conditions, such as using a $C_{1-6}$alkylhalide in the presence of a suitable base in an appropriate solvent, to furnish 44. Heating intermediate 44 with tert-butoxybis(dimethylamino)methane gives aminopropenone 45 which, when reacted with a suitable guanidine in the presence of a base such as sodium methoxide in a protic solvent, such as n-butanol, with heating, yields aminopyrimidine 46. The aryl-$LG^3$ moiety in aminopyrimidine 46 can be reacted with alkynes under palladium-catalyzed Sonogashira coupling conditions, using for example Pd(PPh$_3$)$_4$, CuI and a base such as triethylamine in acetonitrile, with heating, to furnish final products such as 47.

Scheme 10

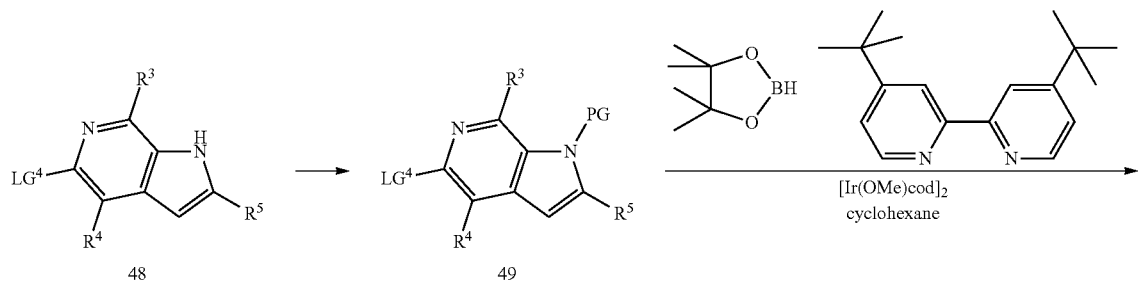

48　　49

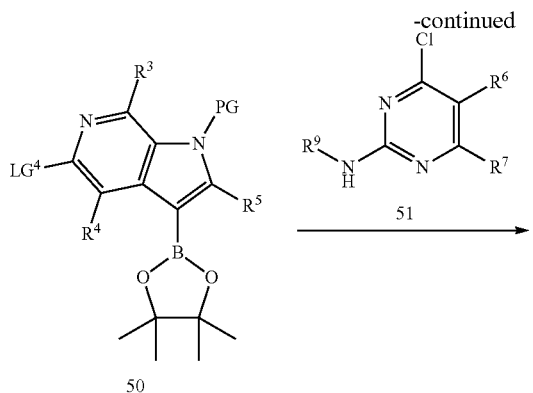
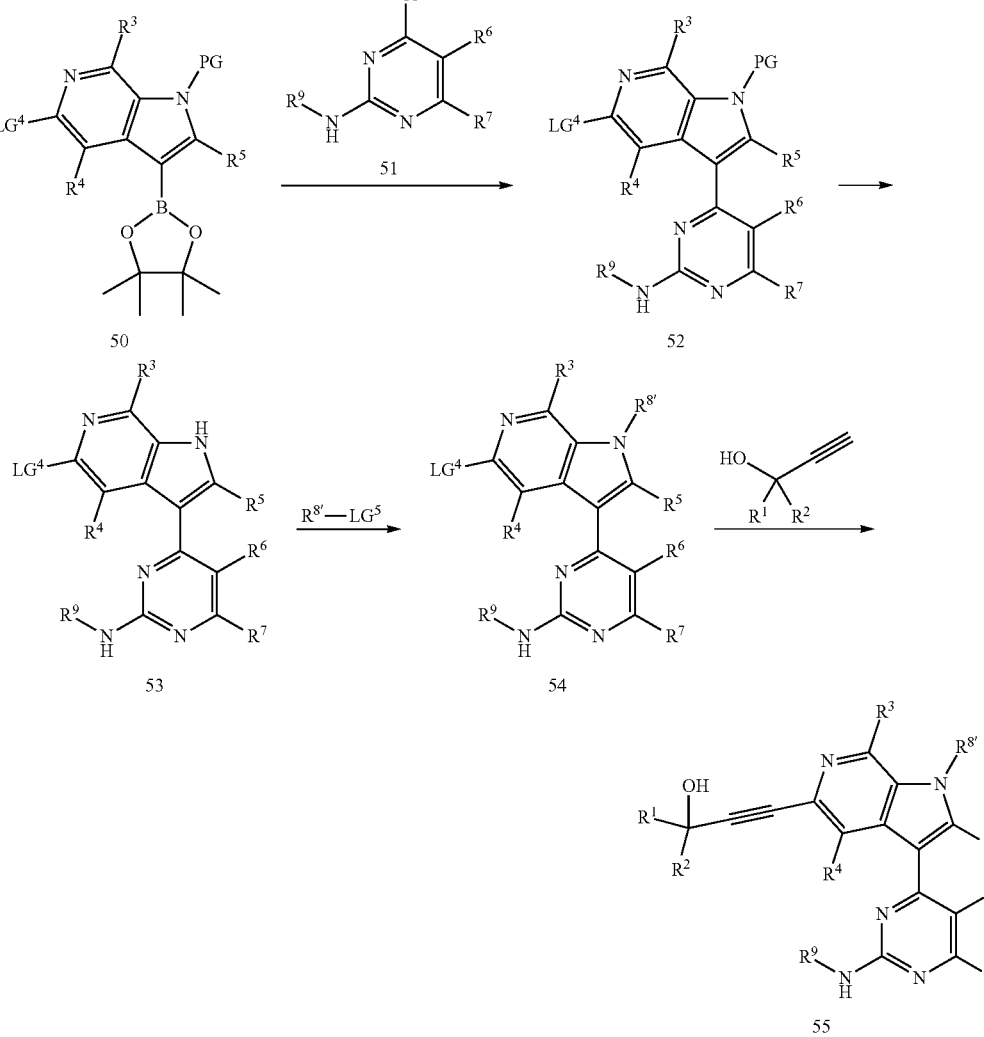

Scheme 10 illustrates methods of preparing compounds of Formula (I) wherein $R^1$-$R^7$ and $R^9$ are as defined in Formula (I), and wherein $R^{8'}$ is as defined before; hereby referred to as compounds of formula 55. Protection of azaindole 48, wherein $LG^4$ is a leaving group such as a suitable halogen, by treatment for instance, with di-tert-butyl dicarbonate, yields azaindole 49, wherein PG is a suitable protecting group, such as a carbamate type, for example tert-butyl carbonate (Boc). The iridium-catalyzed C—H borylation of 49 (e.g. wherein [Ir(OMe)cod]$_2$ means (1,5-cyclooctadiene)(methoxy) iridium(I) dimer) yields boronate 50. Reaction of 50 with heteroaryl chlorides 51 under palladium-catalyzed conditions yields 52 which, after deprotection under suitable conditions, for instance by treatment with TFA when the protecting group is Boc, yields intermediate 53. Intermediate 53 can be N-functionalised by treatment with a suitable electrophile, such as $LG^5$-$R^{8'}$ under suitable conditions, wherein $LG^5$ is a suitable leaving group, for example, mesylate, triflate or halogen, to yield N-substituted azaindoles 54. Alternatively, intermediate 53 can be reacted with a reagent such as Alk$^1$-OH under Mitsunobu type conditions, wherein Alk$^1$ represents $C_{1-6}$alkyl or $C_{2-6}$alkyl optionally substituted as in $R^8$ in Formula (I), to yield N-substituted azaindoles 54. The aryl-$LG^4$ moiety in aminopyrimidine 54 can be reacted with alkynes under palladium-catalyzed Sonogashira coupling conditions, using for example Pd(PPh$_3$)$_4$, CuI and a base such as triethylamine in acetonitrile, with heating, to furnish final products such as 55.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from commercially available starting materials using the general methods illustrated herein.

Pharmacology

It has been found that the compounds of the present invention inhibit NF-κB-inducing kinase (NIK—also known as MAP3K14). The compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Hence, the invention relates to compounds of Formula (I), the tautomers and the stereoisomeric forms thereof, and the pharmaceutically acceptable salts and the solvates thereof, for use as a medicament.

The invention also relates to the use of a compound of Formula (I), a tautomer or a stereoisomeric form thereof or a pharmaceutically acceptable salt or a solvate thereof, or a pharmaceutical composition according to the invention for the manufacture of a medicament.

The present invention also relates to a compound of Formula (I), a tautomer or a stereoisomeric form thereof or a pharmaceutically acceptable salt or a solvate thereof, or a pharmaceutical composition according to the invention for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase. Also, the present invention relates to the use of a compound of Formula (I), a tautomer or a stereoisomeric form thereof or a pharmaceutically acceptable salt or a solvate thereof, or a pharmaceutical composition according to the invention for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof or a pharmaceutically acceptable salt or a solvate thereof, for use in the treatment or prevention of any one of the diseases mentioned hereinbefore.

The invention also relates to a compound of Formula (I), a tautomer or a stereoisomeric form thereof or a pharmaceutically acceptable salt or a solvate thereof, for use in treating or preventing any one of the diseases mentioned hereinbefore.

The invention also relates to the use of a compound of Formula (I), a tautomer or a stereoisomeric form thereof or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof or a pharmaceutically acceptable salt or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof or a pharmaceutically acceptable salt or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of formula (I), a tautomer or a stereoisomeric form thereof or a pharmaceutically acceptable salt or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoïden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, quisinostat, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat;
- Recombinant interleukins for example aldesleukin, denileukin diftitox, interferon alfa 2a, interferon alfa 2b, peginterferon alfa 2b;
- MAPK inhibitors;
- Retinoids for example alitretinoin, bexarotene, tretinoin;
- Arsenic trioxide;
- Asparaginase;
- Steroids for example dromostanolone propionate, megestrol acetate, nandrolone (decanoate, phenpropionate), dexamethasone;
- Gonadotropin releasing hormone agonists or antagonists for example abarelix, goserelin acetate, histrelin acetate, leuprolide acetate;
- Thalidomide, lenalidomide;
- Mercaptopurine, mitotane, pamidronate, pegademase, pegaspargase, rasburicase;
- BH3 mimetics for example ABT-737;
- MEK inhibitors for example PD98059, AZD6244, CI-1040;
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;
- a steroidal cytochrome P450 17alpha-hydroxylase-17,20-lyase inhibitor (CYP17), e.g. abiraterone, abiraterone acetate.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. Unless otherwise noted, all starting materials were obtained from commercial suppliers and used without further purification.

Herein, the term 'Ac' means acetyl, 'Me' means methyl, 'DIPEA' means diisopropylethylamine, 'HPLC' means High Performance Liquid Chromatography, 'DCM' means dichloromethane, 'DMF' means N,N-dimethylformamide, 'DMSO' means dimethylsulfoxide, 'Et$_2$O' means diethyl ether, 'EtOAc' means ethyl acetate, 'HATU' means 1-[bis(dimethylamino)methylene]-1H-[1,2,3]triazolo[4,5-b]pyridin-1-ium 3-oxide hexafluorophosphate, 'HPLC' means high performance liquid chromatography, 'LCMS' means liquid chromatography/mass spectrometry, 'MeOH' means methanol, 'MTBE' means methyl tert-butyl ether, 'NMP' means N-methyl-2-pyrrolidone, 'Rt' means retention time, 'TLC' means thin layer chromatography, 'RT' means room temperature, 'SCX-2' means an ISOLUTE® silica propylsulfonic acid strong cation exchanger (SCX) column and 'SFC' means supercritical fluid chromatography.

When in the Examples below, intermediates or compounds were prepared according to the reaction protocol of a fully described Example, this means that the intermediate or compound was prepared by an analogous reaction protocol (but not necessarily identical) as the Example referred to.

Preparation of Intermediates

Example A1 a) Preparation of Intermediate 1

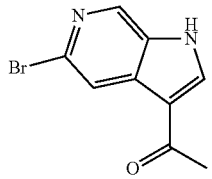

A stirred mixture of 5-bromo-1H-pyrrolo[2,3-c]pyridine (2.00 g, 10.2 mmol) in anhydrous DCM (65 ml) at ambient temperature was treated portionwise with aluminium chloride (2.70 g, 20.3 mmol). After stirring for 15 minutes, the mixture was treated dropwise with acetyl chloride (1.44 ml, 20.3 mmol) and the resulting mixture was stirred at ambient temperature for 24 hours. The mixture was treated cautiously with MeOH until no further effervescence was observed. The mixture was then concentrated in vacuo and the residue partitioned between 2.0 M aqueous sodium hydroxide and EtOAc. The organic phase was washed with brine, dried over sodium sulfate and concentrated in vacuo. The residue was triturated with Et$_2$O to afford the desired product (2.12 g, 87%).

LCMS (Method B): R$_t$=2.29 min, m/z [M+H]$^+$=239/241 b) Preparation of Intermediate 2

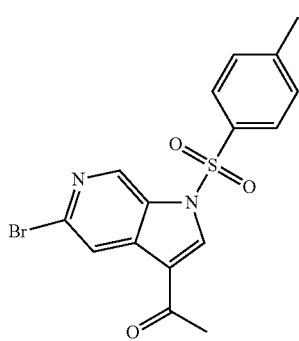 [SMILES: CC(=O)c1cn(S(=O)(=O)c2ccc(C)cc2)c2cnc(Br)cc12]

A stirred mixture of intermediate 1 (2.12 g, 8.87 mmol), 4-methylbenzenesulfonyl chloride (1.86 g, 9.76 mmol), N,N-diisopropylethylamine (3.08 ml, 17.7 mmol) and anhydrous DCM (20 ml) at ambient temperature was treated with 4-dimethylaminopyridine (0.01 g, 0.09 mmol). The resulting mixture was stirred for 3 hours and then concentrated in vacuo. The residue was purified by column chromatography on silica gel, eluting with a mixture of MeOH and DCM (0:1 to 1:99 by volume), to afford the desired product (3.14 g, 90%).

LCMS (Method C): R$_t$=3.91 min, m/z [M+H]$^+$=393/395

Example A2 a) Preparation of Intermediate 3

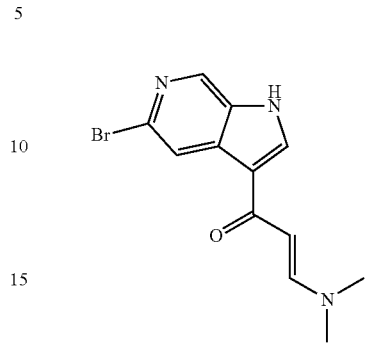

A stirred mixture of intermediate 2 (0.98 g, 2.50 mmol) and tert-butoxy bis(dimethylamino)methane (1.03 ml, 5.0 mmol) was heated at 100° C. for 2.5 hour. The mixture was cooled to ambient temperature and stood for 18 hours. A second aliquot of tert-butoxy bis(dimethylamino)methane (0.52 ml, 2.50 mmol) was added and the mixture was heated at 100° C. for 2.5 hours. The mixture was cooled to ambient temperature and concentrated in vacuo to afford the desired product as a brown semi-solid (1.40 g).

LCMS (Method D): R$_t$=2.04 min, m/z [M+H]$^+$=294/296 b) Preparation of Intermediate 4

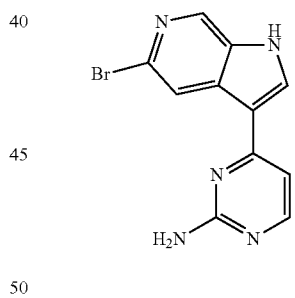

A stirred mixture of guanidine hydrochloride (2.38 g, 25.0 mmol) and 1-butanol (9.0 ml) under a nitrogen atmosphere at ambient temperature was treated portionwise with sodium methoxide (1.35 g, 25.0 mmol). After stirring for 30 minutes, a slurry of intermediate 3 (1.40 g, 4.75 mmol) in 1-butanol (8.0 ml) was added and the resulting mixture heated at 100° C. for 18 hours. The mixture was cooled to ambient temperature and concentrated in vacuo. The residue was diluted with water and extracted with a mixture of EtOAc and MeOH (9:1 by volume). The combined extracts were dried over sodium sulfate and concentrated in vacuo. The residue was triturated with Et$_2$O to afford the desired product as a fawn solid (0.47 g, 64% over two steps).

LCMS (Method D): R$_t$=1.51 min, m/z [M+H]$^+$=290/292 c) Preparation of Intermediate 5

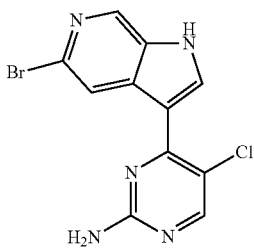 [SMILES: Nc1ncc(Cl)c(-c2c[nH]c3cnc(Br)cc23)n1]

A solution of intermediate 4 (0.47 g, 1.62 mmol) and N-chlorosuccinimide (0.22 g, 1.62 mmol) in acetonitrile (10 ml) was stirred at 85° C. for 5 hours. The mixture was cooled to 0° C. and the resulting precipitate collected by filtration to afford the desired product as a colourless solid (0.24 g, 46%).

LCMS (Method C): $R_t$=2.58 min, m/z [M+H]$^+$=324/326

Example A3 a) Preparation of Intermediate 6

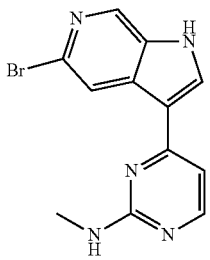 [SMILES: CNc1nccc(-c2c[nH]c3cnc(Br)cc23)n1]

A stirred mixture of N-methylguanidine hydrochloride (1.99 g, 18.2 mmol) and 1-butanol (8.0 ml) under a nitrogen atmosphere at ambient temperature was treated with sodium methoxide (0.98 g, 18.2 mmol). After stirring for 30 minutes, the mixture was treated with a slurry of intermediate 3 (1.05 g, 3.57 mmol) in 1-butanol (3.0 ml) and the resulting mixture heated at 100° C. for 16 hours. The mixture was cooled to ambient temperature and concentrated in vacuo. The residue was diluted with water and extracted sequentially with EtOAc and a mixture of EtOAc and MeOH (9:1 by volume). The combined extracts were dried over sodium sulfate and concentrated in vacuo. The residue was purified by column chromatography on silica gel, eluting with a mixture of MeOH and EtOAc (0:1 to 1:9 by volume), followed by trituration with Et$_2$O to afford the desired product (0.12 g, 22%).

LCMS (Method C): $R_t$=1.88 min, m/z [M+H]$^+$=304/306

Example A4 a) Preparation of Intermediate 7

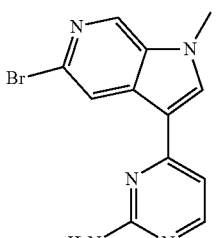

A mixture of intermediate 4 (0.11 g, 0.38 mmol), methyl iodide (0.03 ml, 0.42 mmol), potassium carbonate (0.10 g, 0.76 mmol) and DMF (2.0 ml) was heated by microwave irradiation at 100° C. for 1 hour. The mixture was cooled to ambient temperature, filtered and the filtrate concentrated in vacuo to afford the desired product (0.12 g, 100%).

LCMS (Method D): $R_t$=1.67 min, m/z [M+H]$^+$=304/306

Intermediates 8 to 15, 25 to 32, and 162 to 165 were prepared according to the reaction protocol of example A4 using the appropriate starting materials (Table 1).

TABLE 1

| Intermediate | Structure | Starting Materials | LCMS Data |
| --- | --- | --- | --- |
| 8 | 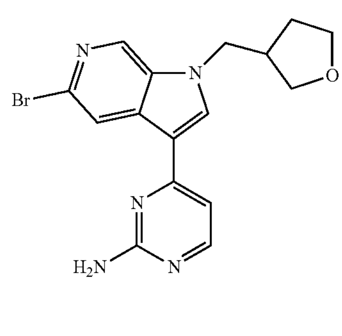 [SMILES: Nc1nccc(-c2cn(CC3CCOC3)c3cnc(Br)cc23)n1] | a) Intermediate 4<br>b) 3-Bromomethyl-tetrahydrofuran | Rt = 2.13 min, m/z [M + H]$^+$ = 374/376 (Method D) |

TABLE 1-continued

| Intermediate | Structure | Starting Materials | LCMS Data |
|---|---|---|---|
| 9 | 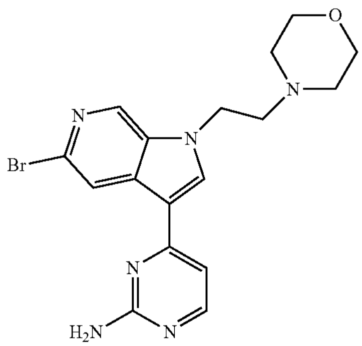 [SMILES: Nc1nccc(-c2cn(CCN3CCOCC3)c3cnc(Br)cc23)n1] | a) Intermediate 4<br>b) 4-(2-Chloroethyl)-morpholine hydrochloride | Rt = 2.07 min, m/z [M + H]$^+$ = 403/405 (Method D) |
| 10 | 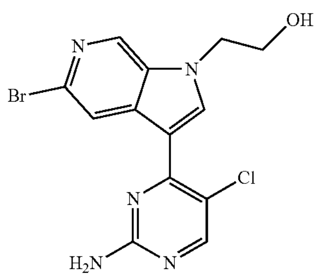 [SMILES: Nc1ncc(Cl)c(-c2cn(CCO)c3cnc(Br)cc23)n1] | a) Intermediate 5<br>b) 2-Bromoethanol | Rt = 2.17 min, m/z [M + H]$^+$ = 368/370 (Method D) |
| 11 | 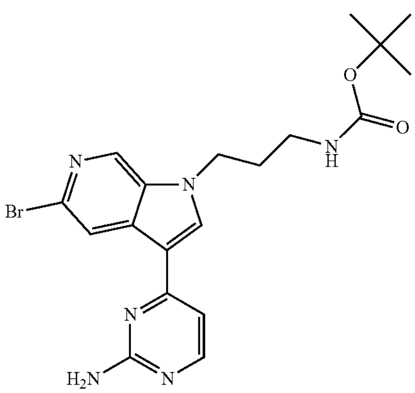 [SMILES: CC(C)(C)OC(=O)NCCCn1cc(-c2ccnc(N)n2)c2cc(Br)ncc21] | a) Intermediate 4<br>b) (3-Bromopropyl)carbamic acid tert-butyl ester | Rt = 1.32 min, m/z [M + H]$^+$ = 447/449 (Method C) |
| 12 | 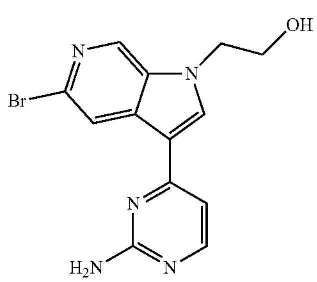 [SMILES: Nc1nccc(-c2cn(CCO)c3cnc(Br)cc23)n1] | a) Intermediate 4<br>b) 2-Bromoethanol | Rt = 1.67 min, m/z [M + H]$^+$ = 334/336 (Method B) |
| 13 | 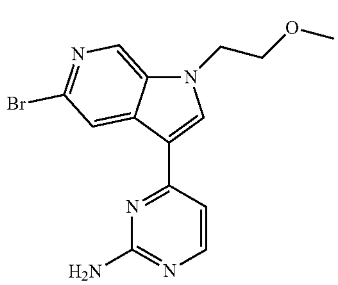 [SMILES: COCCn1cc(-c2ccnc(N)n2)c2cc(Br)ncc21] | a) Intermediate 4<br>b) 2-Bromoethyl methyl ether | Rt = 1.83 min, m/z [M + H]$^+$ = 348/350 (Method B) |

TABLE 1-continued

| Intermediate | Structure | Starting Materials | LCMS Data |
|---|---|---|---|
| 14 | 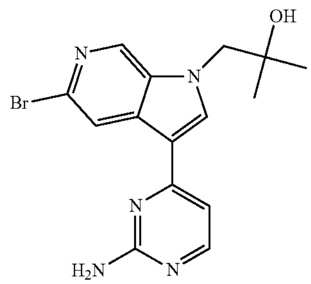 [SMILES: CC(C)(O)Cn1cc(-c2ccnc(N)n2)c2cc(Br)ncc21] | a) Intermediate 4<br>b) 2,2-Dimethyl-oxirane | Rt = 1.70 min, m/z<br>[M + H]⁺ = 362/364<br>(Method D) |
| 15 | 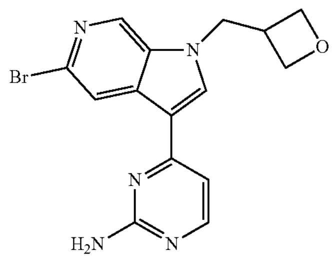 [SMILES: Nc1nccc(-c2cn(CC3COC3)c3cnc(Br)cc23)n1] | a) Intermediate 4<br>b) Toluene-4-sulfonic acid oxetan-3-yl methyl ester | Rt = 1.85 min, m/z<br>[M + H]⁺ = 360/362<br>(Method A) |
| 25 | 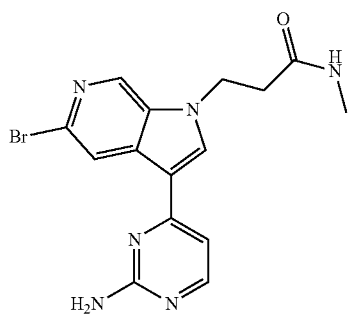 [SMILES: CNC(=O)CCn1cc(-c2ccnc(N)n2)c2cc(Br)ncc21] | a) Intermediate 4<br>b) 3-Chloro(N-methyl)-propanamide | Rt = 1.73 min, m/z<br>[M + H]⁺ = 375/377<br>(Method C) |
| 26 | 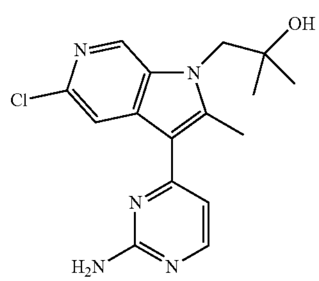 [SMILES: Cc1c(-c2ccnc(N)n2)c2cc(Cl)ncc2n1CC(C)(C)O] | a) Intermediate 123<br>b) 2,2-Dimethyl-oxirane | Rt = 1.85 min, m/z<br>[M + H]⁺ = 332/334<br>(Method C) |
| 27 | 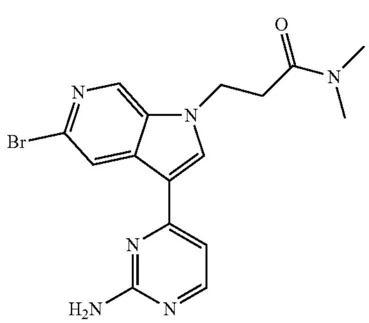 [SMILES: CN(C)C(=O)CCn1cc(-c2ccnc(N)n2)c2cc(Br)ncc21] | a) Intermediate 4<br>b) 3-Chloro(N,N-dimethyl)propanamide | Rt = 1.85 min, m/z<br>[M + H]⁺ = 389/391<br>(Method C) |

TABLE 1-continued

| Intermediate | Structure | Starting Materials | LCMS Data |
| --- | --- | --- | --- |
| 28 | 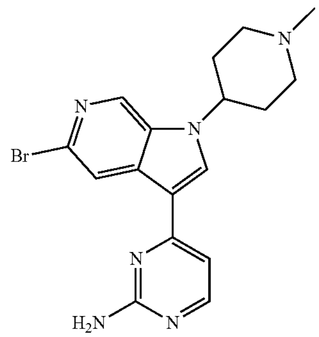 [SMILES: CN1CCC(n2cc(-c3ccnc(N)n3)c3cc(Br)ncc32)CC1] | a) Intermediate 119<br>b) Methyl iodide | Rt = 0.34 min, m/z<br>[M + H]$^+$ = 387/389<br>(Method C) |
| 29 | 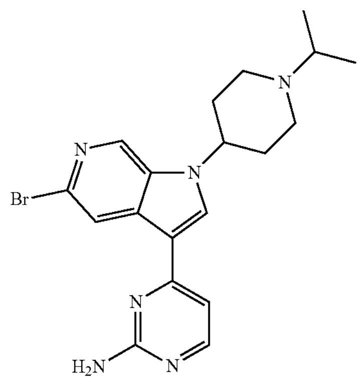 [SMILES: CC(C)N1CCC(n2cc(-c3ccnc(N)n3)c3cc(Br)ncc32)CC1] | a) Intermediate 119<br>b) 2-Iodopropane | Rt = 1.57 min, m/z<br>[M + H]$^+$ = 415/417<br>(Method C) |
| 30 | 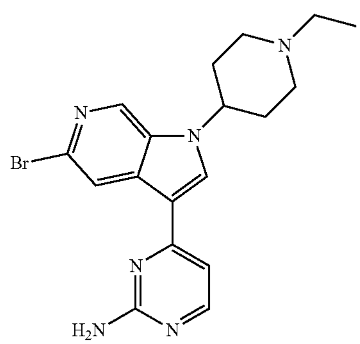 [SMILES: CCN1CCC(n2cc(-c3ccnc(N)n3)c3cc(Br)ncc32)CC1] | a) Intermediate 119<br>b) Ethyl iodide | Rt = 1.62 min, m/z<br>[M + H]$^+$ = 401/403<br>(Method B) |
| 31 | 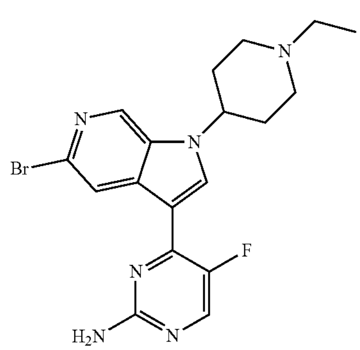 [SMILES: CCN1CCC(n2cc(-c3nc(N)ncc3F)c3cc(Br)ncc32)CC1] | a) Intermediate 120<br>b) Ethyl iodide | Rt = 1.60 min, m/z<br>[M + H]$^+$ = 419/421<br>(Method C) |

TABLE 1-continued
| Intermediate | Structure | Starting Materials | LCMS Data |
| --- | --- | --- | --- |
| 32 | 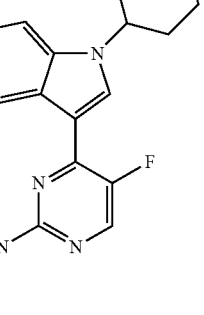 | a) Intermediate 120<br>b) 1-Bromo-2-methoxy-ethane | Rt = 1.83 min, m/z [M + H]$^+$ = 449/451 (Method C) |
| 162 | 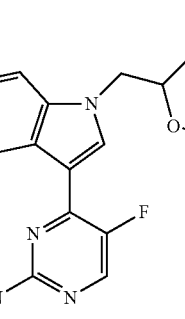 | a) Intermediate 161<br>b) Ethyl iodide | Rt = 1.86 min, m/z [M + H]$^+$ = 435/437 (Method C) |
| 163 | 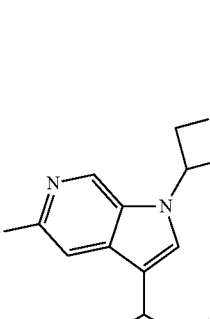 | a) Intermediate 121<br>b) Ethyl iodide | Rt = 1.74 min, m/z [M + H]$^+$ = 391/393 (Method C) |
| 164 | 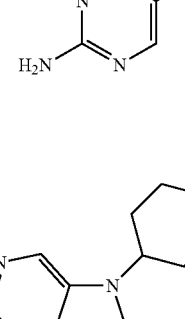 | a) Intermediate 171<br>b) Ethyl iodide | Rt = 1.89 min, m/z [M + H]$^+$ = 419/421 (Method C) |

//141//

TABLE 1-continued

| Intermediate | Structure | Starting Materials | LCMS Data |
|---|---|---|---|
| 165 | 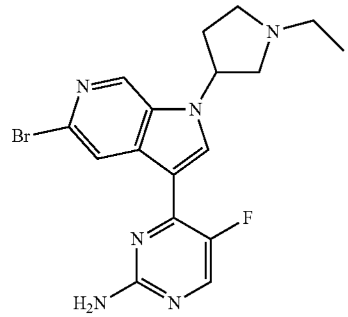 [SMILES: CCN1CCC(n2cc(-c3nc(N)ncc3F)c3cc(Br)ncc32)C1] | a) Intermediate 128<br>b) Ethyl iodide | Rt = 1.80 min, m/z<br>[M + H]⁺ = 405/407<br>(Method C) |

Example A5 a) Preparation of Intermediate 16

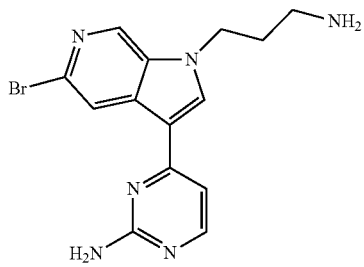 [SMILES: NCCCn1cc(-c2ccnc(N)n2)c2cc(Br)ncc21]

A stirred solution of intermediate 11 (0.17 g, 0.50 mmol) in DCM (3.0 ml) under a nitrogen atmosphere at ambient temperature was treated with trifluoroacetic acid (0.39 ml, 5.0 mmol), and the resulting mixture stirred for 2 hours. The mixture was concentrated in vacuo and the residue purified by ISOLUTE® SCX-2 SPE column, eluting with a mixture of MeOH and 2.0 M ammonia solution in MeOH (1:0 to 0:1 by volume), to afford the desired product as a pale yellow solid (0.13 g, 96%).

LCMS (Method C): $R_t$=1.32 min, m/z [M+H]⁺=347/349

Example A6 a) Preparation of Intermediate 17

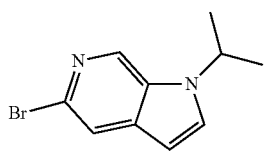

A stirred solution of 5-bromo-1H-pyrrolo[2,3-c]pyridine (2.0 g, 10.2 mmol) in anhydrous DMF (80 ml) under a nitrogen atmosphere at ambient temperature was treated portionwise with sodium hydride (0.49 g, 12.2 mmol, 60% in mineral oil). After stirring for 20 minutes, 2-iodopropane (1.1 ml, 11.2 mmol) was added dropwise and the resulting mixture stirred for 18 hours. The mixture was concentrated in vacuo and the residue partitioned between water and EtOAc. The organic phase was washed with brine, dried over sodium sulfate and concentrated in vacuo. The residue was purified by column chromatography on silica gel, eluting with a mixture of EtOAc and pentane (1:9 to 1:1 by volume), to afford the desired product as a brown oil (1.87 g, 77%).

LCMS (Method C): $R_t$=3.19 min, m/z [M+H]⁺=239/241 b) Preparation of Intermediate 18

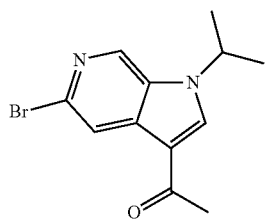 [SMILES: CC(=O)c1cn(C(C)C)c2cnc(Br)cc12]

A stirred mixture of intermediate 17 (1.87 g, 7.81 mmol), aluminium chloride (2.08 g, 15.6 mmol) and anhydrous DCM (40 ml) at ambient temperature was treated dropwise with acetyl chloride (1.1 ml, 15.6 mmol), and the resulting mixture stirred for 4 hours. The mixture was treated sequentially with MeOH (2.0 ml), aqueous ammonium hydroxide (10 ml) and water. The separated aqueous phase was extracted with DCM and the combined organic phases were dried over sodium sulfate and concentrated in vacuo. The residue was purified by column chromatography on silica gel, eluting with a mixture of EtOAc and pentane (1:9 to 1:0 by volume), to afford the desired product as a pale yellow solid (1.67 g, 76%).

LCMS (Method B): $R_t$=2.88 min, m/z [M+H]⁺=281/283 c) Preparation of Intermediate 19

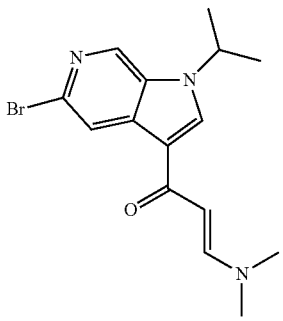 [SMILES: CC(C)n1cc(C(=O)/C=C/N(C)C)c2cc(Br)ncc21]

A mixture of intermediate 18 (1.66 g, 5.92 mmol) and tert-butoxy bis(dimethylamino)methane (2.44 ml, 11.8 mmol) was stirred at 100° C. for 30 minutes. The mixture was cooled to ambient temperature and concentrated in vacuo to afford the desired product as a pale yellow solid (1.99 g, 100%).

LCMS (Method C): $R_t$=2.80 min, m/z [M+H]$^+$=336/338 d) Preparation of Intermediate 20

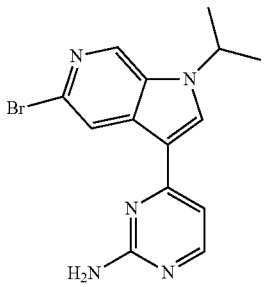 [SMILES: CC(C)n1cc(-c2ccnc(N)n2)c2cc(Br)ncc21]

A stirred mixture of guanidine hydrochloride (5.65 g, 59.2 mmol) and 1-butanol (40 ml) under a nitrogen atmosphere at 0° C. was treated portionwise with sodium methoxide (3.20 g, 59.2 mmol). After stirring for 30 minutes, intermediate 19 (1.99 g, 5.92 mmol) was added and the resulting mixture heated at 100° C. for 18 hours. The mixture was cooled to ambient temperature and concentrated in vacuo. The residue was partitioned between water and EtOAc. The organic phase was washed with brine, dried over sodium sulfate and concentrated in vacuo. The residue was triturated with Et$_2$O to afford the desired product as a colourless solid (1.77 g, 90%).

LCMS (Method C): $R_t$=2.04 min, m/z [M+H]$^+$=332/334 e) Preparation of Intermediate 21

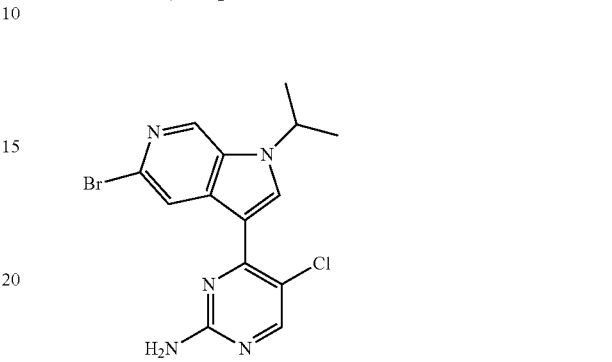

A mixture of intermediate 20 (0.50 g, 1.45 mmol), N-chlorosuccinimide (0.19 g, 1.45 mmol) and acetonitrile (10 ml) under a nitrogen atmosphere was stirred at 85° C. for 3.5 hours. The mixture was cooled to 0° C. and the resulting precipitate collected by filtration. The filtrate was concentrated in vacuo and the residue purified by column chromatography on silica gel, eluting with a mixture of EtOAc and DCM (1:4 by volume). The fractions containing the desired product were combined with the solid recovered by filtration and the mixture was concentrated in vacuo. Purification of the residue by trituration with Et$_2$O, followed by column chromatography on silica gel, eluting with a mixture of EtOAc and DCM (1:9 to 1:4 by volume), afforded the desired product as an off-white solid containing traces of succinimide. The solid was dissolved in EtOAc, washed with saturated aqueous sodium carbonate solution and dried over sodium sulfate. The solvent was removed in vacuo to afford the desired product as an off-white solid (0.42 g, 79%).

LCMS (Method B): $R_t$=3.17 min, m/z [M+H]$^+$=366/368

Intermediates 22 to 24 were prepared according to the reaction protocol of intermediate 21 using the appropriate starting material (Table 2).

TABLE 2

| Intermediate | Structure | Starting Material | Analytical Data |
|---|---|---|---|
| 22 | ![structure] | Intermediate 14 | $^1$H NMR (300 MHz, DMSO-d$_6$) δ ppm: 8.85 (d, J = 0.9 Hz, 1H), 8.68-8.67 (m, 2H), 8.26 (s, 1H), 6.93 (s, 2H), 4.83 (s, 1H), 4.31 (s, 2H), 1.12 (s, 6H). |

TABLE 2-continued

| Intermediate | Structure | Starting Material | Analytical Data |
|---|---|---|---|
| 23 | 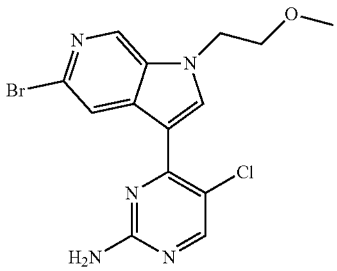 [SMILES: COCCn1cc(-c2nc(N)ncc2Cl)c2cc(Br)ncc21] | Intermediate 13 | LCMS (Method B): Rt = 2.83 min, m/z [M + H]$^+$ = 382/384 |
| 24 | 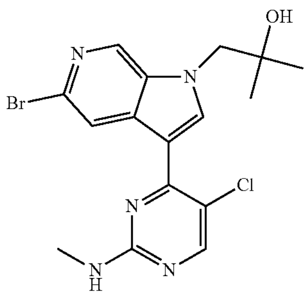 [SMILES: CNc1ncc(Cl)c(-c2cn(CC(C)(C)O)c3cnc(Br)cc23)n1] | Intermediate 90 | LCMS (Method C): Rt = 3.10 min, m/z [M + H]$^+$ = 410/412/414 |

Example A7 a) Preparation of Intermediate 33

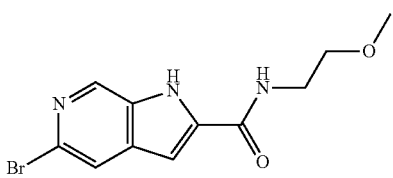 [SMILES: COCCNC(=O)c1cc2cc(Br)ncc2[nH]1]

A stirred mixture of 5-bromo-1H-pyrrolo[2,3-c]pyridine-2-carboxylic acid (0.50 g, 2.07 mmol), HATU (0.94 g, 2.48 mmol), DIPEA (0.79 ml, 4.55 mmol) and DMF (40.0 ml) under a nitrogen atmosphere at ambient temperature was treated with 2-methoxyethylamine (0.32 ml, 3.73 mmol). After stirring for 18 hours, the mixture was filtered and the filtrate concentrated in vacuo. The residue was purified by ISOLUTE® SCX-2 SPE column, eluting with a mixture of MeOH and 2.0 M ammonia solution in MeOH (1:0 to 0:1 by volume). Further purification by trituration with DCM afforded the desired product as a white solid (0.28 g, 46%).

LCMS (Method D): Rt=2.20 min, m/z [M+H]$^+$=298/300

Example A8 a) Preparation of Intermediate 34

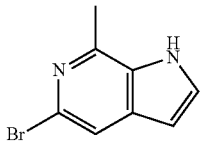

A stirred solution of 6-bromo-2-methyl-3-nitro-pyridine (0.25 g, 1.15 mmol) in anhydrous tetrahydrofuran (11.5 ml) under an argon atmosphere at −40° C. was treated with 1.0 M solution of vinylmagnesium bromide in tetrahydrofuran (3.46 ml, 3.46 mmol), and the resulting mixture was stirred for 1 hour. The mixture was diluted with saturated aqueous ammonium chloride solution (11.5 ml) and partitioned between water and EtOAc. The organic phase was dried over sodium sulfate and concentrated in vacuo. The residue was purified by column chromatography on silica gel, eluting with a mixture of EtOAc and pentane (0:1 to 1:1 by volume), to afford the desired product as a yellow gum (0.07 g, 25%).

LCMS (Method B): Rt=1.84 min, m/z [M+H]$^+$=211/213

Example A9 a) Preparation of Intermediate 35

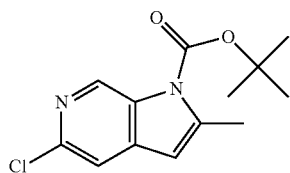 [SMILES: Cc1cc2cc(Cl)ncc2n1C(=O)OC(C)(C)C]

A stirred suspension of 5-chloro-2-methyl-1H-pyrrolo[2,3-c]pyridine (0.40 g, 2.41 mmol) in DCM (10 ml) at 0° C. was treated sequentially with 4-dimethylaminopyridine (0.02 g, 0.14 mmol), triethylamine (0.67 ml, 4.8 mmol) and di-tert-butyldicarbonate (0.63 g, 2.89 mmol). The resulting mixture was warmed to ambient temperature and stirred for 1 hour. The mixture was partitioned between DCM and water. The organic phase was dried over sodium sulfate and concentrated in vacuo. The residue was purified by column chromatography on silica gel, eluting with a mixture of EtOAc and pentane (0:1 to 1:1 by volume), to afford the desired product as a white solid (0.58 g, 90%).

LCMS (Method B): Rt=3.98 min, m/z [M+H]$^+$=267/269

Intermediates 36 to 38 were prepared according to the reaction protocol of example A9 using the appropriate starting materials (Table 3).

TABLE 3

| Intermediate | Structure | Starting Materials | LCMS Data |
|---|---|---|---|
| 36 | 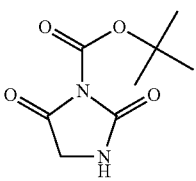 | Imidazolidine-2,4-dione | |
| 37 | 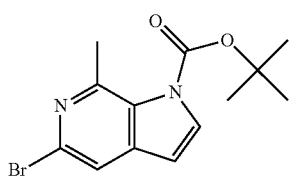 [SMILES: Cc1nc(Br)cc2ccn(C(=O)OC(C)(C)C)c12] | Intermediate 34 | Rt = 4.16 min, m/z [M + H]$^+$ = 311/313 (Method C) |
| 38 | 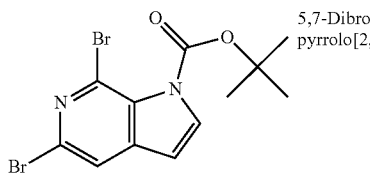 | 5,7-Dibromo-1H-pyrrolo[2,3-c]pyridine | Rt = 4.20 min, m/z [M + H]$^+$ = 375/377/379 (Method B) |

Example A10 a) Preparation of Intermediate 39

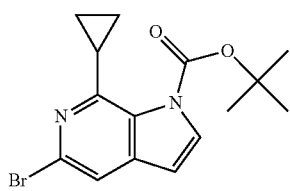 [SMILES: CC(C)(C)OC(=O)n1ccc2cc(Br)nc(C3CC3)c21]

A stirred suspension of intermediate 38 (1.38 g, 3.67 mmol) and tetrakis(triphenylphosphine) palladium (0.21 g, 0.184 mmol) in anhydrous tetrahydrofuran (14 ml) under a nitrogen atmosphere at ambient temperature was treated with 0.5 M solution of cyclopropyl zinc bromide in tetrahydrofuran (11.0 ml, 5.51 mmol), and the resulting mixture was stirred for 4 hours. The mixture was partitioned between EtOAc and saturated aqueous sodium bicarbonate solution. The organic phase was dried over sodium sulfate and concentrated in vacuo. The residue was purified by column chromatography on silica gel, eluting with a mixture of DCM and pentane (0:1 to 2:3 by volume), to afford the desired product as a white solid (0.91 g, 74%).

LCMS (Method C): Rt=4.61 min, m/z [M+H]$^+$=337/339

Example A11 a) Preparation of Intermediate 40

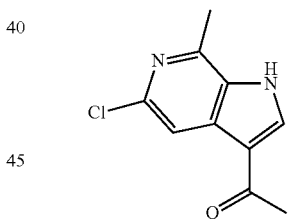

A stirred mixture of 5-chloro-7-methyl-1H-pyrrolo[2,3-c]pyridine (0.95 g, 5.71 mmol) in anhydrous 1,2-dichloroethane (33.3 ml) at ambient temperature was treated portionwise with aluminium chloride (1.52 g, 11.4 mmol). After stirring for 15 minutes, the mixture was treated dropwise with acetyl chloride (0.81 ml, 11.4 mmol) and the resulting mixture was stirred at ambient temperature for 5 hours. The mixture was treated cautiously with MeOH until no further effervescence was observed. The mixture was then concentrated in vacuo and the residue partitioned between 2.0 M aqueous sodium hydroxide solution and EtOAc. The organic phase was washed with brine, dried over sodium sulfate and concentrated in vacuo to afford the desired product (1.06 g, 78%).

LCMS (Method B): Rt=2.25 min, m/z [M+H]$^+$=209/211

Intermediates 41 to 43 and 188 were prepared according to the reaction protocol of intermediate 40 using the appropriate starting materials (Table 4).

TABLE 4

| Intermediate | Structure | Starting Materials | LCMS Data |
|---|---|---|---|
| 41 | 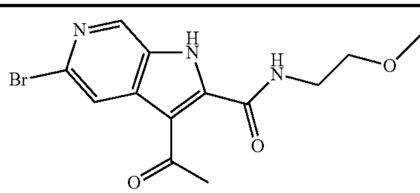 | a) Intermediate 33<br>b) Acetyl chloride | Rt = 2.70 min, m/z<br>[M + H]⁺ = 340/342<br>(Method C) |
| 42 | 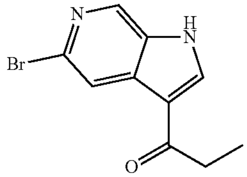 | a) 5-Bromo-1H-pyrrolo[2,3-c]pyridine<br>b) Propionyl chloride | Rt = 2.63 min, m/z<br>[M + H]⁺ = 353/355<br>(Method C) |
| 43 | 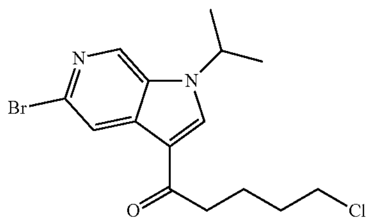 [SMILES: CC(C)n1cc(C(=O)CCCCCl)c2cc(Br)ncc21] | a) Intermediate 17<br>b) 5-Chloro-pentanoyl chloride | |
| 188 | | a) Intermediate 17<br>b) 3-Methoxy-propionyl chloride | Rt = 3.02 min, m/z<br>[M + H]⁺ = 325/327<br>(Method C) | b) Preparation of Intermediate 44

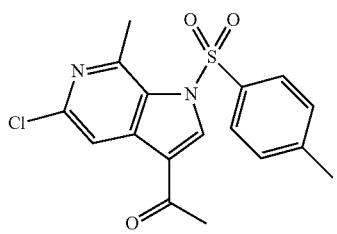 [SMILES: CC(=O)c1cn(S(=O)(=O)c2ccc(C)cc2)c2c(C)nc(Cl)cc12]

A stirred mixture of intermediate 40 (1.06 g, 5.08 mmol), 4-methylbenzenesulfonyl chloride (1.06 g, 5.59 mmol), DIPEA (1.77 ml, 10.2 mmol) and anhydrous DCM (51.6 ml) at ambient temperature was treated with 4-dimethylaminopyridine (0.06 g, 0.51 mmol). The resulting mixture was stirred for 2 hours and then partitioned between water and DCM. The organic phase was washed with brine, dried over sodium sulfate and concentrated in vacuo. The residue was purified by column chromatography on silica gel, eluting with a mixture of EtOAc and pentane (0:1 to 3:1 by volume), to afford the desired product as an off-white solid (1.36 g, 74%).

LCMS (Method B): Rt=3.90 min, m/z [M+H]+=363/365

Intermediates 45 and 46 were prepared according to the reaction protocol of intermediate 44 using the appropriate starting materials (Table 5).

TABLE 5

| Intermediate | Structure | Starting Materials | LCMS Data |
|---|---|---|---|
| 45 | 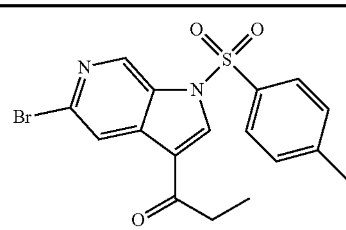 | Intermediate 42 | Rt = 4.20 min, m/z<br>[M + H]⁺ = 407/409<br>(Method B) |

TABLE 5-continued

| Intermediate | Structure | Starting Materials | LCMS Data |
|---|---|---|---|
| 46 | | Intermediate 41 | Rt = 3.61 min, m/z [M + H]$^+$ = 494/496 (Method C) | c) Preparation of Intermediate 47

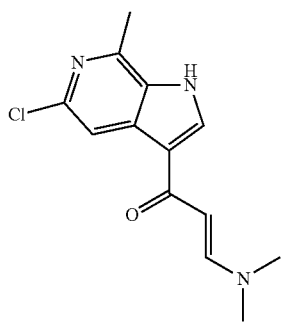 [SMILES: Cc1nc(Cl)cc2c(C(=O)/C=C/N(C)C)c[nH]c12]

A stirred mixture of intermediate 40 (1.36 g, 3.75 mmol) and tert-butoxy bis(dimethylamino)methane (3.09 ml, 14.9 mmol) was heated at 100° C. for 3.5 hours. The mixture was cooled to ambient temperature and concentrated in vacuo to afford the desired product as a brown semi-solid (0.99 g, 100%).

LCMS (Method B): Rt=2.10 min, m/z [M+H]+=264/266

Intermediates 48 to 50 and 180 were prepared according to the reaction protocol of intermediate 47 using the appropriate starting materials (Table 6).

TABLE 6

| Intermediate | Structure | Starting Materials | LCMS Data |
|---|---|---|---|
| 48 | 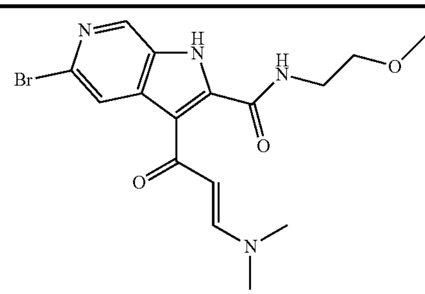 | Intermediate 41 | Rt = 2.61 min, m/z [M + H]$^+$ = 395/397 (Method C) |
| 49 | 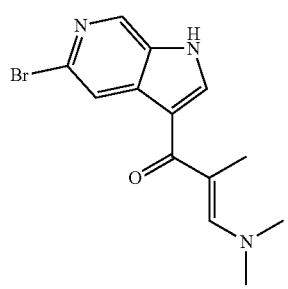 [SMILES: C/C(=C\N(C)C)C(=O)c1c[nH]c2cnc(Br)cc12] | Intermediate 42 | |

TABLE 6-continued

| Intermediate | Structure | Starting Materials | LCMS Data |
|---|---|---|---|
| 50 | 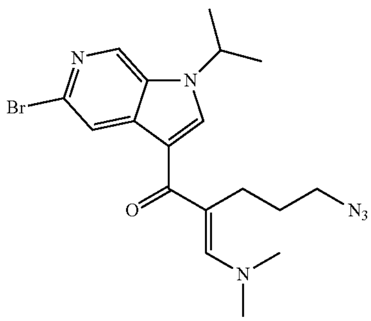 [SMILES: CC(C)n1cc(C(=O)/C(=C/N(C)C)CCCN=[N+]=[N-])c2cc(Br)ncc21] | Intermediate 55 | |
| 180 | | Intermediate 188 | | d) Preparation of Intermediate 51

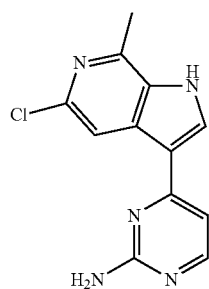 [SMILES: Cc1nc(Cl)cc2c(-c3ccnc(N)n3)c[nH]c12]

A stirred mixture of guanidine hydrochloride (3.58 g, 37.5 mmol) and 1-butanol (38 ml) under a nitrogen atmosphere at ambient temperature was treated portionwise with sodium methoxide (2.02 g, 37.5 mmol). After stirring for 30 minutes, a slurry of intermediate 47 (0.99 g, 37.5 mmol) in 1-butanol (18.0 ml) was added and the resulting mixture heated at 100° C. for 18 hours. The mixture was cooled to ambient temperature and concentrated in vacuo. The residue was diluted with water and extracted with EtOAc. The combined extracts were dried over sodium sulfate and concentrated in vacuo. The residue was triturated with $Et_2O$ to afford the desired product as a brown solid (0.61 g, 63%).

LCMS (Method B): Rt=1.67 min, m/z [M+H]+=260/262

Intermediates 52 to 54 and 181 were prepared according to the reaction protocol of intermediate 51 using the appropriate starting materials (Table 7).

TABLE 7

| Intermediate | Structure | Starting Materials | LCMS Data |
|---|---|---|---|
| 52 | 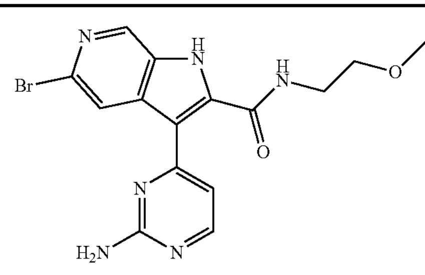 | a) Intermediate 48<br>b) Guanidine hydrochloride | Rt = 2.31 min, m/z [M + H]+ = 391/393 (Method C) |

TABLE 7-continued

| Intermediate | Structure | Starting Materials | LCMS Data |
|---|---|---|---|
| 53 | 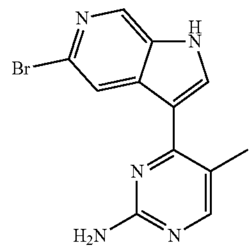 [SMILES: Cc1cnc(N)nc1-c1c[nH]c2cnc(Br)cc12] | a) Intermediate 49<br>b) Guanidine hydrochloride | Rt = 1.73 min, m/z [M + H]$^+$ = 304/306 (Method C) |
| 54 | 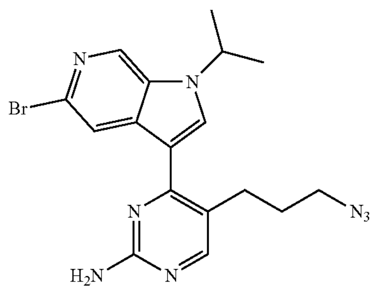 [SMILES: CC(C)n1cc(-c2nc(N)ncc2CCCN=[N+]=[N-])c2cc(Br)ncc21] | a) Intermediate 50<br>b) Guanidine hydrochloride | |
| 181 | 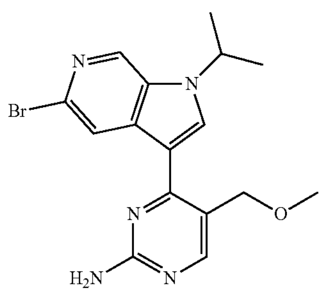 [SMILES: COCc1cnc(N)nc1-c1cn(C(C)C)c2cnc(Br)cc12] | a) Intermediate 180<br>b) Guanidine hydrochloride | Rt = 2.28 min, m/z [M + H]$^+$ = 376/378 (Method B) |

Example A12 a) Preparation of Intermediate 55

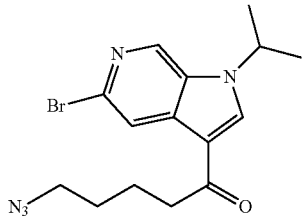 [SMILES: CC(C)n1cc(C(=O)CCCCN=[N+]=[N-])c2cc(Br)ncc21]

A mixture of intermediate 43 (0.3 g, 0.84 mmol), sodium azide (0.1 g, 1.5 mmol), sodium iodide (catalic amount) and DMF (15 ml) was stirred at 55° C. for 18 hours. The mixture was cooled to ambient temperature and concentrated in vacuo to afford the desired product (0.3 g, 97%).

Example A13 a) Preparation of Intermediate 56

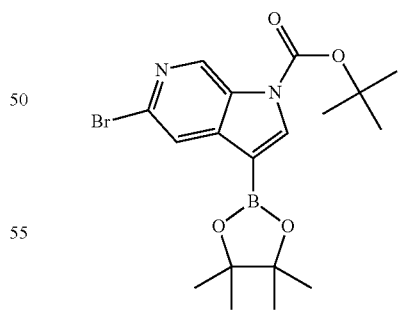

A degassed mixture of 5-bromo-pyrrolo[2,3-c]pyridine-1-carboxylic acid tert-butyl ester (0.10 g, 0.34 mmol), 4,4,-di-tert-butyl-2,2-dipyridyl (9.0 mg, 0.03 mmol) and cyclohexane (2.5 ml) under an argon atmosphere at ambient temperature was treated sequentially with di-μ-methoxobis(1,5-cyclooctadiene)diiridium (0.01 g, 0.02 mmol) and 4,4,5,5-tetramethyl-1,3,2-dioxaborolane (0.24 ml, 1.69 mmol). The resulting mixture was stirred at 60° C. for 2 hours. The mixture was cooled to ambient temperature and concentrated in vacuo. The residue was purified by column chromatography on silica gel, eluting with a mixture of EtOAc and pentane (0:1 to 1:1 by volume), to afford the desired product as a white solid.

LCMS (Method B): Rt=4.83 min, m/z [M+H]$^+$=423/425

Intermediates 57 to 61 and 182 were prepared according to the reaction protocol of intermediate 56 using the appropriate starting materials (Table 8).

TABLE 8

| Intermediate | Structure | Starting Materials | LCMS Data |
|---|---|---|---|
| 57 | 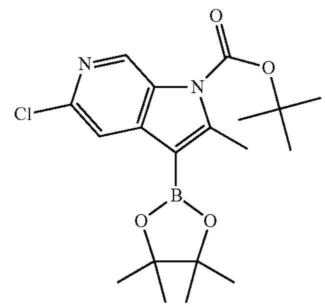 [SMILES: Cc1c(B2OC(C)(C)C(C)(C)O2)c2cc(Cl)ncc2n1C(=O)OC(C)(C)C] | Intermediate 35 | Rt = 4.98 min, m/z [M + H]$^+$ = 393/395 (Method C) |
| 58 | 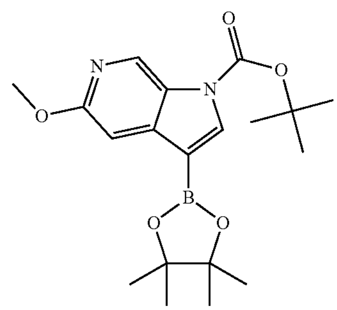 [SMILES: COc1cc2c(B3OC(C)(C)C(C)(C)O3)cn(C(=O)OC(C)(C)C)c2cn1] | 5-Methoxy-pyrrolo[2,3-c]pyridine-1-carboxylic acid tert-butyl ester | Rt = 4.64 min, m/z [M + H-t-Bu]$^+$ = 319 (Method C) |
| 59 | 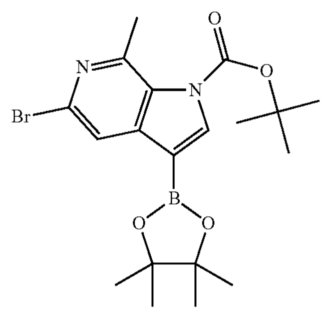 [SMILES: Cc1nc(Br)cc2c(B3OC(C)(C)C(C)(C)O3)cn(C(=O)OC(C)(C)C)c12] | Intermediate 37 | Rt = 5.05 min, m/z [M + H]$^+$ = 381/383 (Method C) |
| 60 | 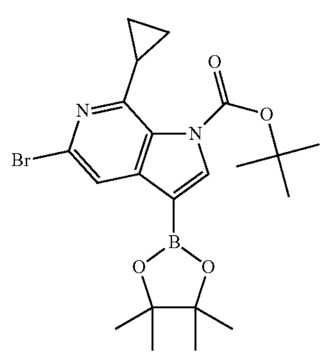 [SMILES: CC(C)(C)OC(=O)n1cc(B2OC(C)(C)C(C)(C)O2)c2cc(Br)nc(C3CC3)c21] | Intermediate 39 | Rt = 5.32 min, m/z [M-(tBu) + H]$^+$ = 407/409 (Method C) |

TABLE 8-continued

| Intermediate | Structure | Starting Materials | LCMS Data |
|---|---|---|---|
| 61 | 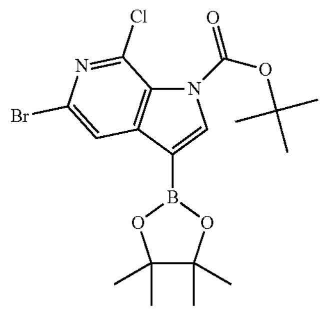 [SMILES: CC(C)(C)OC(=O)n1cc(B2OC(C)(C)C(C)(C)O2)c2cc(Br)nc(Cl)c21] | 5-Bromo-7-chloro-pyrrolo[2,3-c]pyridine-1-carboxylic acid tert-butyl ester | Rt = 5.01 min, m/z [M + H]$^+$ = 457/459 (Method B) |
| 182 | | Intermediate 17 | Rt = 4.18 min, m/z [M + H]$^+$ = 365/367 (Method C) | b) Preparation of Intermediate 62

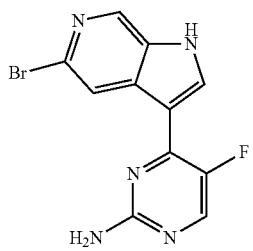 [SMILES: Nc1ncc(F)c(-c2c[nH]c3cnc(Br)cc23)n1]

A mixture of intermediate 56 (0.36 g, 0.84 mmol), 4-chloro-5-fluoropyrimidin-2-amine (0.10 g, 0.67 mmol), tetrakis(triphenylphosphine)palladium (0.08 g, 0.07 mmol), sodium carbonate (1.01 ml, 2.02 mmol), toluene (12.5 ml) and MeOH (1.5 ml) was stirred under an argon atmosphere at 85° C. for 4 hours. The mixture was cooled to ambient temperature and purified by column chromatography on silica gel, eluting with a mixture of EtOAc and pentane (0:1 to 1:0 by volume), to afford the desired product as a yellow solid (0.09 g, 36%).

LCMS (Method C): Rt=2.26 min, m/z [M+H]$^+$=308/310

Intermediates 63 to 71, 183 and 184 were prepared according to the reaction protocol of intermediate 62 using the appropriate starting materials (Table 9).

TABLE 9

| Intermediate | Structure | Starting Materials | LCMS Data |
|---|---|---|---|
| 63 | 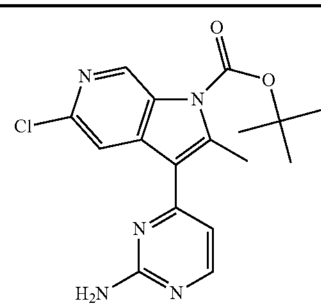 | a) Intermediate 57 b) 4-Chloro-pyrimidin-2-ylamine | Rt = 3.07 min, m/z [M + H]$^+$ = 360/362 (Method C) |

TABLE 9-continued

| Intermediate | Structure | Starting Materials | LCMS Data |
|---|---|---|---|
| 64 | 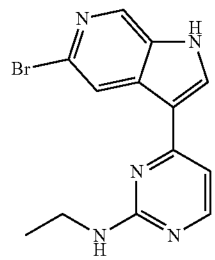 [SMILES: CCNc1nccc(-c2c[nH]c3cnc(Br)cc23)n1] | a) Intermediate 56<br>b) (4-Chloro-pyrimidin-2-yl)-ethyl-amine | Rt = 2.03 min, m/z<br>[M + H]⁺ = 318/320<br>(Method C) |
| 65 | 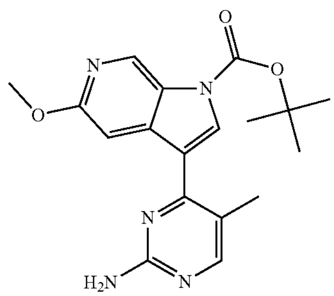 [SMILES: COc1cc2c(-c3nc(N)ncc3C)cn(C(=O)OC(C)(C)C)c2cn1] | a) Intermediate 58<br>b) 4-Chloro-5-methyl-pyrimidin-2-ylamine | Rt = 2.78 min, m/z<br>[M + H]⁺ = 356<br>(Method B) |
| 66 | 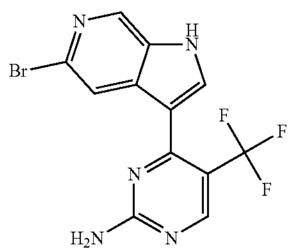 [SMILES: Nc1ncc(C(F)(F)F)c(-c2c[nH]c3cnc(Br)cc23)n1] | a) Intermediate 56<br>b) 4-Chloro-5-trifluoromethyl-pyrimidin-2-ylamine | Rt = 2.80 min, m/z<br>[M + H]⁺ = 358/360<br>(Method C) |
| 67 | 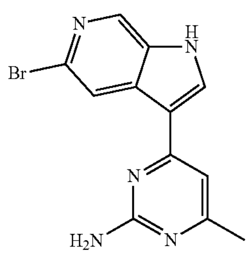 [SMILES: Cc1cc(-c2c[nH]c3cnc(Br)cc23)nc(N)n1] | a) Intermediate 56<br>b) 4-Chloro-6-methyl-pyrimidin-2-ylamine | Rt = 1.72 min, m/z<br>[M + H]+ = 304/306<br>(Method C) |
| 68 | 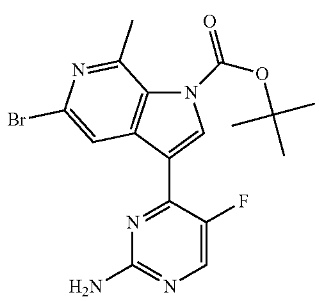 | a) Intermediate 59<br>b) 4-Chloro-5-fluoro-pyrimidin-2-ylamine | Rt = 4.02 min, m/z<br>[M + H]⁺ = 422/424<br>(Method C) |

TABLE 9-continued

| Intermediate | Structure | Starting Materials | LCMS Data |
| --- | --- | --- | --- |
| 69 | 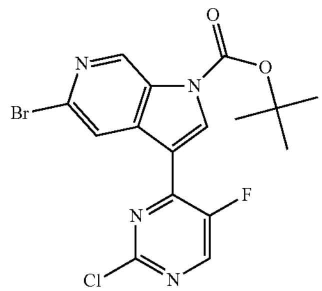 [SMILES: CC(C)(C)OC(=O)n1cc(-c2nc(Cl)ncc2F)c2cc(Br)ncc21] | a) Intermediate 56<br>b) 2,4-Dichloro-5-fluoro-pyrimidine | Rt = 4.52 min, m/z [M + H]$^+$ = 427-430 (Method C) |
| 70 | 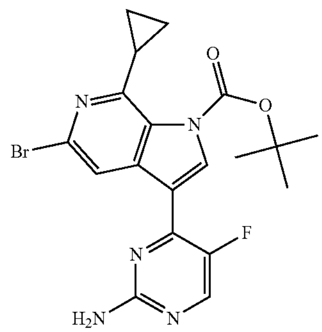 [SMILES: CC(C)(C)OC(=O)n1cc(-c2nc(N)ncc2F)c2cc(Br)nc(C3CC3)c21] | a) Intermediate 60<br>b) 4-Chloro-5-fluoro-pyrimidin-2-ylamine | Rt = 4.52 min, m/z [M + H]$^+$ = 448/450 (Method C) |
| 71 | 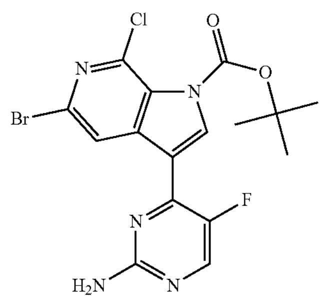 [SMILES: CC(C)(C)OC(=O)n1cc(-c2nc(N)ncc2F)c2cc(Br)nc(Cl)c21] | a) Intermediate 61<br>b) 4-Chloro-5-fluoro-pyrimidin-2-ylamine | Rt = 4.14 min, m/z [M + H]$^+$ = 442 (Method C) |
| 183 | 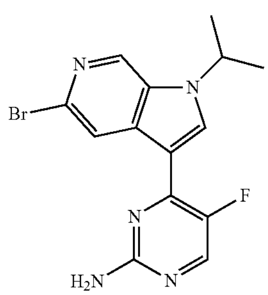 | a) Intermediate 182<br>b) 4-Chloro-5-fluoro-pyrimidin-2-ylamine | Rt = 2.90 min, m/z [M + H]+ = 350/352 (Method C) |
| 184 | 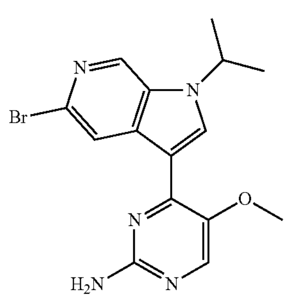 [SMILES: COc1cnc(N)nc1-c1cn(C(C)C)c2cnc(Br)cc12] | a) Intermediate 182<br>b) 4-Chloro-5-methoxy-pyrimidin-2-ylamine | Rt = 2.21 min, m/z [M + H]$^+$ = 362/364 (Method C) |

Example A14 a) Preparation of Intermediate 72

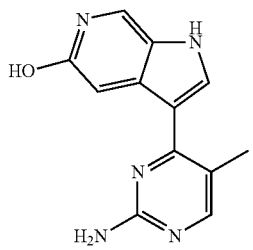

A mixture of intermediate 65 (0.17 g, 0.49 mmol), 48% aqueous hydrobromic acid solution (1.24 ml, 7.38 mmol) and glacial acetic acid (3.5 ml) was stirred at 110° C. for 2 hours and then stood at ambient temperature for 18 hours. The mixture was stirred at 110° C. for further 7 hours, cooled to ambient temperature and the solids were collected by filtration. Purification by ISOLUTE® SCX-2 SPE column, eluting with a mixture of MeOH and 2.0 M ammonia solution in MeOH (1:0 to 0:1 by volume), afforded the desired product as a yellow solid (0.09 g, 71%).

LCMS (Method D): Rt=0.29 min, m/z [M+H]$^+$=242 b) Preparation of Intermediate 73

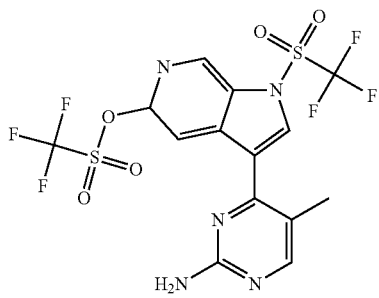 [SMILES: Cc1cnc(N)nc1-c1cn(S(=O)(=O)C(F)(F)F)c2c1=CC(OS(=O)(=O)C(F)(F)F)NC=2]

A solution of intermediate 72 (0.08 g, 0.35 mmol), triethylamine (0.24 ml, 1.76 mmol) and N-phenylbis(trifluoromethanesulphonimide) (0.31 g, 0.880 mmol) in DMF (5 ml) was stirred at ambient temperature for 18 hours. The mixture was concentrated in vacuo and partitioned between EtOAc and water. The organic phase was dried over sodium sulfate and concentrated in vacuo to afford the desired product (0.18 g, 100%).

LCMS (Method C): Rt=4.00 min, m/z [M+H]$^+$=506

Example A15 a) Preparation of Intermediate 74

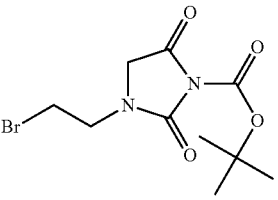 [SMILES: CC(C)(C)OC(=O)N1C(=O)CN(CCBr)C1=O]

A mixture of intermediate 36 (0.23 g, 1.16 mmol), 1,2-dibromoethane (0.11 ml, 1.28 mmol), potassium carbonate (0.53 g, 3.86 mmol) and DMF (4.6 ml) was stirred at 50° C. for 2.5 hours. The mixture was cooled to ambient temperature and partitioned between EtOAc and water. The organic phase was dried over sodium sulfate and concentrated in vacuo. The residue was purified by column chromatography on silica gel, eluting with a mixture of EtOAc and pentane (0:1 to 3:1 by volume), to afford the desired product as a white solid (229 mg, 64%).

Example A16

Preparation of Intermediate 75

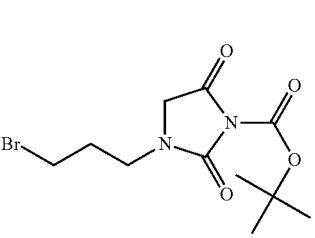 [SMILES: CC(C)(C)OC(=O)N1C(=O)CN(CCCBr)C1=O]

A mixture of intermediate 36 (0.25 g, 1.25 mmol), 1,3-dibromopropane (0.14 ml, 1.37 mmol), potassium carbonate (0.57 g, 4.12 mmol) and DMF (5 ml) was stirred at ambient temperature for 18 hours. The mixture was partitioned between EtOAc and water. The organic phase was dried over sodium sulfate and concentrated in vacuo. The residue was purified by column chromatography on silica gel, eluting with a mixture of EtOAc and pentane (0:1 to 3:1 by volume), to afford the desired product as a colorless oil (0.22 g, 56%).

Example A17 a) Preparation of Intermediate 76

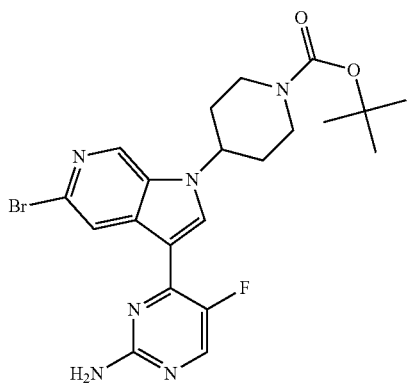 [SMILES: CC(C)(C)OC(=O)N1CCC(n2cc(-c3nc(N)ncc3F)c3cc(Br)ncc32)CC1]

A stirred solution of intermediate 62 (0.81 g, 2.63 mmol) in anhydrous DMF (25 ml), under a nitrogen atmosphere at ambient temperature, was treated portionwise with sodium hydride (0.32 g, 7.89 mmol, 60% in mineral oil). After stirring for 30 minutes, 4-methanesulfonyloxy-piperidine-1-carboxylic acid tert-butyl ester (1.28 g, 4.6 mmol) was added portionwise and the resulting mixture stirred at 100° C. for 24 hours. The mixture was cooled to ambient temperature, quenched with water and partitioned between water and EtOAc. The organic phase was washed with brine, dried over sodium sulfate and concentrated in vacuo. The residue was purified by column chromatography on silica gel, eluting with a mixture of MeOH and DCM (0:1 to 1:9 by volume), to afford the desired product as a yellow solid (0.53 g, 41%).

LCMS (Method C): Rt=3.44 min, m/z [M+H]$^+$=491/493

Intermediates 77 to 79 and 166 to 168 were prepared according to the reaction protocol of example A17 using the appropriate starting materials (Table 10).

TABLE 10

| Intermediate | Structure | Starting Materials | LCMS Data |
|---|---|---|---|
| 77 | 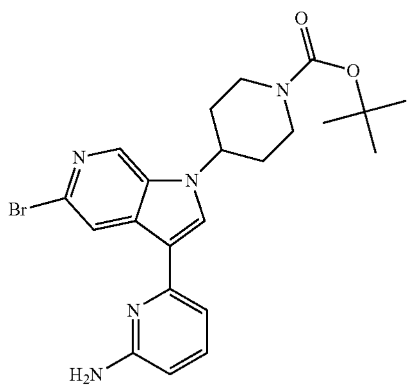 [SMILES: CC(C)(C)OC(=O)N1CCC(n2cc(-c3cccc(N)n3)c3cc(Br)ncc32)CC1] | a) Intermediate 4<br>b) 4-Methanesulfonyloxy-piperidine-1-carboxylic acid tert-butyl ester | Rt = 2.52 min, m/z [M + H]$^+$ = 473/475 (Method C) |
| 78 | 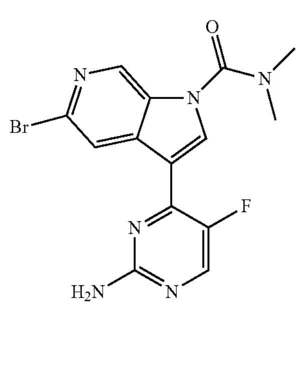 [SMILES: CN(C)C(=O)n1cc(-c2nc(N)ncc2F)c2cc(Br)ncc21] | a) Intermediate 62<br>b) Dimethyl-carbamylchloride | Rt = 2.61 min, m/z [M + H]$^+$ = 379/381 (Method B) |

TABLE 10-continued

| Intermediate | Structure | Starting Materials | LCMS Data |
|---|---|---|---|
| 79 | 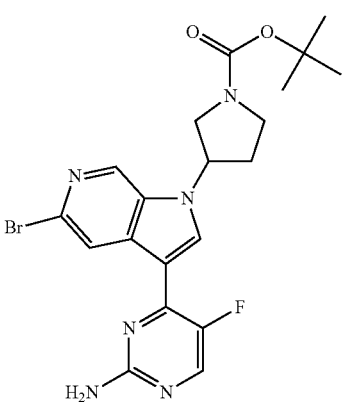 [SMILES: CC(C)(C)OC(=O)N1CCC(n2cc(-c3nc(N)ncc3F)c3cc(Br)ncc32)C1] | a) Intermediate 62<br>b) 3-Methanesulfonyloxy-pyrrolidine-1-carboxylic acid tert-butyl ester | Rt = 3.28 min, m/z [M + H]$^+$ = 477 (Method C) |
| 166 | 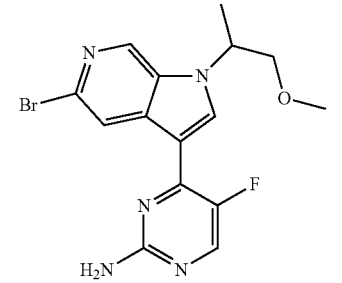 [SMILES: COCC(C)n1cc(-c2nc(N)ncc2F)c2cc(Br)ncc21] | a) Intermediate 62<br>b) 1-Methoxypropan-2-yl-methanesulfonate | Rt = 2.81 min, m/z [M + H]$^+$ = 380/382 (Method B) |
| 167 | 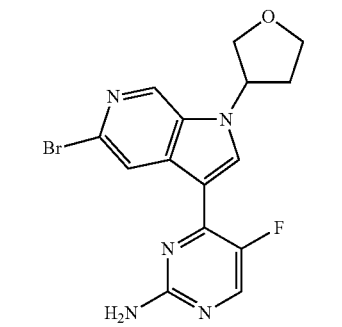 [SMILES: Nc1ncc(F)c(-c2cn(C3CCOC3)c3cnc(Br)cc23)n1] | a) Intermediate 62<br>b) Methanesulfonic acid tetrahydro-furan-3-yl ester | Rt = 2.56 min, m/z [M + H]$^+$ = 378/380 (Method C) |
| 168 | 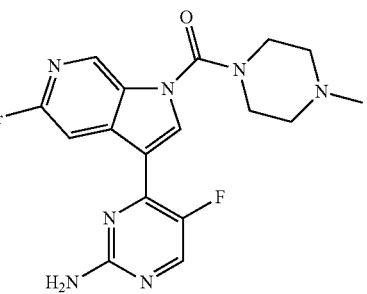 | a) Intermediate 62<br>b) 4-Methyl-piperazine-1-carbonyl chloride | Rt = 2.29 min, m/z [M + H]$^+$ = 436/438 (Method C) |

Example A18 a) Preparation of Intermediate 96

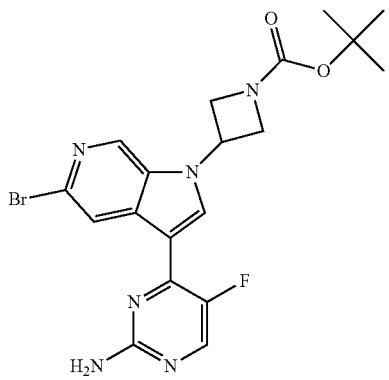 [SMILES: CC(C)(C)OC(=O)N1CC(n2cc(-c3nc(N)ncc3F)c3cc(Br)ncc32)C1]

A mixture of intermediate 62 (0.50 g, 1.62 mmol), 3-iodo-azetidine-1-carboxylic acid tert-butyl ester (0.64 g, 2.27 mmol), caesium carbonate (1.19 g, 3.65 mmol) and DMF (14 ml) was heated by microwave irradiation at 110° C. for 2.5 hours. The mixture was cooled to ambient temperature and partitioned between water and EtOAc. The organic phase was washed with brine, dried over sodium sulfate and concentrated in vacuo. The residue was purified by column chromatography on silica gel, eluting with a mixture of 2.0 M ammonia solution in MeOH and DCM (0:1 to 1:9 by volume), to afford the desired product as an off-white solid (0.50 g, 66%).

LCMS (Method A): Rt=3.30 min, m/z [M+H]+=463/465

Example A19 a) Preparation of Intermediate 100

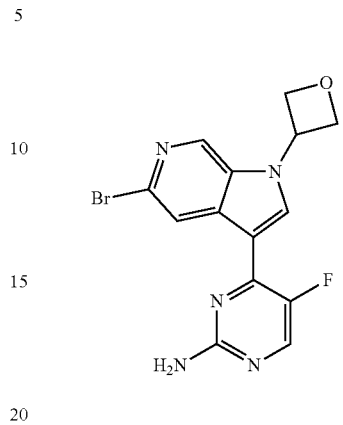

A mixture of intermediate 62 (0.50 g, 1.62 mmol), 3-iodo oxetane (1.45 g, 7.86 mmol), caesium carbonate (2.11 g, 6.48 mmol) and DMF (0.95 ml) was heated at 100° C. for 48 hours. The mixture was cooled to ambient temperature and partitioned between water and EtOAc. The organic phase was washed with brine, dried over sodium sulfate and concentrated in vacuo to afford the desired product as pale yellow solid (0.32 g, 55%).

LCMS (Method C): Rt=2.49 min, m/z [M+H]+=364/366

Intermediates 80 to 116, 160, 169, 170, 176, 185, 193, 194 and 195 were prepared according to the reaction protocol of example A19 using the appropriate starting materials (Table 11).

TABLE 11

| Intermediate | Structure | Starting Materials | LCMS Data |
|---|---|---|---|
| 80 | 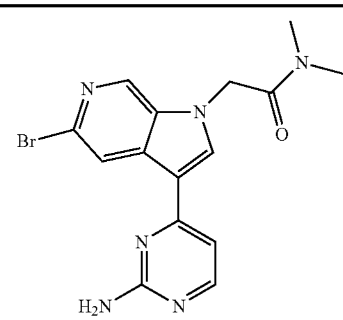 | a) Intermediate 4<br>b) 2-Chloro-N-isopropylacetamide | Rt = 0.30/1.87 min, m/z [M + H]+ = 375/377 (Method A) |
| 81 | 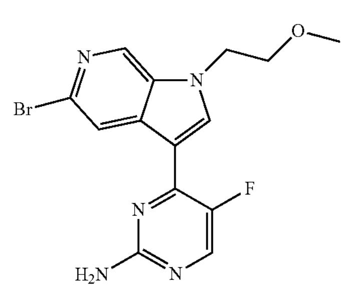 [SMILES: COCCn1cc(-c2nc(N)ncc2F)c2cc(Br)ncc21] | a) Intermediate 62<br>b) 2-Bromoethyl methyl ether | Rt = 2.65 min, m/z [M + H]+ = 366/368 (Method C) |

TABLE 11-continued

| Intermediate | Structure | Starting Materials | LCMS Data |
| --- | --- | --- | --- |
| 82 | 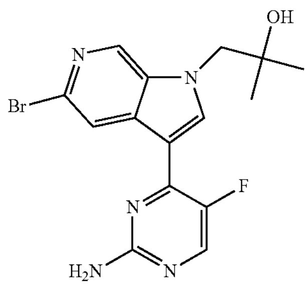 [SMILES: CC(C)(O)Cn1cc(-c2nc(N)ncc2F)c2cc(Br)ncc21] | a) Intermediate 62<br>b) 2,2-Dimethyl-oxirane | Rt = 2.41 min, m/z [M + H]⁺ = 380/382 (Method A) |
| 83 | 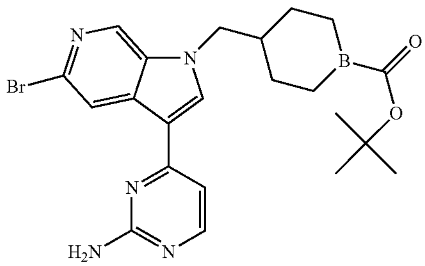 | a) Intermediate 4<br>b) 4-Bromomethyl-piperidine-1-carboxylic acid tert-butyl ester | Rt = 2.32 min, m/z [M + H]⁺ = 487/489 (Method D) |
| 84 | 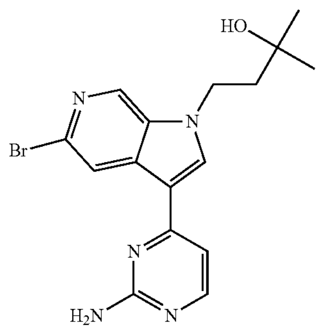 [SMILES: CC(C)(O)CCn1cc(-c2ccnc(N)n2)c2cc(Br)ncc21] | a) Intermediate 4<br>b) 4-Bromo-2-methylbutanol | Rt = 1.60 min, m/z [M + H]⁺ = 376/378 (Method D) |
| 85 | 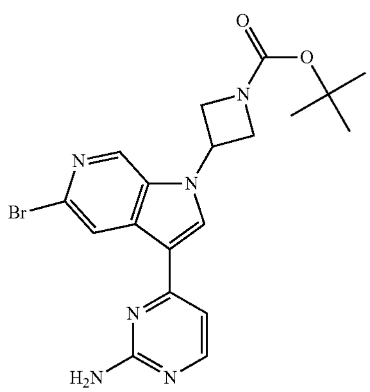 [SMILES: CC(C)(C)OC(=O)N1CC(n2cc(-c3ccnc(N)n3)c3cc(Br)ncc32)C1] | a) Intermediate 4<br>b) 3-Iodo-azetidine-1-carboxylic acid tert-butyl ester | Rt = 2.39 min, m/z [M + H]⁺ = 445/447 (Method B) |
| 86 | 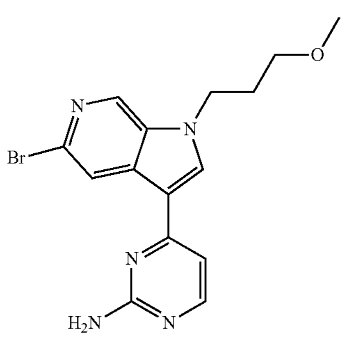 [SMILES: COCCCn1cc(-c2ccnc(N)n2)c2cc(Br)ncc21] | a) Intermediate 4<br>b) 1-Bromo-3-methoxypropane | Rt = 1.73 min, m/z [M + H]⁺ = 362/364 (Method C) |

TABLE 11-continued

| Intermediate | Structure | Starting Materials | LCMS Data |
|---|---|---|---|
| 87 | 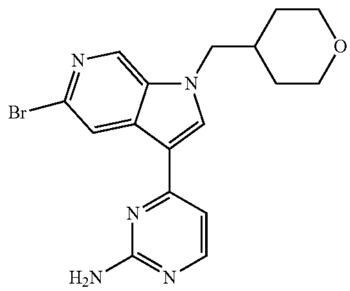 [SMILES: Nc1nccc(-c2cn(CC3CCOCC3)c3cnc(Br)cc23)n1] | a) Intermediate 4<br>b) 4-Bromomethyl-tetrahydro-pyran | Rt = 1.78 min, m/z<br>[M + H]⁺ = 388/390<br>(Method C) |
| 88 | 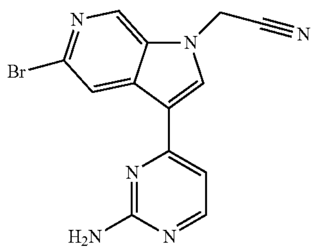 [SMILES: N#CCn1cc(-c2ccnc(N)n2)c2cc(Br)ncc21] | a) Intermediate 4<br>b) Chloro-acetonitrile | Rt = 1.85 min, m/z<br>[M + H]⁺ = 329/331<br>(Method C) |
| 89 | 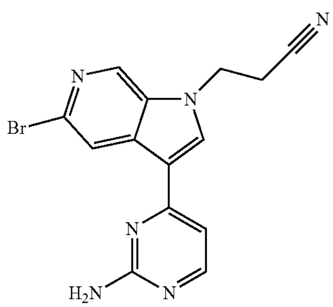 [SMILES: N#CCCn1cc(-c2ccnc(N)n2)c2cc(Br)ncc21] | a) Intermediate 4<br>b) 3-Chloro-propionitrile | Rt = 1.81 min, m/z<br>[M + H]⁺ = 343/345<br>(Method C) |
| 90 | 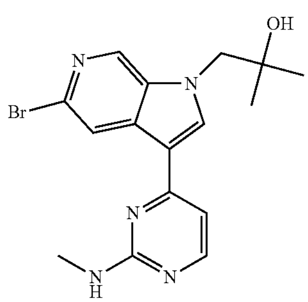 [SMILES: CNc1nccc(-c2cn(CC(C)(C)O)c3cnc(Br)cc23)n1] | a) Intermediate 6<br>b) 2,2-Dimethyl-oxirane | Rt = 2.01 min, m/z<br>[M + H]⁺ = 376/378<br>(Method C) |
| 91 | 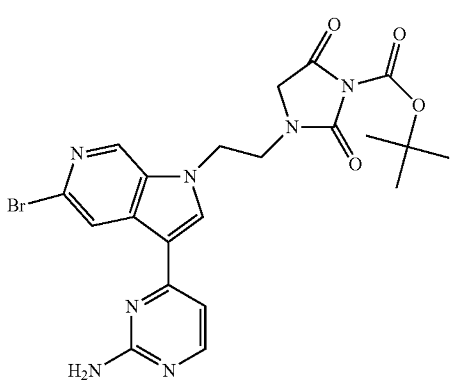 [SMILES: CC(C)(C)OC(=O)N1C(=O)CN(CCn2cc(-c3ccnc(N)n3)c3cc(Br)ncc32)C1=O] | a) Intermediate 4<br>b) Intermediate 74 | Rt = 2.22 min, m/z<br>[M + H]⁺ = 516/518<br>(Method C) |

TABLE 11-continued

| Intermediate | Structure | Starting Materials | LCMS Data |
|---|---|---|---|
| 92 | 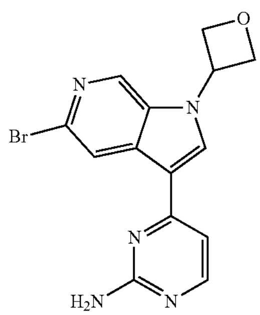 [SMILES: Nc1nccc(-c2cn(C3COC3)c3cnc(Br)cc23)n1] | a) Intermediate 4<br>b) 3-Iodo-oxetane | Rt = 1.83 min, m/z<br>[M + H]⁺ = 346/348<br>(Method B) |
| 93 | 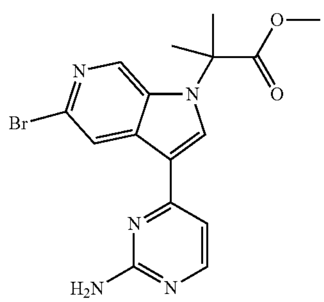 [SMILES: COC(=O)C(C)(C)n1cc(-c2ccnc(N)n2)c2cc(Br)ncc21] | a) Intermediate 4<br>b) Methyl 2-bromoisobutyrate | Rt = 1.89 min, m/z<br>[M + H]⁺ = 390/392<br>(Method C) |
| 94 | 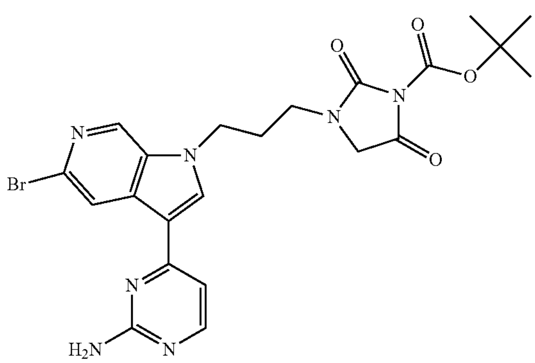 [SMILES: CC(C)(C)OC(=O)N1C(=O)CN(CCCn2cc(-c3ccnc(N)n3)c3cc(Br)ncc32)C1=O] | a) Intermediate 4<br>b) Intermediate 75 | Rt = 2.28 min, m/z<br>[M + H]⁺ = 530/532<br>(Method C) |
| 95 | 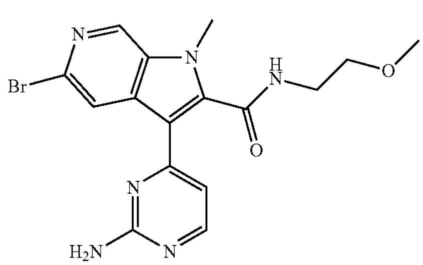 [SMILES: COCCNC(=O)c1c(-c2ccnc(N)n2)c2cc(Br)ncc2n1C] | a) Intermediate 52<br>b) Methyl iodide | Rt = 1.83 min, m/z<br>[M + H]⁺ = 405/407<br>(Method C) |
| 97 | 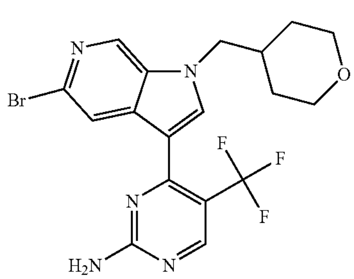 [SMILES: Nc1ncc(C(F)(F)F)c(-c2cn(CC3CCOCC3)c3cnc(Br)cc23)n1] | a) Intermediate 66<br>b) 4-(Bromomethyl)tetrahydropyran | Rt = 3.21 min, m/z<br>[M + H]⁺ = 456/458<br>(Method C) |

TABLE 11-continued

| Intermediate | Structure | Starting Materials | LCMS Data |
|---|---|---|---|
| 98 | 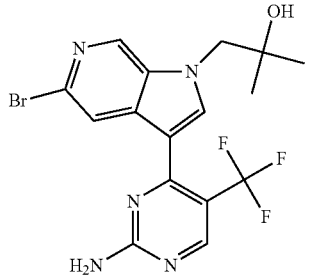 [SMILES: CC(C)(O)Cn1cc(-c2nc(N)ncc2C(F)(F)F)c2cc(Br)ncc21] | a) Intermediate 66<br>b) 2,2-Dimethyl-oxirane | Rt = 2.93 min, m/z [M + H]$^+$ = 430/432 (Method C) |
| 99 | 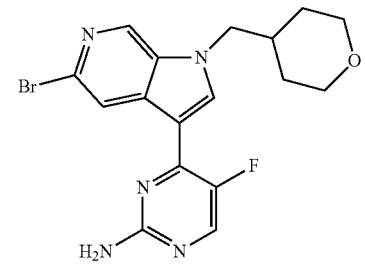 | a) Intermediate 62<br>b) 4-Bromomethyl-tetrahydro-pyran | Rt = 2.76 min, [M + H]$^+$ = 406/408 (Method C) |
| 101 | 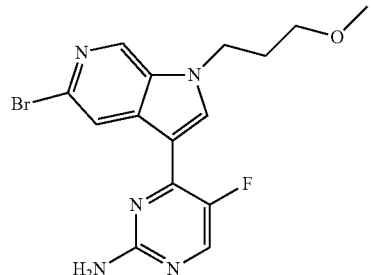 | a) Intermediate 62<br>b) 1-Bromo-3-methoxy-propane | Rt = 2.72 min, m/z [M + H]$^+$ = 380/382 (Method B) |
| 102 | 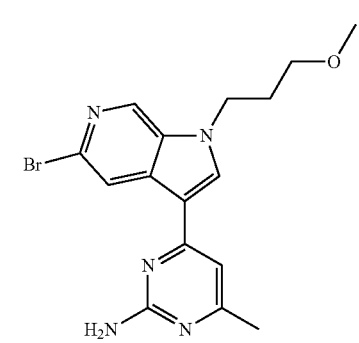 [SMILES: COCCCn1cc(-c2cc(C)nc(N)n2)c2cc(Br)ncc21] | a) Intermediate 67<br>b) 1-Bromo-3-methoxy-propane | Rt = 1.89 min, m/z [M + H]$^+$ = 376/.78 (Method C) |
| 103 | 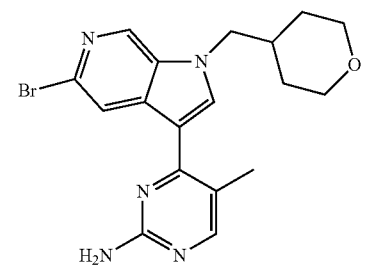 | a) Intermediate 53<br>b) 4-Bromomethyl-tetrahydro-pyran | Rt = 2.01 min, m/z [M + H]$^+$ = 402/404 (Method C) |

TABLE 11-continued

| Intermediate | Structure | Starting Materials | LCMS Data |
|---|---|---|---|
| 104 | 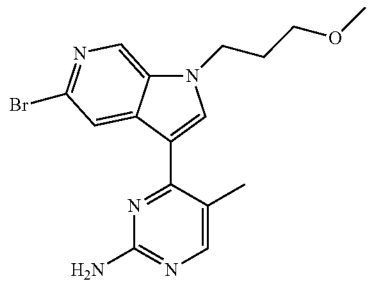 [SMILES: COCCCn1cc(-c2nc(N)ncc2C)c2cc(Br)ncc21] | a) Intermediate 53<br>b) 1-Bromo-3-methoxy-propane | Rt = 2.00 min, m/z [M + H]$^+$ = 376/378 (Method C) |
| 105 | 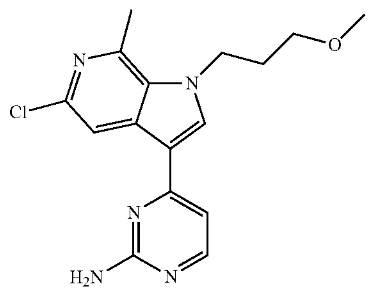 [SMILES: COCCCn1cc(-c2ccnc(N)n2)c2cc(Cl)nc(C)c21] | a) Intermediate 51<br>b) 1-Bromo-3-methoxy-propane | Rt = 1.96 min, m/z [M + H]$^+$ = 332/334 (Method B) |
| 106 | 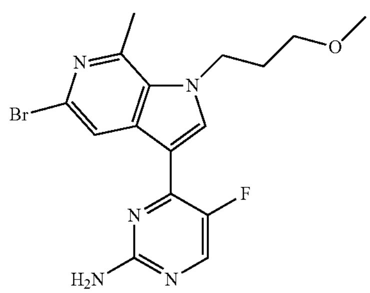 [SMILES: COCCCn1cc(-c2nc(N)ncc2F)c2cc(Br)nc(C)c21] | a) Intermediate 117<br>b) 1-Bromo-3-methoxy-propane | Rt = 2.83 min, m/z [M + H]$^+$ = 394/396 (Method C) |
| 107 | 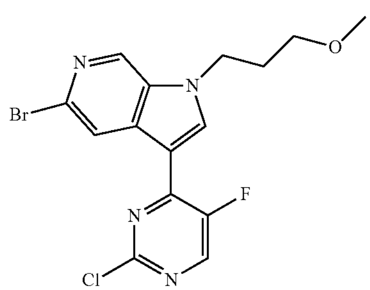 [SMILES: COCCCn1cc(-c2nc(Cl)ncc2F)c2cc(Br)ncc21] | a) Intermediate 118<br>b) 1-Bromo-3-methoxy-propane | Rt = 3.70 min, m/z [M + H]$^+$ = 399/401 (Method B) |
| 108 | 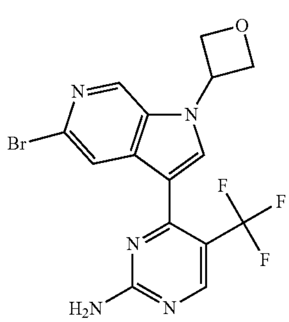 [SMILES: Nc1ncc(C(F)(F)F)c(-c2cn(C3COC3)c3cnc(Br)cc23)n1] | a) Intermediate 66<br>b) 3-Iodo-oxetane | Rt = 2.69 min, m/z [M + H]$^+$ = 414/416 (Method D) |

TABLE 11-continued

| Intermediate | Structure | Starting Materials | LCMS Data |
|---|---|---|---|
| 109 | 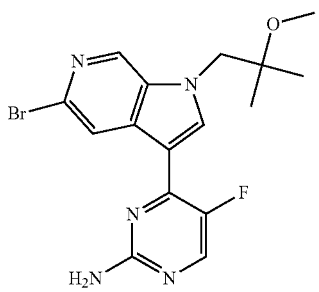 [SMILES: COC(C)(C)Cn1cc(-c2nc(N)ncc2F)c2cc(Br)ncc21] | a) Intermediate 62<br>b) 1-Iodo-2-methoxy-2-methyl-propane | Rt = 3.00 min, m/z<br>[M + H]$^+$ = 394/396<br>(Method C) |
| 110 | 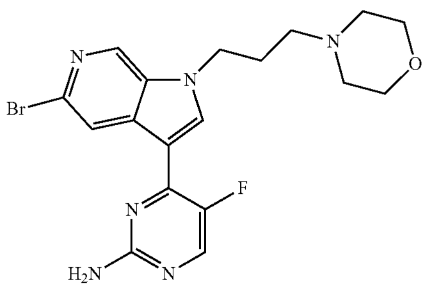 [SMILES: Nc1ncc(F)c(-c2cn(CCCN3CCOCC3)c3cnc(Br)cc23)n1] | a) Intermediate 62<br>b) 4-(3-Chloro-propyl)-morpholine | Rt = 1.78 min, m/z<br>[M + H]$^+$ = 435/437<br>(Method B) |
| 111 | 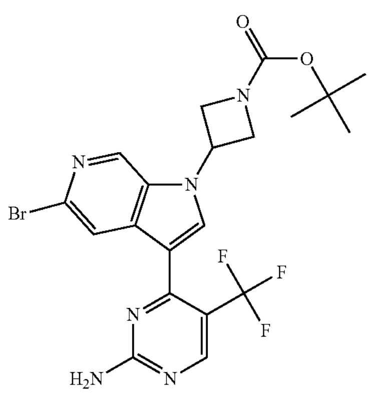 [SMILES: CC(C)(C)OC(=O)N1CC(n2cc(-c3nc(N)ncc3C(F)(F)F)c3cc(Br)ncc32)C1] | a) Intermediate 66<br>b) 3-Iodo-azetidine-1-carboxylic acid tert-butyl ester | Rt = 3.21 min, m/z<br>[M + H]$^+$ = 513/515<br>(Method D) |
| 112 | 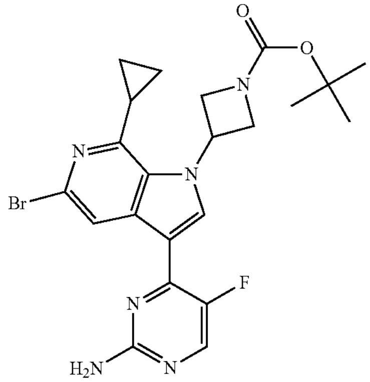 [SMILES: CC(C)(C)OC(=O)N1CC(n2cc(-c3nc(N)ncc3F)c3cc(Br)nc(C4CC4)c32)C1] | a) Intermediate 125<br>b) 3-Iodo-azetidine-1-carboxylic acid tert-butyl ester | Rt = 3.34 min, m/z<br>[M + H]$^+$ = 503/505<br>(Method D) |

TABLE 11-continued

| Intermediate | Structure | Starting Materials | LCMS Data |
| --- | --- | --- | --- |
| 113 | 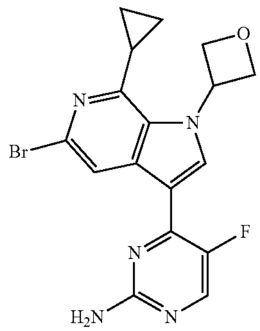 [SMILES: Nc1ncc(F)c(-c2cn(C3COC3)c3c(C4CC4)nc(Br)cc23)n1] | a) Intermediate 125<br>b) 3-Iodo-oxetane | Rt = 2.82 min, m/z<br>[M + H]⁺ = 404/406<br>(Method C) |
| 114 | 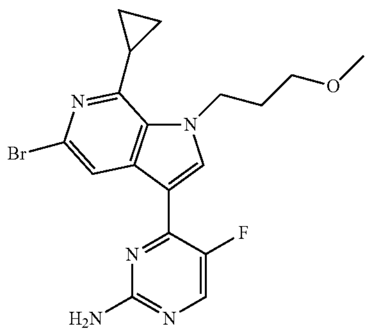 [SMILES: COCCCn1cc(-c2nc(N)ncc2F)c2cc(Br)nc(C3CC3)c21] | a) Intermediate 125<br>b) 1-Bromo-3-methoxypropane | Rt = 3.11 min, m/z<br>[M + H]⁺ = 420/422<br>(Method C) |
| 115 | 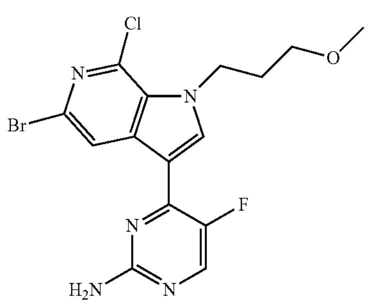 [SMILES: COCCCn1cc(-c2nc(N)ncc2F)c2cc(Br)nc(Cl)c21] | a) Intermediate 127<br>b) 1-Bromo-3-methoxypropane | Rt = 3.43 min, m/z<br>[M + H]⁺ = 414/416<br>(Method C) |
| 116 | 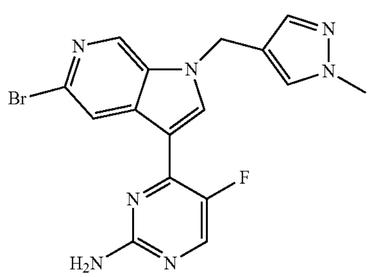 [SMILES: Cn1cc(Cn2cc(-c3nc(N)ncc3F)c3cc(Br)ncc32)cn1] | a) Intermediate 62<br>b) Methanesulfonic acid 1-methyl-1H-pyrazol-4-ylmethyl ester | Rt = 2.44 min, m/z<br>[M + H]⁺ = 402/404<br>(Method C) |
| 160 | 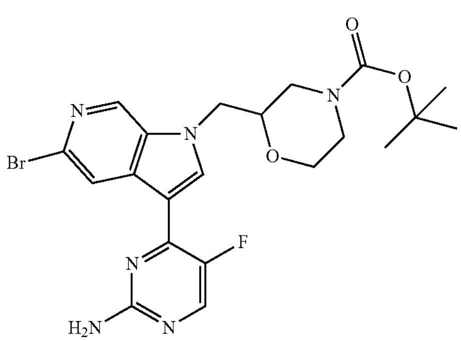 [SMILES: CC(C)(C)OC(=O)N1CCOC(Cn2cc(-c3nc(N)ncc3F)c3cc(Br)ncc32)C1] | a) Intermediate 62<br>b) 2-Chloromethyl-morpholine-4-carboxylic acid tert-butyl ester | Rt = 3.35 min, m/z<br>[M + H]⁺ = 507/509<br>(Method C) |

TABLE 11-continued

| Intermediate | Structure | Starting Materials | LCMS Data |
|---|---|---|---|
| 169 | 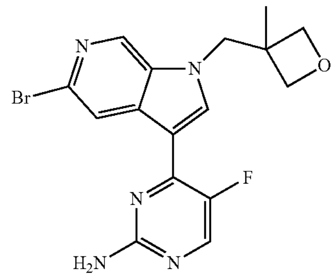 [SMILES: CC1(Cn2cc(-c3nc(N)ncc3F)c3cc(Br)ncc32)COC1] | a) Intermediate 62<br>b) Methanesulfonic acid 3-methyl-oxetan-3-ylmethyl ester | Rt = 2.57 min, m/z [M + H]+ = 392/394 (Method B) |
| 170 | 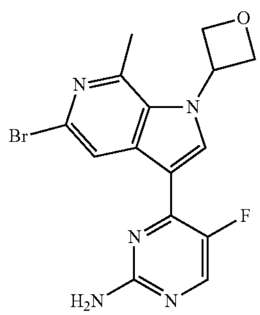 [SMILES: Cc1nc(Br)cc2c(-c3nc(N)ncc3F)cn(C3COC3)c12] | a) Intermediate 117<br>b) 3-Iodo-oxetane | Rt = 2.51 min, m/z [M + H]+ = 378/380 (Method C) |
| 176 | 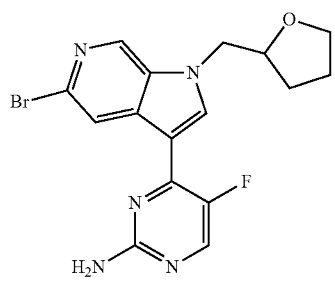 [SMILES: Nc1ncc(F)c(-c2cn(CC3CCCO3)c3cnc(Br)cc23)n1] | a) Intermediate 62<br>b) 2-Bromomethyl-tetrahydro-furan | Rt = 2.82 min, m/z [M + H]+ = 392/394 (Method C) |
| 185 | 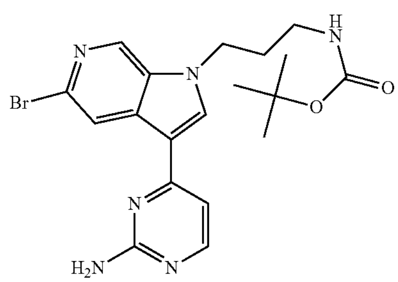 [SMILES: CC(C)(C)OC(=O)NCCCn1cc(-c2ccnc(N)n2)c2cc(Br)ncc21] | a) Intermediate 4<br>b) (3-Bromo-propyl)-carbamic acid tert-butyl ester | Rt = 2.19 min, m/z [M + H]+ = 447/449 (Method B) |
| 193 | 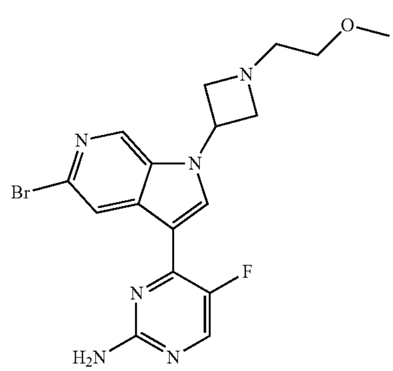 [SMILES: COCCN1CC(n2cc(-c3nc(N)ncc3F)c3cc(Br)ncc32)C1] | a) Intermediate 121<br>b) 1-Bromo-2-methoxy-ethane | Rt = 1.80 min, m/z [M + H]+ = 421/423 (Method A) |

TABLE 11-continued

| Intermediate | Structure | Starting Materials | LCMS Data |
|---|---|---|---|
| 194 | 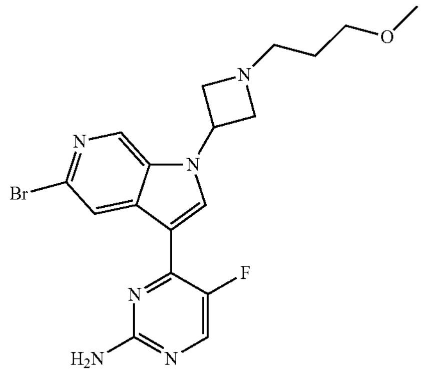 [SMILES: COCCCN1CC(n2cc(-c3nc(N)ncc3F)c3cc(Br)ncc32)C1] | a) Intermediate 121<br>b) 1-Bromo-3-methoxy-propane | Rt = 1.80 min, m/z<br>[M + H]+ = 435/437<br>(Method B) |
| 195 | 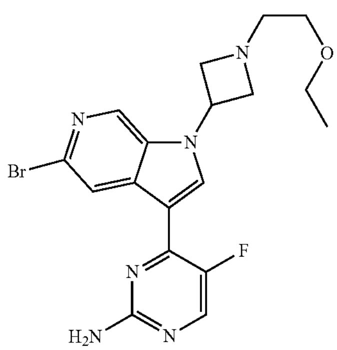 [SMILES: CCOCCN1CC(n2cc(-c3nc(N)ncc3F)c3cc(Br)ncc32)C1] | a) Intermediate 121<br>b) 1-Bromo-2-ethoxy-ethane | Rt = 1.84 min, m/z<br>[M + H]+ = 435/437<br>(Method C) |

Example A20 a) Preparation of Intermediate 121

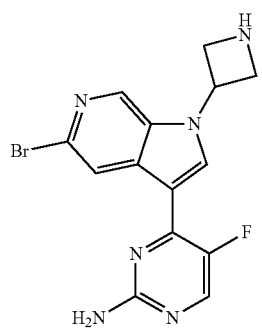

A stirred solution of intermediate 96 (0.50 g, 1.073 mmol) in DCM (20 ml) under a nitrogen atmosphere at ambient temperature was treated with trifluoroacetic acid (5.0 ml, 65.0 mmol) and the resulting mixture stirred for 1 hours. The mixture was concentrated in vacuo and the residue was triturated with MeOH to afford the desired product as an off-white solid (0.41 g, 100%).

LCMS (Method B): Rt=1.98 min, m/z [M+H]+=363/365

Intermediates 117 to 128, 161, 171 and 186 were prepared according to the reaction protocol of example A20 using the appropriate starting materials (Table 12).

TABLE 12

| Intermediate | Structure | Starting Materials | LCMS Data |
|---|---|---|---|
| 117 | 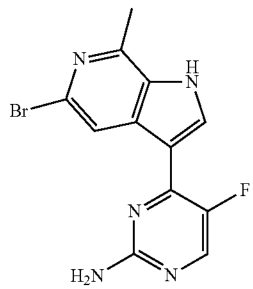 [SMILES: Cc1nc(Br)cc2c(-c3nc(N)ncc3F)c[nH]c12] | Intermediate 68 | Rt = 2.22 min, m/z [M + H]+ = 322/324 (Method C) |
| 118 | 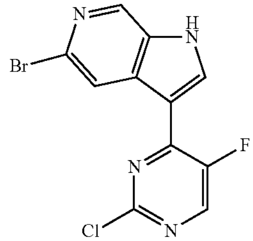 [SMILES: Fc1cnc(Cl)nc1-c1c[nH]c2cnc(Br)cc12] | Intermediate 69 | Rt = 3.25 min, m/z [M + H]$^+$ = 327/329 (Method B) |
| 119 | 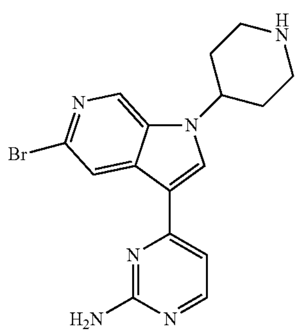 [SMILES: Nc1nccc(-c2cn(C3CCNCC3)c3cnc(Br)cc23)n1] | Intermediate 77 | |
| 120 | 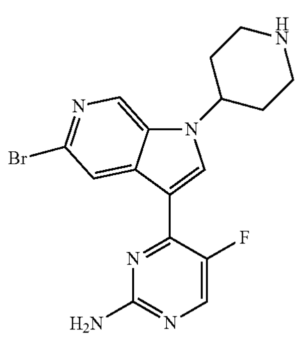 [SMILES: Nc1ncc(F)c(-c2cn(C3CCNCC3)c3cnc(Br)cc23)n1] | Intermediate 76 | Rt = 1.47 min, m/z [M + H]$^+$ = 391/393 (Method C) |
| 122 | 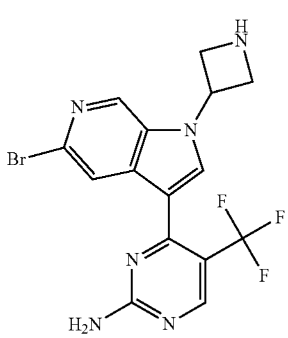 [SMILES: Nc1ncc(C(F)(F)F)c(-c2cn(C3CNC3)c3cnc(Br)cc23)n1] | Intermediate 111 | Rt = 1.98 min, m/z [M + H]$^+$ = 413/415 (Method D) |

TABLE 12-continued

| Intermediate | Structure | Starting Materials | LCMS Data |
|---|---|---|---|
| 123 | 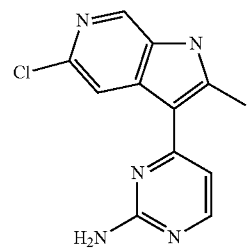 [SMILES: Cc1[nH]c2cnc(Cl)cc2c1-c1ccnc(N)n1] | Intermediate 63 | Rt = 1.73 min, m/z [M + H]⁺ = 260 (Method B) |
| 124 | 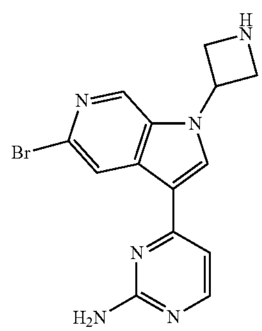 [SMILES: Nc1nccc(-c2cn(C3CNC3)c3cnc(Br)cc23)n1] | Intermediate 85 | Rt = 0.83 min, m/z [M + H]⁺ = 345/347 (Method C) |
| 125 | 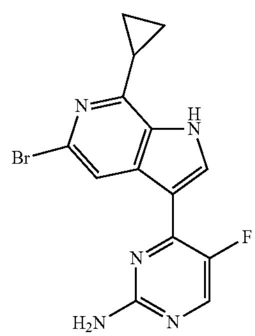 [SMILES: Nc1ncc(F)c(-c2c[nH]c3c(C4CC4)nc(Br)cc23)n1] | Intermediate 70 | Rt = 2.93 min, m/z [M + H]⁺ = 348/350 (Method C) |
| 126 | 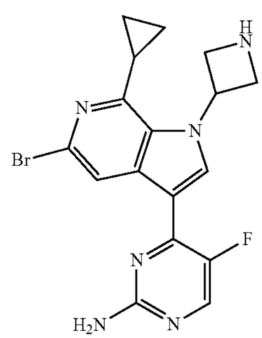 [SMILES: Nc1ncc(F)c(-c2cn(C3CNC3)c3c(C4CC4)nc(Br)cc23)n1] | Intermediate 112 | Rt = 2.10 min, m/z [M + H]⁺ = 403/405 (Method D) |
| 127 | 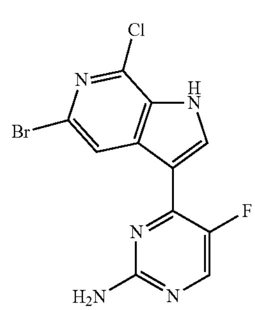 [SMILES: Nc1ncc(F)c(-c2c[nH]c3c(Cl)nc(Br)cc23)n1] | Intermediate 71 | Rt = 2.67 min, m/z [M + H]⁺ = 42/444/346 (Method D) |

TABLE 12-continued

| Intermediate | Structure | Starting Materials | LCMS Data |
|---|---|---|---|
| 128 | 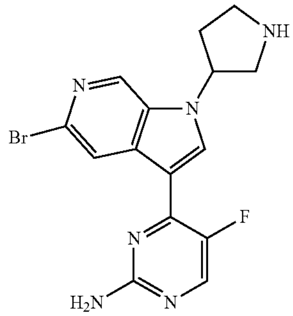 [SMILES: Nc1ncc(F)c(-c2cn(C3CCNC3)c3cnc(Br)cc23)n1] | Intermediate 79 | Rt = 1.76 min, m/z [M + H]+ = 377/379 (Method C) |
| 161 | 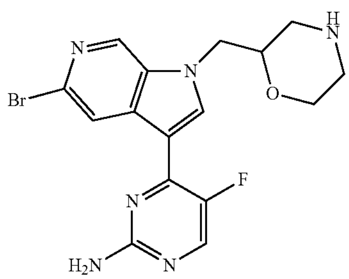 [SMILES: Nc1ncc(F)c(-c2cn(CC3CNCCO3)c3cnc(Br)cc23)n1] | Intermediate 160 | Rt = 1.80 min, m/z [M + H]+ = 407/409 (Method C) |
| 171 | 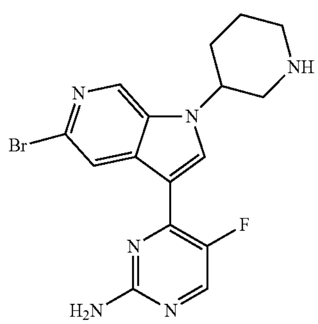 [SMILES: Nc1ncc(F)c(-c2cn(C3CCCNC3)c3cnc(Br)cc23)n1] | Intermediate 175 | Rt = 0.33 min, m/z [M + H]+ = 391/393 (Method C) |
| 186 | 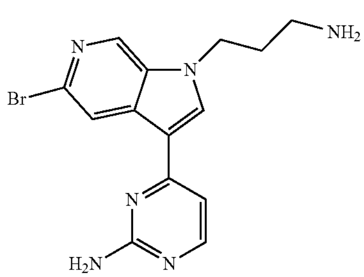 [SMILES: NCCCn1cc(-c2ccnc(N)n2)c2cc(Br)ncc21] | Intermediate 185 | |

Example A21

Preparation of Intermediate 129

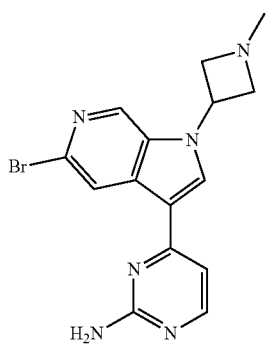 [SMILES: CN1CC(n2cc(-c3ccnc(N)n3)c3cc(Br)ncc32)C1]

A stirred solution of intermediate 124 (0.38 g, 0.83 mmol) in a mixture of MeOH (13 ml) and 1,2-dichloroethane (7.6 ml) under a nitrogen atmosphere at ambient temperature was treated sequentially with sodium acetate (0.07 g, 0.832 mmol), formaldehyde solution (37 wt % in water) (0.12 ml, 1.664 mmol) and sodium triacetoxyborohydride (0.35 g, 1.664 mmol), and the resulting mixture was stirred for 3 hours. The mixture was purified by ISOLUTE® SCX-2 SPE column, eluting with a mixture of MeOH and 2.0 M ammonia solution in MeOH (1:0 to 0:1 by volume), to afford the desired product as a yellow solid (231 mg, 77%).

LCMS (Method C): Rt=0.86 min, m/z [M+H]$^+$=359/361

Intermediates 130 to 134, 172, 173, 176, 187, 189, 196 and 197 were prepared according to the reaction protocol of example A21 using the appropriate starting materials (Table 13).

TABLE 13

| Intermediate | Structure | Starting Materials | LCMS Data |
|---|---|---|---|
| 130 | 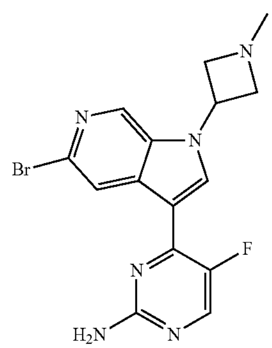 [SMILES: CN1CC(n2cc(-c3nc(N)ncc3F)c3cc(Br)ncc32)C1] | a) Intermediate 121<br>b) Formaldehyde solution (37 wt % in water) | Rt = 1.82 min, m/z [M + H]$^+$ = 377/379 (Method C) |
| 131 | 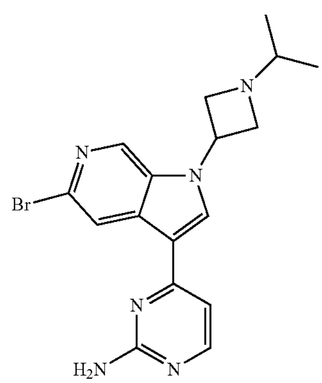 [SMILES: CC(C)N1CC(n2cc(-c3ccnc(N)n3)c3cc(Br)ncc32)C1] | a) Intermediate 124<br>b) Acetone | Rt = 1.20 min, m/z [M + H]$^+$ = 387/389 (Method C) |
| 132 | 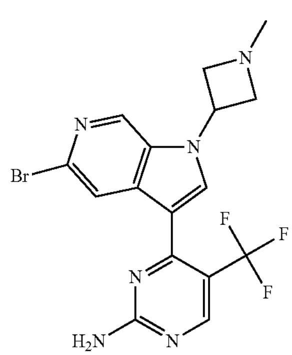 [SMILES: CN1CC(n2cc(-c3nc(N)ncc3C(F)(F)F)c3cc(Br)ncc32)C1] | a) Intermediate 122<br>b) Formaldehyde solution (37 wt % in water) | Rt = 2.04 min, m/z [M + H]$^+$ = 427/429 (Method D) |

TABLE 13-continued

| Intermediate | Structure | Starting Materials | LCMS Data |
|---|---|---|---|
| 133 | 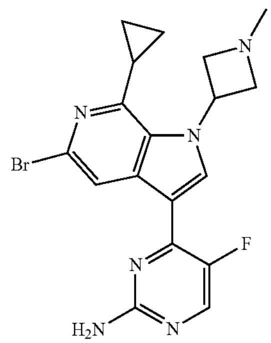 [SMILES: CN1CC(n2cc(-c3nc(N)ncc3F)c3cc(Br)nc(C4CC4)c32)C1] | a) Intermediate 126<br>b) Formaldehyde solution (37 wt % in water) | Rt = 1.98 min, m/z [M + H]$^+$ = 417/419 (Method D) |
| 134 | 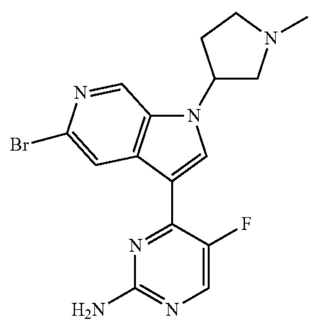 [SMILES: CN1CCC(n2cc(-c3nc(N)ncc3F)c3cc(Br)ncc32)C1] | a) Intermediate 128<br>b) Formaldehyde solution (37 wt % in water) | Rt = 1.76 min, m/z [M + H]$^+$ = 391/393 (Method C) |
| 172 | 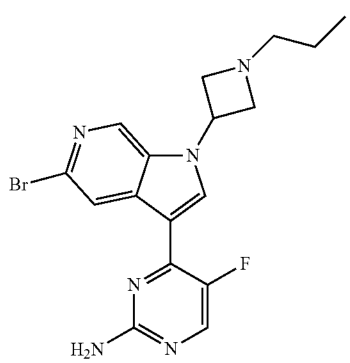 [SMILES: CCCN1CC(n2cc(-c3nc(N)ncc3F)c3cc(Br)ncc32)C1] | a) Intermediate 121<br>b) Propionaldehyde | Rt = 1.80 min, m/z [M + H]$^+$ = 405/407 (Method C) |
| 173 | 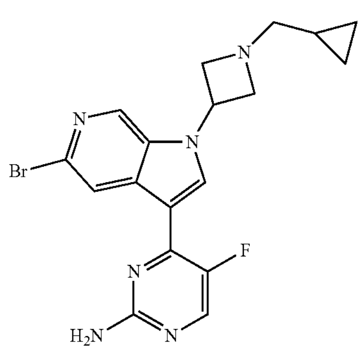 [SMILES: Nc1ncc(F)c(-c2cn(C3CN(CC4CC4)C3)c3cnc(Br)cc23)n1] | a) Intermediate 121<br>b) Cyclopropane carbaldehyde | Rt = 1.85 min, m/z [M + H]$^+$ = 417/419 (Method C) |

TABLE 13-continued

| Intermediate | Structure | Starting Materials | LCMS Data |
|---|---|---|---|
| 189 | 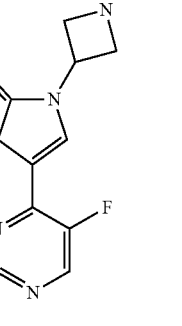 | a) Intermediate 121<br>b) Cyclopentanone | Rt = 1.88 min, m/z<br>[M + H]$^+$ = 431/433<br>(Method B) |
| 187 | 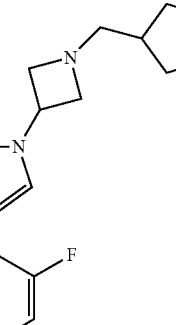 | a) Intermediate 121<br>b) Cyclopentane-<br>carbaldehyde | Rt = 2.06 min, m/z<br>[M + H]$^+$ = 445/447<br>(Method C) |
| 196 | 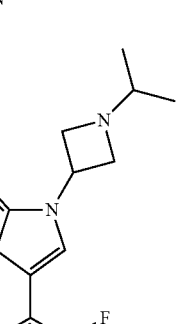 | a) Intermediate 121<br>b) Acetone | Rt = 1.80 min, m/z<br>[M + H]$^+$ = 405/407<br>(Method C) |
| 197 | 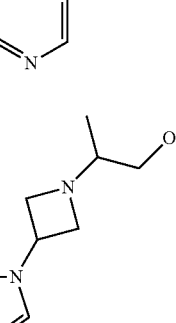 | a) Intermediate 121<br>b) 1-Methoxy-propan-<br>2-one | Rt = 1.72 min, m/z<br>[M + H]$^+$ = 435/437<br>(Method C) |

Example A22 a) Preparation of Intermediate 135

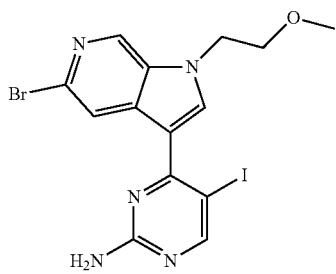

A mixture of intermediate 13 (0.15 g, 0.43 mmol), N-iodosuccinimide (0.29 g, 1.29 mmol) and DMF (3 ml) was stirred at 100° C. for 1 hour. The mixture was cooled to ambient temperature and concentrated in vacuo. The residue was partitioned between water and EtOAc. The organic phase was washed with brine, dried over sodium sulfate and concentrated in vacuo. The residue was purified by column chromatography on silica gel, eluting with a mixture of MeOH in DCM (0:1 to 1:19 by volume), to afford the desired product (0.30 g, 51%).

LCMS (Method C): Rt=2.96 min, m/z $[M+H]^+$=474/476

Intermediates 136, 137 and 202 were prepared according to the reaction protocol of intermediate 135 using the appropriate starting materials (Table 14).

TABLE 14

| Intermediate | Structure | Starting Materials | LCMS Data |
|---|---|---|---|
| 136 | 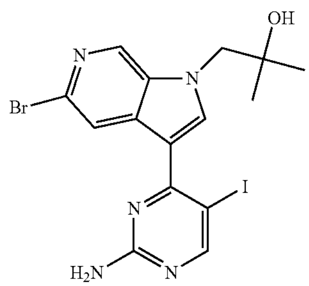 [SMILES: CC(C)(O)Cn1cc(-c2nc(N)ncc2I)c2cc(Br)ncc21] | Intermediate 14 | Rt = 2.72 min, m/z $[M + H]^+$ = 488/490 (Method C) |
| 137 | 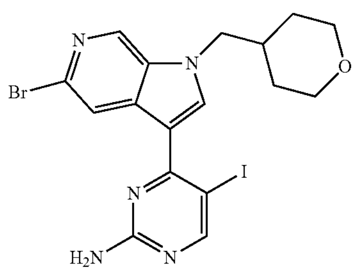 [SMILES: Nc1ncc(I)c(-c2cn(CC3CCOCC3)c3cnc(Br)cc23)n1] | Intermediate 87 | |
| 202 | | Intermediate 20 | Rt = 3.26 min, m/z $[M + H]^+$ = 458/460 (Method C) | b) Preparation of Intermediate 138

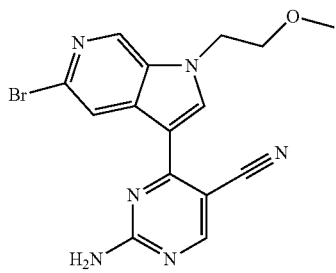 [SMILES: COCCn1cc(-c2nc(N)ncc2C#N)c2cc(Br)ncc21]

A mixture of intermediate 135 (0.10 g, 0.22 mmol), copper cyanide (0.02 g, 0.22 mmol) and DMF (1.0 ml) was stirred under a nitrogen atmosphere at 100° C. for 9 hours. The mixture was cooled to ambient temperature and partitioned between EtOAc and water. The organic phase was dried over sodium sulfate and concentrated in vacuo. The residue was purified by column chromatography on silica gel, eluting with a mixture of EtOAc and pentane (0:1 to 1:0 by volume), to afford the desired product (0.06 g, 68%).

LCMS (Method A): Rt=2.78 min, m/z [M+H]$^+$=373/375

Intermediates 139 and 140 were prepared according to the reaction protocol of intermediate 138 using the appropriate starting materials (Table 15).

TABLE 15

| Intermediate | Structure | Starting Materials | LCMS Data |
|---|---|---|---|
| 139 | 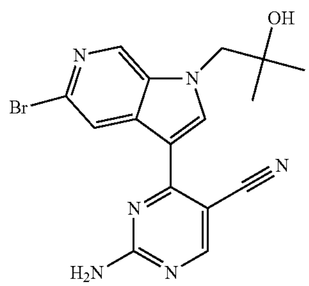 [SMILES: CC(C)(O)Cn1cc(-c2nc(N)ncc2C#N)c2cc(Br)ncc21] | Intermediate 136 | Rt = 2.59 min, m/z [M + H]$^+$ = 387/389 (Method C) |
| 140 | 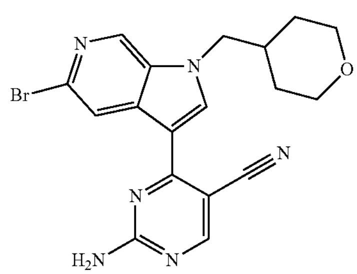 [SMILES: N#Cc1cnc(N)nc1-c1cn(CC2CCOCC2)c2cnc(Br)cc12] | Intermediate 137 | Rt = 2.92 min, m/z [M + H]$^+$ = 413/415 (Method C) |

Example A23
a) Preparation of Intermediate 141

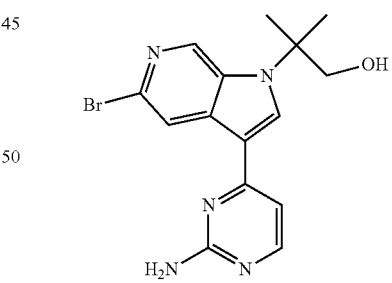

A stirred solution of intermediate 93 (0.10 g, 0.26 mmol) in anhydrous tetrahydrofuran (6 ml) under nitrogen atmosphere at 0° C. was treated with a 1 M solution of lithium aluminium hydride in tetrahydrofuran (0.38 ml, 0.38 mmol). After 0.5 hour, the mixture was diluted sequentially with water (1.0 ml) and 3.75 M aqueous solution of sodium hydroxide (0.5 ml), and the resulting mixture was stirred for 10 minutes. The mixture was filtered through celite, dried over magnesium sulfate and concentrated in vacuo. The residue was purified by column chromatography on silica gel, eluting with a mixture of DCM and MeOH (1:0 to 9:1 by volume), to afford the desired product (0.06 g, 65%).

LCMS (Method C): Rt=1.88 min, m/z [M+H]$^+$=362/364

Example A24 a) Preparation of Intermediate 142

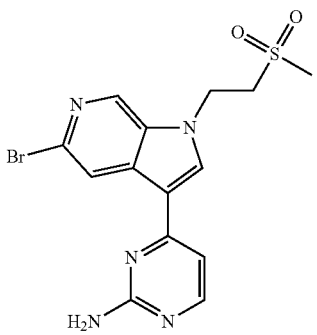 [SMILES: CS(=O)(=O)CCn1cc(-c2ccnc(N)n2)c2cc(Br)ncc21]

A mixture of intermediate 4 (0.10 g, 0.35 mmol), methanesulfonyl-ethene (0.26 ml, 2.92 mmol), triethylamine (0.12 ml, 0.828 mmol) and MeOH (2.0 ml) was heated by microwave irradiation at 120° C. for 0.5 hour. The mixture was cooled to ambient temperature and concentrated in vacuo. The residue was purified by column chromatography on silica gel, eluting with a mixture of DCM and 2 M ammonia solution in MeOH (1:0 to 19:1 by volume), to afford the desired product as a beige solid (0.11 g, 81%).

LCMS (Method B): Rt=1.59/1.72 min, m/z [M+H]$^+$=396/398

Example A25 a) Preparation of Intermediate 143

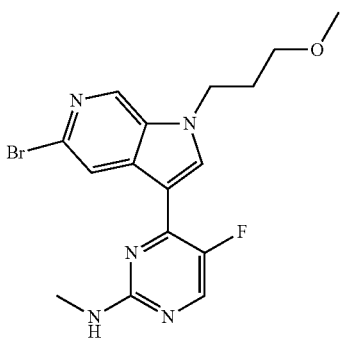 [SMILES: CNc1ncc(F)c(-c2cn(CCCOC)c3cnc(Br)cc23)n1]

A mixture of intermediate 107 (0.21 g, 0.52 mmol), methylamine hydrochloride (0.14 g, 2.10 mmol), DIPEA (0.55 ml, 3.15 mmol), 1-butanol (2.5 ml) and tetrahydrofuran (1.5 ml) was heated by microwave irradiation at 150° C. for 8 hours. The mixture was cooled to ambient temperature and concentrated in vacuo. The residue was purified by column chromatography on silica gel, eluting with a mixture of EtOAc and cyclohexane (0:1 to 1:0 by volume), to afford the desired product as a white solid (0.18 g, 86%).

LCMS (Method C): Rt=3.14 min, m/z [M+H]$^+$=394/396

Example A26 a) Preparation of Intermediate 144

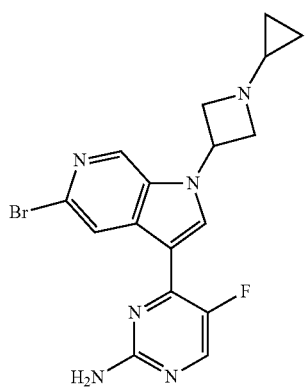 [SMILES: Nc1ncc(F)c(-c2cn(C3CN(C4CC4)C3)c3cnc(Br)cc23)n1]

A stirred solution of intermediate 121 (0.34 g, 0.94 mmol) in a mixture of MeOH (9 ml) and acetic acid (4.5 ml) under nitrogen atmosphere at ambient temperature was treated with (1-ethoxycyclopropoxy)trimethylsilane (0.94 ml, 4.68 mmol). After stirring for 10 minutes, the mixture was treated with sodium cyanoborohydride (0.35 g, 5.62 mmol) and the resulting mixture was stirred at 55° C. for 1.5 hours. The mixture was cooled to ambient temperature and purified by ISOLUTE® SCX-2 SPE column, eluting with a mixture of MeOH and 2.0 M ammonia solution in MeOH (1:0 to 0:1 by volume). Further purification by column chromatography on silica gel, eluting with a mixture of 2.0 M ammonia solution in MeOH and DCM (0:1 to 1:19 by volume), afforded the desired product as a white solid (0.09 g, 25%).

LCMS (Method B): Rt=1.82 min, m/z [M+H]$^+$=403/405

Intermediate 199 was prepared according to the reaction protocol of example A26 using the appropriate starting materials (Table 16).

TABLE 16

| Intermediate | Structure | Starting Materials | LCMS Data |
|---|---|---|---|
| 199 | 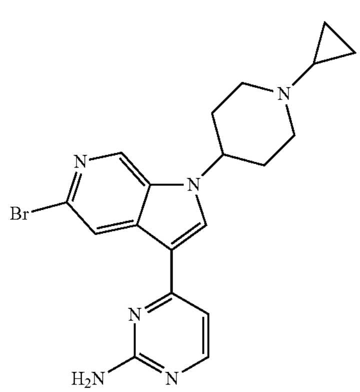 [SMILES: Nc1nccc(-c2cn(C3CCN(C4CC4)CC3)c3cnc(Br)cc23)n1] | a) Intermediate 119<br>b) (1-ethoxycyclopropoxy)trimethylsilane | Rt = 1.39 min, m/z [M + H]$^+$ = 413/415 (Method C) |

Example A27 a) Preparation of Intermediate 145

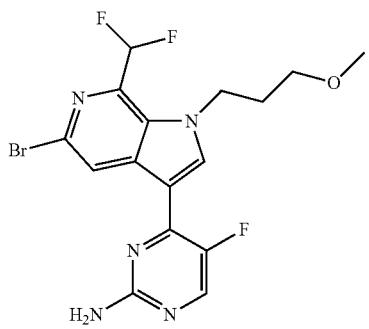 [SMILES: COCCCn1cc(-c2nc(N)ncc2F)c2cc(Br)nc(C(F)F)c21]

A stirred suspension of intermediate 101 (0.20 g, 0.526 mmol) and zinc difluoromethanesulfinate (0.31 g, 1.05 mmol) in a mixture of DCM (8.0 ml) and water (3.2 ml) at ambient temperature was treated sequentially with trifluoroacetic acid (0.04 ml, 0.52 mmol) and tert-butylhydroperoxide 70% solution in water (1.84 mmol). After stirring for 24 hours, the mixture was treated sequentially with zinc difluoromethanesulfinate (0.31 g, 1.05 mmol) and tert-butylhydroperoxide 70% solution in water (0.94 mmol), and the resulting mixture was stirred for 48 hours. The mixture was partitioned between DCM and saturated aqueous sodium bicarbonate solution. The organic phase was dried over magnesium sulfate and concentrated in vacuo. The residue was purified by column chromatography on silica gel, eluting with a mixture of MeOH and DCM (0:100 to 1:19 by volume), to afford the desired product (0.06 g, 24%).

LCMS (Method B): Rt=3.22 min, m/z [M+H]$^+$=430/432

Example A28 a) Preparation of Intermediate 146

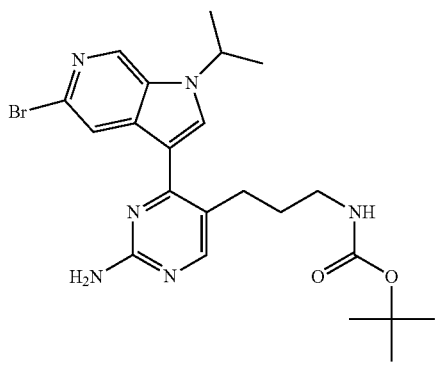 [SMILES: CC(C)n1cc(-c2nc(N)ncc2CCCNC(=O)OC(C)(C)C)c2cc(Br)ncc21]

A stirred solution of intermediate 54 (0.2 g, 0.48 mmol) in a mixture of tetrahydrofuran (3.6 ml) and water (0.4 ml) at ambient temperature was treated sequentially with triethylamine (0.15 g, 1.44 mmol), di-tert-butyldicarbonate (0.2 g, 0.96 mmol) and triphenyl phosphine (0.25 g, 0.96 mmol), and the resulting mixture was stirred at 30° C. for 18 hours. The mixture was cooled to ambient temperature and concentrated in vacuo. The residue was purified by preparative TLC to afford the desired product (0.05 g, 21%).

Example A29 a) Preparation of Intermediate 147

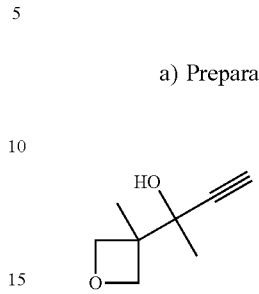

A stirred solution of 1-(3-methyl-oxetan-3-yl)-ethanone (0.5 g, 4.4 mmol) in anhydrous tetrahydrofuran (7.0 ml) under a nitrogen atmosphere at −78° C. was treated with 0.5 M solution of ethynylmagnesium bromide in tetrahydrofuran (9.7 ml, 4.85 mmol). The resulting mixture was warmed to ambient temperature and stirred for 3.5 hours. The mixture was cooled to 0° C., diluted with a saturated aqueous solution of ammonium chloride and extracted with Et$_2$O. The combined extracts were washed with water and dried over sodium sulfate. The solvent was removed in vacuo to afford the desired product (0.67 g, 100%).

Intermediates 148, 149, 159 and 174 were prepared according to the reaction protocol of example A29 using the appropriate starting materials (Table 17).

TABLE 17

| Intermediate | Structure | Starting Materials |
|---|---|---|
| 148 | 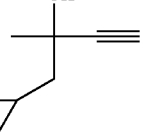 | 1-Cyclopropyl-propan-2-one |
| 149 | 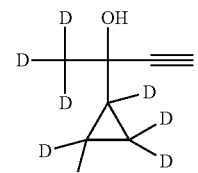 | Cyclopropyl methyl ketone-d8 |
| 159 | 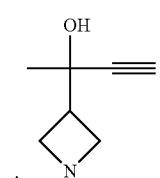 | 3-Acetyl azetidine-1-carboxylic acid tert-butyl ester |
| 174 | 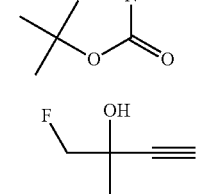 | 1-Cyclopropyl-2-fluoro-ethanone |

Example A30 a) Preparation of Intermediate 150

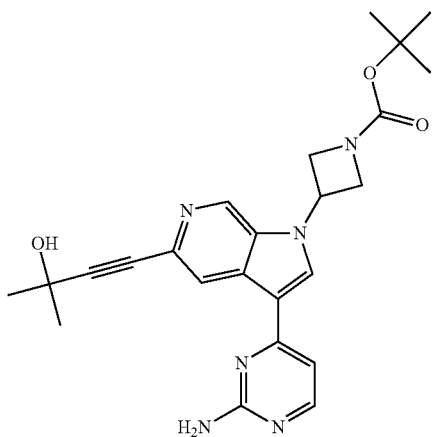 [SMILES: CC(C)(O)C#Cc1cc2c(-c3ccnc(N)n3)cn(C3CN(C(=O)OC(C)(C)C)C3)c2cn1]

A degassed suspension of intermediate 85 (0.07 g, 0.16 mmol), 2-methyl-but-3-yn-2-ol (0.02 ml, 0.20 mmol), tetrakis(triphenylphosphine) palladium (0.04 g, 0.04 mmol), copper iodide (3.7 mg, 0.020 mmol) and triethylamine (0.191 ml, 1.37 mmol) in acetonitrile (2.6 ml) was heated by microwave irradiation at 100° C. for 1.25 hours. The mixture was cooled to ambient temperature, filtered and concentrated in vacuo. The residue was purified by column chromatography on silica gel, eluting with a mixture of MeOH in DCM (0:1 to 1:10 by volume), to afford the desired product (0.04 g, 55%).

LCMS (Method B): Rt=2.18 min, m/z [M+H]$^+$=449

Intermediates 151 to 158 were prepared according to the reaction protocol of example A30 using the appropriate starting materials (Table 18).

TABLE 18

| Intermediate | Structure | Starting Materials | LCMS Data |
|---|---|---|---|
| 151 | 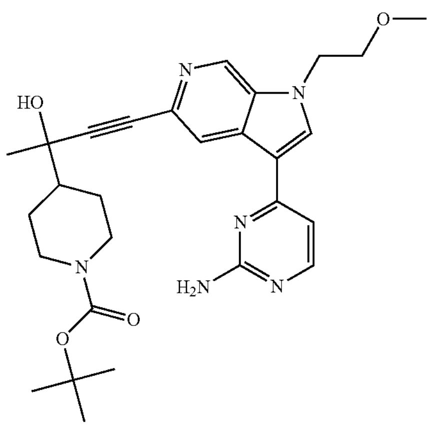 [SMILES: COCCn1cc(-c2ccnc(N)n2)c2cc(C#CC(C)(O)C3CCN(C(=O)OC(C)(C)C)CC3)ncc21] | a) Intermediate 13<br>b) 4-(1-Hydroxy-1-methyl-prop-2-ynyl)-piperidine-1-carboxylic acid tert-butyl ester | Rt = 2.92 min, m/z [M + H]$^+$ = 521 (Method E) |
| 152 | 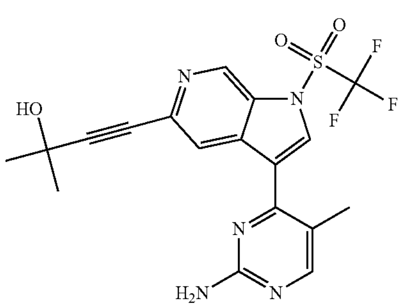 [SMILES: Cc1cnc(N)nc1-c1cn(S(=O)(=O)C(F)(F)F)c2cnc(C#CC(C)(C)O)cc12] | a) Intermediate 73<br>b) 2-Methyl-but-3-yn-2-ol | Rt = 2.94 min, m/z [M + H]$^+$ = 440 (Method B) |

TABLE 18-continued

| Intermediate | Structure | Starting Materials | LCMS Data |
| --- | --- | --- | --- |
| 153 | 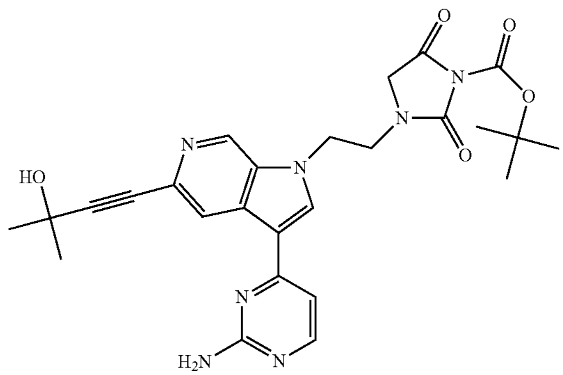 [SMILES: CC(C)(O)C#Cc1cc2c(-c3ccnc(N)n3)cn(CCN3CC(=O)N(C(=O)OC(C)(C)C)C3=O)c2cn1] | a) Intermediate 91<br>b) 2-Methyl-but-3-yn-2-ol | Rt = 1.99 min, m/z [M + H]$^+$ = 520 (Method C) |
| 154 | 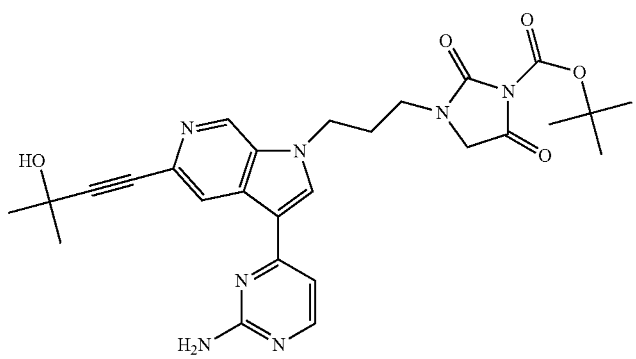 [SMILES: CC(C)(O)C#Cc1cc2c(-c3ccnc(N)n3)cn(CCCN3CC(=O)N(C(=O)OC(C)(C)C)C3=O)c2cn1] | a) Intermediate 94<br>b) 2-Methyl-but-3-yn-2-ol | Rt = 2.02 min, m/z [M + H]$^+$ = 534 (Method C) |
| 155 | 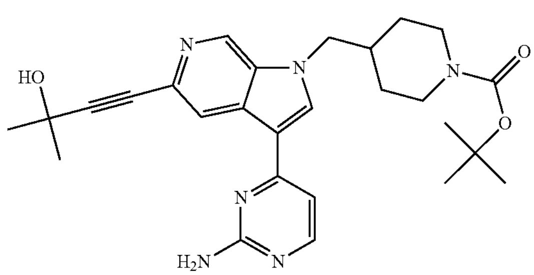 [SMILES: CC(C)(O)C#Cc1cc2c(-c3ccnc(N)n3)cn(CC3CCN(C(=O)OC(C)(C)C)CC3)c2cn1] | a) Intermediate 83<br>b) 2-Methyl-but-3-yn-2-ol | Rt = 1.95 min, m/z [M + H]$^+$ = 491 (Method A) |
| 156 | 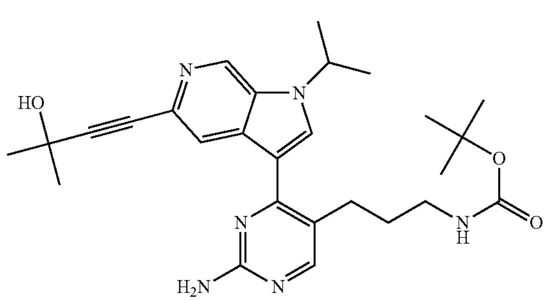 [SMILES: CC(C)n1cc(-c2nc(N)ncc2CCCNC(=O)OC(C)(C)C)c2cc(C#CC(C)(C)O)ncc21] | a) Intermediate 146<br>b) 2-Methyl-but-3-yn-2-ol | |

TABLE 18-continued

| Intermediate | Structure | Starting Materials | LCMS Data |
|---|---|---|---|
| 157 | 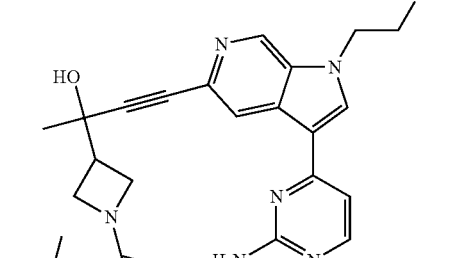 | a) Intermediate 13<br>b) Intermediate 159 | Rt = 2.10 min, m/z<br>[M + H]$^+$ = 493<br>(Method B) |
| 158 | 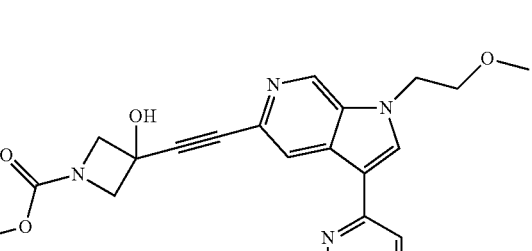 | a) Intermediate 13<br>b) 3-Ethynyl-3-hydroxy-azetidine-1-carboxylic acid tert-butyl ester | Rt = 1.90 min, m/z<br>[M + H]$^+$ = 465<br>(Method C) |

Example A31 a) Preparation of Intermediate 175

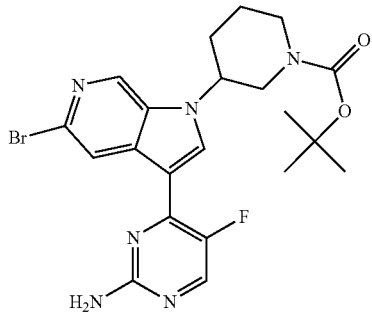 [SMILES: CC(C)(C)OC(=O)N1CCCC(n2cc(-c3nc(N)ncc3F)c3cc(Br)ncc32)C1]

A stirred mixture of intermediate 62 (0.70 g, 1.66 mmol), powdered potassium hydroxide (0.11 g, 1.96 mmol), toluene (15.0 ml) and DMF (1.0 ml) under a nitrogen atmosphere at 80° C. was treated portionwise with 3-methanesulfonyloxy-piperidine-1-carboxylic acid tert-butyl ester (0.27 g, 0.98 mmol) over 1 hour. After 6 hours, a second aliquot of 3-methanesulfonyloxy-piperidine-1-carboxylic acid tert-butyl ester (0.27 g, 0.98 mmol) was added and the resulting mixture stirred at 80° C. for 18 hours. The mixture was cooled to ambient temperature and concentrated in vacuo. The residue was partitioned between water and DCM. The organic phase was dried over sodium sulfate and concentrated in vacuo to afford the desired product as a yellow oil (0.79 g, 97%).

LCMS (Method C): Rt=3.51 min, m/z [M+H]$^+$=491/493

Example A32 a) Preparation of Intermediate 177

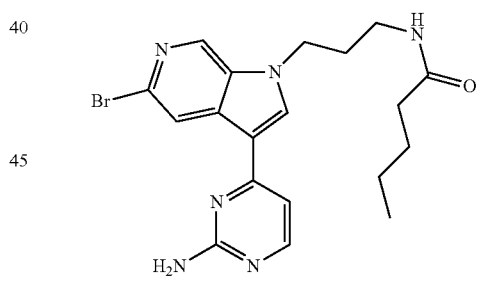

A stirred mixture of intermediate 186 (0.17 g, 0.49 mmol), triethylamine (0.10 ml, 0.73 mmol) and DMF (5.0 ml) at ambient temperature was treated with pentanoyl chloride (0.06 ml, 0.54 mmol). After 0.5 hour, the mixture was concentrated in vacuo and the residue purified by ISOLUTE® SCX-2 SPE column, eluting with a mixture of MeOH and 2.0 M ammonia solution in MeOH (1:0 to 0:1 by volume). Further purification by column chromatography on silica gel, eluting with a mixture of 2.0 M ammonia solution in MeOH and DCM (0:1 to 1:9 by volume) afforded the desired product as a yellow foam (0.12 g, 57%). LCMS (Method C): Rt=2.08 min, m/z [M+H]$^+$=431/433

Intermediate 191 was prepared according to the reaction protocol of example A32 using the appropriate starting materials (Table 19).

TABLE 19

| Intermediate | Structure | Starting Materials | LCMS Data |
| --- | --- | --- | --- |
| 191 | 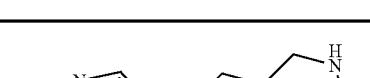 | a) Intermediate 186<br>b) Acetyl chloride | Rt = 1.81 min, m/z<br>[M + H]⁺ = 359/391<br>(Method B) |

Example A33 a) Preparation of Intermediate 178

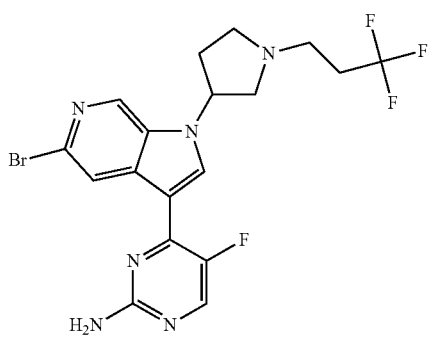 [SMILES: Nc1ncc(F)c(-c2cn(C3CCN(CCC(F)(F)F)C3)c3cnc(Br)cc23)n1]

A stirred mixture of intermediate 128 (0.23 g, 0.61 mmol), DIPEA (0.16 ml, 0.92 mmol) and DMF (6.0 ml) at ambient temperature was treated with 1,1,1-trifluoro-3-iodo-propane (0.09 ml, 0.79 mmol), and the resulting mixture was heated at 50° C. for 72 hours and then at 70° C. for 10 hours. The mixture was cooled to ambient temperature and concentrated in vacuo. The residue was purified by ISOLUTE® SCX-2 SPE column, eluting with a mixture of MeOH and 2.0 M ammonia solution in MeOH (1:0 to 0:1 by volume). Further purification by column chromatography on silica gel, eluting with a mixture of 2.0 M ammonia solution in MeOH and DCM (0:1 to 1:19 by volume), afforded the desired product as a cream solid (0.12 g, 43%).

LCMS (Method C): Rt=2.18 min, m/z [M+H]⁺=473/475

Intermediate 179, 198, 200 and 201 were prepared according to the reaction protocol of example A33 using the appropriate starting materials (Table 20).

TABLE 20

| Intermediate | Structure | Starting Materials | LCMS Data |
| --- | --- | --- | --- |
| 179 | 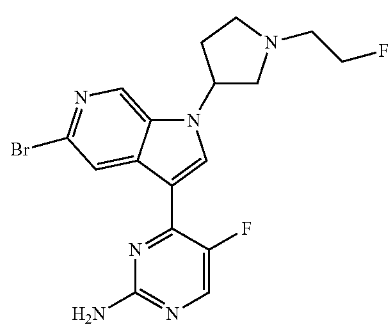 [SMILES: Nc1ncc(F)c(-c2cn(C3CCN(CCF)C3)c3cnc(Br)cc23)n1] | a) Intermediate 128<br>b) 1-Bromo-2-fluoro-ethane | Rt = 1.81 min, m/z<br>[M + H]⁺ = 423/425<br>(Method C) |

TABLE 20-continued

| Intermediate | Structure | Starting Materials | LCMS Data |
| --- | --- | --- | --- |
| 198 | 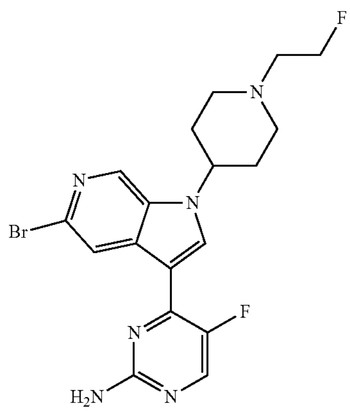 [SMILES: Nc1ncc(F)c(-c2cn(C3CCN(CCF)CC3)c3cnc(Br)cc23)n1] | a) Intermediate 120<br>b) 1-Bromo-2-fluoro-ethane | Rt = 1.84 min, m/z<br>[M + H]⁺ = 437/439<br>(Method B) |
| 200 | 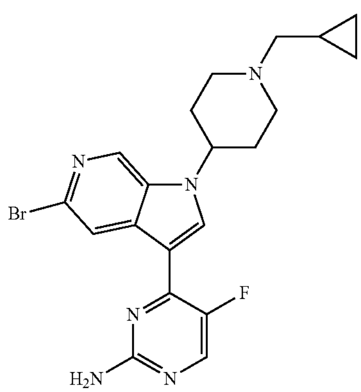 [SMILES: Nc1ncc(F)c(-c2cn(C3CCN(CC4CC4)CC3)c3cnc(Br)cc23)n1] | a) Intermediate 120<br>b) Iodomethyl-cyclopropane | Rt = 1.91 min, m/z<br>[M + H]⁺ = 445/447<br>(Method B) |
| 201 | 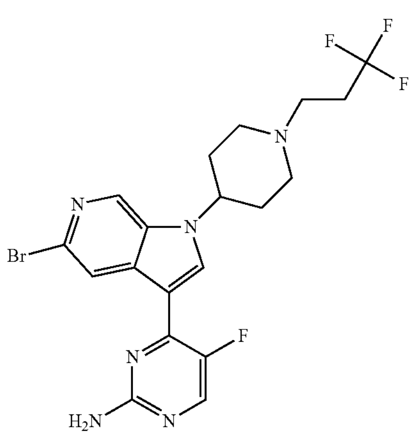 [SMILES: Nc1ncc(F)c(-c2cn(C3CCN(CCC(F)(F)F)CC3)c3cnc(Br)cc23)n1] | a) Intermediate 120<br>b) 1,1,1-Trifluoro-3-iodo-propane | Rt = 2.01 min, m/z<br>[M + H]⁺ = 487/489<br>(Method C) |

Example A34 a) Preparation of Intermediate 190

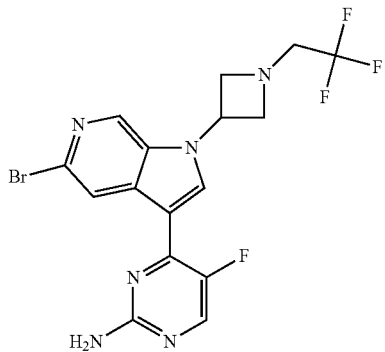 [SMILES: Nc1ncc(F)c(-c2cn(C3CN(CC(F)(F)F)C3)c3cnc(Br)cc23)n1]

A stirred mixture of intermediate 121 (0.25 g, 0.52 mmol), DIPEA (0.27 ml, 1.57 mmol) and tetrahydrofuran (7.0 ml) under a nitrogen atmosphere at 0° C. was treated with trifluoro-methanesulfonic acid 2,2,2-trifluoro-ethyl ester (0.08 ml, 0.55 mmol). After stirring at ambient temperature for 2 hours, a second aliquot of trifluoro-methanesulfonic acid 2,2,2-trifluoro-ethyl ester (0.18 ml, 1.24 mmol) was added and the resulting mixture was stirred at 50° C. for 2.5 hours. The mixture was cooled to ambient temperature and concentrated in vacuo. The residue was purified by column chromatography on silica gel, eluting with a mixture of MeOH and DCM (0:1 to 1:19 by volume), to afford the desired product as a white solid (0.12 g, 74%).

LCMS (Method B): Rt=3.12 min, m/z [M+H]$^+$=445/447

Example A35 a) Preparation of Intermediate 192

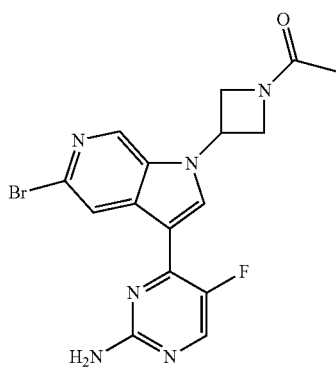 [SMILES: CC(=O)N1CC(n2cc(-c3nc(N)ncc3F)c3cc(Br)ncc32)C1]

A stirred mixture of intermediate 121 (0.20 g, 0.42 mmol), triethylamine (0.17 ml, 1.22 mmol) and tetrahydrofuran (4.0 ml) under a nitrogen atmosphere at 0° C. was treated with acetyl chloride (0.04 ml, 0.61 mmol), and the resulting mixture was stirred at ambient temperature for 1.5 hours. The mixture was concentrated in vacuo and the residue was purified by column chromatography on silica gel, eluting with a mixture of 2 M ammonia solution in MeOH and DCM (0:1 to 1:9 by volume), to afford the desired product as a white solid (0.10 g, 59%).

LCMS (Method B): Rt=2.29 min, m/z [M+H]$^+$=405/407

Example A36 a) Preparation of Intermediate 203

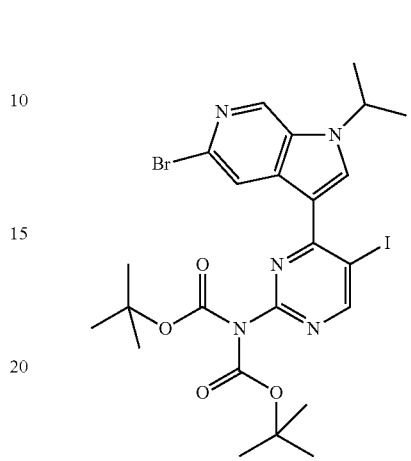

A stirred suspension of intermediate 202 (0.47 g, 1.03 mmol) in THF (12 ml) under a nitrogen atmosphere at ambient temperature was treated sequentially with 4-dimethylaminopyridine (0.03 g, 0.21 mmol), triethylamine (0.43 ml, 3.09 mmol) and di-tert-butyldicarbonate (0.49 g, 2.27 mmol). The resulting mixture was stirred at 50° C. for 2 hour. A second aliquot of di-tert-butyldicarbonate (0.49 g, 2.27 mmol) was added and the mixture was heated at 50° C. for 3 hours. The mixture was cooled to ambient temperature and partitioned between water and EtOAc. The organic phase was dried over sodium sulfate and concentrated in vacuo. The residue was purified by column chromatography on silica gel, eluting with a mixture of EtOAc and pentane (0:1 to 7:3 by volume), to afford the desired product as a brown solid (0.55 g, 81%).

LCMS (Method B): Rt=4.64 min, m/z [M+H]+=658/660b)

Preparation of Intermediate 204

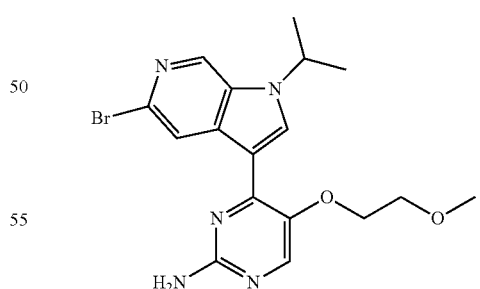

A stirred mixture of intermediate 203 (0.50 g, 0.76 mmol), copper iodide (0.06 g, 0.30 mmol), 1,10-phenanthroline (0.11 g, 0.608 mmol), caesium carbonate (0.49 g, 1.52 mmol) and 2-methoxyethanol (10.0 ml, 127 mmol) was heated by microwave irradiation at 100° C. for 0.5 hour. The mixture was cooled to ambient temperature, filtered and the filtrate concentrated in vacuo. The residue was diluted with DCM (10 ml) and treated with trifluoroacetic acid (5 ml).

223

The resulting mixture was stirred at ambient temperature for 1 hour. The mixture was then concentrated in vacuo and the residue purified by ISOLUTE® SCX-2 SPE column, eluting with a mixture of MeOH and 2.0 M ammonia solution in MeOH (1:0 to 0:1 by volume). Further purification by column chromatography on silica gel, eluting with a mixture of EtOAc and pentane (0:1 to 1:0) followed by 2.0 M ammonia solution in MeOH and DCM (0:1 to 1:19 by volume), afforded the desired product as a white solid (0.09 g, 30%).

LCMS (Method B): Rt=2.28 min, m/z [M+H]+=406/408

Example A37 a) Preparation of Intermediate 205

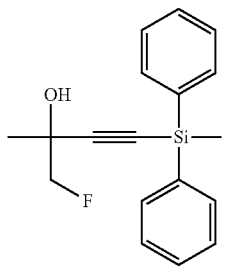 [SMILES: CC(O)(C#C[Si](C)(c1ccccc1)c1ccccc1)CF]

A stirred solution of (methyldiphenylsilyl)acetylene (1.10 ml, 4.99 mmol) in anhydrous tetrahydrofuran (20 ml) under an argon atmosphere at −78° C. was treated with 1.6 M solution of n-butyllithium in hexanes (3.2 ml, 5.12 mmol) maintaining the temperature below −70° C. After stirring for 1 hour, the mixture was treated with 1-fluoro-2-propanone (0.36 ml, 5.00 mmol) and the resulting mixture stirred at 0° C. for 1.5 hours. The mixture was quenched by the addition of water and partitioned between water and diethyl ether. The organic phase was washed with brine, dried over sodium sulfate and concentrated in vacuo. The residue was purified by column chromatography on silica gel, eluting with a mixture of diethyl ether and pentane (0:1 to 1:19 by volume), to afford the desired product as a colourless oil (0.91 g, 61%).

Intermediate 206 was prepared according to the reaction protocol of example A37 using the appropriate starting materials (Table 21).

TABLE 21

| Intermediate | Structure | Starting Materials |
|---|---|---|
| 206 | 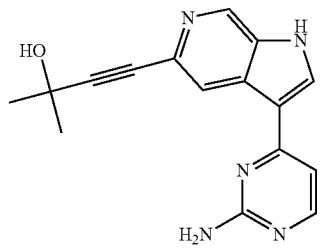 [SMILES: CC(C)(O)C#Cc1cc2c(-c3ccnc(N)n3)c[nH]c2cn1] | 1-Cyclopropyl-ethanone |

224

Example A38 a) Preparation of Intermediate 207

Intermediate 206 (1.40 g, 4.57 mmol) was purified by chiral preparative HPLC with the following conditions: column, Diacel Chiralpak IC, 250×20 mm, 5 μm; mobile phase, DCM in Heptane (40%), flow 18 ml/min; detector, UV 254 nm. The first eluting enantiomer was isolated as a colourless oil (0.45 g, 32%) and second eluting enantiomer (intermediate 207) as a colourless oil (0.49 g, 35%).

Preparation of Compounds

The values of acid content (e.g. formic acid or acetic acid) in the compounds as provided herein, are those obtained experimentally and may vary when using different analytical methods. The content of formic acid or acetic acid reported herein was determined by $^1$H NMR integration and is reported together with the $^1$H NMR results. Compounds with an acid content of below 0.5 equivalents may be considered as free bases.

Example B1

Example B1.a

Preparation of Compound 1

A mixture of intermediate 4 (0.07 g, 0.21 mmol), 2-methylbut-3-yn-2-ol (0.02 g, 0.23 mmol), tetrakis(triphenylphosphine) palladium (0.05 g, 0.04 mmol), copper(I) iodide (4.0 mg, 0.02 mmol), triethylamine (0.24 ml, 1.43 mmol) and acetonitrile (1.5 ml) was heated by microwave irradiation at 100° C. for 15 minutes. The mixture was cooled to ambient temperature and concentrated in vacuo. The residue was purified by column chromatography on silica gel, eluting with a mixture of MeOH and DCM (1:19 to 1:4 by volume), followed by trituration with Et$_2$O to afford the desired product as a pale yellow solid (0.022 g, 31%).

LCMS (Method E): R$_t$=1.69 min, m/z [M+H]$^+$=294

$^1$H NMR (400 MHz, DMSO-d$_6$) δ ppm: 12.27 (s, 1H), 8.73 (d, J=1.1 Hz, 1H), 8.51 (s, 1H), 8.45 (d, J=2.9 Hz, 1H), 8.16 (d, J=5.3 Hz, 1H), 7.04 (d, J=5.3 Hz, 1H), 6.56 (s, 2H), 5.47 (s, 1H), 1.52 (s, 6H).

A second batch was isolated with 1.0 equivalents of formic acid present.

Example B1.b

Preparation of Compound 97

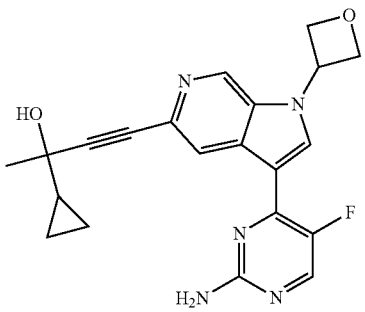 [SMILES: CC(O)(C#Cc1cc2c(-c3nc(N)ncc3F)cn(C3COC3)c2cn1)C1CC1]

A mixture of intermediate 100 (0.35 g, 0.96 mmol), 2-cyclopropyl-but-3-yn-2-ol (0.33 g, 2.96 mmol), tetrakis (triphenylphosphine) palladium (0.22 g, 0.19 mmol), copper (I) iodide (0.02 g, 0.09 mmol), triethylamine (0.95 ml, 6.82 mmol) and acetonitrile (15 ml) was heated by microwave irradiation at 100° C. for 2 hours. The mixture was cooled to ambient temperature and concentrated in vacuo. The residue was purified by ISOLUTE® SCX-2 SPE column, eluting with a mixture of MeOH and 2.0 M ammonia solution in MeOH (1:0 to 0:1 by volume). Further purification by column chromatography on silica gel, eluting with a mixture of 2.0 M ammonia solution in MeOH and DCM (1:19 by volume), afforded the desired product as a pale yellow solid (0.24 g, 62%).

LCMS (Method E): Rt=2.62 min, m/z [M+H]$^+$=394

$^1$H NMR (400 MHz, DMSO-d$_6$) δ ppm: 9.03 (d, J=0.9 Hz, 1H), 8.60 (d, J=0.9 Hz, 1H), 8.54 (d, J=2.1 Hz, 1H), 8.30 (d, J=3.7 Hz, 1H), 6.67 (s, 2H), 6.01-5.93 (m, 1H), 5.35 (s, 1H), 5.11 (t, J=7.5 Hz, 2H), 5.00 (t, J=6.6 Hz, 2H), 1.55 (s, 3H), 1.22-1.14 (m, 1H), 0.60-0.39 (m, 4H).

Example B1.c a) Preparation of Compound 104

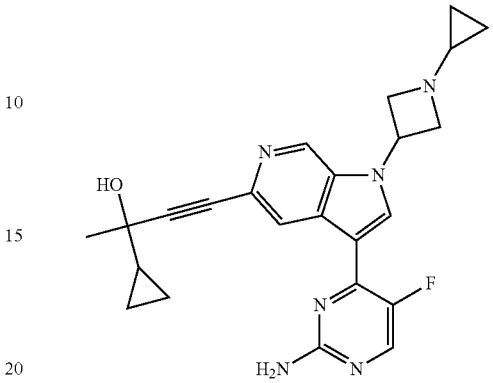

A mixture of intermediate 144 (0.09 g, 0.23 mmol), 2-cyclopropyl-but-3-yn-2-ol (0.07 g, 0.69 mmol), tetrakis (triphenylphosphine) palladium (0.05 g, 0.04 mmol), copper (I) iodide (4.0 mg, 0.02 mmol), triethylamine (0.23 ml, 1.62 mmol) and acetonitrile (3.0 ml) was heated by microwave irradiation at 100° C. for 1 hour. The mixture was cooled to ambient temperature and concentrated in vacuo. The residue was purified by column chromatography on silica gel, eluting with a mixture of 2.0 M ammonia solution in MeOH and DCM (1:0 to 1:19 by volume). Further purification by reverse phase preparative HPLC, eluting with a mixture of acetonitrile and water containing 0.1% ammonium hydroxide (1:19 to 7:3 by volume over 20 min), afforded the desired product as a white solid (0.044 g, 43%).

LCMS (Method E): Rt=2.25 min, m/z [M+H]$^+$=433

$^1$H NMR (400 MHz, DMSO-d$_6$) δ ppm: 9.01 (d, J=1.0 Hz, 1H), 8.56 (d, J=1.0 Hz, 1H), 8.45 (d, J=2.2 Hz, 1H), 8.28 (d, J=3.7 Hz, 1H), 6.66 (s, 2H), 5.37-5.29 (m, 2H), 3.90-3.85 (m, 2H), 3.63-3.58 (m, 2H), 2.13-2.07 (m, 1H), 1.54 (s, 3H), 1.21-1.14 (m, 1H), 0.61-0.48 (m, 2H), 0.48-0.36 (m, 4H), 0.34-0.30 (m, 2H).

Compounds 2 to 96, 98 to 103, 105 to 110, 123, 126 to 156, 158 to 160, and 162 to 168 were prepared according to the reaction protocols of example B1 (B1.a, B1.b, B1.c) (Table 22).

TABLE 22

| Compound | Structure | Starting Materials |
| --- | --- | --- |
| 2 | (structure) | a) Intermediate 13<br>b) 2-Methylbut-3-yn-2-ol |

TABLE 22-continued
| Compound | Structure | Starting Materials |
|---|---|---|
| 3 | 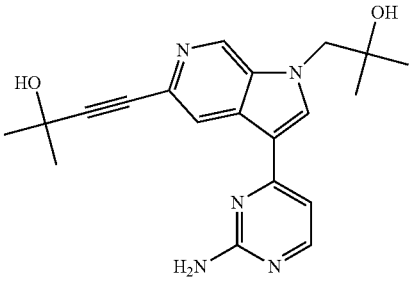 [SMILES: CC(C)(O)C#Cc1cc2c(-c3ccnc(N)n3)cn(CC(C)(C)O)c2cn1] | a) Intermediate 14<br>b) 2-Methylbut-3-yn-2-ol |
| 4 | 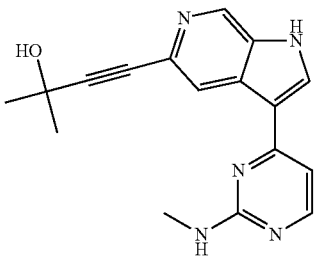 [SMILES: CNc1nccc(-c2c[nH]c3cnc(C#CC(C)(C)O)cc23)n1] | a) Intermediate 6<br>b) 2-Methylbut-3-yn-2-ol |
| 5 | 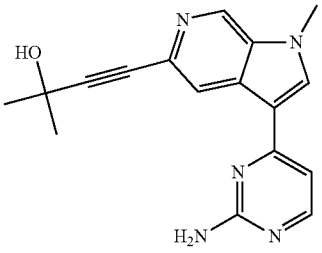 [SMILES: Cn1cc(-c2ccnc(N)n2)c2cc(C#CC(C)(C)O)ncc21] | a) Intermediate 7<br>b) 2-Methylbut-3-yn-2-ol |
| 6 | 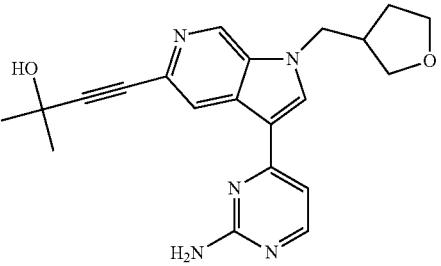 [SMILES: CC(C)(O)C#Cc1cc2c(-c3ccnc(N)n3)cn(CC3CCOC3)c2cn1] | a) Intermediate 8<br>b) 2-Methylbut-3-yn-2-ol |
| 7 | 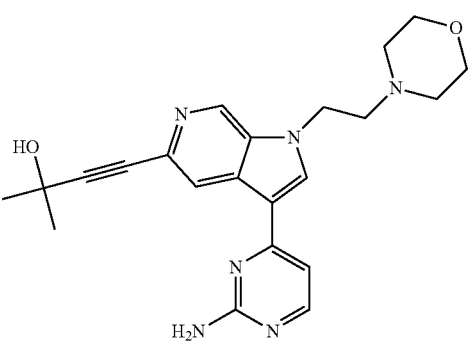 [SMILES: CC(C)(O)C#Cc1cc2c(-c3ccnc(N)n3)cn(CCN3CCOCC3)c2cn1] | a) Intermediate 9<br>b) 2-Methylbut-3-yn-2-ol |

TABLE 22-continued
| Compound | Structure | Starting Materials |
|---|---|---|
| 8 | 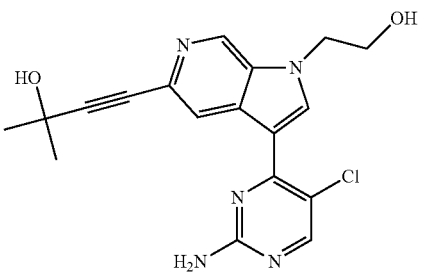 [SMILES: CC(C)(O)C#Cc1cc2c(-c3nc(N)ncc3Cl)cn(CCO)c2cn1] | a) Intermediate 10<br>b) 2-Methylbut-3-yn-2-ol |
| 9 | 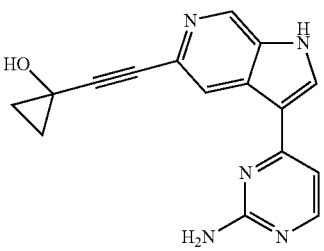 [SMILES: Nc1nccc(-c2c[nH]c3cnc(C#CC4(O)CC4)cc23)n1] | a) Intermediate 4<br>b) 1-Ethynyl-cyclopropanol |
| 10 | 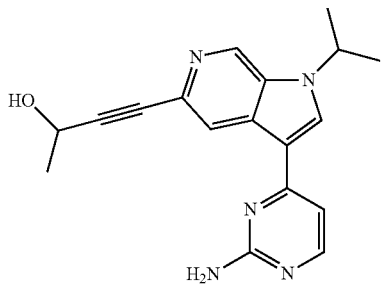 [SMILES: CC(O)C#Cc1cc2c(-c3ccnc(N)n3)cn(C(C)C)c2cn1] | a) Intermediate 20<br>b) But-3-yn-2-ol |
| 11 | 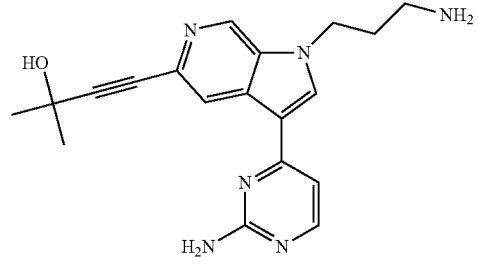 [SMILES: CC(C)(O)C#Cc1cc2c(-c3ccnc(N)n3)cn(CCCN)c2cn1] | a) Intermediate 16<br>b) 2-Methylbut-3-yn-2-ol |
| 12 | 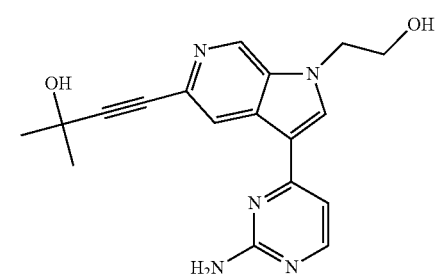 [SMILES: CC(C)(O)C#Cc1cc2c(-c3ccnc(N)n3)cn(CCO)c2cn1] | a) Intermediate 12<br>b) 2-Methylbut-3-yn-2-ol |

TABLE 22-continued

| Compound | Structure | Starting Materials |
| --- | --- | --- |
| 13 | 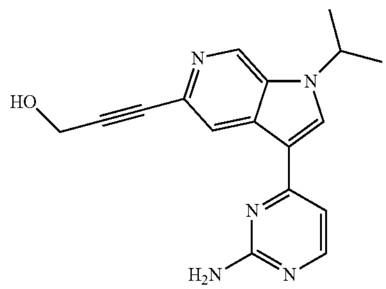 [SMILES: CC(C)n1cc(-c2ccnc(N)n2)c2cc(C#CCO)ncc21] | a) Intermediate 20<br>b) Prop-2-yn-1-ol |
| 14 | 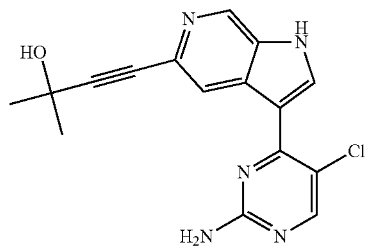 [SMILES: CC(C)(O)C#Cc1cc2c(-c3nc(N)ncc3Cl)c[nH]c2cn1] | a) Intermediate 5<br>b) 2-Methylbut-3-yn-2-ol |
| 15 | 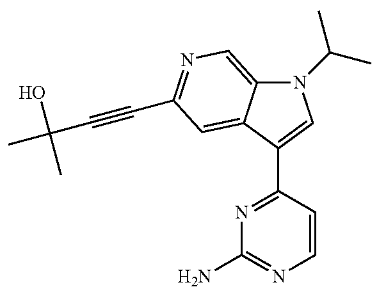 [SMILES: CC(C)n1cc(-c2ccnc(N)n2)c2cc(C#CC(C)(C)O)ncc21] | a) Intermediate 20<br>b) 2-Methylbut-3-yn-2-ol |
| 16 | 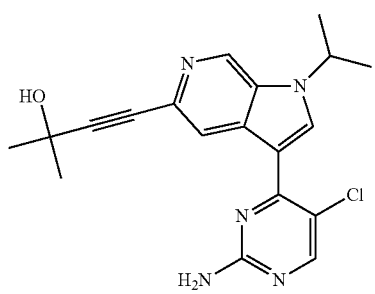 [SMILES: CC(C)n1cc(-c2nc(N)ncc2Cl)c2cc(C#CC(C)(C)O)ncc21] | a) Intermediate 21<br>b) 2-Methylbut-3-yn-2-ol |
| 17 | 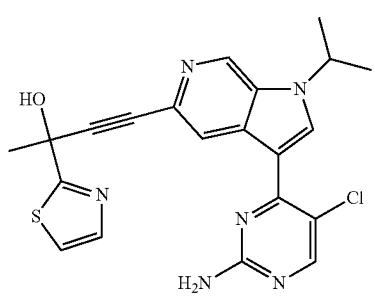 [SMILES: CC(C)n1cc(-c2nc(N)ncc2Cl)c2cc(C#CC(C)(O)c3nccs3)ncc21] | a) Intermediate 21<br>b) 2-Thiazol-2-yl-but-3-yn-2-ol |

TABLE 22-continued

| Compound | Structure | Starting Materials |
| --- | --- | --- |
| 18 | 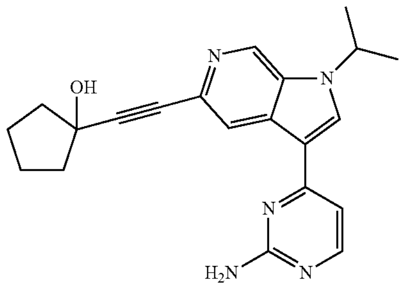 [SMILES: CC(C)n1cc(-c2ccnc(N)n2)c2cc(C#CC3(O)CCCC3)ncc21] | a) Intermediate 20<br>b) 1-Ethynylcyclopentanol |
| 19 | 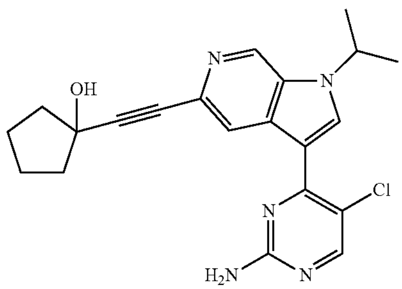 [SMILES: CC(C)n1cc(-c2nc(N)ncc2Cl)c2cc(C#CC3(O)CCCC3)ncc21] | a) Intermediate 21<br>b) 1-Ethynylcyclopentanol |
| 20 | 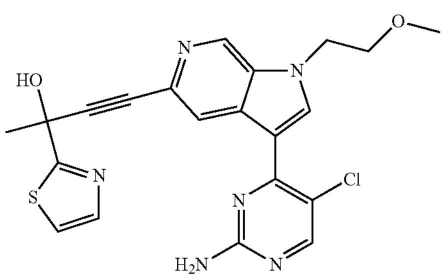 [SMILES: COCCn1cc(-c2nc(N)ncc2Cl)c2cc(C#CC(C)(O)c3nccs3)ncc21] | a) Intermediate 23<br>b) 2-Thiazol-2-yl-but-3-yn-2-ol |
| 21 | 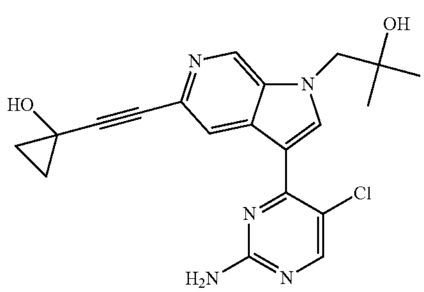 [SMILES: CC(C)(O)Cn1cc(-c2nc(N)ncc2Cl)c2cc(C#CC3(O)CC3)ncc21] | a) Intermediate 22<br>b) 1-Ethynyl-cyclopropanol |
| 22 | 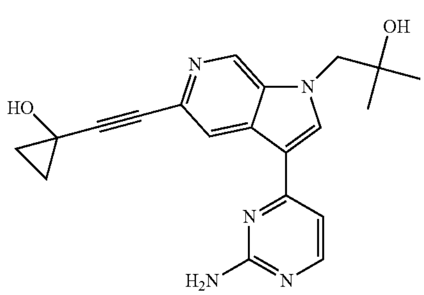 [SMILES: CC(C)(O)Cn1cc(-c2ccnc(N)n2)c2cc(C#CC3(O)CC3)ncc21] | a) Intermediate 14<br>b) 1-Ethynyl-cyclopropanol |

TABLE 22-continued

| Compound | Structure | Starting Materials |
|---|---|---|
| 23 | 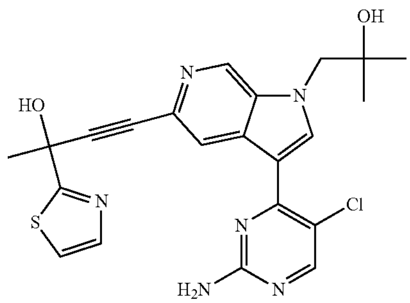 [SMILES: CC(C)(O)Cn1cc(-c2nc(N)ncc2Cl)c2cc(C#CC(C)(O)c3nccs3)ncc21] | a) Intermediate 22<br>b) 2-Thiazol-2-yl-but-3-yn-2-ol |
| 24 | 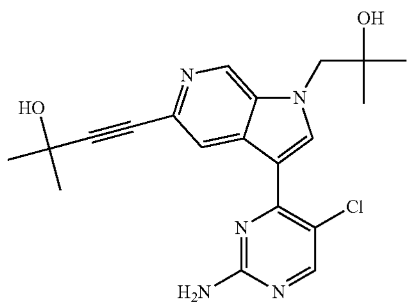 [SMILES: CC(C)(O)C#Cc1cc2c(-c3nc(N)ncc3Cl)cn(CC(C)(C)O)c2cn1] | a) Intermediate 22<br>b) 2-Methylbut-3-yn-2-ol |
| 25 | 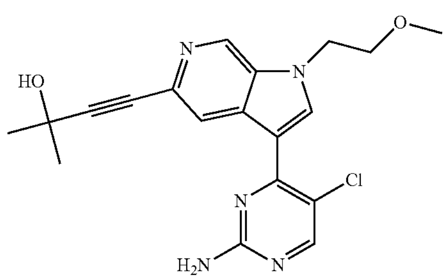 [SMILES: COCCn1cc(-c2nc(N)ncc2Cl)c2cc(C#CC(C)(C)O)ncc21] | a) Intermediate 23<br>b) 2-Methylbut-3-yn-2-ol |
| 26 | 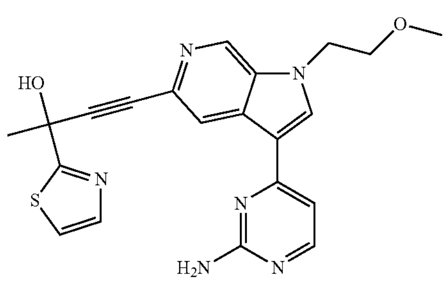 [SMILES: COCCn1cc(-c2ccnc(N)n2)c2cc(C#CC(C)(O)c3nccs3)ncc21] | a) Intermediate 13<br>b) 2-Thiazol-2-yl-but-3-yn-2-ol |
| 27 | 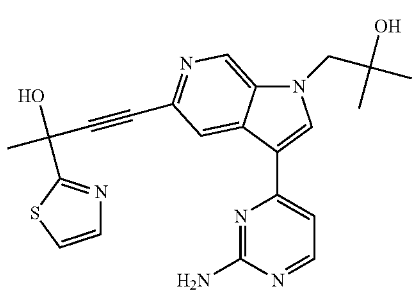 [SMILES: CC(C)(O)Cn1cc(-c2ccnc(N)n2)c2cc(C#CC(C)(O)c3nccs3)ncc21] | a) Intermediate 14<br>b) 2-Thiazol-2-yl-but-3-yn-2-ol |

TABLE 22-continued

| Compound | Structure | Starting Materials |
|---|---|---|
| 28 | 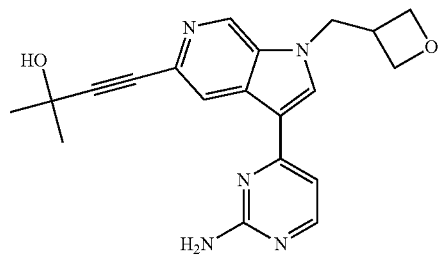 [SMILES: CC(C)(O)C#Cc1cc2c(-c3ccnc(N)n3)cn(CC3COC3)c2cn1] | a) Intermediate 15<br>b) 2-Methylbut-3-yn-2-ol |
| 29 | 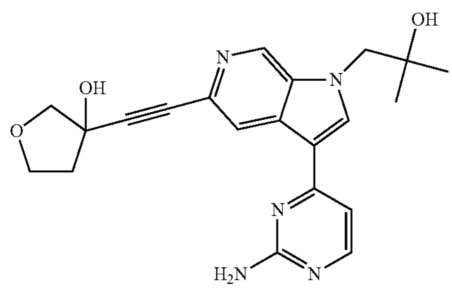 [SMILES: CC(C)(O)Cn1cc(-c2ccnc(N)n2)c2cc(C#CC3(O)CCOC3)ncc21] | a) Intermediate 14<br>b) 3-Ethynyl-tetrahydro-furan-3-ol |
| 30 | 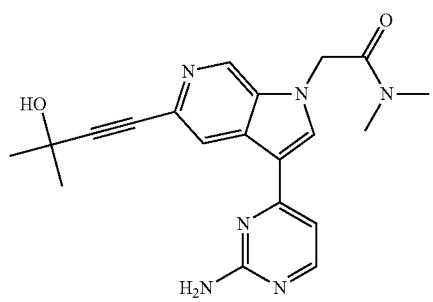 [SMILES: CN(C)C(=O)Cn1cc(-c2ccnc(N)n2)c2cc(C#CC(C)(C)O)ncc21] | a) Intermediate 80<br>b) 2-Methylbut-3-yn-2-ol |
| 31 | 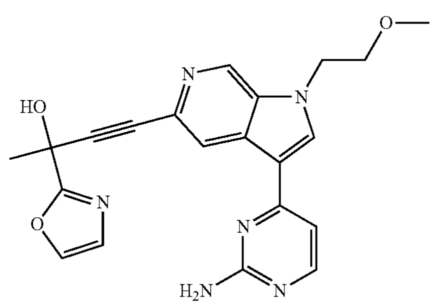 [SMILES: COCCn1cc(-c2ccnc(N)n2)c2cc(C#CC(C)(O)c3ncco3)ncc21] | a) Intermediate 13<br>b) 2-Oxazol-2-yl-but-3-yn-2-ol |
| 32 | 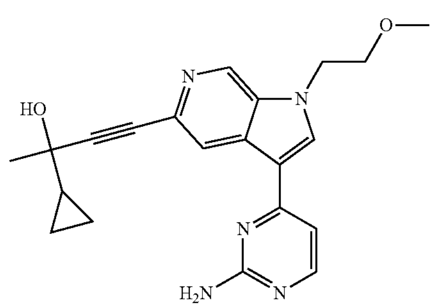 [SMILES: COCCn1cc(-c2ccnc(N)n2)c2cc(C#CC(C)(O)C3CC3)ncc21] | a) Intermediate 13<br>b) 2-Cyclopropyl-but-3-yn-2-ol |

TABLE 22-continued

| Compound | Structure | Starting Materials |
|---|---|---|
| 33 | 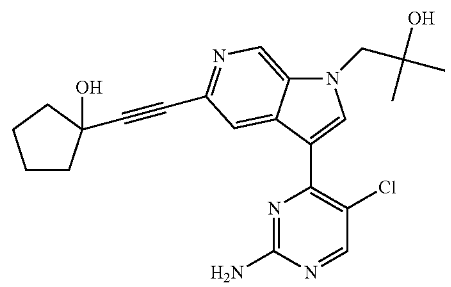 [SMILES: CC(C)(O)Cn1cc(-c2nc(N)ncc2Cl)c2cc(C#CC3(O)CCCC3)ncc21] | a) Intermediate 22<br>b) 1-Ethynyl-cyclopentanol |
| 34 | 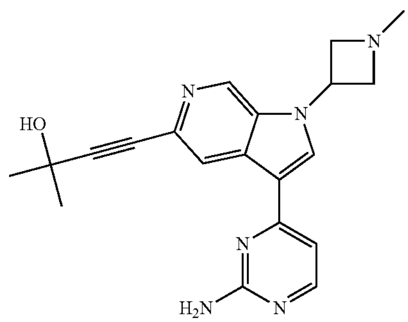 [SMILES: CN1CC(n2cc(-c3ccnc(N)n3)c3cc(C#CC(C)(C)O)ncc32)C1] | a) Intermediate 129<br>b) 2-Methylbut-3-yn-2-ol |
| 35 | 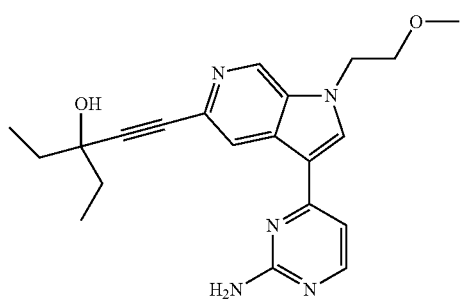 [SMILES: CCC(O)(C#Cc1cc2c(-c3ccnc(N)n3)cn(CCOC)c2cn1)CC] | a) Intermediate 13<br>b) 3-Ethyl-pent-1-yn-3-ol |
| 36 | 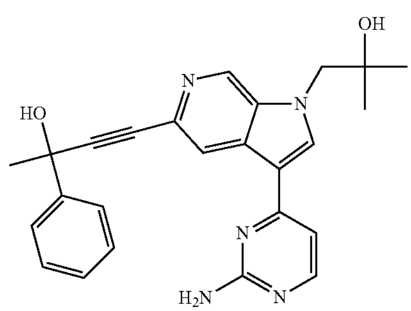 [SMILES: CC(C)(O)Cn1cc(-c2ccnc(N)n2)c2cc(C#CC(C)(O)c3ccccc3)ncc21] | a) Intermediate 14<br>b) 2-Phenyl-but-3-yn-2-ol |
| 37 | 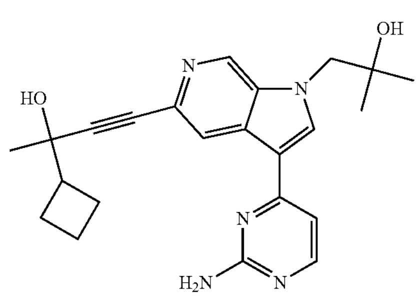 [SMILES: CC(C)(O)Cn1cc(-c2ccnc(N)n2)c2cc(C#CC(C)(O)C3CCC3)ncc21] | a) Intermediate 14<br>b) 2-Cyclobutyl-but-3-yn-2-ol |

TABLE 22-continued

| Compound | Structure | Starting Materials |
|---|---|---|
| 38 | 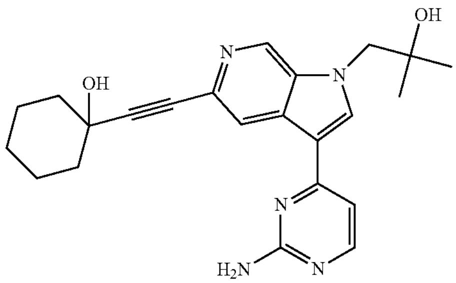 [SMILES: CC(C)(O)Cn1cc(-c2ccnc(N)n2)c2cc(C#CC3(O)CCCCC3)ncc21] | a) Intermediate 14<br>b) 1-Ethynyl-cyclohexanol |
| 39 | 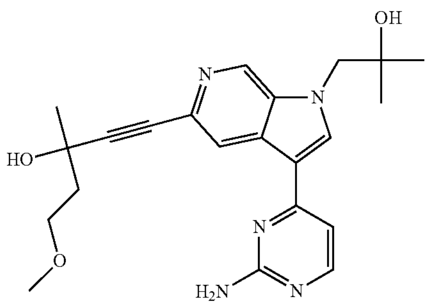 [SMILES: COCCC(C)(O)C#Cc1cc2c(-c3ccnc(N)n3)cn(CC(C)(C)O)c2cn1] | a) Intermediate 14<br>b) 5-Methoxy-3-methyl-pent-1-yn-3-ol |
| 40 | 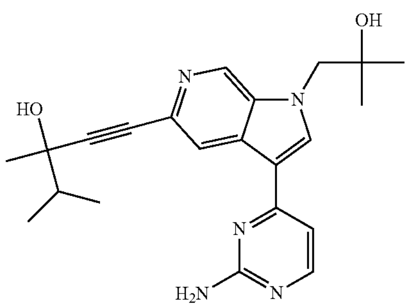 [SMILES: CC(C)C(C)(O)C#Cc1cc2c(-c3ccnc(N)n3)cn(CC(C)(C)O)c2cn1] | a) Intermediate 14<br>b) 3,4-Dimethyl-pent-1-yn-3-ol |
| 41 | 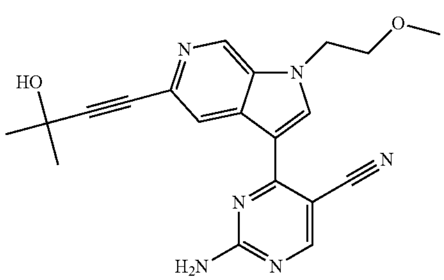 [SMILES: COCCn1cc(-c2nc(N)ncc2C#N)c2cc(C#CC(C)(C)O)ncc21] | a) Intermediate 138<br>b) 2-Methylbut-3-yn-2-ol |
| 42 | 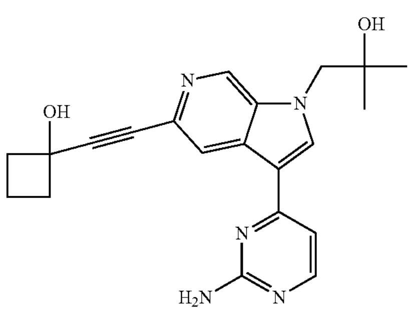 [SMILES: CC(C)(O)Cn1cc(-c2ccnc(N)n2)c2cc(C#CC3(O)CCC3)ncc21] | a) Intermediate 14<br>b) 1-Ethynyl-cyclobutanol |

TABLE 22-continued
| Compound | Structure | Starting Materials |
|---|---|---|
| 43 | 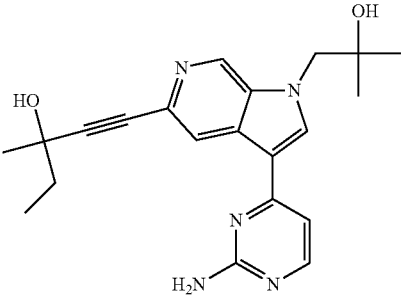 [SMILES: CCC(C)(O)C#Cc1cc2c(-c3ccnc(N)n3)cn(CC(C)(C)O)c2cn1] | a) Intermediate 14<br>b) 3-Methyl-pent-1-yn-3-ol |
| 44 | 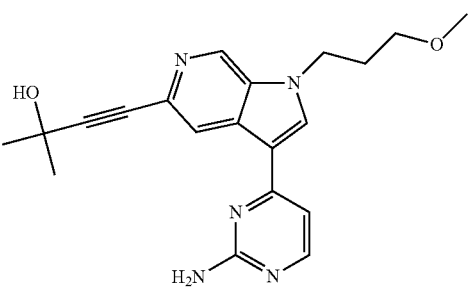 [SMILES: COCCCn1cc(-c2ccnc(N)n2)c2cc(C#CC(C)(C)O)ncc21] | a) Intermediate 86<br>b) 2-Methylbut-3-yn-2-ol |
| 45 | 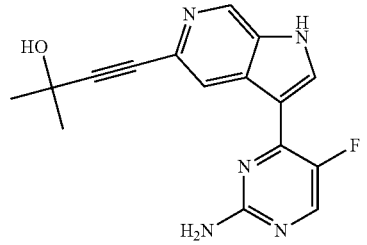 [SMILES: CC(C)(O)C#Cc1cc2c(-c3nc(N)ncc3F)c[nH]c2cn1] | a) Intermediate 62<br>b) 2-Methylbut-3-yn-2-ol |
| 46 | 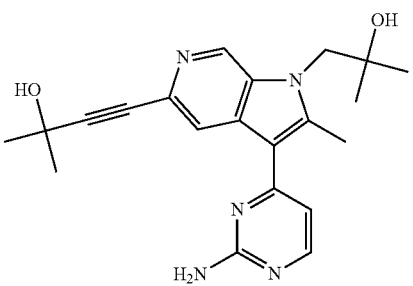 [SMILES: Cc1c(-c2ccnc(N)n2)c2cc(C#CC(C)(C)O)ncc2n1CC(C)(C)O] | a) Intermediate 26<br>b) 2-Methylbut-3-yn-2-ol |
| 47 | 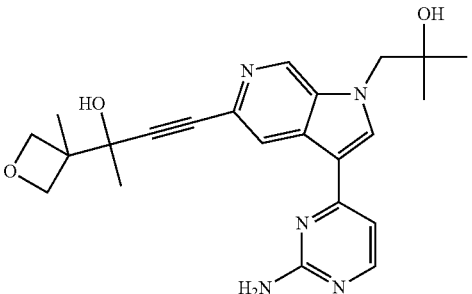 | a) Intermediate 14<br>b) Intermediate 147 |

TABLE 22-continued
| Compound | Structure | Starting Materials |
|---|---|---|
| 48 | 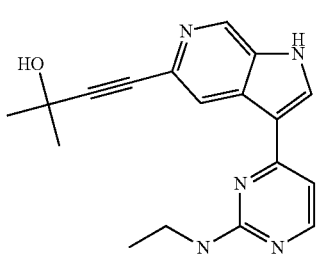 | a) Intermediate 64<br>b) 2-Methylbut-3-yn-2-ol |
| 49 | 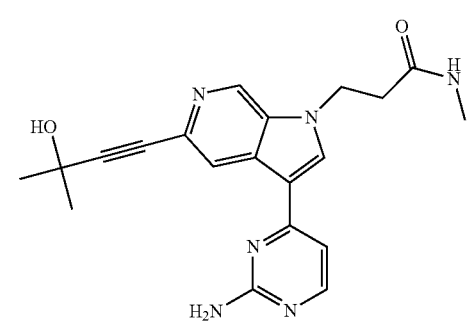 [SMILES: CNC(=O)CCn1cc(-c2ccnc(N)n2)c2cc(C#CC(C)(C)O)ncc21] | a) Intermediate 25<br>b) 2-Methylbut-3-yn-2-ol |
| 50 | 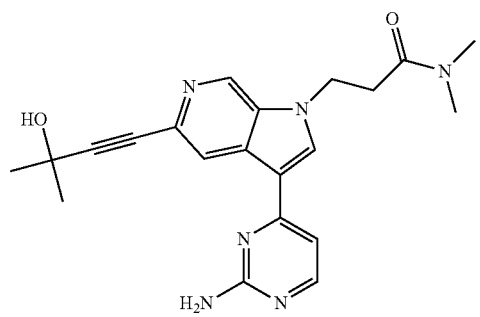 [SMILES: CN(C)C(=O)CCn1cc(-c2ccnc(N)n2)c2cc(C#CC(C)(C)O)ncc21] | a) Intermediate 27<br>b) 2-Methylbut-3-yn-2-ol |
| 51 | 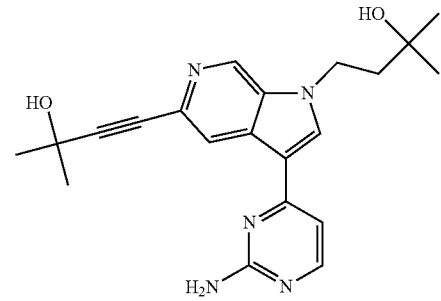 [SMILES: CC(C)(O)C#Cc1cc2c(-c3ccnc(N)n3)cn(CCC(C)(C)O)c2cn1] | a) Intermediate 84<br>b) 2-Methylbut-3-yn-2-ol |
| 52 | 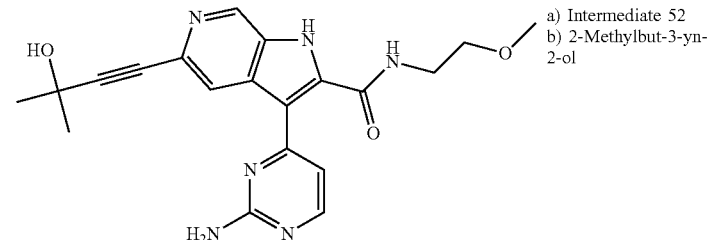 | a) Intermediate 52<br>b) 2-Methylbut-3-yn-2-ol |

TABLE 22-continued

| Compound | Structure | Starting Materials |
| --- | --- | --- |
| 53 | 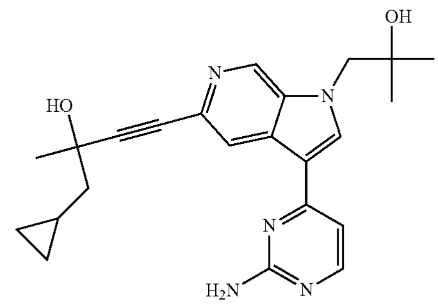 [SMILES: CC(C)(O)Cn1cc(-c2ccnc(N)n2)c2cc(C#CC(C)(O)CC3CC3)ncc21] | a) Intermediate 14<br>b) Intermediate 148 |
| 54 | 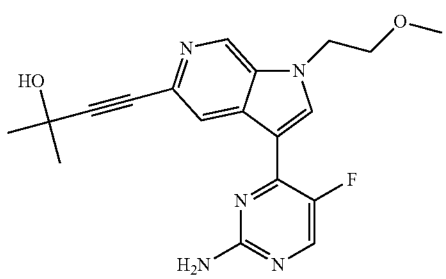 [SMILES: COCCn1cc(-c2nc(N)ncc2F)c2cc(C#CC(C)(C)O)ncc21] | a) Intermediate 81<br>b) 2-Methylbut-3-yn-2-ol |
| 55 | 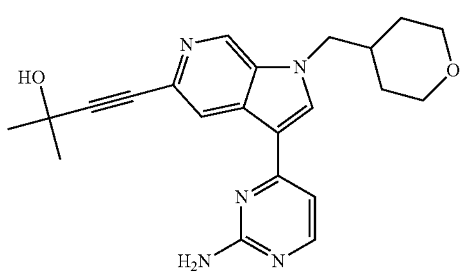 [SMILES: CC(C)(O)C#Cc1cc2c(-c3ccnc(N)n3)cn(CC3CCOCC3)c2cn1] | a) Intermediate 87<br>b) 2-Methylbut-3-yn-2-ol |
| 56 | 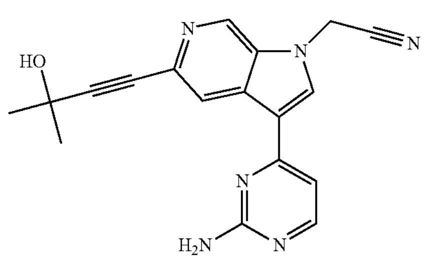 [SMILES: CC(C)(O)C#Cc1cc2c(-c3ccnc(N)n3)cn(CC#N)c2cn1] | a) Intermediate 88<br>b) 2-Methylbut-3-yn-2-ol |
| 57 | 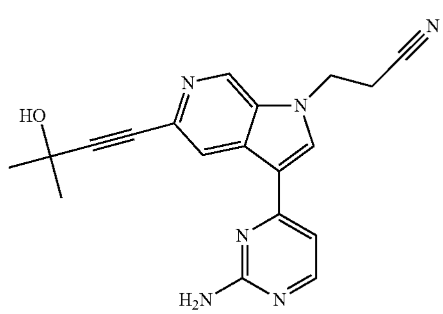 [SMILES: CC(C)(O)C#Cc1cc2c(-c3ccnc(N)n3)cn(CCC#N)c2cn1] | a) Intermediate 89<br>b) 2-Methylbut-3-yn-2-ol |

TABLE 22-continued

| Compound | Structure | Starting Materials |
|---|---|---|
| 58 | 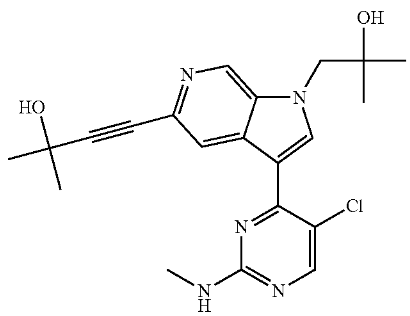 [SMILES: CNc1ncc(Cl)c(-c2cn(CC(C)(C)O)c3cnc(C#CC(C)(C)O)cc23)n1] | a) Intermediate 24<br>b) 2-Methylbut-3-yn-2-ol |
| 59 | 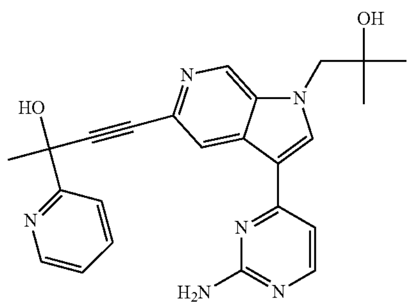 | a) Intermediate 14<br>b) 2-Pyridin-2-yl-but-3-yn-2-ol |
| 60 | 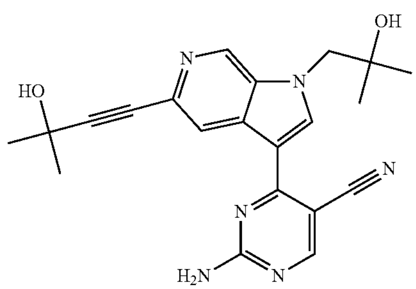 [SMILES: CC(C)(O)C#Cc1cc2c(-c3nc(N)ncc3C#N)cn(CC(C)(C)O)c2cn1] | a) Intermediate 139<br>b) 2-Methylbut-3-yn-2-ol |
| 61 | 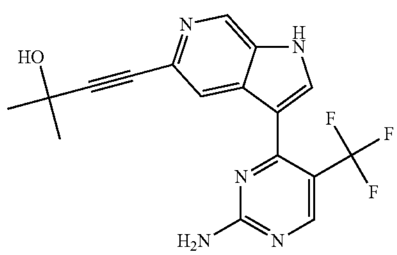 [SMILES: CC(C)(O)C#Cc1cc2c(-c3nc(N)ncc3C(F)(F)F)c[nH]c2cn1] | a) Intermediate 66<br>b) 2-Methylbut-3-yn-2-ol |
| 62 | 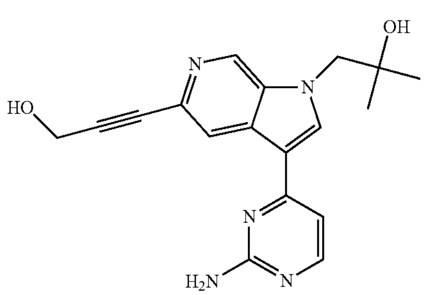 [SMILES: CC(C)(O)Cn1cc(-c2ccnc(N)n2)c2cc(C#CCO)ncc21] | a) Intermediate 14<br>b) Prop-2-yn-1-ol |

TABLE 22-continued

| Compound | Structure | Starting Materials |
| --- | --- | --- |
| 63 | 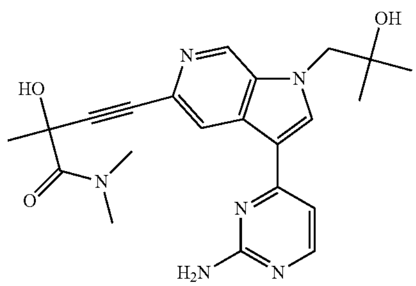 [SMILES: CN(C)C(=O)C(C)(O)C#Cc1cc2c(-c3ccnc(N)n3)cn(CC(C)(C)O)c2cn1] | a) Intermediate 14<br>b) 2,2-Dimethyl-but-3-ynoic acid dimethylamide |
| 64 | 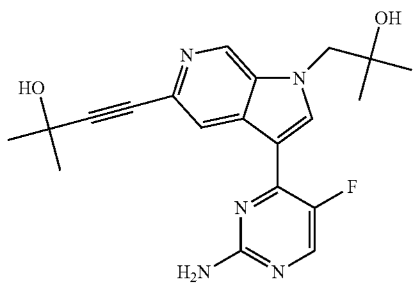 [SMILES: CC(C)(O)C#Cc1cc2c(-c3nc(N)ncc3F)cn(CC(C)(C)O)c2cn1] | a) Intermediate 82<br>b) 2-Methylbut-3-yn-2-ol |
| 65 | 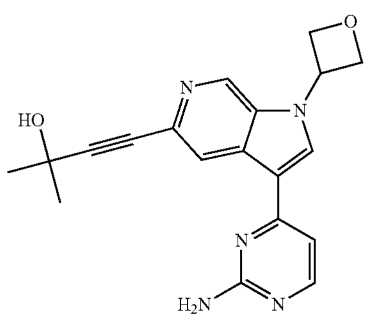 [SMILES: CC(C)(O)C#Cc1cc2c(-c3ccnc(N)n3)cn(C3COC3)c2cn1] | a) Intermediate 92<br>b) 2-Methylbut-3-yn-2-ol |
| 66 | 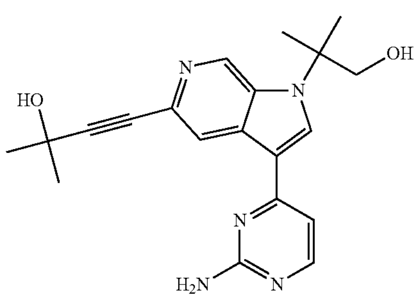 [SMILES: CC(C)(O)C#Cc1cc2c(-c3ccnc(N)n3)cn(C(C)(C)CO)c2cn1] | a) Intermediate 141<br>b) 2-Methylbut-3-yn-2-ol |
| 67 | 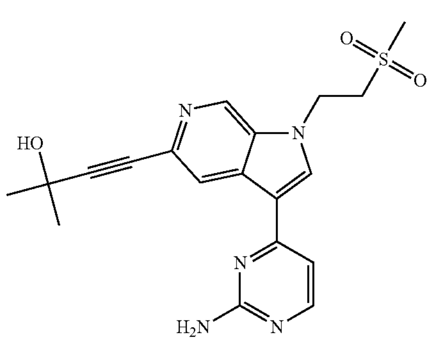 [SMILES: CC(C)(O)C#Cc1cc2c(-c3ccnc(N)n3)cn(CCS(C)(=O)=O)c2cn1] | a) Intermediate 142<br>b) 2-Methylbut-3-yn-2-ol |

TABLE 22-continued

| Compound | Structure | Starting Materials |
|---|---|---|
| 68 | 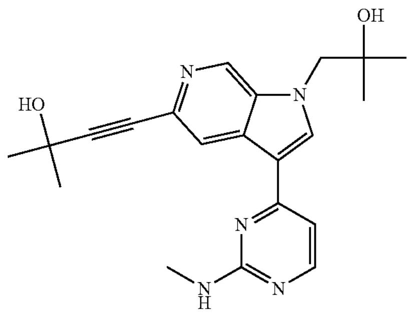 [SMILES: CNc1nccc(-c2cn(CC(C)(C)O)c3cnc(C#CC(C)(C)O)cc23)n1] | a) Intermediate 90<br>b) 2-Methylbut-3-yn-2-ol |
| 69 | 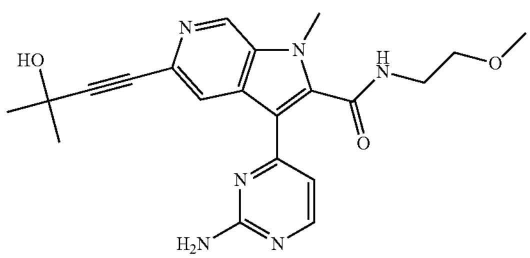 [SMILES: COCCNC(=O)c1c(-c2ccnc(N)n2)c2cc(C#CC(C)(C)O)ncc2n1C] | a) Intermediate 95<br>b) 2-Methylbut-3-yn-2-ol |
| 70 | 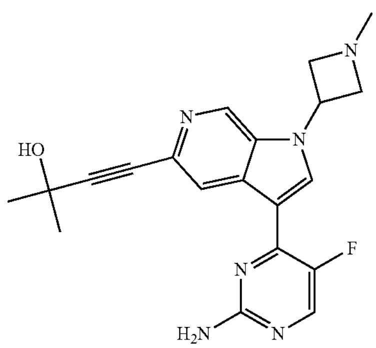 [SMILES: CN1CC(n2cc(-c3nc(N)ncc3F)c3cc(C#CC(C)(C)O)ncc32)C1] | a) Intermediate 130<br>b) 2-Methylbut-3-yn-2-ol |
| 71 | 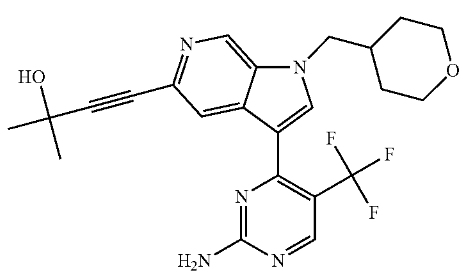 [SMILES: CC(C)(O)C#Cc1cc2c(-c3nc(N)ncc3C(F)(F)F)cn(CC3CCOCC3)c2cn1] | a) Intermediate 97<br>b) 2-Methylbut-3-yn-2-ol |
| 72 | 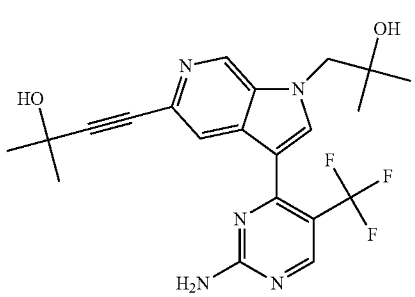 [SMILES: CC(C)(O)C#Cc1cc2c(-c3nc(N)ncc3C(F)(F)F)cn(CC(C)(C)O)c2cn1] | a) Intermediate 98<br>b) 2-Methylbut-3-yn-2-ol |

TABLE 22-continued

| Compound | Structure | Starting Materials |
|---|---|---|
| 73 | 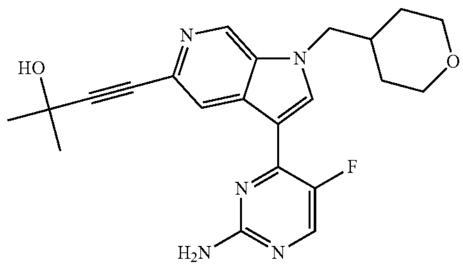 [SMILES: CC(C)(O)C#Cc1cc2c(-c3nc(N)ncc3F)cn(CC3CCOCC3)c2cn1] | a) Intermediate 99<br>b) 2-Methylbut-3-yn-2-ol |
| 74 | 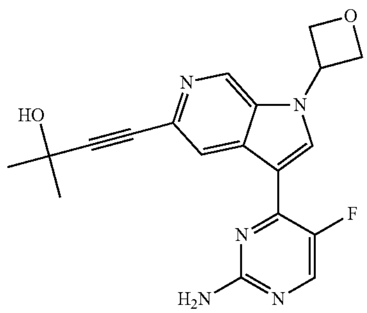 [SMILES: CC(C)(O)C#Cc1cc2c(-c3nc(N)ncc3F)cn(C3COC3)c2cn1] | a) Intermediate 100<br>b) 2-Methylbut-3-yn-2-ol |
| 75 | 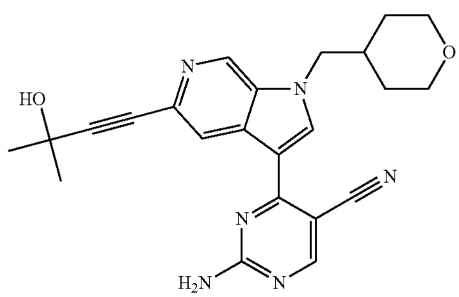 [SMILES: CC(C)(O)C#Cc1cc2c(-c3nc(N)ncc3C#N)cn(CC3CCOCC3)c2cn1] | a) Intermediate 140<br>b) 2-Methylbut-3-yn-2-ol |
| 76 | 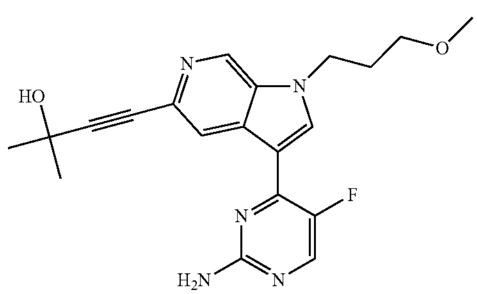 [SMILES: COCCCn1cc(-c2nc(N)ncc2F)c2cc(C#CC(C)(C)O)ncc21] | a) Intermediate 101<br>b) 2-Methylbut-3-yn-2-ol |
| 77 | 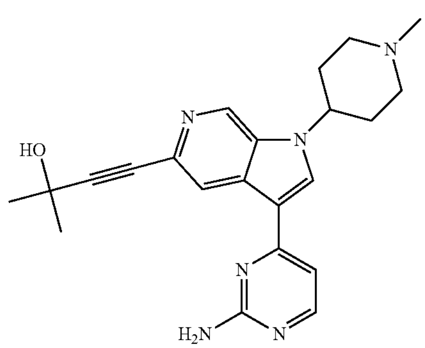 [SMILES: CN1CCC(n2cc(-c3ccnc(N)n3)c3cc(C#CC(C)(C)O)ncc32)CC1] | a) Intermediate 28<br>b) 2-Methylbut-3-yn-2-ol |

TABLE 22-continued

| Compound | Structure | Starting Materials |
|---|---|---|
| 78 | 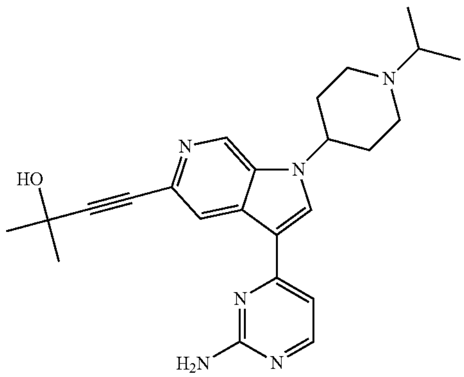 [SMILES: CC(C)N1CCC(n2cc(-c3ccnc(N)n3)c3cc(C#CC(C)(C)O)ncc32)CC1] | a) Intermediate 29<br>b) 2-Methylbut-3-yn-2-ol |
| 79 | 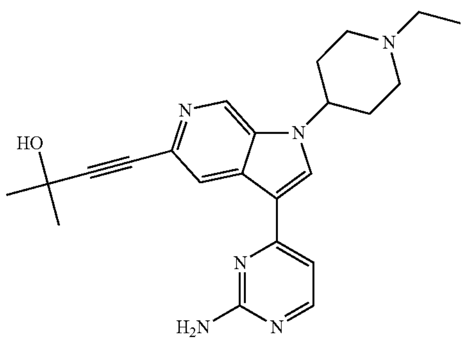 [SMILES: CCN1CCC(n2cc(-c3ccnc(N)n3)c3cc(C#CC(C)(C)O)ncc32)CC1] | a) Intermediate 30<br>b) 2-Methylbut-3-yn-2-ol |
| 80 | 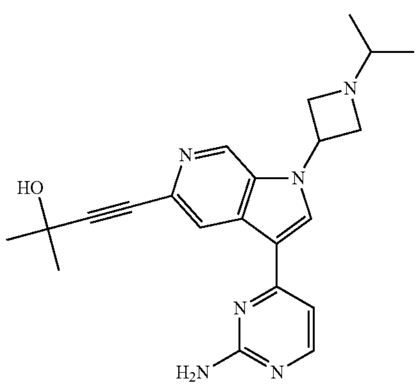 [SMILES: CC(C)N1CC(n2cc(-c3ccnc(N)n3)c3cc(C#CC(C)(C)O)ncc32)C1] | a) Intermediate 131<br>b) 2-Methylbut-3-yn-2-ol |
| 81 | 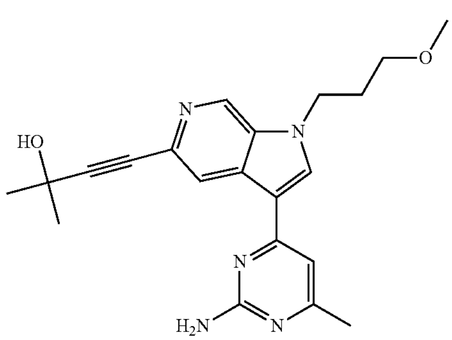 [SMILES: COCCCn1cc(-c2cc(C)nc(N)n2)c2cc(C#CC(C)(C)O)ncc21] | a) Intermediate 102<br>b) 2-Methylbut-3-yn-2-ol |

TABLE 22-continued

| Compound | Structure | Starting Materials |
|---|---|---|
| 82 | 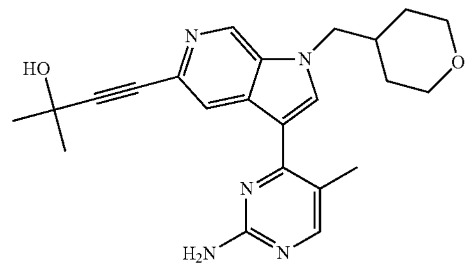 | a) Intermediate 103<br>b) 2-Methylbut-3-yn-2-ol |
| 83 | 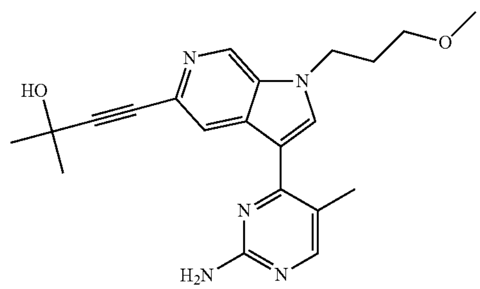 [SMILES: COCCCn1cc(-c2nc(N)ncc2C)c2cc(C#CC(C)(C)O)ncc21] | a) Intermediate 104<br>b) 2-Methylbut-3-yn-2-ol |
| 84 | 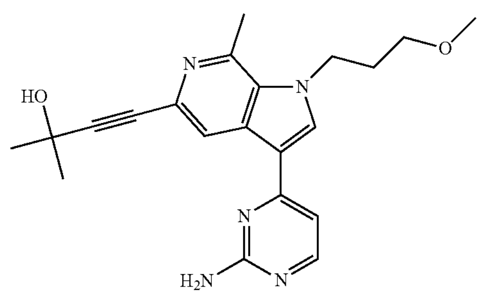 [SMILES: COCCCn1cc(-c2ccnc(N)n2)c2cc(C#CC(C)(C)O)nc(C)c21] | a) Intermediate 105<br>b) 2-Methylbut-3-yn-2-ol |
| 85 | 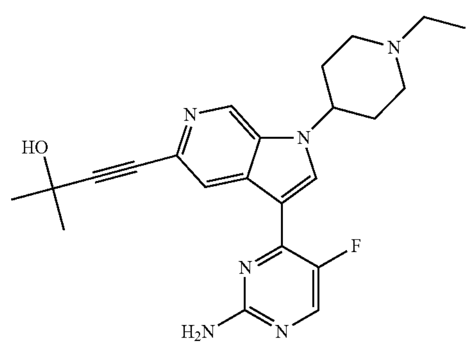 [SMILES: CCN1CCC(n2cc(-c3nc(N)ncc3F)c3cc(C#CC(C)(C)O)ncc32)CC1] | a) Intermediate 31<br>b) 2-Methylbut-3-yn-2-ol |
| 86 | 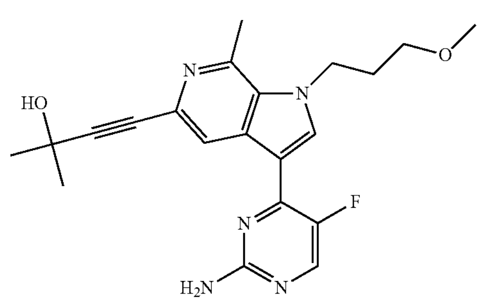 [SMILES: COCCCn1cc(-c2nc(N)ncc2F)c2cc(C#CC(C)(C)O)nc(C)c21] | a) Intermediate 106<br>b) 2-Methylbut-3-yn-2-ol |

TABLE 22-continued

| Compound | Structure | Starting Materials |
|---|---|---|
| 87 | 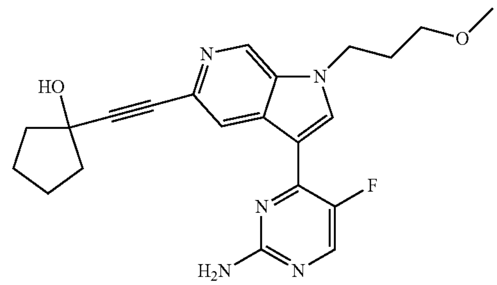 [SMILES: COCCCn1cc(-c2nc(N)ncc2F)c2cc(C#CC3(O)CCCC3)ncc21] | a) Intermediate 101<br>b) 1-Ethynyl-cyclopentanol |
| 88 | 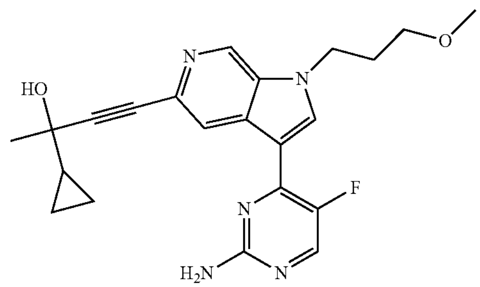 [SMILES: COCCCn1cc(-c2nc(N)ncc2F)c2cc(C#CC(C)(O)C3CC3)ncc21] | a) Intermediate 101<br>b) 2-Cyclopropyl-but-3-yn-2-ol |
| 89 | 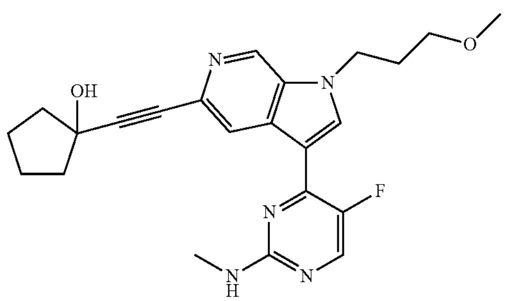 [SMILES: CNc1ncc(F)c(-c2cn(CCCOC)c3cnc(C#CC4(O)CCCC4)cc23)n1] | a) Intermediate 143<br>b) 1-Ethynyl-cyclopentanol |
| 90 | 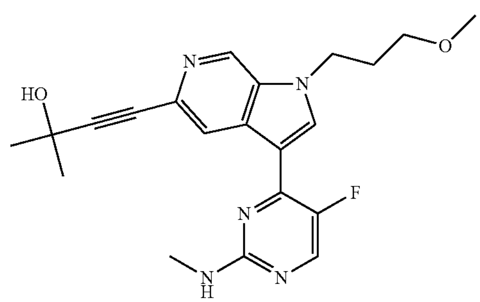 [SMILES: CNc1ncc(F)c(-c2cn(CCCOC)c3cnc(C#CC(C)(C)O)cc23)n1] | a) Intermediate 143<br>b) 2-Methylbut-3-yn-2-ol |
| 91 | 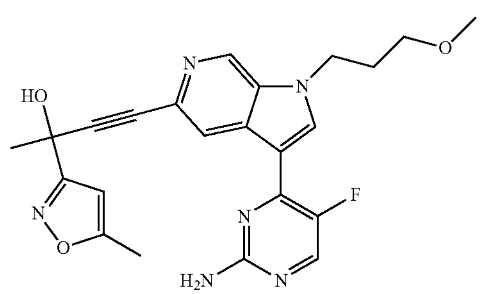 [SMILES: COCCCn1cc(-c2nc(N)ncc2F)c2cc(C#CC(C)(O)c3cc(C)on3)ncc21] | a) Intermediate 101<br>b) 2-(5-Methyl-isoxazol-3-yl)-but-3-yn-2-ol |

TABLE 22-continued

| Compound | Structure | Starting Materials |
|---|---|---|
| 92 | 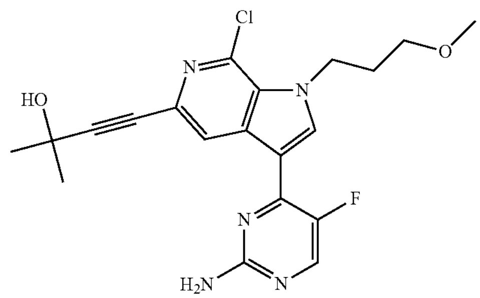 [SMILES: COCCCn1cc(-c2nc(N)ncc2F)c2cc(C#CC(C)(C)O)nc(Cl)c21] | a) Intermediate 115<br>b) 2-Methylbut-3-yn-2-ol |
| 93 | 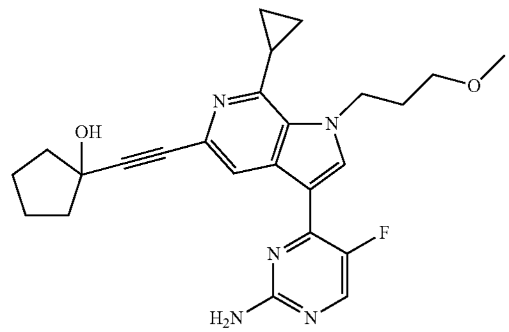 [SMILES: COCCCn1cc(-c2nc(N)ncc2F)c2cc(C#CC3(O)CCCC3)nc(C3CC3)c21] | a) Intermediate 114<br>b) 1-Ethynyl-cyclopentanol |
| 94 | 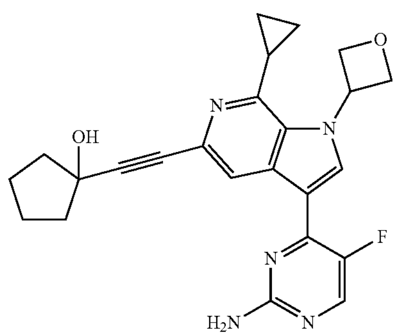 [SMILES: Nc1ncc(F)c(-c2cn(C3COC3)c3c(C4CC4)nc(C#CC4(O)CCCC4)cc23)n1] | a) Intermediate 113<br>b) 1-Ethynyl-cyclopentanol |
| 95 | 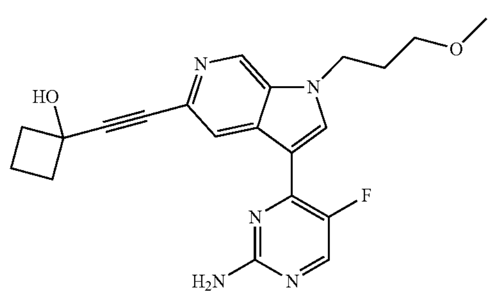 [SMILES: COCCCn1cc(-c2nc(N)ncc2F)c2cc(C#CC3(O)CCC3)ncc21] | a) Intermediate 101<br>b) 2-Cyclobutyl-but-3-yn-2-ol |
| 96 | 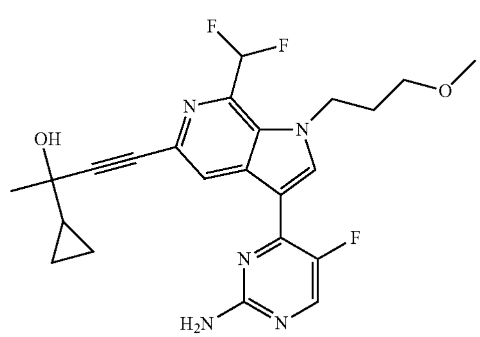 [SMILES: COCCCn1cc(-c2nc(N)ncc2F)c2cc(C#CC(C)(O)C3CC3)nc(C(F)F)c21] | a) Intermediate 145<br>b) 2-Cyclopropyl-but-3-yn-2-ol |

TABLE 22-continued

| Compound | Structure | Starting Materials |
|---|---|---|
| 98 | 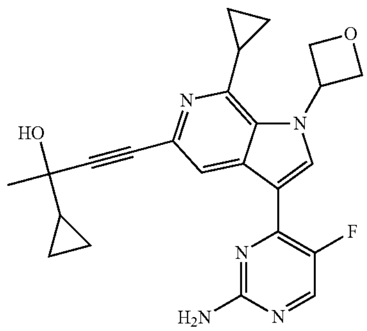 [SMILES: CC(O)(C#Cc1cc2c(-c3nc(N)ncc3F)cn(C3COC3)c2c(C2CC2)n1)C1CC1] | a) Intermediate 113<br>b) 2-Cyclopropyl-but-3-yn-2-ol |
| 99 | 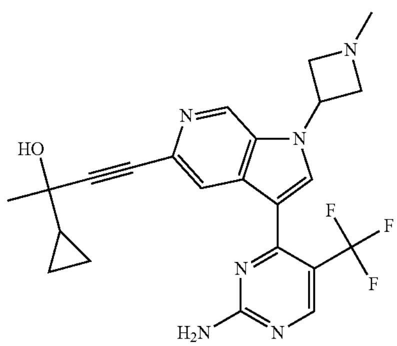 [SMILES: CN1CC(n2cc(-c3nc(N)ncc3C(F)(F)F)c3cc(C#CC(C)(O)C4CC4)ncc32)C1] | a) Intermediate 132<br>b) 2-Cyclopropyl-but-3-yn-2-ol |
| 100 | 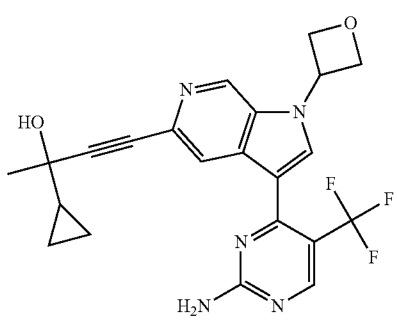 [SMILES: CC(O)(C#Cc1cc2c(-c3nc(N)ncc3C(F)(F)F)cn(C3COC3)c2cn1)C1CC1] | a) Intermediate 108<br>b) 2-Cyclopropyl-but-3-yn-2-ol |
| 101 | 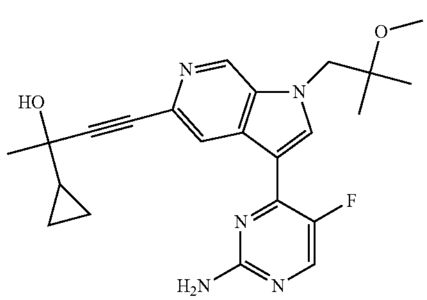 [SMILES: COC(C)(C)Cn1cc(-c2nc(N)ncc2F)c2cc(C#CC(C)(O)C3CC3)ncc21] | a) Intermediate 109<br>b) 2-Cyclopropyl-but-3-yn-2-ol |

TABLE 22-continued
| Compound | Structure | Starting Materials |
|---|---|---|
| 102 | 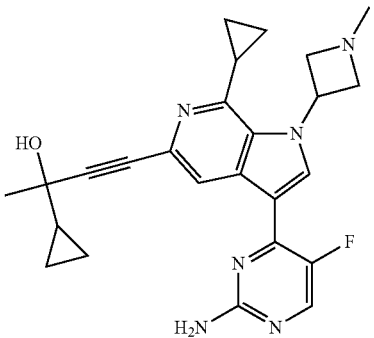 [SMILES: CN1CC(n2cc(-c3nc(N)ncc3F)c3cc(C#CC(C)(O)C4CC4)nc(C4CC4)c32)C1] | a) Intermediate 133<br>b) 2-Cyclopropyl-but-3-yn-2-ol |
| 103 | 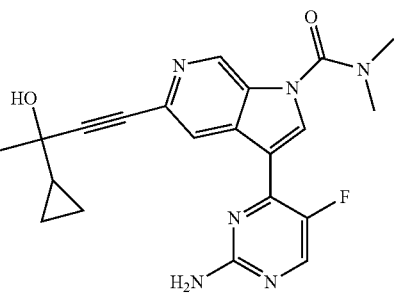 [SMILES: CN(C)C(=O)n1cc(-c2nc(N)ncc2F)c2cc(C#CC(C)(O)C3CC3)ncc21] | a) Intermediate 78<br>b) 2-Cyclopropyl-but-3-yn-2-ol |
| 105 | 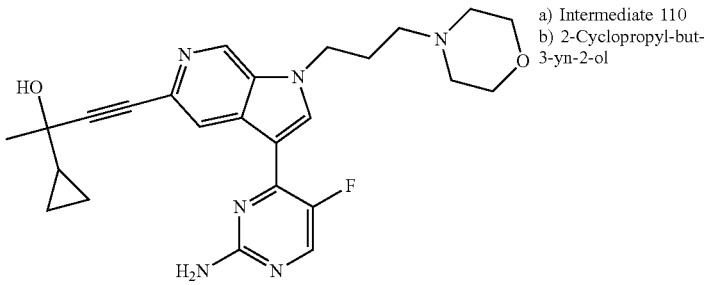 | a) Intermediate 110<br>b) 2-Cyclopropyl-but-3-yn-2-ol |
| 106 | 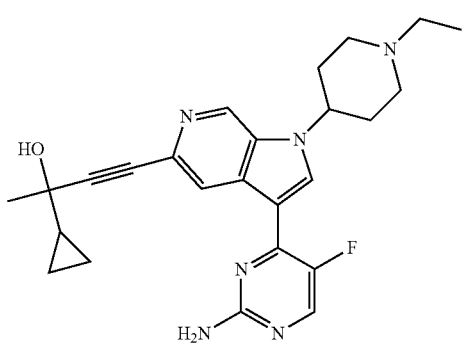 [SMILES: CCN1CCC(n2cc(-c3nc(N)ncc3F)c3cc(C#CC(C)(O)C4CC4)ncc32)CC1] | a) Intermediate 31<br>b) 2-Cyclopropyl-but-3-yn-2-ol |
| 107 | 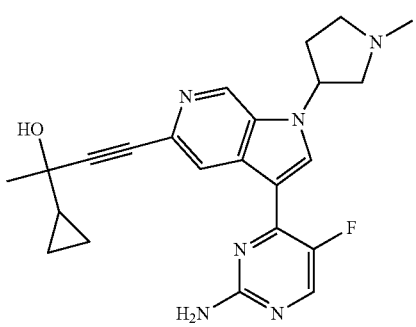 [SMILES: CN1CCC(n2cc(-c3nc(N)ncc3F)c3cc(C#CC(C)(O)C4CC4)ncc32)C1] | a) Intermediate 134<br>b) 2-Cyclopropyl-but-3-yn-2-ol |

TABLE 22-continued

| Compound | Structure | Starting Materials |
|---|---|---|
| 108 | 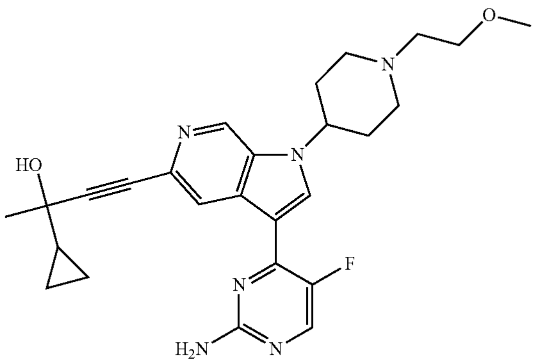 [SMILES: COCCN1CCC(n2cc(-c3nc(N)ncc3F)c3cc(C#CC(C)(O)C4CC4)ncc32)CC1] | a) Intermediate 32<br>b) 2-Cyclopropyl-but-3-yn-2-ol |
| 109 | 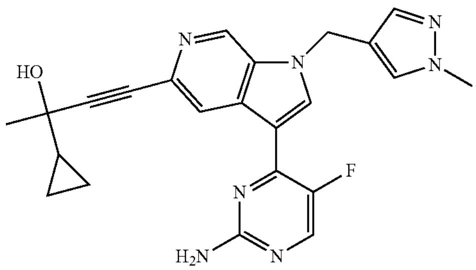 [SMILES: Cn1cc(Cn2cc(-c3nc(N)ncc3F)c3cc(C#CC(C)(O)C4CC4)ncc32)cn1] | a) Intermediate 116<br>b) 2-Cyclopropyl-but-3-yn-2-ol |
| 110 | 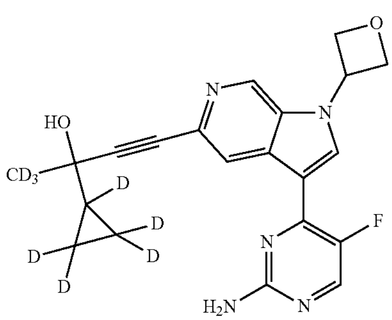 [SMILES: [2H]C([2H])([2H])C(O)(C#Cc1cc2c(-c3nc(N)ncc3F)cn(C3COC3)c2cn1)C1([2H])C([2H])([2H])C1([2H])[2H]] | a) Intermediate 100<br>b) Intermediate 149 |
| 123 | 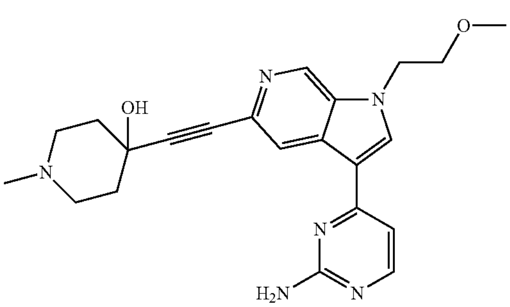 | a) Intermediate 13<br>b) 4-Ethynyl-1-methyl-piperidin-4-ol |

TABLE 22-continued
| Compound | Structure | Starting Materials |
|---|---|---|
| 126 | 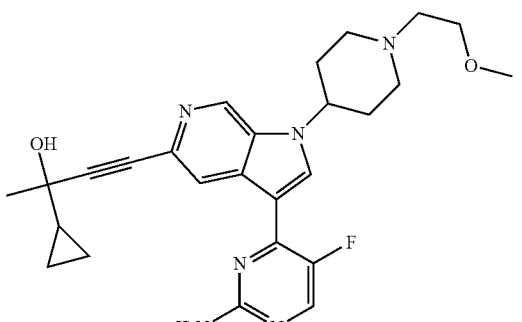 | a) Intermediate 32<br>b) 2-Cyclopropyl-but-3-yn-2-ol |
| 127 | 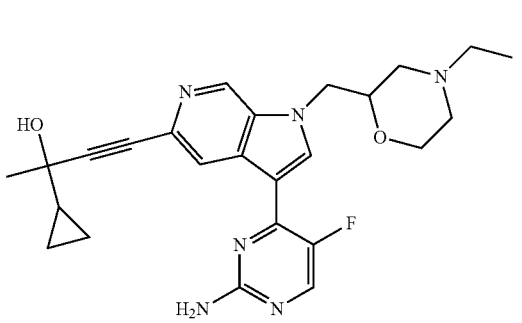 [SMILES: CCN1CCOC(Cn2cc(-c3nc(N)ncc3F)c3cc(C#CC(C)(O)C4CC4)ncc32)C1] | a) Intermediate 162<br>b) 2-Cyclopropyl-but-3-yn-2-ol |
| 128 | 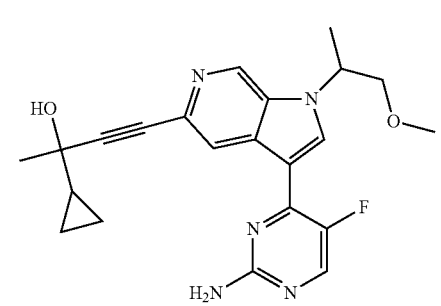 [SMILES: COCC(C)n1cc(-c2nc(N)ncc2F)c2cc(C#CC(C)(O)C3CC3)ncc21] | a) Intermediate 166<br>b) 2-Cyclopropyl-but-3-yn-2-ol |
| 129 | 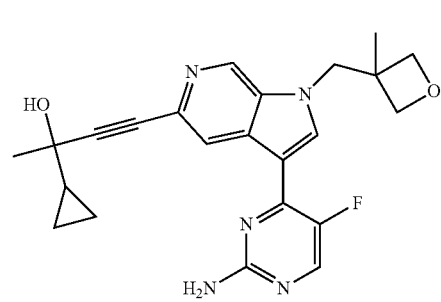 [SMILES: CC1(Cn2cc(-c3nc(N)ncc3F)c3cc(C#CC(C)(O)C4CC4)ncc32)COC1] | a) Intermediate 169<br>b) 2-Cyclopropyl-but-3-yn-2-ol |
| 130 | 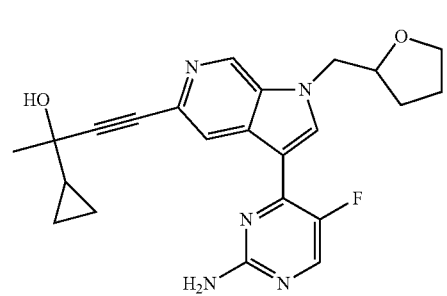 [SMILES: CC(O)(C#Cc1cc2c(-c3nc(N)ncc3F)cn(CC3CCCO3)c2cn1)C1CC1] | a) Intermediate 176<br>b) 2-Cyclopropyl-but-3-yn-2-ol |

TABLE 22-continued

| Compound | Structure | Starting Materials |
|---|---|---|
| 131 | 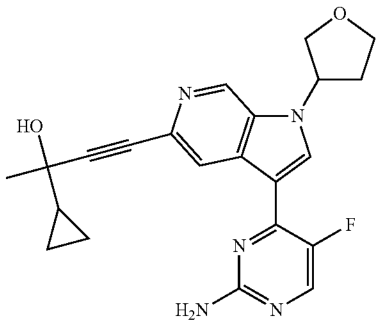 [SMILES: CC(O)(C#Cc1cc2c(-c3nc(N)ncc3F)cn(C3CCOC3)c2cn1)C1CC1] | a) Intermediate 167<br>b) 2-Cyclopropyl-but-3-yn-2-ol |
| 132 | 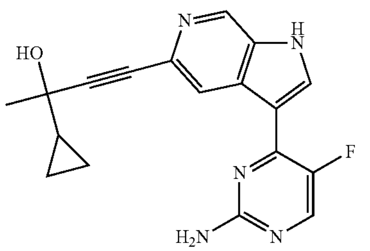 [SMILES: CC(O)(C#Cc1cc2c(-c3nc(N)ncc3F)c[nH]c2cn1)C1CC1] | a) Intermediate 62<br>b) 2-Cyclopropyl-but-3-yn-2-ol |
| 133 | 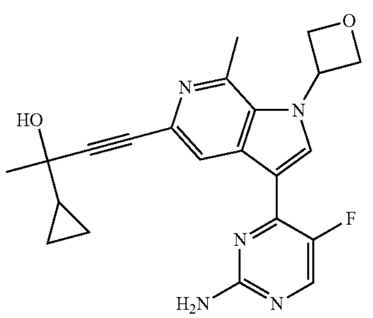 [SMILES: Cc1nc(C#CC(C)(O)C2CC2)cc2c(-c3nc(N)ncc3F)cn(C3COC3)c12] | a) Intermediate 170<br>b) 2-Cyclopropyl-but-3-yn-2-ol |
| 134 | 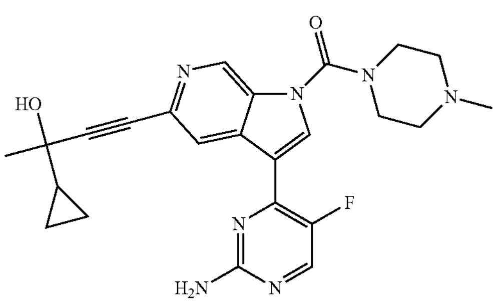 [SMILES: CN1CCN(C(=O)n2cc(-c3nc(N)ncc3F)c3cc(C#CC(C)(O)C4CC4)ncc32)CC1] | a) Intermediate 168<br>b) 2-Cyclopropyl-but-3-yn-2-ol |
| 135 | 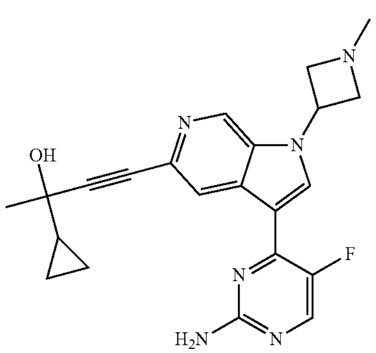 [SMILES: CN1CC(n2cc(-c3nc(N)ncc3F)c3cc(C#CC(C)(O)C4CC4)ncc32)C1] | a) Intermediate 130<br>b) 2-Cyclopropyl-but-3-yn-2-ol |

TABLE 22-continued

| Compound | Structure | Starting Materials |
|---|---|---|
| 136 | 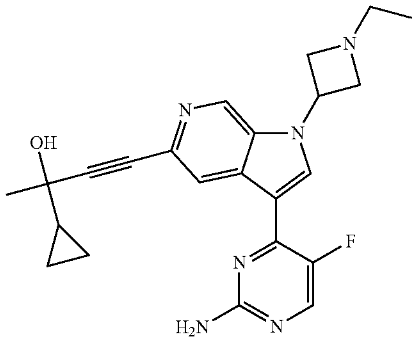 [SMILES: CCN1CC(n2cc(-c3nc(N)ncc3F)c3cc(C#CC(C)(O)C4CC4)ncc32)C1] | a) Intermediate 163<br>b) 2-Cyclopropyl-but-3-yn-2-ol |
| 137 | 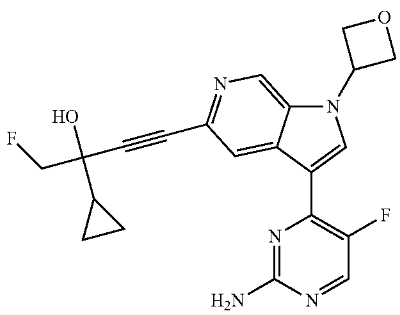 [SMILES: Nc1ncc(F)c(-c2cn(C3COC3)c3cnc(C#CC(O)(CF)C4CC4)cc23)n1] | a) Intermediate 100<br>b) Intermediate 174 |
| 138 | 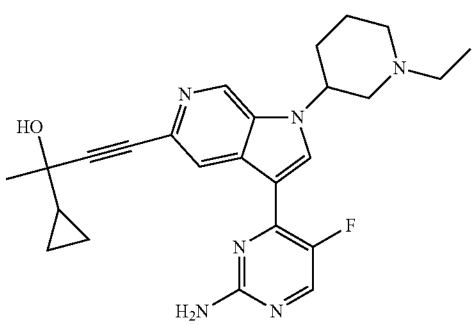 [SMILES: CCN1CCCC(n2cc(-c3nc(N)ncc3F)c3cc(C#CC(C)(O)C4CC4)ncc32)C1] | a) Intermediate 164<br>b) 2-Cyclopropyl-but-3-yn-2-ol |
| 139 | 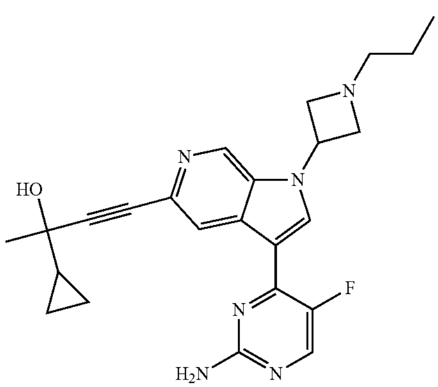 [SMILES: CCCN1CC(n2cc(-c3nc(N)ncc3F)c3cc(C#CC(C)(O)C4CC4)ncc32)C1] | a) Intermediate 172<br>b) 2-Cyclopropyl-but-3-yn-2-ol |

TABLE 22-continued

| Compound | Structure | Starting Materials |
| --- | --- | --- |
| 140 | 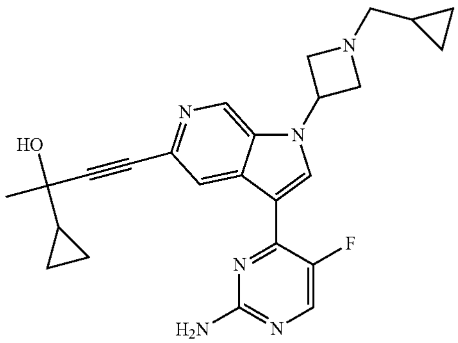 [SMILES: CC(O)(C#Cc1cc2c(-c3nc(N)ncc3F)cn(C3CN(CC4CC4)C3)c2cn1)C1CC1] | a) Intermediate 173<br>b) 2-Cyclopropyl-but-3-yn-2-ol |
| 141 | 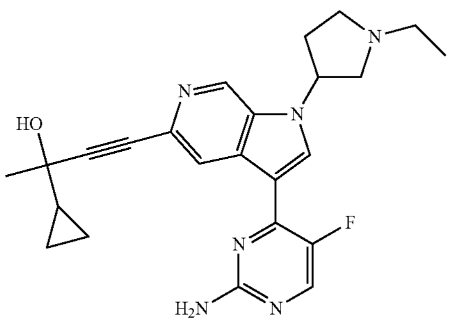 [SMILES: CCN1CCC(n2cc(-c3nc(N)ncc3F)c3cc(C#CC(C)(O)C4CC4)ncc32)C1] | a) Intermediate 165<br>b) 2-Cyclopropyl-but-3-yn-2-ol |
| 142 | 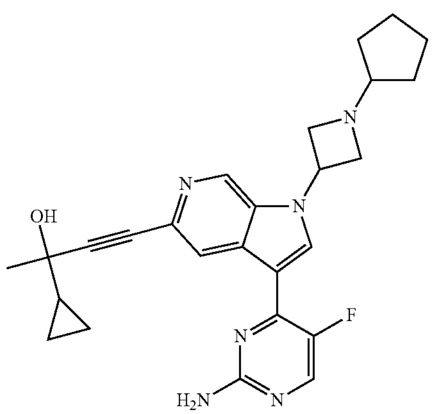 [SMILES: CC(O)(C#Cc1cc2c(-c3nc(N)ncc3F)cn(C3CN(C4CCCC4)C3)c2cn1)C1CC1] | a) Intermediate 189<br>b) 2-Cyclopropyl-but-3-yn-2-ol |
| 143 | 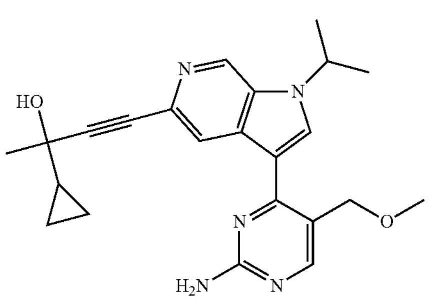 [SMILES: COCc1cnc(N)nc1-c1cn(C(C)C)c2cnc(C#CC(C)(O)C3CC3)cc12] | a) Intermediate 181<br>b) 2-Cyclopropyl-but-3-yn-2-ol |

TABLE 22-continued

| Compound | Structure | Starting Materials |
|---|---|---|
| 144 | 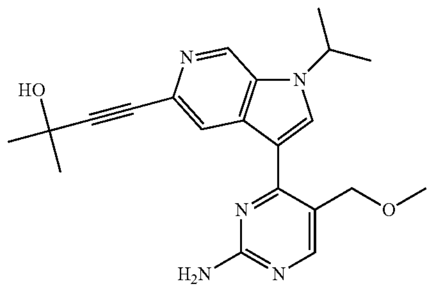 [SMILES: COCc1cnc(N)nc1-c1cn(C(C)C)c2cnc(C#CC(C)(C)O)cc12] | a) Intermediate 181<br>b) 2-Methylbut-3-yn-2-ol |
| 145 | 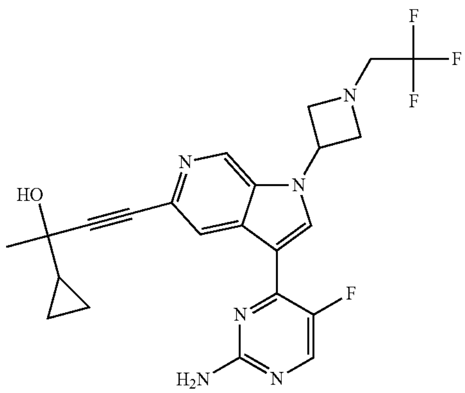 [SMILES: CC(O)(C#Cc1cc2c(-c3nc(N)ncc3F)cn(C3CN(CC(F)(F)F)C3)c2cn1)C1CC1] | a) Intermediate 190<br>b) 2-Cyclopropyl-but-3-yn-2-ol |
| 146 | 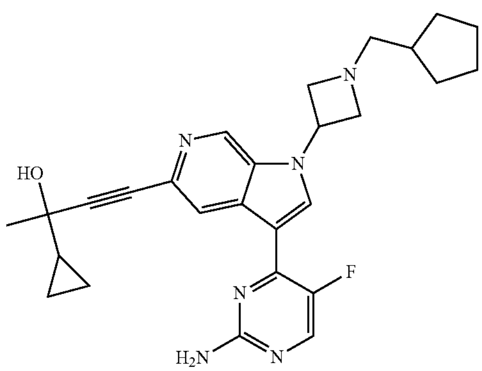 [SMILES: CC(O)(C#Cc1cc2c(-c3nc(N)ncc3F)cn(C3CN(CC4CCCC4)C3)c2cn1)C1CC1] | a) Intermediate 187<br>b) 2-Cyclopropyl-but-3-yn-2-ol |
| 147 | 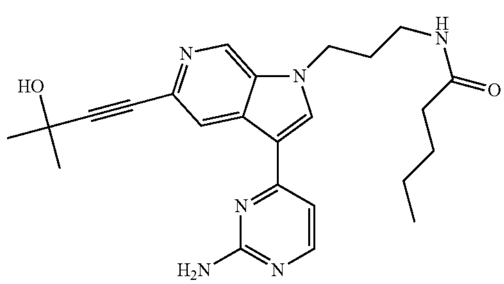 [SMILES: CCCCC(=O)NCCCn1cc(-c2ccnc(N)n2)c2cc(C#CC(C)(C)O)ncc21] | a) Intermediate 177<br>b) 2-Methylbut-3-yn-2-ol |
| 148 | 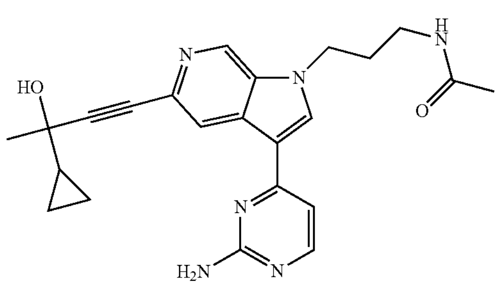 [SMILES: CC(=O)NCCCn1cc(-c2ccnc(N)n2)c2cc(C#CC(C)(O)C3CC3)ncc21] | a) Intermediate 191<br>b) 2-Methylbut-3-yn-2-ol |

TABLE 22-continued

| Compound | Structure | Starting Materials |
|---|---|---|
| 149 | 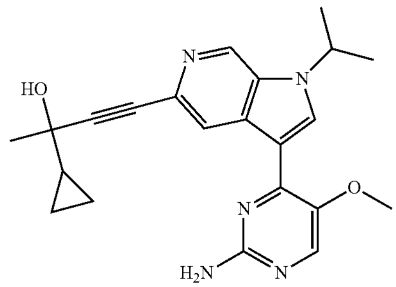 [SMILES: COc1cnc(N)nc1-c1cn(C(C)C)c2cnc(C#CC(C)(O)C3CC3)cc12] | a) Intermediate 184<br>b) 2-Cyclopropyl-but-3-yn-2-ol |
| 150 | 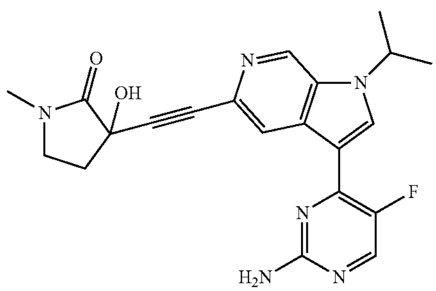 [SMILES: CC(C)n1cc(-c2nc(N)ncc2F)c2cc(C#CC3(O)CCN(C)C3=O)ncc21] | a) Intermediate 183<br>b) 3-Ethynyl-3-hydroxy-1-methyl-pyrrolidin-2-one |
| 151 | 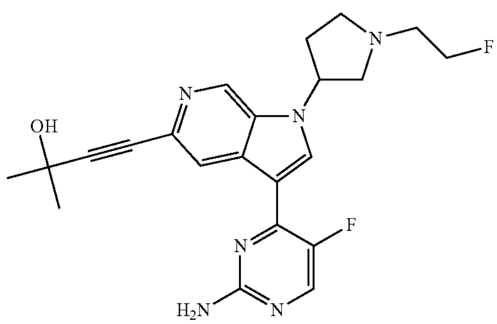 [SMILES: CC(C)(O)C#Cc1cc2c(-c3nc(N)ncc3F)cn(C3CCN(CCF)C3)c2cn1] | a) Intermediate 179<br>b) 2-Methylbut-3-yn-2-ol |
| 152 | 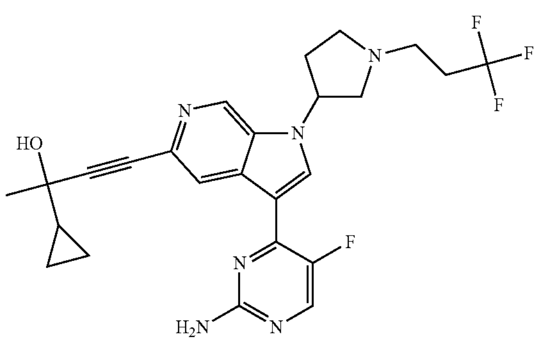 [SMILES: CC(O)(C#Cc1cc2c(-c3nc(N)ncc3F)cn(C3CCN(CCC(F)(F)F)C3)c2cn1)C1CC1] | a) Intermediate 178<br>b) 2-Cyclopropyl-but-3-yn-2-ol |
| 153 | 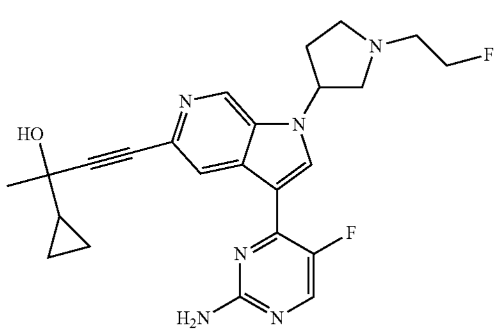 [SMILES: CC(O)(C#Cc1cc2c(-c3nc(N)ncc3F)cn(C3CCN(CCF)C3)c2cn1)C1CC1] | a) Intermediate 179<br>b) 2-Cyclopropyl-but-3-yn-2-ol |

TABLE 22-continued

| Compound | Structure | Starting Materials |
|---|---|---|
| 154 | 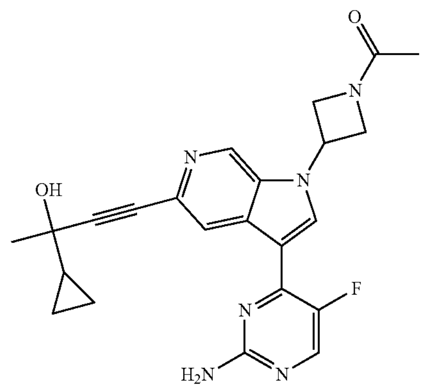 [SMILES: CC(=O)N1CC(n2cc(-c3nc(N)ncc3F)c3cc(C#CC(C)(O)C4CC4)ncc32)C1] | a) Intermediate 192<br>b) 2-Cyclopropyl-but-3-yn-2-ol |
| 155 | 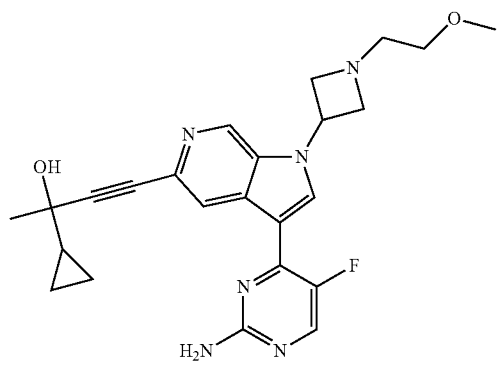 [SMILES: COCCN1CC(n2cc(-c3nc(N)ncc3F)c3cc(C#CC(C)(O)C4CC4)ncc32)C1] | a) Intermediate 193<br>b) 2-Cyclopropyl-but-3-yn-2-ol |
| 156 | 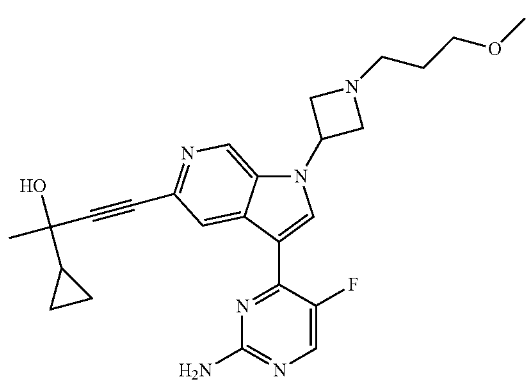 [SMILES: COCCCN1CC(n2cc(-c3nc(N)ncc3F)c3cc(C#CC(C)(O)C4CC4)ncc32)C1] | a) Intermediate 194<br>b) 2-Cyclopropyl-but-3-yn-2-ol |
| 158 | 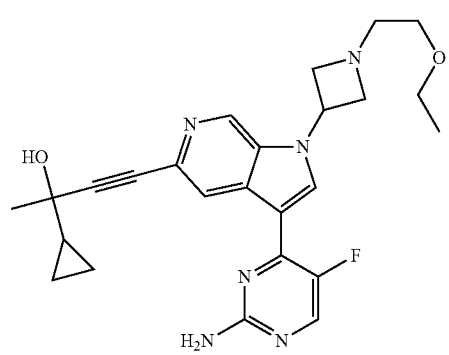 [SMILES: CCOCCN1CC(n2cc(-c3nc(N)ncc3F)c3cc(C#CC(C)(O)C4CC4)ncc32)C1] | a) Intermediate 195<br>b) 2-Cyclopropyl-but-3-yn-2-ol |

TABLE 22-continued

| Compound | Structure | Starting Materials |
| --- | --- | --- |
| 159 | 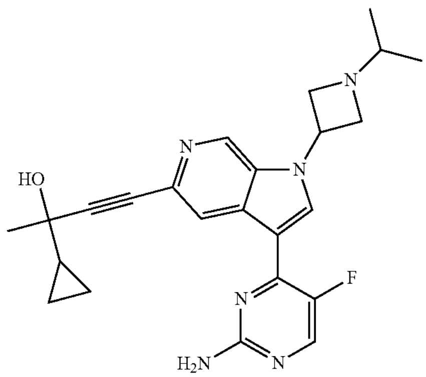 [SMILES: CC(C)N1CC(n2cc(-c3nc(N)ncc3F)c3cc(C#CC(C)(O)C4CC4)ncc32)C1] | a) Intermediate 196<br>b) 2-Cyclopropyl-but-3-yn-2-ol |
| 160 | 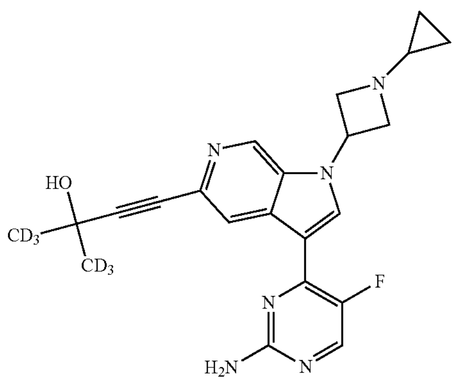 [SMILES: [2H]C([2H])([2H])C(O)(C#Cc1cc2c(-c3nc(N)ncc3F)cn(C3CN(C4CC4)C3)c2cn1)C([2H])([2H])[2H]] | a) Intermediate 144<br>b) 1,1,1-Trideutero-2-trideutermethyl-3-butyn-2-ol |
| 162 | 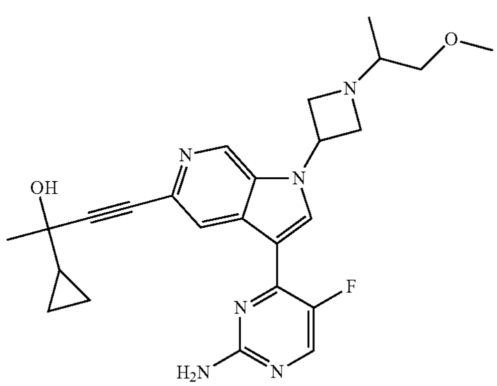 [SMILES: COCC(C)N1CC(n2cc(-c3nc(N)ncc3F)c3cc(C#CC(C)(O)C4CC4)ncc32)C1] | a) Intermediate 197<br>b) 2-Cyclopropyl-but-3-yn-2-ol |
| 163 | 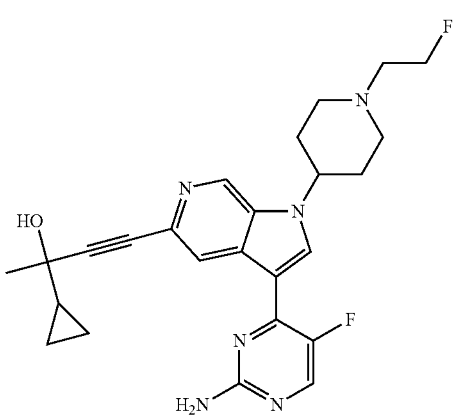 [SMILES: CC(O)(C#Cc1cc2c(-c3nc(N)ncc3F)cn(C3CCN(CCF)CC3)c2cn1)C1CC1] | a) Intermediate 198<br>b) 2-Cyclopropyl-but-3-yn-2-ol |

TABLE 22-continued

| Compound | Structure | Starting Materials |
|---|---|---|
| 164 | 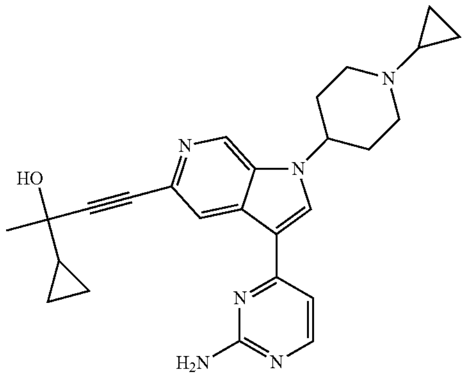 [SMILES: CC(O)(C#Cc1cc2c(-c3ccnc(N)n3)cn(C3CCN(C4CC4)CC3)c2cn1)C1CC1] | a) Intermediate 199<br>b) 2-Cyclopropyl-but-3-yn-2-ol |
| 165 | 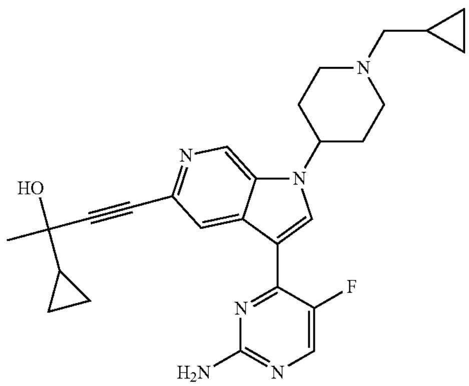 [SMILES: CC(O)(C#Cc1cc2c(-c3nc(N)ncc3F)cn(C3CCN(CC4CC4)CC3)c2cn1)C1CC1] | a) Intermediate 200<br>b) 2-Cyclopropyl-but-3-yn-2-ol |
| 166 | 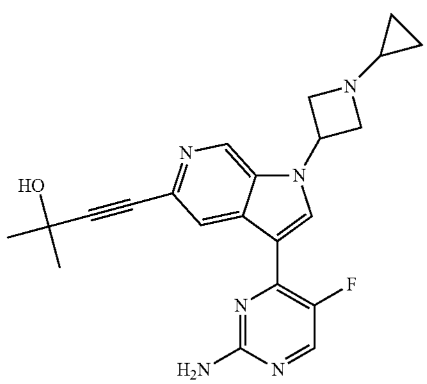 [SMILES: CC(C)(O)C#Cc1cc2c(-c3nc(N)ncc3F)cn(C3CN(C4CC4)C3)c2cn1] | a) Intermediate 144<br>b) 2-Methylbut-3-yn-2-ol |
| 167 | 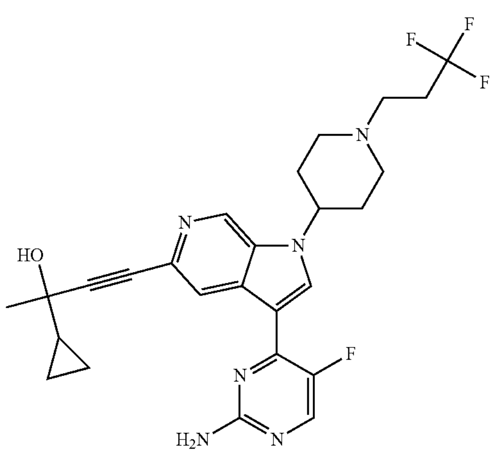 [SMILES: CC(O)(C#Cc1cc2c(-c3nc(N)ncc3F)cn(C3CCN(CCC(F)(F)F)CC3)c2cn1)C1CC1] | a) Intermediate 201<br>b) 2-Cyclopropyl-but-3-yn-2-ol |

TABLE 22-continued

| Compound | Structure | Starting Materials |
|---|---|---|
| 168 | 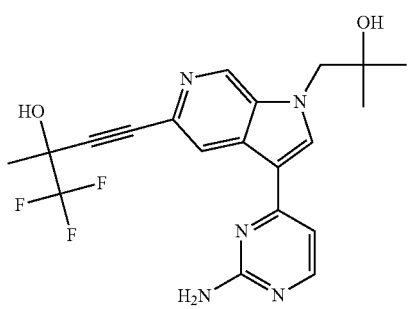 [SMILES: CC(C)(O)Cn1cc(-c2ccnc(N)n2)c2cc(C#CC(C)(O)C(F)(F)F)ncc21] | a) Intermediate 204<br>b) 2-Cyclopropyl-but-3-yn-2-ol |

Example B2 a) Preparation of Compound 111

A degassed mixture of intermediate 14 (0.06 g, 0.166 mmol), 1,1,1-trifluoro-2-methyl-4-trimethylsilanyl-but-3-yn-2-ol (0.35 g, 1.67 mmol), tetrakis(triphenylphosphine)palladium (0.04 g, 0.033 mmol), copper iodide (3.2 mg, 0.017 mmol), triethylamine (0.17 ml, 1.20 mmol) and acetonitrile (1.5 ml) was treated with 1.0 M solution of tetrabutylammonium fluoride in tetrahydrofuran (1.67 ml, 1.67 mmol). The resulting mixture was heated by microwave irradiation at 100° C. for 1 hour. The mixture cooled to ambient temperature and concentrated in vacuo. The residue was purified by column chromatography on silica gel, eluting with a mixture of MeOH and DCM (0:1 to 1:9 by volume). Further purification by ISOLUTE® SCX-2 SPE column, eluting with a mixture of MeOH and 2.0 M ammonia solution in MeOH (1:0 to 0:1 by volume), afforded the desired product (0.03 g, 50%).

$^1$H NMR (400 MHz, DMSO-$d_6$) δ ppm: 8.99 (d, J=1.0 Hz, 1H), 8.56 (d, J=1.0 Hz, 1H), 8.36 (s, 1H), 8.18 (d, J=5.3 Hz, 1H), 7.13 (s, 1H), 6.98 (d, J=5.3 Hz, 1H), 6.57 (s, 2H), 4.83 (s, 1H), 4.28 (s, 2H), 1.68 (s, 3H), 1.13 (s, 6H).

LCMS (Method E): Rt=2.49 min, m/z [M+H]$^+$=420

Compounds 157 and 161 were prepared according to the reaction protocols of example B2 (Table 23). Compound 157 is an enantiomerically pure compound of unknown configuration (S or R enantiomer).

TABLE 23

| Compound | Structure | Starting Materials |
|---|---|---|
| 157 | S or R enantiomer | a) Intermediate 144<br>b) Intermediate 207 |

TABLE 23-continued

| Compound | Structure | Starting Materials |
|---|---|---|
| 161 | 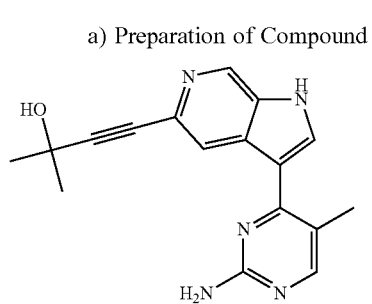 | a) Intermediate 144<br>b) Intermediate 205 |

Example B3 a) Preparation of Compound 112

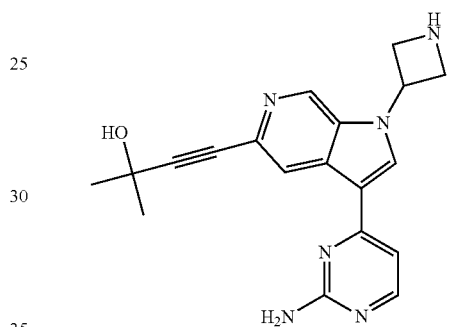

A mixture of intermediate 152 (0.17 mmol), 2.0 M aqueous lithium hydroxide solution (3 ml) and dioxane (3 ml) was stirred at ambient temperature for 2 hours. The mixture was partitioned between EtOAc and water. The organic phase was dried over sodium sulfate and concentrated in vacuo. The residue was purified by reverse phase preparative HPLC, eluting with a mixture of acetonitrile and water containing 0.1% formic acid (1:19 to 1:1 by volume over 20 min), to afford the desired product as a white solid (0.02 g, 35%).

$^1$H NMR (400 MHz, DMSO-$d_6$) δ ppm: 12.22 (s, 1H), 8.74 (d, J=1.0 Hz, 1H), 8.47 (d, J=0.9 Hz, 1H), 8.16 (d, J=2.6 Hz, 1H), 8.14 (s, 1H), 8.09 (s, 1H), 6.35 (s, 2H), 5.44 (s, 1H), 2.28 (s, 3H), 1.51 (s, 6H).

LCMS (Method E): Rt=1.78 min, m/z [M+H]$^+$=308

Example B4 a) Preparation of Compound 113

A mixture of intermediate 150 (0.04 g, 0.09 mmol), trifluoroacetic acid (0.4 ml) and DCM (1.6 ml) under an argon atmosphere at ambient temperature was stirred for 2 hours. The mixture was concentrated in vacuo and the residue purified by ISOLUTE® SCX-2 SPE column, eluting with a mixture of DCM, MeOH and 2.0 M ammonia solution in MeOH (1:1:0 to 1:0:1 by volume), followed by trituration in Et$_2$O to afford the desired product as an off-white solid (0.03 g, 92%).

$^1$H NMR (400 MHz, CD$_3$OD) δ ppm: 8.79 (d, J=0.9 Hz, 1H), 8.67 (s, 1H), 8.65 (d, J=0.9 Hz, 1H), 8.18 (d, J=5.4 Hz, 1H), 7.12 (d, J=5.5 Hz, 1H), 5.64-5.58 (m, 1H), 4.19-4.05 (m, 4H), 1.62 (s, 6H).

LCMS (Method E): Rt=1.55 min, m/z [M+H]$^+$=349

Compounds 114 to 118, 124 and 125 were prepared according to the reaction protocol of example B4 (Table 24).

TABLE 24

| Compound | Structure | Starting Materials |
|---|---|---|
| 114 | ![structure] | Intermediate 155 |

TABLE 24-continued

| Compound | Structure | Starting Materials |
|---|---|---|
| 115 | 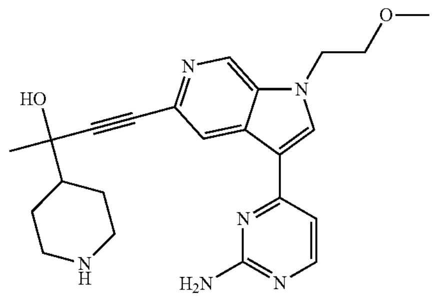 [SMILES: COCCn1cc(-c2ccnc(N)n2)c2cc(C#CC(C)(O)C3CCNCC3)ncc21] | Intermediate 151 |
| 116 | 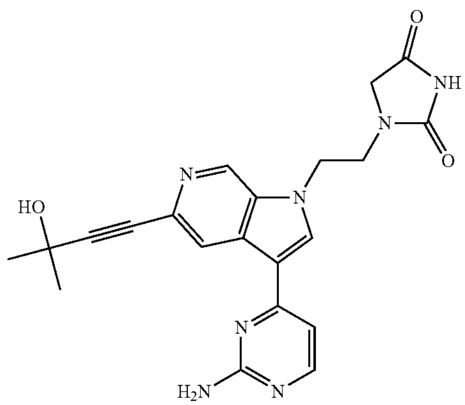 [SMILES: CC(C)(O)C#Cc1cc2c(-c3ccnc(N)n3)cn(CCN3CC(=O)NC3=O)c2cn1] | Intermediate 153 |
| 117 | 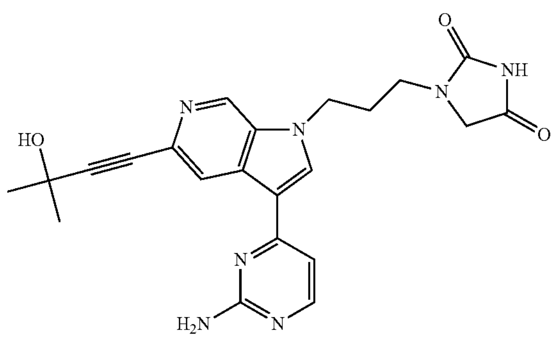 [SMILES: CC(C)(O)C#Cc1cc2c(-c3ccnc(N)n3)cn(CCCN3CC(=O)NC3=O)c2cn1] | Intermediate 154 |
| 118 | 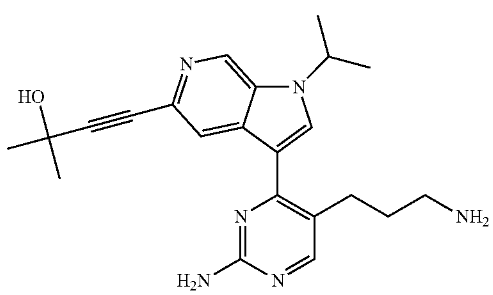 [SMILES: CC(C)n1cc(-c2nc(N)ncc2CCCN)c2cc(C#CC(C)(C)O)ncc21] | Intermediate 156 |
| 124 | 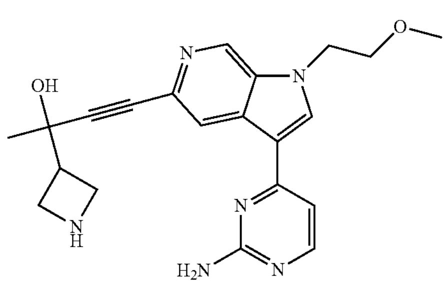 [SMILES: COCCn1cc(-c2ccnc(N)n2)c2cc(C#CC(C)(O)C3CNC3)ncc21] | Intermediate 157 |

TABLE 24-continued

| Compound | Structure | Starting Materials |
|---|---|---|
| 125 | 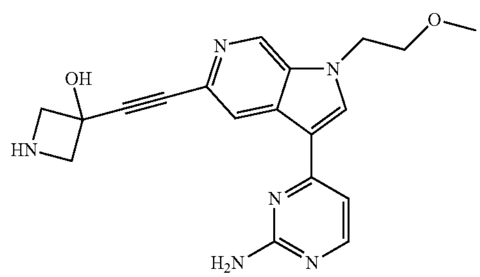 [SMILES: COCCn1cc(-c2ccnc(N)n2)c2cc(C#CC3(O)CNC3)ncc21] | Intermediate 158 |

Example C1 a) Preparation of Compounds 119 and 120

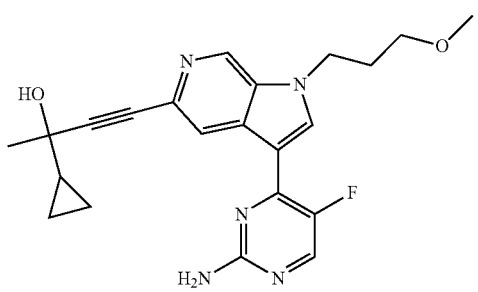

Compound 119 (first eluting enantiomer; R or S)
Compound 120 (second eluting enantiomer; S or R)

Compound 88 (0.04 g, 0.09 mmol) was purified by chiral preparative SFC with the following conditions: column, Phenomenex Lux® 5u Cellulose-4, 250×21.2 mm, 5 µm; mobile phase, $CO_2$ (60%), MeOH (40%); detector, UV 240 nm. This afforded Compound 119 (first eluting enantiomer; R or S) as a pale yellow solid (0.01 g, 33%) and Compound 120 (second eluting enantiomer; S or R) as a pale yellow solid (0.01 g, 32%).

Example C2 a) Preparation of Compound 121 and 122

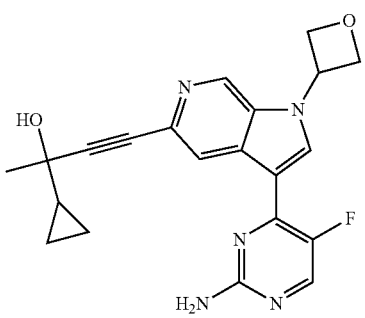

Compound 121 (first eluting enantiomer; R or S)
Compound 122 (second eluting enantiomer; S or R)

Compound 97 (0.20 g, 0.51 mmol) was purified by chiral preparative SFC with the following conditions: column, Phenomenex Lux® 5u Cellulose-4, 250×21.2 mm, 5 µm; mobile phase, $CO_2$ (45%), isopropyl alcohol (55%); detector, UV 240 nm. This afforded Compound 121 (first eluting enantiomer; R or S) as a pale yellow solid (0.08 g, 41%) and Compound 122 (second eluting enantiomer; S or R) as a pale yellow solid (0.08 g, 42%).

Analytical Part

LCMS

Mass Spectrometry (LCMS) experiments to determine retention times and associated mass ions were performed using the following methods:

Method A: Experiments were performed on a Waters ZMD quadrupole mass spectrometer linked to a Waters 1525 LC system with a diode array detector. The spectrometer had an electrospray source operating in positive and negative ion mode. Additional detection was achieved using a Sedex 85 evaporative light scattering detector. LC was carried out using a Luna 3 micron 30×4.6 mm C18 column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 min. The final solvent system was held constant for a further 1 minute.

Method B: Experiments were performed on a Waters VG Platform II quadrupole spectrometer linked to a Hewlett Packard 1050 LC system with a diode array detector. The spectrometer had an electrospray source operating in positive and negative ion mode. Additional detection was achieved using a Sedex 85 evaporative light scattering detector. LC was carried out using a Luna 3 micron 30×4.6 mm C18 column and a 2 ml/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 min. The final solvent system was held constant for a further 1 minute.

Method C: Experiments were performed on a Waters Platform LC quadrupole mass spectrometer linked to a Hewlett Packard HP1100 LC system with diode array detector. The spectrometer had an electrospray source operating in positive and negative ion mode. Additional detection was achieved using a Sedex 85 evaporative light scattering detector. LC was carried out using a Phenomenex Luna 3 micron 30×4.6 mm C18 column and a 2 ml/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 min. The final solvent system was held constant for a further 1 minute.

Method D: Experiments were performed on a Waters ZQ quadrupole mass spectrometer linked to a Hewlett Packard HP1100 LC system with quaternary pump and PDA detector. The spectrometer had an electrospray source operating in positive and negative ion mode. Additional detection was achieved using a Sedex 65 evaporative light scattering detector. LC was carried out using a Phenomenex Luna 3 micron 30×4.6 mm C18 column and a 2 ml/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 min. The final solvent system was held constant for a further 1 minute.

Method E: Experiments were performed on a Waters Micromass ZQ2000 quadrupole mass spectrometer linked to a Waters Acquity UPLC system with a PDA UV detector. The spectrometer had an electrospray source operating in positive and negative ion mode. LC was carried out using an Acquity BEH 1.7 micron C18 column, an Acquity BEH Shield 1.7 micron RP18 column or an Acquity HST 1.8 micron column. Each column has dimensions of 100×2.1 mm and was maintained at 40° C. with a flow rate of 0.4 ml/minute. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.2 min. The final solvent system was held constant for a further 0.8 min.

NMR Data

The values of acid content (e.g. formic acid or acetic acid) in the compounds as provided herein, are those obtained experimentally and may vary when using different analytical methods. The content of formic acid or acetic acid reported herein was determined by $^1$H NMR integration. Compounds with an acid content of below 0.5 equivalents may be considered as free bases.

The NMR experiments herein were carried out using a Varian Unity Inova spectrometer with standard pulse sequences, operating at 400 MHz at ambient temperature. Chemical shifts ($\delta$) are reported in parts per million (ppm) downfield from tetramethylsilane (TMS), which was used as internal standard.

Compound 2

$^1$H NMR (400 MHz, DMSO-$d_6$) $\delta$ ppm: 8.90 (d, J=1.1 Hz, 1H), 8.48 (d, J=1.1 Hz, 1H), 8.42 (s, 1H), 8.17 (d, J=5.3 Hz, 1H), 6.98 (d, J=5.3 Hz, 1H), 6.57 (s, 2H), 5.48 (s, 1H), 4.52 (t, J=5.0 Hz, 2H), 3.73 (t, J=5.0 Hz, 2H), 3.23 (s, 3H), 1.52 (s, 6H).

LCMS (Method E): Rt=1.96 min, m/z [M+H]$^+$=352

Compound 3

$^1$H NMR (400 MHz, DMSO-$d_6$) $\delta$ ppm: 8.94 (d, J=1.1 Hz, 1H), 8.45 (d, J=1.1 Hz, 1H), 8.32 (s, 1H), 8.17 (d, J=5.3 Hz, 1H), 6.97 (d, J=5.3 Hz, 1H), 6.56 (s, 2H), 5.47 (s, 1H), 4.82 (s, 1H), 4.26 (s, 2H), 1.52 (s, 6H), 1.13 (s, 6H).

LCMS (Method E): Rt=1.89 min, m/z [M+H]$^+$=366

Compound 4

$^1$H NMR (400 MHz, DMSO-$d_6$) $\delta$ ppm: 12.30-12.10 (br s, 1H), 8.73 (d, J=1.1 Hz, 1H), 8.53 (d, J=1.1 Hz, 1H), 8.47 (s, 1H), 8.20 (d, J=5.2 Hz, 1H), 7.04-7.03 (m, 2H), 5.47 (s, 1H), 2.91 (s, 3H), 1.50 (s, 6H).

LCMS (Method E): Rt=1.89 min, m/z [M+H]$^+$=308

Compound 5

$^1$H NMR (400 MHz, DMSO-$d_6$) $\delta$ ppm: 8.84 (d, J=1.1 Hz, 1H), 8.48 (d, J=1.1 Hz, 1H), 8.41 (s, 1H), 8.16 (d, J=5.3 Hz, 1H), 6.95 (d, J=5.3 Hz, 1H), 6.55 (s, 2H), 5.47 (s, 1H), 3.96 (s, 3H), 1.51 (s, 6H).

LCMS (Method E): Rt=1.78 min, m/z [M+H]$^+$=308

Compound 6 (Formic Acid 0.5 Equivalents)

$^1$H NMR (400 MHz, DMSO-$d_6$) $\delta$ ppm: 8.95 (d, J=1.1 Hz, 1H), 8.52 (s, 1H), 8.50 (d, J=1.1 Hz, 1H), 8.33 (s, 0.5H), 8.17 (d, J=5.3 Hz, 1H), 6.99 (d, J=5.3 Hz, 1H), 6.56 (s, 2H), 5.47 (s, 1H), 4.36-4.32 (m, 2H), 3.86-3.81 (m, 1H), 3.69-3.64 (m, 2H), 3.49-3.47 (m, 1H), 2.86-2.83 (m, 1H), 1.93-1.88 (m, 1H), 1.65-1.61 (m, 1H), 1.51 (s, 6H).

LCMS (Method E): Rt=2.01 min, m/z [M+H]$^+$=378

Compound 7

$^1$H NMR (400 MHz, DMSO-$d_6$) $\delta$ ppm: 8.91 (d, J=1.1 Hz, 1H), 8.47 (d, J=1.1 Hz, 1H), 8.46 (s, 1H), 8.16 (d, J=5.3 Hz, 1H), 6.96 (d, J=5.3 Hz, 1H), 6.55 (s, 2H), 5.47 (s, 1H), 4.45 (t, J=6.1 Hz, 2H), 3.50 (t, J=4.4 Hz, 4H), 2.74 (t, J=6.1 Hz, 2H), 2.45-2.40 (m, 4H), 1.51 (s, 6H).

LCMS (Method E): Rt=1.67 min, m/z [M+H]$^+$=407

Compound 8

$^1$H NMR (400 MHz, DMSO-$d_6$) $\delta$ ppm: 8.93 (d, J=1.1 Hz, 1H), 8.65 (s, 1H), 8.52 (d, J=1.0 Hz, 1H), 8.27 (s, 1H), 6.90 (s, 2H), 5.46 (s, 1H), 5.00 (t, J=5.0 Hz, 1H), 4.46 (t, J=5.0 Hz, 2H), 3.81-3.75 (m, 2H), 1.52 (s, 6H).

LCMS (Method E): Rt=2.29 min, m/z [M+H]$^+$=372/374

Compound 9

$^1$H NMR (400 MHz, DMSO-$d_6$) $\delta$ ppm: 12.28 (br s, 1H), 8.73 (d, J=1.1 Hz, 1H), 8.54 (d, J=1.1 Hz, 1H), 8.45 (s, 1H), 8.15 (d, J=5.3 Hz, 1H), 7.04 (d, J=5.3 Hz, 1H), 6.56 (s, 2H), 6.29 (s, 1H), 1.01 (s, 4H).

LCMS (Method E): Rt=1.64 min, m/z [M+H]$^+$=292

Compound 10

$^1$H NMR (400 MHz, DMSO-$d_6$) $\delta$ ppm: 8.96 (d, J=1.0 Hz, 1H), 8.61 (s, 1H), 8.56 (d, J=1.0 Hz, 1H), 8.17 (d, J=5.3 Hz, 1H), 7.08 (d, J=5.3 Hz, 1H), 6.57 (s, 2H), 5.48 (d, J=5.4 Hz, 1H), 4.99-4.98 (m, 1H), 4.64-4.63 (m, 1H), 1.55 (d, J=6.6 Hz, 6H), 1.44 (d, J=6.6 Hz, 3H).

LCMS (Method E): Rt=1.06 min, m/z [M+H]$^+$=322

Compound 11

$^1$H NMR (400 MHz, DMSO-$d_6$, trifluoroacetic acid) $\delta$ ppm: 9.51 (s, 1H), 9.39 (s, 1H), 8.97 (s, 1H), 8.37 (d, J=6.6 Hz, 1H), 7.41 (d, J=6.6 Hz, 1H), 4.55 (t, J=7.1 Hz, 2H), 2.82 (t, J=7.1 Hz, 2H), 2.18-2.11 (m, 2H), 1.52 (s, 6H).

LCMS (Method E): Rt=1.55 min, m/z [M+H]$^+$=351

Compound 12

$^1$H NMR (400 MHz, DMSO-$d_6$) $\delta$ ppm: 8.89 (d, J=1.0 Hz, 1H), 8.48 (d, J=1.0 Hz, 1H), 8.42 (s, 1H), 8.17 (d, J=5.3 Hz, 1H), 6.98 (d, J=5.3 Hz, 1H), 6.56 (s, 2H), 5.47 (s, 1H), 5.01 (t, J=5.2 Hz, 1H), 4.39 (t, J=5.2 Hz, 2H), 3.79 (q, J=5.2 Hz, 2H), 1.52 (s, 6H).

LCMS (Method E): Rt=1.71 min, m/z [M+H]$^+$=338

A second batch was isolated with 1.5 equivalents of formic acid present.

Compound 13

$^1$H NMR (400 MHz, DMSO-$d_6$) $\delta$ ppm: 8.97 (d, J=1.1 Hz, 1H), 8.61 (s, 1H), 8.60 (d, J=1.1 Hz, 1H), 8.16 (d, J=5.3 Hz, 1H), 7.08 (d, J=5.3 Hz, 1H), 6.57 (s, 2H), 5.36 (t, J=5.9 Hz, 1H), 4.99-4.98 (m, 1H), 4.35 (d, J=5.9 Hz, 2H), 1.55 (d, J=6.6 Hz, 6H).

LCMS (Method E): Rt=1.83 min, m/z [M+H]$^+$=308

Compound 14 (Formic Acid 0.5 Equivalents)

$^1$H NMR (400 MHz, DMSO-$d_6$) $\delta$ ppm: 12.39 (s, 1H), 8.79 (s, 1H), 8.63 (d, J=2.7 Hz, 1H), 8.50 (s, 1H), 8.27 (s, 1H), 8.17 (s, 0.5H), 6.90 (s, 2H), 5.46 (s, 1H), 1.51 (s, 6H).

LCMS (Method E): Rt=2.33 min, m/z [M+H]$^+$=328/330

Compound 15 (Formic Acid 1.8 Equivalents)

$^1$H NMR (400 MHz, DMSO-d$_6$) δ ppm: 8.94 (d, J=0.9 Hz, 1H), 8.59 (s, 1H), 8.52 (d, J=0.9 Hz, 1H), 8.17 (d, J=5.5 Hz, 1H), 8.14 (s, 1.8H), 7.08 (d, J=5.4 Hz, 1H), 6.56 (s, 2H), 5.47 (s, 1H), 5.02-4.93 (m, 1H), 1.54 (d, J=6.6 Hz, 6H), 1.52 (s, 6H).

LCMS (Method E): Rt=2.07 min, m/z [M+H]$^+$=336

Compound 16

$^1$H NMR (400 MHz, DMSO-d$_6$) δ ppm: 8.99 (d, J=1.1 Hz, 1H), 8.62 (s, 1H), 8.46 (d, J=1.1 Hz, 1H), 8.28 (s, 1H), 6.90 (s, 2H), 5.47 (s, 1H), 5.06-4.98 (m, 1H), 1.56 (d, J=6.6 Hz, 6H), 1.51 (s, 6H).

LCMS (Method E): Rt=2.88 min, m/z [M+H]$^+$=370/372

A second batch was isolated with 1.0 equivalents of formic acid present.

Compound 17 (Formic Acid 1.0 Equivalents)

$^1$H NMR (400 MHz, DMSO-d$_6$) δ ppm: 9.01 (d, J=1.1 Hz, 1H), 8.62 (s, 1H), 8.48 (d, J=1.1 Hz, 1H), 8.29 (s, 1H), 7.78 (d, J=3.2 Hz, 1H), 7.69 (d, J=3.2 Hz, 1H), 7.05 (s, 1H), 6.90 (s, 2H), 5.04-5.03 (m, 1H), 1.93 (s, 3H), 1.56 (d, J=6.7 Hz, 6H).

LCMS (Method E): Rt=3.19 min, m/z [M+H]$^+$=439/441

Compound 18 (Formic Acid 1.5 Equivalents)

$^1$H NMR (400 MHz, DMSO-d$_6$) δ ppm: 8.94 (d, J=1.1 Hz, 1H), 8.59 (s, 1H), 8.53 (d, J=1.1 Hz, 1H), 8.16 (d, J=5.3 Hz, 1H), 8.15 (s, 1.5H), 7.08 (d, J=5.3 Hz, 1H), 6.56 (s, 2H), 5.46-5.20 (br s, 1H), 4.98-4.97 (m, 1H), 1.96-1.93 (m, 4H), 1.78-1.72 (m, 4H), 1.55 (d, J=6.6 Hz, 6H).

LCMS (Method E): Rt=2.33 min, m/z [M+H]$^+$=362

Compound 19

$^1$H NMR (400 MHz, DMSO-d$_6$) δ ppm: 9.00 (d, J=1.0 Hz, 1H), 8.62 (s, 1H), 8.47 (d, J=1.0 Hz, 1H), 8.28 (s, 1H), 6.90 (s, 2H), 5.32 (s, 1H), 5.02-5.01 (m, 1H), 1.96-1.93 (m, 4H), 1.75-1.72 (m, 4H), 1.57 (d, J=6.7 Hz, 6H).

LCMS (Method E): Rt=3.17 min, m/z [M+H]$^+$=396/398

Compound 20 (Formic Acid 0.2 Equivalents)

$^1$H NMR (400 MHz, DMSO-d$_6$) δ ppm: 8.95 (d, J=1.1 Hz, 1H), 8.63 (s, 1H), 8.52 (d, J=1.1 Hz, 1H), 8.28 (s, 1H), 8.25 (s, 0.2H), 7.78 (d, J=3.2 Hz, 1H), 7.69 (d, J=3.2 Hz, 1H), 7.04 (s, 1H), 6.90 (s, 2H), 4.60 (t, J=5.0 Hz, 2H), 3.72 (t, J=5.0 Hz, 2H), 3.23 (s, 3H), 1.93 (s, 3H).

LCMS (Method E): Rt=2.92 min, m/z [M+H]$^+$=455/457

Compound 21

$^1$H NMR (400 MHz, DMSO-d$_6$) δ ppm: 8.98 (d, J=1.1 Hz, 1H), 8.62 (s, 1H), 8.53 (d, J=1.1 Hz, 1H), 8.26 (s, 1H), 6.90 (s, 2H), 6.28 (s, 1H), 4.82 (s, 1H), 4.31 (s, 2H), 1.13 (s, 6H), 1.01 (s, 4H).

LCMS (Method E): Rt=2.53 min, m/z [M+H]$^+$=398/400

Compound 22

$^1$H NMR (400 MHz, DMSO-d$_6$) δ ppm: 8.94 (d, J=1.1 Hz, 1H), 8.49 (d, J=1.1 Hz, 1H), 8.33 (s, 1H), 8.16 (d, J=5.3 Hz, 1H), 6.97 (d, J=5.3 Hz, 1H), 6.56 (s, 2H), 6.29 (s, 1H), 4.81 (s, 1H), 4.25 (s, 2H), 1.13 (s, 6H), 1.01 (s, 4H).

LCMS (Method E): Rt=1.85 min, m/z [M+H]$^+$=364

Compound 23

$^1$H NMR (400 MHz, DMSO-d$_6$) δ ppm: 9.00 (d, J=1.1 Hz, 1H), 8.60 (s, 1H), 8.52 (d, J=1.1 Hz, 1H), 8.27 (s, 1H), 7.78 (d, J=3.2 Hz, 1H), 7.69 (d, J=3.2 Hz, 1H), 7.03 (s, 1H), 6.89 (s, 2H), 4.83 (s, 1H), 4.32 (s, 2H), 1.93 (s, 3H), 1.12 (s, 6H).

LCMS (Method E): Rt=2.76 min, m/z [M+H]$^+$=469/471

Compound 24

$^1$H NMR (400 MHz, DMSO-d$_6$) δ ppm: 8.98 (d, J=1.1 Hz, 1H), 8.61 (s, 1H), 8.50 (d, J=1.1 Hz, 1H), 8.27 (s, 1H), 6.90 (s, 2H), 5.46 (s, 1H), 4.83 (s, 1H), 4.32 (s, 2H), 1.51 (s, 6H), 1.13 (s, 6H).

LCMS (Method E): Rt=2.54 min, m/z [M+H]$^+$=400/402

Compound 25 (Formic Acid 0.2 Equivalents)

$^1$H NMR (400 MHz, DMSO-d$_6$) δ ppm: 8.93 (d, J=1.1 Hz, 1H), 8.63 (s, 1H), 8.50 (d, J=1.1 Hz, 1H), 8.27 (s, 1H), 8.22 (s, 0.2H), 6.90 (s, 2H), 5.46 (s, 1H), 4.59 (t, J=5.0 Hz, 2H), 3.72 (t, J=5.0 Hz, 2H), 3.23 (s, 3H), 1.51 (s, 6H).

LCMS (Method E): Rt=2.69 min, m/z [M+H]$^+$=386/388

Compound 26 (Formic Acid 0.2 Equivalents)

$^1$H NMR (400 MHz, DMSO-d$_6$) δ ppm: 8.92 (d, J=1.1 Hz, 1H), 8.51 (d, J=1.1 Hz, 1H), 8.43 (s, 1H), 8.26 (s, 0.2H), 8.17 (d, J=5.3 Hz, 1H), 7.78 (d, J=3.2 Hz, 1H), 7.69 (d, J=3.2 Hz, 1H), 7.06 (s, 1H), 6.98 (d, J=5.3 Hz, 1H), 6.56 (s, 2H), 4.53 (t, J=5.0 Hz, 2H), 3.73 (t, J=5.0 Hz, 2H), 3.23 (s, 3H), 1.93 (s, 3H).

LCMS (Method E): Rt=2.20 min, m/z [M+H]$^+$=421

Compound 27 (Formic Acid 0.4 Equivalents)

$^1$H NMR (400 MHz, DMSO-d$_6$) δ ppm: 8.96 (d, J=1.0 Hz, 1H), 8.48 (d, J=1.0 Hz, 1H), 8.34 (s, 1H), 8.29 (s, 0.4H), 8.17 (d, J=5.3 Hz, 1H), 7.78 (d, J=3.2 Hz, 1H), 7.69 (d, J=3.2 Hz, 1H), 7.11-7.00 (br s, 1H), 6.97 (d, J=5.3 Hz, 1H), 6.56 (s, 2H), 4.90-4.74 (br s, 1H), 4.26 (s, 2H), 1.93 (s, 3H), 1.12 (s, 6H).

LCMS (Method E): Rt=2.13 min, m/z [M+H]$^+$=435

Compound 28

$^1$H NMR (400 MHz, DMSO-d$_6$) δ ppm: 8.96 (d, J=1.1 Hz, 1H), 8.53 (s, 1H), 8.51 (d, J=1.1 Hz, 1H), 8.18 (d, J=5.3 Hz, 1H), 7.01 (d, J=5.3 Hz, 1H), 6.64 (s, 2H), 5.48 (s, 1H), 4.65-4.66 (m, 4H), 4.44 (t, J=6.1 Hz, 2H), 3.55-3.57 (m, 1H), 1.52 (s, 6H).

LCMS (Method E): Rt=1.91 min, m/z [M+H]$^+$=364

Compound 29

$^1$H NMR (400 MHz, DMSO-d$_6$) δ ppm: 8.91 (s, 1H), 8.53 (s, 1H), 8.31 (s, 1H), 8.15 (d, J=4.8 Hz, 1H), 6.98 (d, J=5.3 Hz, 1H), 6.48 (s, 2H), 6.05 (s, 1H), 5.00 (s, 1H), 4.24 (s, 2H), 3.93-3.85 (m, 4H), 2.32-2.18 (m, 2H), 1.10 (s, 6H).

LCMS (Method E): Rt=1.84 min, m/z [M+H]$^+$=394

Compound 30

$^1$H NMR (400 MHz, CD$_3$OD) δ ppm: 8.63 (d, J=1.0 Hz, 1H), 8.60 (d, J=1.0 Hz, 1H), 8.19 (s, 1H), 8.12 (d, J=5.5 Hz, 1H), 7.00-6.98 (m, 1H), 5.35 (s, 2H), 3.19 (s, 3H), 2.96 (s, 3H), 1.59 (s, 6H).

LCMS (Method E): Rt=1.82 min, m/z [M+H]$^+$=379

Compound 31 (Formic Acid 0.5 Equivalents).

$^1$H NMR (400 MHz, DMSO-d$_6$) δ ppm: 8.93 (d, J=1.0 Hz, 1H), 8.54 (d, J=1.0 Hz, 1H), 8.44 (s, 1H), 8.18 (d, J=5.3 Hz, 1.5H), 8.15 (d, J=0.6 Hz, 1H), 7.23 (s, 1H), 6.99 (d, J=5.3 Hz, 1H), 6.72 (s, 1H), 6.57 (s, 2H), 4.54 (t, J=5.0 Hz, 2H), 3.74 (t, J=5.0, 2H), 3.23 (s, 3H), 1.93 (s, 3H).

LCMS (Method E): Rt=2.11 min, m/z [M+H]$^+$=405

Compound 32 (Formic Acid 0.5 Equivalents).

$^1$H NMR (400 MHz, DMSO-d$_6$) δ ppm: 8.90 (d, J=1.1 Hz, 1H), 8.45 (d, J=1.1 Hz, 1H), 8.41 (s, 1H), 8.18 (d, J=5.3 Hz, 1H), 8.15 (s, 0.5H), 6.98 (d, J=5.3 Hz, 1H), 6.56 (s, 2H), 5.33 (s, 1H), 4.52 (t, J=5.0 Hz, 2H), 3.73 (t, J=5.1 Hz, 2H), 3.23 (s, 3H), 1.54 (s, 3H), 1.21-1.13 (m, 1H), 0.60-0.38 (m, 4H).

LCMS (Method E): Rt=2.26 min, m/z [M+H]$^+$=378

Compound 33

$^1$H NMR (400 MHz, DMSO-d$_6$) δ ppm: 8.98 (d, J=0.9 Hz, 1H), 8.61 (s, 1H), 8.50 (d, J=0.8 Hz, 1H), 8.27 (s, 1H), 6.89 (s, 2H), 5.29 (s, 1H), 4.84 (s, 1H), 4.32 (s, 2H), 1.98-1.91 (m, 4H), 1.79-1.68 (m, 4H), 1.13 (s, 6H).

LCMS (Method E): Rt=2.84 min, m/z [M+H]$^+$=426/428

Compound 34 (Formic Acid 1.7 Equivalents)

$^1$H NMR (400 MHz, CD$_3$OD) δ ppm: 8.92 (d, J=1.0 Hz, 1H), 8.72 (s, 1H), 8.51 (d, J=1.0 Hz, 1H), 8.19 (d, J=5.2 Hz, 1H), 8.16 (s, 1.7H), 7.14 (d, J=5.2 Hz, 1H), 6.59 (s, 2H), 5.33-5.26 (m, 1H), 3.81 (t, J=7.0 Hz, 2H), 3.48 (t, J=7.0 Hz, 2H), 2.39 (s, 3H), 1.51 (s, 6H).

LCMS (Method E): Rt=1.56 min, m/z [M+H]⁺=363
A second batch was isolated as a free base.
Compound 35
¹H NMR (400 MHz, DMSO-d₆) δ ppm: 8.90 (d, J=1.0 Hz, 1H), 8.45 (d, J=1.0 Hz, 1H), 8.41 (s, 1H), 8.18 (d, J=5.3 Hz, 1H), 6.98 (d, J=5.3 Hz, 1H), 6.54 (s, 2H), 5.16-5.12 (s, 1H), 4.52 (t, J=5.0 Hz, 2H), 3.73 (t, J=5.0 Hz, 2H), 3.23 (s, 3H), 1.72-1.64 (m, 4H), 1.03 (t, J=7.4 Hz, 6H).
LCMS (Method E): Rt=2.38 min, m/z [M+H]⁺=380
Compound 36
¹H NMR (400 MHz, DMSO-d₆) δ ppm: d 8.97 (d, J=0.9 Hz, 1H), 8.51 (d, J=0.9 Hz, 1H), 8.34 (s, 1H), 8.18 (d, J=5.3 Hz, 1H), 7.71-7.68 (m, 2H), 7.42-7.37 (m, 2H), 7.32-7.26 (m, 1H), 6.98 (d, J=5.3 Hz, 1H), 6.56 (s, 2H), 6.21 (s, 1H), 4.82 (s, 1H), 4.26 (s, 2H), 1.77 (s, 3H), 1.13 (s, 6H).
LCMS (Method E): Rt=2.56 min, m/z [M+H]⁺=428
Compound 37
¹H NMR (400 MHz, DMSO-d₆) δ ppm: 8.95 (d, J=0.9 Hz, 1H), 8.44 (d, J=0.9 Hz, 1H), 8.32 (s, 1H), 8.18 (d, J=5.2 Hz, 1H), 6.97 (d, J=5.3 Hz, 1H), 6.54 (s, 2H), 5.28 (s, 1H), 4.82 (s, 1H), 4.26 (s, 2H), 2.57-2.53 (m, 1H), 2.15-2.02 (m, 2H), 1.97-1.68 (m, 4H), 1.36 (s, 3H), 1.13 (s, 6H).
LCMS (Method E): Rt=2.40 min, m/z [M+H]⁺=406
Compound 38 (Formic Acid 1.5 Equivalents)
¹H NMR (400 MHz, CD₃OD) δ ppm: 8.87 (s, 1H), 8.64 (s, 1H), 8.34 (s, 1H), 8.16 (s, 1H), 8.15 (s, 1.5H), 7.08 (d, J=5.6 Hz, 1H), 4.32 (s, 2H), 2.07-2.02 (m, 2H), 1.78-1.67 (m, 6H), 1.67-1.58 (m, 1H), 1.41-1.28 (m, 1H), 1.25 (s, 6H).
LCMS (Method E): Rt=2.36 min, m/z [M+H]⁺=406
Compound 39 (Formic Acid 0.5 Equivalents)
¹H NMR (400 MHz, CD₃OD) δ ppm: 8.87 (s, 1H), 8.66 (s, 1H), 8.35 (s, 1H), 8.15 (d, J=4.9 Hz, 1.5H), 7.08 (d, J=5.6 Hz, 1H), 4.33 (s, 2H), 3.84-3.72 (m, 2H), 3.38 (s, 3H), 2.11-2.05 (m, 2H), 1.61 (s, 3H), 1.25 (s, 6H).
LCMS (Method E): Rt=2.05 min, m/z [M+H]⁺=410
Compound 40
¹H NMR (400 MHz, DMSO-d₆) δ ppm: 8.94 (d, J=0.9 Hz, 1H), 8.42 (d, J=0.9 Hz, 1H), 8.32 (s, 1H), 8.18 (d, J=5.4 Hz, 1H), 6.97 (d, J=5.3 Hz, 1H), 6.55 (s, 2H), 5.25 (s, 1H), 4.82 (s, 1H), 4.26 (s, 2H), 1.86-1.78 (m, 1H), 1.43 (s, 3H), 1.13 (s, 6H), 1.03 (dd, J=6.8, 15.7 Hz, 6H).
LCMS (Method E): Rt=2.32 min, m/z [M+H]⁺=394
Compound 41
¹H NMR (400 MHz, DMSO-d₆) δ ppm: 8.97 (s, 1H), 8.63 (d, J=3.2 Hz, 2H), 8.51 (s, 1H), 7.89 (s, 2H), 5.48 (s, 1H), 4.61 (t, J=4.9 Hz, 2H), 3.73 (t, J=4.9 Hz, 2H), 3.25 (s, 3H), 1.52 (s, 6H).
LCMS (Method E): Rt=2.63 min, m/z [M+H]⁺=377
Compound 42 (Formic Acid 0.5 Equivalents)
¹H NMR (400 MHz, DMSO-d₆) δ ppm: 8.96 (d, J=0.9 Hz, 1H), 8.51 (d, J=0.9 Hz, 1H), 8.34 (s, 1H), 8.17 (d, J=5.5 Hz, 1H), 8.13 (s, 0.5H), 6.98 (d, J=5.3 Hz, 1H), 6.57 (s, 2H), 5.88 (s, 1H), 4.82 (s, 1H), 4.26 (s, 2H), 2.48-2.40 (m, 2H), 2.29-2.20 (m, 2H), 1.87-1.79 (m, 2H), 1.13 (s, 6H).
LCMS (Method E): Rt=2.04 min, m/z [M+H]⁺=378
Compound 43 (Formic Acid 0.6 Equivalents)
¹H NMR (400 MHz, DMSO-d₆) δ ppm: 8.89 (d, J=0.9 Hz, 1H), 8.39 (d, J=0.9 Hz, 1H), 8.27 (s, 1H), 8.13 (d, J=5.3 Hz, 1H), 8.10 (s, 0.6H), 6.92 (d, J=5.3 Hz, 1H), 6.50 (s, 2H), 5.29 (s, 1H), 4.77 (s, 1H), 4.21 (s, 2H), 1.69-1.61 (m, 2H), 1.42 (s, 3H), 1.08 (s, 6H), 0.99 (t, J=7.4 Hz, 3H).
LCMS (Method E): Rt=2.10 min, m/z [M+H]⁺=380
Compound 44 (Formic Acid 0.6 Equivalents)
¹H NMR (400 MHz, DMSO-d₆) δ ppm: 8.87 (d, J=1.0 Hz, 1H), 8.51-8.46 (m, 2H), 8.17 (d, J=5.2 Hz, 1H), 8.14 (s, 0.6H), 6.99 (d, J=5.3 Hz, 1H), 6.57 (s, 2H), 5.46 (s, 1H), 4.40 (t, J=7.1 Hz, 2H), 3.27 (t, J=6.2 Hz, 2H), 3.21 (s, 3H), 2.12-2.04 (m, 2H), 1.52 (s, 6H).
LCMS (Method E): Rt=2.10 min, m/z [M+H]⁺=366
Compound 45 (Formic Acid 0.9 Equivalents)
¹H NMR (400 MHz, DMSO-d₆) δ ppm: 12.40 (s, 1H), 8.78 (d, J=1.0 Hz, 1H), 8.59 (d, J=1.1 Hz, 1H), 8.30 (d, J=2.6 Hz, 1H), 8.24 (d, J=4.0 Hz, 1H), 8.16 (s, 0.9H), 6.62 (s, 2H), 5.47 (s, 1H), 1.52 (s, 6H).
LCMS (Method E): Rt=2.19 min, m/z [M+H]⁺=312
Compound 46 (Formic Acid 0.8 Equivalents)
¹H NMR (400 MHz, DMSO-d₆) δ ppm: 8.87 (s, 1H), 8.25 (d, J=5.3 Hz, 1H), 8.22 (s, 0.8H), 7.98 (s, 1H), 6.79 (d, J=5.2 Hz, 1H), 6.54 (s, 2H), 5.44 (s, 1H), 4.77 (s, 1H), 4.26 (s, 2H), 2.75 (s, 3H), 1.49 (s, 6H), 1.17 (s, 6H).
LCMS (Method E): Rt=1.94 min, m/z [M+H]⁺=380
Compound 47
¹H NMR (400 MHz, DMSO-d₆) δ ppm: 8.95 (d, J=1.0 Hz, 1H), 8.45 (d, J=1.0 Hz, 1H), 8.33 (s, 1H), 8.18 (d, J=5.3 Hz, 1H), 6.97 (d, J=5.3 Hz, 1H), 6.53 (s, 2H), 5.80 (s, 1H), 4.81 (dd, J=5.5, 15.4 Hz, 3H), 4.26 (s, 2H), 4.15 (dd, J=5.5, 7.4 Hz, 2H), 1.49 (s, 3H), 1.40 (s, 3H), 1.12 (s, 6H).
LCMS (Method E): Rt=2.04 min, m/z [M+H]⁺=422
Compound 48 (Formic Acid 1.0 Equivalents)
¹H NMR (400 MHz, DMSO-d₆) δ ppm: 12.29 (s, 1H), 8.73 (d, J=1.0 Hz, 1H), 8.55 (s, 1H), 8.47 (s, 1H), 8.19 (d, J=5.1 Hz, 2H), 7.12-7.06 (m, 1H), 7.03 (d, J=5.3 Hz, 1H), 5.47 (s, 1H), 3.35-3.17 (m, 2H), 1.50 (s, 6H), 1.22 (t, J=6.7 Hz, 3H).
LCMS (Method E): Rt=2.10 min, m/z [M+H]⁺=322
Compound 49 (Formic Acid 1.0 Equivalents)
¹H NMR (400 MHz, DMSO-d₆) δ ppm: 8.89 (d, J=1.0 Hz, 1H), 8.46 (d, J=1.0 Hz, 1H), 8.39 (s, 1H), 8.29 (s, 1H), 8.17 (d, J=5.2 Hz, 1H), 7.88-7.82 (m, 1H), 6.95 (d, J=5.3 Hz, 1H), 6.57 (s, 2H), 5.47 (s, 1H), 4.57 (t, J=6.6 Hz, 2H), 2.68 (t, J=6.6 Hz, 2H), 2.50 (s, 3H), 1.51 (s, 6H).
LCMS (Method E): Rt=1.82 min, m/z [M+H]⁺=379
Compound 50 (Formic Acid 1.0 Equivalents)
¹H NMR (400 MHz, DMSO-d₆) δ ppm: 8.92 (d, J=1.0 Hz, 1H), 8.47-8.45 (m, 2H), 8.18-8.16 (m, 2H), 6.95 (d, J=5.3 Hz, 1H), 6.56 (s, 2H), 5.47 (s, 1H), 4.55 (t, J=6.7 Hz, 2H), 2.96 (t, J=6.7 Hz, 2H), 2.89 (s, 3H), 2.79 (s, 3H), 1.52 (s, 6H).
LCMS (Method E): Rt=1.96 min, m/z [M+H]⁺=393
Compound 51
¹H NMR (400 MHz, DMSO-d₆) δ ppm: 8.86 (d, J=1.0 Hz, 1H), 8.50 (d, J=1.2 Hz, 1H), 8.49 (s, 1H), 8.17 (s, 1H), 6.99 (d, J=5.4 Hz, 1H), 6.55 (s, 2H), 5.47 (s, 1H), 4.55 (s, 1H), 4.41 (dd, J=5.7, 10.5 Hz, 2H), 1.98-1.92 (m, 2H), 1.52 (s, 6H), 1.18 (s, 6H).
LCMS (Method E): Rt=2.04 min, m/z [M+H]⁺=380
Compound 52
¹H NMR (400 MHz, DMSO-d₆) δ ppm: 12.82 (s, 1H), 11.23 (s, 1H), 8.82 (s, 1H), 8.41 (d, J=5.2 Hz, 1H), 7.93 (s, 1H), 7.02 (d, J=5.2 Hz, 1H), 6.86 (s, 2H), 5.48 (s, 1H), 3.63-3.53 (m, 4H), 3.28 (s, 3H), 1.49 (s, 6H).
LCMS (Method E): Rt=2.28 min, m/z [M+H]⁺=395
Compound 53
¹H NMR (400 MHz, DMSO-d₆) δ ppm: 8.95 (d, J=1.0 Hz, 1H), 8.44 (d, J=1.0 Hz, 1H), 8.32 (s, 1H), 8.18 (d, J=5.4 Hz, 1H), 6.97 (d, J=5.4 Hz, 1H), 6.54 (s, 2H), 5.37 (s, 1H), 4.81 (s, 1H), 4.25 (s, 2H), 1.75 (dd, J=6.3, 13.6 Hz, 1H), 1.57-1.50 (m, 4H), 1.13 (s, 6H), 0.99-0.90 (m, 1H), 0.51-0.45 (m, 2H), 0.20-0.15 (m, 2H).
LCMS (Method E): Rt=2.33 min, m/z [M+H]⁺=406
Compound 54
¹H NMR (400 MHz, DMSO-d₆) δ ppm: 8.94 (d, J=1.1 Hz, 1H), 8.60 (d, J=1.1 Hz, 1H), 8.31 (d, J=2.8 Hz, 1H), 8.25 (d, J=3.9 Hz, 1H), 6.64 (s, 2H), 5.47 (s, 1H), 4.59 (t, J=5.0 Hz, 2H), 3.72 (t, J=5.0 Hz, 2H), 3.23 (s, 3H), 1.52 (s, 6H).

LCMS (Method E): Rt=2.46 min, m/z [M+H]⁺=370

Compound 55

¹H NMR (400 MHz, DMSO-d₆) δ ppm: 8.96 (d, J=0.9 Hz, 1H), 8.49 (d, J=1.1 Hz, 1H), 8.46 (s, 1H), 8.18-8.16 (m, 1H), 6.98 (d, J=5.3 Hz, 1H), 6.56 (s, 2H), 5.47 (s, 1H), 4.26 (d, J=7.3 Hz, 2H), 3.86-3.79 (m, 2H), 3.27-3.18 (m, 2H), 2.17-2.08 (m, 1H), 1.52 (s, 6H), 1.43-1.29 (m, 4H).

LCMS (Method E): Rt=2.07 min, m/z [M+H]⁺=392

Compound 56 (Formic Acid 1.0 Equivalents)

¹H NMR (400 MHz, DMSO-d₆) δ ppm: 9.01 (d, J=1.0 Hz, 1H), 8.53-8.50 (m, 2H), 8.28 (s, 1H), 8.22 (d, J=5.3 Hz, 1H), 6.99 (d, J=5.3 Hz, 1H), 6.66 (s, 2H), 5.73 (s, 2H), 5.55-5.49 (m, 1H), 1.52 (s, 6H).

LCMS (Method E): Rt=1.99 min, m/z [M+H]⁺=333

Compound 57 (Formic Acid 1.0 Equivalents)

¹H NMR (400 MHz, DMSO-d₆) δ ppm: 9.01 (s, 1H), 8.50 (d, J=5.1 Hz, 2H), 8.20 (d, J=5.4 Hz, 1H), 8.15 (s, 1H), 6.95 (d, J=5.3 Hz, 1H), 6.60 (s, 2H), 5.49 (s, 1H), 4.69 (t, J=6.5 Hz, 2H), 3.19 (t, J=6.5 Hz, 2H), 1.52 (s, 6H).

LCMS (Method E): Rt=1.87 min, m/z [M+H]⁺=347

Compound 58

¹H NMR (400 MHz, DMSO-d₆) δ ppm: 8.98 (s, 1H), 8.65 (s, 1H), 8.60 (s, 1H), 8.32 (s, 1H), 7.36 (s, 1H), 5.46 (s, 1H), 4.83 (s, 1H), 4.32 (s, 2H), 2.97-2.92 (m, 3H), 1.49 (s, 6H), 1.13 (s, 6H).

LCMS (Method E): Rt=2.90 min, m/z [M+H]⁺=414/416

Compound 59 (Acetic Acid 0.87 Equivalents)

¹H NMR (400 MHz, DMSO-d₆) δ ppm: 8.94 (d, J=0.9 Hz, 1H), 8.59-8.56 (m, 1H), 8.45 (d, J=1.0 Hz, 1H), 8.32 (s, 1H), 8.17 (d, J=5.2 Hz, 1H), 7.93-7.80 (m, 2H), 7.35-7.31 (m, 1H), 6.97 (d, J=5.4 Hz, 1H), 6.55 (s, 2H), 6.34 (s, 1H), 4.81 (s, 1H), 4.25 (s, 2H), 1.91 (s, 2.6H), 1.86 (s, 3H), 1.12 (s, 6H).

LCMS (Method E): Rt=1.95 min, m/z [M+H]⁺=429

Compound 60

¹H NMR (400 MHz, DMSO-d₆) δ ppm: 9.01 (d, J=0.9 Hz, 1H), 8.62 (d, J=4.3 Hz, 2H), 8.50 (d, J=1.0 Hz, 1H), 7.89 (s, 1H), 7.67 (s, 1H), 5.47-5.45 (m, 1H), 4.87 (s, 1H), 4.33 (s, 2H), 1.52 (s, 6H), 1.13 (s, 6H).

LCMS (Method E): Rt=2.42 min, m/z [M+H]⁺=391

Compound 61 (Formic Acid 0.5 Equivalents)

¹H NMR (400 MHz, DMSO-d₆) δ ppm: 12.30 (d, J=2.3 Hz, 1H), 8.77 (d, J=1.1 Hz, 1H), 8.56 (s, 1H), 8.21-8.19 (m, 1.5H), 8.02 (s, 1H), 7.49 (s, 2H), 5.48 (s, 1H), 1.50 (s, 6H).

LCMS (Method E): Rt=2.54 min, m/z [M+H]⁺=362

Compound 62 (Formic Acid 0.6 Equivalents)

¹H NMR (400 MHz, DMSO-d₆) δ ppm: 8.91 (d, J=0.9 Hz, 1H), 8.49 (d, J=0.9 Hz, 1H), 8.29 (s, 1H), 8.15 (s, 0.6H), 8.12 (d, J=5.2 Hz, 1H), 6.92 (d, J=5.3 Hz, 1H), 6.51 (s, 2H), 5.29 (s, 1H), 4.76 (s, 1H), 4.30 (s, 2H), 4.21 (s, 2H), 1.08 (s, 6H).

LCMS (Method E): Rt=1.62 min, m/z [M+H]⁺=338

Compound 63

¹H NMR (400 MHz, DMSO-d₆) δ ppm: 8.97 (d, J=0.9 Hz, 1H), 8.50 (d, J=1.0 Hz, 1H), 8.34 (s, 1H), 8.17 (d, J=5.4 Hz, 1H), 6.98 (d, J=5.4 Hz, 1H), 6.57 (s, 2H), 6.18 (s, 1H), 4.83 (s, 1H), 4.26 (s, 2H), 3.40 (s, 3H), 2.91 (s, 3H), 1.68 (s, 3H), 1.12 (s, 6H).

LCMS (Method E): Rt=1.95 min, m/z [M+H]⁺=423

Compound 64

¹H NMR (400 MHz, DMSO-d₆) δ ppm: 8.99 (s, 1H), 8.60 (d, J=0.9 Hz, 1H), 8.27 (s, 1H), 8.25 (d, J=3.9 Hz, 1H), 6.64 (s, 2H), 5.48 (s, 1H), 4.83 (s, 1H), 4.32 (s, 2H), 1.52 (s, 6H), 1.12 (s, 6H).

LCMS (Method E): Rt=2.34 min, m/z [M+H]⁺=384

A second batch was isolated with 1.0 equivalents of formic acid present.

Compound 65 (Formic Acid 0.5 Equivalents)

¹H NMR (400 MHz, DMSO-d₆) δ ppm: 8.93 (d, J=1.1 Hz, 1H), 8.90 (s, 1H), 8.56 (d, J=1.0 Hz, 1H), 8.20 (d, J=5.2 Hz, 1H), 8.17 (s, 0.5H), 7.15 (d, J=5.3 Hz, 1H), 6.61 (s, 2H), 5.99-5.92 (m, 1H), 5.49 (s, 1H), 5.11-4.98 (m, 4H), 1.52 (s, 6H).

LCMS (Method E): Rt=1.87 min, m/z [M+H]⁺=350

Compound 66 (Formic Acid 0.6 Equivalents)

¹H NMR (400 MHz, DMSO-d₆) δ ppm: 9.07 (d, J=0.9 Hz, 1H), 8.56 (d, J=0.9 Hz, 1H), 8.38 (s, 1H), 8.20 (s, 0.6H), 8.18-8.15 (m, 1H), 7.11 (d, J=5.3 Hz, 1H), 6.54 (s, 2H), 5.48 (s, 1H), 5.18 (s, 1H), 3.84 (s, 2H), 1.70 (s, 6H), 1.52 (s, 6H).

LCMS (Method E): Rt=1.93 min, m/z [M+H]⁺=366

Compound 67

¹H NMR (400 MHz, DMSO-d₆) δ ppm: 8.96 (d, J=1.0 Hz, 1H), 8.51 (s, 1H), 8.50 (d, J=1.2 Hz, 1H), 8.19 (d, J=5.2 Hz, 1H), 6.96 (d, J=5.3 Hz, 1H), 6.60 (s, 2H), 5.49 (s, 1H), 4.80 (t, J=6.9 Hz, 2H), 3.83 (t, J=6.9 Hz, 2H), 3.00 (s, 3H), 1.52 (s, 6H).

LCMS (Method E): Rt=1.81 min, m/z [M+H]⁺=400

Compound 68

¹H NMR (400 MHz, DMSO-d₆) δ ppm: 8.94 (d, J=0.9 Hz, 1H), 8.49 (s, 1H), 8.35 (s, 1H), 8.21 (d, J=5.4 Hz, 1H), 7.05 (s, 1H), 6.96 (d, J=5.3 Hz, 1H), 5.49 (s, 1H), 4.80 (s, 1H), 4.25 (s, 2H), 2.92 (s, 3H), 1.50 (s, 6H), 1.13 (s, 6H).

LCMS (Method E): Rt=2.06 min, m/z [M+H]⁺=380

Compound 69

¹H NMR (400 MHz, DMSO-d₆) δ ppm: 9.27-9.21 (m, 1H), 8.93 (d, J=1.0 Hz, 1H), 8.38 (d, J=1.0 Hz, 1H), 8.20 (d, J=5.2 Hz, 1H), 6.75 (d, J=5.2 Hz, 1H), 6.65 (s, 2H), 5.48 (s, 1H), 3.87 (s, 3H), 3.52-3.49 (m, 4H), 3.28 (s, 3H), 1.51 (s, 6H).

LCMS (Method E): Rt=1.96 min, m/z [M+H]⁺=409

Compound 70

¹H NMR (400 MHz, DMSO-d₆) δ ppm: 9.01 (d, J=1.0 Hz, 1H), 8.59 (d, J=1.0 Hz, 1H), 8.48 (d, J=2.3 Hz, 1H), 8.28 (d, J=3.7 Hz, 1H), 6.67 (s, 2H), 5.49 (s, 1H), 5.39-5.31 (m, 1H), 3.80-3.75 (m, 2H), 3.51-3.46 (m, 2H), 2.37 (s, 3H), 1.52 (s, 6H).

LCMS (Method E): Rt=1.82 min, m/z [M+H]⁺=381

Compound 71

¹H NMR (400 MHz, DMSO-d₆) δ ppm: 8.99 (d, J=1.0 Hz, 1H), 8.57 (s, 1H), 8.15 (d, J=1.0 Hz, 1H), 7.99 (s, 1H), 7.50 (s, 2H), 5.46 (s, 1H), 4.34 (d, J=7.3 Hz, 2H), 3.85-3.79 (m, 2H), 3.26-3.17 (m, 2H), 2.12-2.03 (m, 1H), 1.50 (s, 6H), 1.43-1.20 (m, 4H).

LCMS (Method E): Rt=2.98 min, m/z [M+H]⁺=460

Compound 72

¹H NMR (400 MHz, DMSO-d₆) δ ppm: 8.98 (s, 1H), 8.56 (s, 1H), 8.20 (d, J=0.8 Hz, 1H), 8.01 (s, 1H), 7.49 (s, 2H), 5.48 (s, 1H), 4.82 (s, 1H), 4.31 (s, 2H), 1.50 (s, 6H), 1.11 (s, 6H).

LCMS (Method E): Rt=2.75 min, m/z [M+H]⁺=434

Compound 73

¹H NMR (400 MHz, DMSO-d₆) δ ppm: 8.96 (d, J=1.0 Hz, 1H), 8.56 (d, J=1.1 Hz, 1H), 8.28 (d, J=2.6 Hz, 1H), 8.20 (d, J=3.7 Hz, 1H), 6.59 (s, 2H), 5.45 (s, 1H), 4.28 (d, J=7.3 Hz, 2H), 3.80-3.74 (m, 2H), 3.21-3.12 (m, 2H), 2.11-2.03 (m, 1H), 1.47 (s, 6H), 1.33-1.24 (m, 4H).

LCMS (Method E): Rt=2.57 min, m/z [M+H]⁺=410

A second batch was isolated with 1.3 equivalents of formic acid present.

Compound 74

¹H NMR (400 MHz, DMSO-d₆) δ ppm: 9.03 (d, J=0.9 Hz, 1H), 8.63 (d, J=0.9 Hz, 1H), 8.54 (d, J=2.2 Hz, 1H), 8.29 (d, J=3.7 Hz, 1H), 6.69 (s, 2H), 6.02-5.93 (m, 1H), 5.50 (s, 1H), 5.11 (t, J=7.4 Hz, 2H), 5.00 (t, J=6.6 Hz, 2H), 1.52 (s, 6H).

LCMS (Method E): Rt=2.32 min, m/z [M+H]$^+$=368

Compound 75

$^1$H NMR (400 MHz, DMSO-d$_6$) δ ppm: d 9.03 (s, 1H), 8.63 (s, 1H), 8.56 (s, 1H), 8.48-8.46 (m, 2H), 6.83 (s, 2H), 5.50 (s, 1H), 4.36 (d, J=7.3 Hz, 2H), 3.82 (dd, J=2.5, 11.3 Hz, 2H), 3.27-3.18 (m, 2H), 2.15-2.06 (m, 1H), 1.52 (s, 6H), 1.42-1.23 (m, 4H).

LCMS (Method E): Rt=2.68 min, m/z [M+H]$^+$=417

Compound 76

$^1$H NMR (400 MHz, DMSO-d$_6$) δ ppm: 8.91 (d, J=1.0 Hz, 1H), 8.61 (d, J=1.0 Hz, 1H), 8.31 (d, J=2.6 Hz, 1H), 8.25 (d, J=3.8 Hz, 1H), 6.64 (s, 2H), 5.48 (s, 1H), 4.46 (t, J=6.8 Hz, 2H), 3.28-3.23 (m, 2H), 3.21 (s, 3H), 2.10-2.02 (m, 2H), 1.52 (s, 6H).

LCMS (Method E): Rt=2.57 min, m/z [M+H]$^+$=384

Compound 77 (Formic Acid 1.7 Equivalents)

$^1$H NMR (400 MHz, DMSO-d$_6$) δ ppm: 8.98 (d, J=0.9 Hz, 1H), 8.61 (s, 1H), 8.54 (d, J=1.0 Hz, 1H), 8.17-8.15 (m, 2.7H), 7.09 (d, J=5.3 Hz, 1H), 6.56 (s, 2H), 5.48 (s, 1H), 4.64-4.54 (m, 1H), 2.94 (d, J=11.1 Hz, 2H), 2.27 (s, 3H), 2.24-1.99 (m, 6H), 1.52 (s, 6H).

LCMS (Method E): Rt=1.56 min, m/z [M+H]$^+$=391

Compound 78 (Formic Acid 1.0 Equivalents)

$^1$H NMR (400 MHz, DMSO-d$_6$) δ ppm: 8.97 (d, J=1.0 Hz, 1H), 8.65 (s, 1H), 8.55 (d, J=1.0 Hz, 1H), 8.20 (s, 1H), 8.15 (d, J=5.3 Hz, 1H), 7.10 (d, J=5.4 Hz, 1H), 6.55 (s, 2H), 5.48 (s, 1H), 4.63-4.54 (m, 1H), 2.95 (d, J=11.5 Hz, 2H), 2.86-2.76 (m, 1H), 2.46-2.38 (m, 2H), 2.08-2.00 (m, 4H), 1.52 (s, 6H), 1.03 (d, J=6.6 Hz, 6H).

LCMS (Method E): Rt=1.67 min, m/z [M+H]$^+$=419

Compound 79 (Formic Acid 1.0 Equivalents)

$^1$H NMR (400 MHz, DMSO-d$_6$) δ ppm: 8.98 (d, J=0.9 Hz, 1H), 8.63 (s, 1H), 8.55 (d, J=1.0 Hz, 1H), 8.17-8.14 (m, 2H), 7.09 (d, J=5.3 Hz, 1H), 6.56 (s, 2H), 5.48 (s, 1H), 4.69-4.59 (m, 1H), 3.14-3.05 (m, 2H), 2.51-2.49 (m, 2H), 2.32-2.24 (m, 2H), 2.14-2.01 (m, 4H), 1.52 (s, 6H), 1.07 (t, J=7.2 Hz, 3H).

LCMS (Method E): Rt=1.59 min, m/z [M+H]$^+$=405

Compound 80 (Formic Acid 1.0 Equivalents)

$^1$H NMR (400 MHz, DMSO-d$_6$) δ ppm: 8.93 (d, J=0.9 Hz, 1H), 8.70 (s, 1H), 8.52 (d, J=0.9 Hz, 1H), 8.19 (d, J=5.3 Hz, 1H), 8.15 (s, 1H), 7.13 (d, J=5.4 Hz, 1H), 6.59 (s, 2H), 5.49 (s, 1H), 5.28-5.23 (m, 1H), 3.84-3.78 (m, 2H), 3.45-3.38 (m, 2H), 2.51-2.50 (m, 1H), 1.51 (s, 6H), 0.94 (d, J=6.2 Hz, 6H).

LCMS (Method E): Rt=1.61 min, m/z [M+H]$^+$=391

Compound 81

$^1$H NMR (400 MHz, DMSO-d$_6$) δ ppm: 8.86 (d, J=1.0 Hz, 1H), 8.49 (d, J=1.0 Hz, 1H), 8.42 (s, 1H), 6.91 (s, 1H), 6.46 (s, 2H), 5.48 (s, 1H), 4.39 (t, J=6.9 Hz, 2H), 3.29-3.23 (m, 2H), 3.21 (s, 3H), 2.25 (s, 3H), 2.12-2.03 (m, 2H), 1.51 (s, 6H).

LCMS (Method E): Rt=2.11 min, m/z [M+H]$^+$=380

Compound 82 (Formic Acid 1.0 Equivalents)

$^1$H NMR (400 MHz, DMSO-d$_6$) δ ppm: 8.96 (d, J=0.9 Hz, 1H), 8.47 (d, J=1.0 Hz, 1H), 8.20-8.19 (m, 2H), 8.09 (s, 1H), 6.36 (s, 2H), 5.46 (s, 1H), 4.30 (d, J=7.4 Hz, 2H), 3.86-3.79 (m, 2H), 3.27-3.17 (m, 2H), 2.28 (s, 3H), 2.17-2.09 (m, 1H), 1.51 (s, 6H), 1.40-1.30 (m, 4H).

LCMS (Method E): Rt=2.16 min, m/z [M+H]$^+$=406

Compound 83 (Formic Acid 1.0 Equivalents)

$^1$H NMR (400 MHz, DMSO-d$_6$) δ ppm: d 8.87 (s, 1H), 8.49 (d, J=1.0 Hz, 1H), 8.18-8.17 (m, 2H), 8.09 (s, 1H), 6.36 (s, 2H), 5.46 (s, 1H), 4.44 (t, J=6.9 Hz, 2H), 3.30-3.24 (m, 2H), 3.21 (s, 3H), 2.29 (s, 3H), 2.12-2.03 (m, 2H), 1.51 (s, 6H).

LCMS (Method E): Rt=2.16 min, m/z [M+H]$^+$=380

Compound 84

$^1$H NMR (400 MHz, DMSO-d$_6$) δ ppm: d 8.43 (s, 1H), 8.37 (s, 1H), 8.16 (d, J=5.3 Hz, 1H), 6.96 (d, J=5.3 Hz, 1H), 6.55 (s, 2H), 5.46 (s, 1H), 4.51 (t, J=7.3 Hz, 2H), 3.39-3.33 (m, 2H), 3.24 (s, 3H), 2.84 (s, 3H), 2.08-2.00 (m, 2H), 1.51 (s, 6H).

LCMS (Method E): Rt=1.98 min, m/z [M+H]$^+$=380

Compound 85 (Formic Acid 1.2 Equivalents)

$^1$H NMR (400 MHz, DMSO-d$_6$) δ ppm: 9.04 (d, J=0.9 Hz, 1H), 8.60 (d, J=1.0 Hz, 1H), 8.30 (d, J=2.2 Hz, 1H), 8.26 (d, J=3.9 Hz, 1H), 8.16 (s, 1.2H), 6.64 (s, 2H), 5.50 (s, 1H), 4.73-4.65 (m, 1H), 3.09 (d, J=11.6 Hz, 2H), 2.49-2.45 (m, 2H), 2.32-2.22 (m, 2H), 2.14-2.04 (m, 4H), 1.52 (s, 6H), 1.07 (t, J=7.2 Hz, 3H).

LCMS (Method E): Rt=1.91 min, m/z [M+H]$^+$=423

Compound 86

$^1$H NMR (400 MHz, DMSO-d$_6$) δ ppm: 8.54 (s, 1H), 8.25-8.21 (m, 2H), 6.62 (s, 2H), 5.48 (s, 1H), 4.60-4.54 (m, 2H), 3.41-3.26 (m, 2H), 3.24 (s, 3H), 2.86 (s, 3H), 2.07-1.99 (m, 2H), 1.51 (s, 6H).

LCMS (Method E): Rt=2.55 min, m/z [M+H]$^+$=398

Compound 87

$^1$H NMR (400 MHz, DMSO-d$_6$) δ ppm: 8.91 (d, J=1.1 Hz, 1H), 8.61 (d, J=1.0 Hz, 1H), 8.31 (d, J=2.7 Hz, 1H), 8.25 (d, J=3.9 Hz, 1H), 6.65 (s, 2H), 5.34 (s, 1H), 4.46 (t, J=6.9 Hz, 2H), 3.26 (t, J=6.0 Hz, 2H), 3.21 (s, 3H), 2.10-2.01 (m, 2H), 1.99-1.92 (m, 4H), 1.79-1.68 (m, 4H).

LCMS (Method E): Rt=2.86 min, m/z [M+H]$^+$=410

Compound 88

$^1$H NMR (400 MHz, CDCl$_3$) δ ppm: 8.79 (d, J=1.0 Hz, 1H), 8.66 (d, J=1.0 Hz, 1H), 8.15 (d, J=3.6 Hz, 1H), 8.04 (d, J=2.2 Hz, 1H), 5.03 (s, 2H), 4.41 (t, J=6.6 Hz, 2H), 3.33 (s, 3H), 3.27 (t, J=5.7 Hz, 2H), 2.17-2.09 (m, 2H), 1.73 (s, 3H), 1.33-1.24 (m, 1H), 0.80-0.50 (m, 4H).

LCMS (Method E): Rt=2.87 min, m/z [M+H]$^+$=410

Compound 89

$^1$H NMR (400 MHz, DMSO-d$_6$) δ ppm: 8.92 (d, J=1.0 Hz, 1H), 8.64 (d, J=0.8 Hz, 1H), 8.34-8.31 (m, 2H), 7.15 (s, 1H), 5.36 (s, 1H), 4.47 (t, J=6.8 Hz, 2H), 3.25 (t, J=5.9 Hz, 2H), 3.21 (s, 3H), 2.90 (d, J=4.4 Hz, 3H), 2.11-2.02 (m, 2H), 1.92 (dd, J=2.6, 4.3 Hz, 4H), 1.79-1.68 (m, 4H).

LCMS (Method E): Rt=3.26 min, m/z [M+H]$^+$=424

Compound 90

$^1$H NMR (400 MHz, DMSO-d$_6$) δ ppm: 8.92 (d, J=1.0 Hz, 1H), 8.64 (s, 1H), 8.34-8.31 (m, 2H), 7.15 (s, 1H), 5.49 (s, 1H), 4.47 (t, J=6.9 Hz, 2H), 3.26 (t, J=6.0 Hz, 2H), 3.20 (s, 3H), 2.90 (d, J=4.4 Hz, 3H), 2.10-2.02 (m, 2H), 1.50 (s, 6H).

LCMS (Method E): Rt=2.97 min, m/z [M+H]$^+$=398

Compound 91

$^1$H NMR (400 MHz, CDCl$_3$) δ ppm: d 8.79 (d, J=0.9 Hz, 1H), 8.72 (d, J=0.9 Hz, 1H), 8.14 (d, J=3.6 Hz, 1H), 8.03 (d, J=2.3 Hz, 1H), 6.24 (s, 1H), 5.10 (s, 2H), 4.41 (t, J=6.6 Hz, 2H), 3.32 (s, 3H), 3.26 (t, J=5.6 Hz, 2H), 2.43 (s, 3H), 2.17-2.08 (m, 2H), 2.02 (s, 3H).

LCMS (Method E): Rt=2.95 min, m/z [M+H]$^+$=451

Compound 92

$^1$H NMR (400 MHz, DMSO-d$_6$) δ ppm: 8.70 (s, 1H), 8.36 (d, J=2.5 Hz, 1H), 8.29 (d, J=3.7 Hz, 1H), 6.72 (s, 2H), 5.54 (s, 1H), 4.69 (t, J=7.1 Hz, 2H), 3.35-3.32 (m, 2H), 3.22 (s, 3H), 2.11-2.03 (m, 2H), 1.52 (s, 6H).

LCMS (Method E): Rt=3.83 min, m/z [M+H]$^+$=418/420

Compound 93

$^1$H NMR (400 MHz, DMSO-d$_6$) δ ppm: 8.50 (s, 1H), 8.25-8.22 (m, 2H), 6.62 (s, 2H), 5.31 (s, 1H), 4.71 (t, J=7.1 Hz, 2H), 3.35-3.33 (m, 2H), 3.23 (s, 3H), 2.66-2.58 (m, 1H), 2.16-2.06 (m, 2H), 1.97-1.90 (m, 4H), 1.78-1.67 (m, 4H), 1.20-1.13 (m, 2H), 1.06-0.99 (m, 2H).
LCMS (Method E): Rt=3.32 min, m/z [M+H]⁺=450

Compound 94

¹H NMR (400 MHz, DMSO-d₆) δ ppm: 8.53 (d, J=2.1 Hz, 1H), 8.48 (s, 1H), 8.30 (d, J=3.8 Hz, 1H), 6.67 (s, 2H), 6.38-6.30 (m, 1H), 5.32 (s, 1H), 5.14 (t, J=7.3 Hz, 2H), 4.97 (t, J=6.5 Hz, 2H), 2.45-2.39 (m, 1H), 1.97-1.91 (m, 4H), 1.78-1.67 (m, 4H), 1.15-1.02 (m, 4H).
LCMS (Method E): Rt=2.97 min, m/z [M+H]⁺=434

Compound 95

¹H NMR (400 MHz, CDCl₃) δ ppm: 8.82 (d, J=1.0 Hz, 1H), 8.73 (d, J=1.0 Hz, 1H), 8.16 (d, J=3.6 Hz, 1H), 8.06 (d, J=2.3 Hz, 1H), 5.04 (s, 2H), 4.44 (t, J=6.6 Hz, 2H), 3.34 (s, 3H), 3.29 (t, J=5.6 Hz, 2H), 2.70-2.62 (m, 2H), 2.44-2.35 (m, 2H), 2.19-2.13 (m, 2H), 2.01-1.88 (m, 2H), 1.27 (s, 1H).
LCMS (Method E): Rt=2.72 min, m/z [M+H]⁺=396

Compound 96

¹H NMR (400 MHz, DMSO-d₆) δ ppm: 9.06 (d, J=1.0 Hz, 1H), 8.42 (d, J=2.4 Hz, 1H), 7.70 (dd, J=1.0, 2.5 Hz, 1H), 7.55 (t, J=51.6 Hz, 1H), 6.77 (s, 2H), 5.38 (s, 1H), 4.59 (t, J=7.6 Hz, 2H), 3.41 (t, J=5.9 Hz, 2H), 3.24 (s, 3H), 2.12-2.03 (m, 2H), 1.51 (s, 3H), 1.19-1.12 (m, 1H), 0.57-0.35 (m, 4H).
LCMS (Method E): Rt=3.68 min, m/z [M+H]⁺=460

Compound 98

¹H NMR (400 MHz, DMSO-d₆) δ ppm: 8.53 (d, J=2.0 Hz, 1H), 8.44 (s, 1H), 8.30 (d, J=3.8 Hz, 1H), 6.66 (s, 2H), 6.38-6.30 (m, 1H), 5.32 (s, 1H), 5.14 (t, J=7.2 Hz, 2H), 4.98 (t, J=6.5 Hz, 2H), 2.45-2.37 (m, 1H), 1.53 (s, 3H), 1.20-1.03 (m, 5H), 0.59-0.48 (m, 2H), 0.47-0.35 (m, 2H).
LCMS (Method E): Rt=3.04 min, m/z [M+H]⁺=434

Compound 99

¹H NMR (400 MHz, DMSO-d₆) δ ppm: 9.00 (d, J=1.0 Hz, 1H), 8.60 (s, 1H), 8.24 (s, 1H), 8.11 (d, J=1.0 Hz, 1H), 7.54 (s, 2H), 5.40-5.31 (m, 2H), 3.80 (t, J=7.7 Hz, 2H), 3.45-3.37 (m, 2H), 2.37 (s, 3H), 1.52 (s, 3H), 1.19-1.11 (m, 1H), 0.57-0.37 (m, 4H).
LCMS (Method E): Rt=2.46 min, m/z [M+H]⁺=457

Compound 100

¹H NMR (400 MHz, DMSO-d₆) δ ppm: 9.02 (d, J=1.0 Hz, 1H), 8.61 (s, 1H), 8.26 (s, 1H), 8.10 (d, J=1.0 Hz, 1H), 7.55 (s, 2H), 6.03-5.95 (m, 1H), 5.34 (s, 1H), 5.13 (t, J=7.5 Hz, 2H), 4.94-4.89 (m, 2H), 1.52 (s, 3H), 1.20-1.12 (m, 1H), 0.57-0.37 (m, 4H).
LCMS (Method E): Rt=3.07 min, m/z [M+H]⁺=444

Compound 101

¹H NMR (400 MHz, DMSO-d₆) δ ppm: 8.98 (d, J=1.0 Hz, 1H), 8.56 (d, J=1.0 Hz, 1H), 8.25 (d, J=3.8 Hz, 1H), 8.18 (d, J=2.7 Hz, 1H), 6.63 (s, 2H), 5.33 (s, 1H), 4.43 (s, 2H), 3.16 (s, 3H), 1.55 (s, 3H), 1.22-1.14 (m, 1H), 1.11 (s, 6H), 0.60-0.39 (m, 4H).
LCMS (Method E): Rt=3.12 min, m/z [M+H]⁺=424

Compound 102

¹H NMR (400 MHz, DMSO-d₆) δ ppm: 8.47 (d, J=2.3 Hz, 1H), 8.43 (s, 1H), 8.28 (d, J=3.8 Hz, 1H), 6.63 (s, 2H), 5.75-5.68 (m, 1H), 5.32 (s, 1H), 3.76 (t, J=7.6 Hz, 2H), 3.54-3.49 (m, 2H), 2.47-2.43 (m, 1H), 2.35 (s, 3H), 1.53 (s, 3H), 1.19-1.09 (m, 3H), 1.06-1.00 (m, 2H), 0.58-0.37 (m, 4H).
LCMS (Method E): Rt=2.29 min, m/z [M+H]⁺=447

Compound 103

¹H NMR (400 MHz, DMSO-d₆) δ ppm: 8.91 (d, J=1.0 Hz, 1H), 8.61 (d, J=1.0 Hz, 1H), 8.42 (d, J=2.1 Hz, 1H), 8.35 (d, J=3.5 Hz, 1H), 6.78 (s, 2H), 5.38 (s, 1H), 3.07 (s, 6H), 1.55 (s, 3H), 1.23-1.14 (m, 1H), 0.60-0.39 (m, 4H).
LCMS (Method E): Rt=3.04 min, m/z [M+H]⁺=409

Compound 105 (Formic Acid 1.0 Equivalents)

¹H NMR (400 MHz, DMSO-d₆) δ ppm: 8.96 (d, J=1.0 Hz, 1H), 8.58 (d, J=1.0 Hz, 1H), 8.35 (d, J=2.6 Hz, 1H), 8.25 (d, J=3.8 Hz, 1H), 8.14 (s, 1H), 6.62 (s, 2H), 5.33 (s, 1H), 4.45 (t, J=6.5 Hz, 2H), 3.52 (t, J=4.5 Hz, 4H), 2.30-2.23 (m, 4H), 2.21 (t, J=6.5 Hz, 2H), 2.04-1.94 (m, 2H), 1.55 (s, 3H), 1.22-1.14 (m, 1H), 0.62-0.49 (m, 2H), 0.48-0.36 (m, 2H).
LCMS (Method E): Rt=2.14 min, m/z [M+H]⁺=465

Compound 106 (Formic Acid 1.0 Equivalents)

¹H NMR (400 MHz, DMSO-d₆) δ ppm: 9.03 (d, J=1.0 Hz, 1H), 8.57 (d, J=1.0 Hz, 1H), 8.30 (d, J=2.2 Hz, 1H), 8.26 (d, J=3.7 Hz, 1H), 8.16 (s, 1H), 6.62 (s, 2H), 5.39-5.38 (m, 1H), 4.72-4.62 (m, 1H), 3.05 (d, J=11.4 Hz, 2H), 2.45 (q, J=7.2 Hz, 2H), 2.23-2.03 (m, 6H), 1.54 (s, 3H), 1.22-1.14 (m, 1H), 1.05 (t, J=7.1 Hz, 3H), 0.60-0.38 (m, 4H).
LCMS (Method E): Rt=2.16 min, m/z [M+H]⁺=449

Compound 107

¹H NMR (400 MHz, DMSO-d₆) δ ppm: 9.10 (d, J=1.0 Hz, 1H), 8.56 (d, J=1.0 Hz, 1H), 8.39 (d, J=2.4 Hz, 1H), 8.25 (d, J=3.8 Hz, 1H), 6.63 (s, 2H), 5.42-5.35 (m, 1H), 5.33 (s, 1H), 3.13-3.01 (m, 2H), 2.68-2.52 (m, 2H), 2.36 (s, 3H), 2.27 (q, J=8.5 Hz, 1H), 2.04-1.94 (m, 1H), 1.54 (s, 3H), 1.21-1.13 (m, 1H), 0.60-0.38 (m, 4H).
LCMS (Method E): Rt=2.12 min, m/z [M+H]⁺=421

Compound 108 (Formic Acid 0.7 Equivalents)

¹H NMR (400 MHz, DMSO-d₆) δ ppm: 9.03 (d, J=1.0 Hz, 1H), 8.57 (d, J=1.0 Hz, 1H), 8.31 (d, J=2.2 Hz, 1H), 8.26 (d, J=3.7 Hz, 1H), 8.17 (s, 0.7H), 6.63 (s, 2H), 5.34 (s, 1H), 4.70-4.60 (m, 1H), 3.48 (t, J=5.8 Hz, 2H), 3.26 (s, 3H), 3.06 (d, J=12.0 Hz, 2H), 2.57 (t, J=5.8 Hz, 2H), 2.34-2.24 (m, 2H), 2.11-2.00 (m, 4H), 1.55 (s, 3H), 1.22-1.14 (m, 1H), 0.60-0.38 (m, 4H).
LCMS (Method E): Rt=2.22 min, m/z [M+H]⁺=479

Compound 109

¹H NMR (400 MHz, DMSO-d₆) δ ppm: 9.01 (d, J=1.1 Hz, 1H), 8.56 (d, J=1.1 Hz, 1H), 8.42 (d, J=2.5 Hz, 1H), 8.25 (d, J=3.7 Hz, 1H), 7.80 (s, 1H), 7.52 (s, 1H), 6.62 (s, 2H), 5.48 (s, 2H), 5.33 (s, 1H), 3.77 (s, 3H), 1.54 (s, 3H), 1.21-1.13 (m, 1H), 0.60-0.38 (m, 4H).
LCMS (Method E): Rt=2.67 min, m/z [M+H]⁺=432

Compound 110

¹H NMR (400 MHz, CDCl₃) δ ppm: 8.92 (d, J=1.0 Hz, 1H), 8.69 (d, J=1.0 Hz, 1H), 8.35 (d, J=1.8 Hz, 1H), 8.20 (d, J=3.5 Hz, 1H), 5.73-5.65 (m, 1H), 5.27 (t, J=7.5 Hz, 2H), 5.11-5.03 (m, 4H).
LCMS (Method E): Rt=2.61 min, m/z [M+H]⁺=402

Compound 114

¹H NMR (400 MHz, DMSO-d₆) δ ppm: 8.92 (d, J=1.0 Hz, 1H), 8.49 (d, J=1.0 Hz, 1H), 8.44 (s, 1H), 8.17 (d, J=5.3 Hz, 1H), 6.99 (d, J=5.3 Hz, 1H), 6.56 (s, 2H), 5.47 (s, 1H), 4.21 (d, J=7.1 Hz, 2H), 2.88 (d, J=12.0 Hz, 2H), 2.40-2.31 (m, 2H), 1.96-1.88 (m, 1H), 1.52 (s, 6H), 1.39 (d, J=10.5 Hz, 2H), 1.19-1.06 (m, 2H).
LCMS (Method E): Rt=1.60 min, m/z [M+H]⁺=391

Compound 115

¹H NMR (400 MHz, DMSO-d₆) δ ppm: 8.91 (d, J=1.0 Hz, 1H), 8.51 (d, J=1.0 Hz, 1H), 8.43 (s, 1H), 8.37 (s, 1H), 8.18 (d, J=5.3 Hz, 1H), 6.98 (d, J=5.3 Hz, 1H), 6.62 (s, 2H), 5.75 (s, 1H), 4.52 (t, J=5.0 Hz, 2H), 3.73 (t, J=5.1 Hz, 2H), 3.29-3.26 (m, 2H), 3.23 (s, 3H), 2.82-2.71 (m, 2H), 2.08-1.88 (m, 2H), 1.74-1.57 (m, 3H), 1.48 (s, 3H).
LCMS (Method E): Rt=1.61 min, m/z [M+H]⁺=421

Compound 116 (Formic Acid 1.0 Equivalents)

¹H NMR (400 MHz, DMSO-d₆) δ ppm: 8.79 (d, J=1.0 Hz, 1H), 8.48 (d, J=1.0 Hz, 1H), 8.43 (s, 1H), 8.25 (s, 1H), 8.16 (d, J=5.2 Hz, 1H), 8.03 (s, 1H), 6.96 (d, J=5.3 Hz, 1H), 6.56

(s, 2H), 5.50 (s, 1H), 4.52 (t, J=5.8 Hz, 2H), 3.81 (t, J=5.8 Hz, 2H), 3.75 (s, 2H), 1.51 (s, 6H).
LCMS (Method E): Rt=1.79 min, m/z [M+H]⁺=420

Compound 117 (Formic Acid 0.85 Equivalents)
¹H NMR (400 MHz, DMSO-d₆) δ ppm: 8.91 (d, J=1.1 Hz, 1H), 8.50-8.49 (m, 2H), 8.17 (d, J=5.2 Hz, 1H), 8.15 (s, 1H), 8.04 (s, 1H), 6.95 (d, J=5.3 Hz, 1H), 6.57 (s, 2H), 5.48 (s, 1H), 4.37 (t, J=7.0 Hz, 2H), 3.87 (s, 2H), 3.41 (t, J=6.8 Hz, 2H), 2.16-2.06 (m, 2H), 1.51 (s, 6H).
LCMS (Method E): Rt=1.85 min, m/z [M+H]⁺=434

Compound 118
¹H NMR (400 MHz, DMSO-d₆, trifluoroacetic acid) δ ppm: 9.64 (s, 1H), 9.00 (s, 1H), 8.88 (s, 1H), 8.34 (s, 1H), 5.30-5.21 (m, 1H), 2.98 (t, J=7.4 Hz, 2H), 2.84 (t, J=7.4 Hz, 2H), 1.87-1.77 (m, 2H), 1.66 (d, J=6.7 Hz, 6H), 1.59 (s, 6H).
LCMS (Method E): Rt=1.70 min, m/z [M+H]⁺=393

Compound 119
¹H NMR (400 MHz, CDCl₃) δ ppm: 8.79 (d, J=1.0 Hz, 1H), 8.66 (d, J=1.0 Hz, 1H), 8.15 (d, J=3.6 Hz, 1H), 8.04 (d, J=2.3 Hz, 1H), 5.02 (s, 2H), 4.42 (t, J=6.6 Hz, 2H), 3.33 (s, 3H), 3.27 (t, J=5.6 Hz, 2H), 2.18-2.09 (m, 2H), 1.73 (s, 3H), 1.33-1.25 (m, 1H), 0.80-0.51 (m, 4H).
LCMS (Method E): Rt=2.83 min, m/z [M+H]⁺=410

Compound 120
¹H NMR (400 MHz, CDCl₃) δ ppm: 8.79 (d, J=1.0 Hz, 1H), 8.66 (d, J=1.0 Hz, 1H), 8.15 (d, J=3.6 Hz, 1H), 8.04 (d, J=2.3 Hz, 1H), 5.02 (s, 2H), 4.42 (t, J=6.6 Hz, 2H), 3.33 (s, 3H), 3.27 (t, J=5.6 Hz, 2H), 2.17-2.09 (m, 2H), 1.73 (s, 3H), 1.33-1.25 (m, 1H), 0.80-0.50 (m, 4H).
LCMS (Method E): Rt=2.83 min, m/z [M+H]⁺=410

Compound 121
¹H NMR (400 MHz, CDCl₃) δ ppm: 8.92 (s, 1H), 8.70 (s, 1H), 8.36 (d, J=1.5 Hz, 1H), 8.20 (d, J=3.5 Hz, 1H), 5.73-5.65 (m, 1H), 5.28 (t, J=7.5 Hz, 2H), 5.10 (t, J=6.6 Hz, 2H), 5.04 (s, 2H), 2.21 (s, 1H), 1.74 (s, 3H), 1.34-1.26 (m, 1H), 0.80-0.52 (m, 4H).
LCMS (Method E): Rt=2.62 min, m/z [M+H]⁺=394

Compound 122
¹H NMR (400 MHz, CDCl₃) δ ppm: 8.91 (s, 1H), 8.69 (d, J=1.0 Hz, 1H), 8.35 (d, J=1.8 Hz, 1H), 8.20 (d, J=3.5 Hz, 1H), 5.73-5.65 (m, 1H), 5.28 (t, J=7.5 Hz, 2H), 5.11-5.07 (m, 2H), 5.04 (s, 2H), 2.26 (s, 1H), 1.74 (s, 3H), 1.34-1.26 (m, 1H), 0.80-0.52 (m, 4H).
LCMS (Method E): Rt=2.62 min, m/z [M+H]⁺=394

Compound 123 (Formic Acid 1.8 Equivalents)
¹H NMR (400 MHz, DMSO-d₆) δ ppm: 8.91 (d, J=1.1 Hz, 1H), 8.50 (d, J=1.0 Hz, 1H), 8.42 (s, 1H), 8.19-8.16 (m, 2.8H), 6.98 (d, J=5.3 Hz, 1H), 6.56 (s, 2H), 4.52 (t, J=4.9 Hz, 2H), 3.75 (t, J=5.2 Hz, 4H), 3.23 (s, 3H), 2.68-2.57 (m, 2H), 2.26 (s, 3H), 1.99-1.90 (m, 2H), 1.87-1.77 (m, 2H).
LCMS (Method E): Rt=1.55 min, m/z [M+H]⁺=407

Compound 124
¹H NMR (400 MHz, DMSO-d₆, trifluoroacetic acid) δ ppm: 9.58 (s, 1H), 9.43 (s, 1H), 9.09 (s, 1H), 8.43 (d, J=6.8 Hz, 1H), 7.54 (d, J=6.8 Hz, 1H), 4.75 (t, J=4.8 Hz, 2H), 4.14-3.99 (m, 4H), 3.81 (t, J=4.8 Hz, 2H), 3.25 (s, 3H), 3.22-3.12 (m, 1H), 1.50 (s, 3H).
LCMS (Method E): Rt=1.59 min, m/z [M+H]⁺=393

Compound 125
¹H NMR (400 MHz, CD₃OD) δ ppm: 8.79 (s, 1H), 8.69 (s, 1H), 8.29 (s, 1H), 8.12 (d, J=5.5 Hz, 1H), 7.01 (d, J=5.5 Hz, 1H), 4.51 (t, J=4.9 Hz, 2H), 3.97-3.94 (m, 2H), 3.80-3.73 (m, 4H) 3.23 (s, 3H).
LCMS (Method E): Rt=1.55 min, m/z [M+H]⁺=365

Compound 126 (Formic Acid 0.7 Equivalents)
¹H NMR (400 MHz, DMSO-d₆) δ ppm: 9.03 (d, J=0.9 Hz, 1H), 8.57 (d, J=1.0 Hz, 1H), 8.31 (d, J=2.2 Hz, 1H), 8.26 (d, J=3.7 Hz, 1H), 8.17 (s, 0.7H), 6.63 (s, 2H), 5.34 (s, 1H), 4.70-4.60 (m, 1H), 3.48 (t, J=5.8 Hz, 2H), 3.26 (s, 3H), 3.06 (d, J=12.0 Hz, 2H), 2.57 (t, J=5.8 Hz, 2H), 2.34-2.24 (m, 2H), 2.11-2.00 (m, 4H), 1.55 (s, 3H), 1.22-1.14 (m, 1H), 0.60-0.38 (m, 4H).
LCMS (Method E): Rt=2.22 min, m/z [M+H]⁺=479

Compound 127
¹H NMR (400 MHz, DMSO-d₆) δ ppm: 8.97 (d, J=1.0 Hz, 1H), 8.59 (d, J=1.0 Hz, 1H), 8.30 (d, J=2.7 Hz, 1H), 8.27 (d, J=3.8 Hz, 1H), 6.65 (s, 2H), 5.35 (s, 1H), 4.59-4.42 (m, 2H), 3.85-3.77 (m, 2H), 3.47-3.38 (m, 1H), 2.94 (d, J=10.8 Hz, 1H), 2.69-2.63 (m, 1H), 2.36-2.30 (m, 2H), 2.01-1.92 (m, 1H), 1.75 (t, J=10.5 Hz, 1H), 1.56 (s, 3H), 1.23-1.15 (m, 1H), 1.01 (t, J=7.1 Hz, 3H), 0.62-0.40 (m, 4H).
LCMS (Method E): Rt=2.17 min, m/z [M+H]⁺=465

Compound 128
¹H NMR (400 MHz, DMSO-d₆) δ ppm: 9.00 (d, J=1.0 Hz, 1H), 8.56 (d, J=1.0 Hz, 1H), 8.33 (d, J=2.2 Hz, 1H), 8.26 (d, J=3.8 Hz, 1H), 6.63 (s, 2H), 5.36 (s, 1H), 5.13-5.06 (m, 1H), 3.79 (dd, J=7.5, 10.4 Hz, 1H), 3.69 (dd, J=4.2, 10.4 Hz, 1H), 3.21 (s, 3H), 1.56-1.53 (m, 6H), 1.22-1.14 (m, 1H), 0.60-0.39 (m, 4H).
LCMS (Method E): Rt=2.92 min, m/z [M+H]⁺=410

Compound 129
¹H NMR (400 MHz, DMSO-d₆) δ ppm: 9.00 (d, J=1.0 Hz, 1H), 8.56 (d, J=1.0 Hz, 1H), 8.34 (d, J=2.5 Hz, 1H), 8.25 (d, J=3.7 Hz, 1H), 6.63 (s, 2H), 5.32 (s, 1H), 4.64 (s, 2H), 4.58 (d, J=6.0 Hz, 2H), 4.21 (d, J=6.0 Hz, 2H), 1.53 (s, 3H), 1.22 (s, 3H), 1.20-1.12 (m, 1H), 0.59-0.37 (m, 4H).
LCMS (Method E): Rt=2.78 min, m/z [M+H]⁺=422

Compound 130
¹H NMR (400 MHz, DMSO-d₆) δ ppm: 8.96 (d, J=0.9 Hz, 1H), 8.57 (d, J=0.9 Hz, 1H), 8.32 (d, J=2.7 Hz, 1H), 8.26 (d, J=4.0 Hz, 1H), 6.63 (s, 2H), 5.34 (s, 1H), 4.56 (dd, J=3.2, 14.4 Hz, 1H), 4.41 (dd, J=7.6, 14.4 Hz, 1H), 4.25-4.17 (m, 1H), 3.78-3.71 (m, 1H), 3.66-3.59 (m, 1H), 2.07-1.97 (m, 1H), 1.82-1.73 (m, 2H), 1.55 (s, 4H), 1.22-1.14 (m, 1H), 0.60-0.39 (m, 4H).
LCMS (Method E): Rt=2.89 min, m/z [M+H]⁺=422

Compound 131
¹H NMR (400 MHz, DMSO-d₆) δ ppm: 9.03 (d, J=1.0 Hz, 1H), 8.58 (d, J=1.0 Hz, 1H), 8.27 (d, J=4.0 Hz, 1H), 8.23 (d, J=2.2 Hz, 1H), 6.66 (s, 2H), 5.57-5.50 (m, 1H), 5.36 (s, 1H), 4.16-4.09 (m, 2H), 3.98 (dd, J=5.7, 10.1 Hz, 1H), 3.88-3.80 (m, 1H), 2.65-2.55 (m, 1H), 2.25-2.15 (m, 1H), 1.55 (s, 3H), 1.22-1.14 (m, 1H), 0.61-0.39 (m, 4H).
LCMS (Method E): Rt=2.73 min, m/z [M+H]⁺=408

Compound 132
¹H NMR (400 MHz, DMSO-d₆) δ ppm: 12.42 (s, 1H), 8.79 (d, J=1.1 Hz, 1H), 8.57 (d, J=1.1 Hz, 1H), 8.30 (d, J=2.8 Hz, 1H), 8.25 (d, J=3.8 Hz, 1H), 6.62 (s, 2H), 5.33 (s, 1H), 1.55 (s, 3H), 1.22-1.14 (m, 1H), 0.61-0.39 (m, 4H).
LCMS (Method E): Rt=2.39 min, m/z [M+H]⁺=338

Compound 133
¹H NMR (400 MHz, DMSO-d₆) δ ppm: 8.56 (d, J=1.9 Hz, 1H), 8.48 (s, 1H), 8.30 (d, J=3.7 Hz, 1H), 6.66 (s, 2H), 6.16-6.09 (m, 1H), 5.34 (s, 1H), 5.09 (t, J=7.3 Hz, 2H), 4.94 (t, J=6.5 Hz, 2H), 2.79 (s, 3H), 1.53 (s, 3H), 1.21-1.13 (m, 1H), 0.58-0.37 (m, 4H).
LCMS (Method E): Rt=2.52 min, m/z [M+H]⁺=408

Compound 134
¹H NMR (400 MHz, CDCl₃) δ ppm: 8.80 (s, 1H), 8.66 (s, 1H), 8.16 (d, J=3.5 Hz, 1H), 8.06 (d, J=2.2 Hz, 1H), 5.04 (s, 2H), 4.47 (t, J=5.7 Hz, 2H), 3.61 (t, J=5.8 Hz, 2H), 3.14-3.09 (m, 2H), 2.81 (s, 3H), 2.78 (s, 3H), 1.73 (s, 3H), 1.34-1.25 (m, 1H), 0.80-0.51 (m, 4H).
LCMS (Method E): Rt=2.56 min, m/z [M+H]⁺=464

Compound 135

¹H NMR (400 MHz, DMSO-d₆) δ ppm: 9.02 (d, J=1.0 Hz, 1H), 8.57 (d, J=1.0 Hz, 1H), 8.48 (d, J=2.3 Hz, 1H), 8.29 (d, J=3.7 Hz, 1H), 6.66 (s, 2H), 5.37-5.31 (m, 2H), 3.78 (t, J=7.7 Hz, 2H), 3.52-3.46 (m, 2H), 2.38 (s, 3H), 1.55 (s, 3H), 1.22-1.14 (m, 1H), 0.60-0.38 (m, 4H).

LCMS (Method E): Rt=2.09 min, m/z [M+H]⁺=407

Compound 136

¹H NMR (400 MHz, DMSO-d₆) δ ppm: 9.03 (d, J=1.0 Hz, 1H), 8.57 (d, J=1.1 Hz, 1H), 8.46 (d, J=2.2 Hz, 1H), 8.28 (d, J=3.7 Hz, 1H), 6.66 (s, 2H), 5.40-5.30 (m, 2H), 3.77 (t, J=7.7 Hz, 2H), 3.48-3.41 (m, 2H), 2.59-2.52 (m, 2H), 1.55 (s, 3H), 1.22-1.14 (m, 1H), 0.95 (t, J=7.1 Hz, 3H), 0.60-0.38 (m, 4H).

LCMS (Method E): Rt=2.16 min, m/z [M+H]⁺=421

Compound 137

¹H NMR (400 MHz, CDCl₃) δ ppm: 8.92 (d, J=0.9 Hz, 1H), 8.72 (d, J=0.9 Hz, 1H), 8.36 (d, J=1.8 Hz, 1H), 8.20 (d, J=3.5 Hz, 1H), 5.72-5.65 (m, 1H), 5.28 (t, J=7.5 Hz, 2H), 5.08 (dd, J=6.0, 7.4 Hz, 4H), 4.71-4.48 (m, 2H), 2.88 (s, 1H), 1.35-1.27 (m, 1H), 0.90-0.83 (m, 1H), 0.77-0.59 (m, 3H).

LCMS (Method E): Rt=2.71 min, m/z [M+H]⁺=412

Compound 138 (Formic Acid 1.0 Equivalents)

¹H NMR (400 MHz, CDCl₃) δ ppm: 8.90 (s, 1H), 8.66 (s, 1H), 8.37 (s, 1H), 8.26 (s, 1H), 8.14 (d, J=3.7 Hz, 1H), 5.21 (s, 2H), 4.85-4.77 (m, 1H), 3.28 (dd, J=1.3, 8.6 Hz, 1H), 2.99 (d, J=10.8 Hz, 1H), 2.65-2.53 (m, 3H), 2.38-2.30 (m, 1H), 2.23 (d, J=9.0 Hz, 1H), 1.99-1.89 (m, 3H), 1.73 (s, 3H), 1.33-1.24 (m, 1H), 1.16 (t, J=7.2 Hz, 3H), 0.79-0.50 (m, 4H).

LCMS (Method E): Rt=2.37 min, m/z [M+H]⁺=449

Compound 139

¹H NMR (400 MHz, DMSO-d₆) δ ppm: 9.05 (d, J=1.0 Hz, 1H), 8.57 (d, J=0.9 Hz, 1H), 8.48 (d, J=2.3 Hz, 1H), 8.28 (d, J=3.7 Hz, 1H), 6.67 (s, 2H), 5.41-5.32 (m, 2H), 3.76 (t, J=7.6 Hz, 2H), 3.58-3.42 (m, 2H), 2.48-2.47 (m, 2H), 1.55 (s, 3H), 1.40-1.33 (m, 2H), 1.22-1.13 (m, 1H), 0.90 (t, J=7.4 Hz, 3H), 0.60-0.38 (m, 4H).

LCMS (Method E): Rt=2.26 min, m/z [M+H]⁺=435

Compound 140

¹H NMR (400 MHz, DMSO-d₆) δ ppm: 9.04 (s, 1H), 8.56 (s, 1H), 8.47 (d, J=2.0 Hz, 1H), 8.29 (d, J=3.7 Hz, 1H), 5.39-5.31 (m, 2H), 3.83 (t, J=7.5 Hz, 2H), 3.48 (dd, J=5.8, 7.6 Hz, 2H), 2.42 (d, J=6.6 Hz, 2H), 1.55 (s, 3H), 1.22-1.13 (m, 1H), 0.83-0.76 (m, 1H), 0.58-0.39 (m, 6H), 0.17-011 (m, 2H).

LCMS (Method E): Rt=2.41 min, m/z [M+H]⁺=447

Compound 141

¹H NMR (400 MHz, DMSO-d₆) δ ppm: 9.13 (d, J=1.0 Hz, 1H), 8.57 (d, J=1.0 Hz, 1H), 8.46 (d, J=2.4 Hz, 1H), 8.25 (d, J=3.8 Hz, 1H), 6.63 (s, 2H), 5.41-5.35 (m, 1H), 5.34 (s, 1H), 3.18-3.11 (m, 2H), 2.68-2.55 (m, 4H), 2.33-2.25 (m, 1H), 2.02-1.91 (m, 1H), 1.55 (s, 3H), 1.22-1.14 (m, 1H), 1.11 (t, J=7.2 Hz, 3H), 0.60-0.39 (m, 4H).

LCMS (Method E): Rt=2.24 min, m/z [M+H]⁺=435

Compound 142

¹H NMR (400 MHz, DMSO-d₆) δ ppm: 9.06 (d, J=1.0 Hz, 1H), 8.57 (d, J=1.0 Hz, 1H), 8.46 (d, J=2.2 Hz, 1H), 8.28 (d, J=3.8 Hz, 1H), 6.66 (s, 2H), 5.34 (s, 1H), 5.33-5.27 (m, 1H), 3.74 (t, J=7.6 Hz, 2H), 3.44-3.39 (m, 2H), 2.91-2.85 (m, 1H), 1.72-1.62 (m, 2H), 1.60-1.47 (m, 7H), 1.44-1.36 (m, 2H), 1.22-1.14 (m, 1H), 0.60-0.38 (m, 4H).

LCMS (Method E): Rt=2.49 min, m/z [M+H]⁺=461

Compound 143

¹H NMR (400 MHz, DMSO-d₆) δ ppm: 8.96 (d, J=1.0 Hz, 1H), 8.36 (d, J=1.0 Hz, 1H), 8.24 (s, 1H), 8.21 (s, 1H), 6.71 (s, 2H), 5.33 (s, 1H), 5.06-4.95 (m, 1H), 4.28 (s, 2H), 3.37 (s, 3H), 1.57-1.53 (m, 9H), 1.20-1.12 (m, 1H), 0.59-0.38 (m, 4H).

LCMS (Method E): Rt=2.68 min, m/z [M+H]⁺=406

Compound 144

¹H NMR (400 MHz, DMSO-d₆) δ ppm: 8.96 (d, J=0.9 Hz, 1H), 8.39 (d, J=1.0 Hz, 1H), 8.23 (s, 1H), 8.22 (s, 1H), 6.72 (s, 2H), 5.47 (s, 1H), 5.05-4.96 (m, 1H), 4.29 (s, 2H), 3.37 (s, 3H), 1.56 (d, J=6.8 Hz, 6H), 1.51 (s, 6H).

LCMS (Method E): Rt=2.42 min, m/z [M+H]⁺=380

Compound 145

¹H NMR (400 MHz, DMSO-d₆) δ ppm: d 9.06 (d, J=1.0 Hz, 1H), 8.57 (d, J=1.0 Hz, 1H), 8.53 (d, J=2.2 Hz, 1H), 8.30 (d, J=3.7 Hz, 1H), 6.67 (s, 2H), 5.48 (tt, J=6.4, 6.5 Hz, 1H), 5.35 (s, 1H), 4.02 (t, J=7.7 Hz, 2H), 3.79-3.74 (m, 2H), 3.44 (q, J=10.1 Hz, 2H), 1.55 (s, 3H), 1.22-1.14 (m, 1H), 0.60-0.38 (m, 4H).

LCMS (Method E): Rt=3.41 min, m/z [M+H]⁺=475

Compound 146

¹H NMR (400 MHz, DMSO-d₆) δ ppm: 9.07 (d, J=1.0 Hz, 1H), 8.56 (d, J=1.0 Hz, 1H), 8.49 (d, J=2.3 Hz, 1H), 8.27 (d, J=3.7 Hz, 1H), 6.65 (s, 2H), 5.33 (s, 2H), 3.76 (t, J=7.6 Hz, 2H), 3.48-3.43 (m, 2H), 2.47-2.44 (m, 2H), 1.93-1.80 (m, 1H), 1.75-1.65 (m, 2H), 1.59-1.44 (m, 7H), 1.25-1.12 (m, 3H), 0.59-0.37 (m, 4H).

LCMS (Method E): Rt=2.73 min, m/z [M+H]⁺=475

Compound 147

¹H NMR (400 MHz, DMSO-d₆) δ ppm: 8.89 (d, J=0.9 Hz, 1H), 8.50 (d, J=1.0 Hz, 1H), 8.48 (s, 1H), 8.18 (d, J=5.3 Hz, 1H), 7.88-7.82 (m, 1H), 6.98 (d, J=5.3 Hz, 1H), 6.57 (s, 2H), 5.48 (s, 1H), 4.35 (t, J=6.9 Hz, 2H), 3.07 (q, J=6.3 Hz, 2H), 2.07 (t, J=7.5 Hz, 2H), 2.02-1.93 (m, 2H), 1.52 (s, 6H), 1.51-1.42 (m, 2H), 1.29-1.22 (m, 2H), 0.86 (t, J=7.4 Hz, 3H).

LCMS (Method E): Rt=2.32 min, m/z [M+H]⁺=435

Compound 148 (Formic Acid 0.6 Equivalents)

¹H NMR (400 MHz, DMSO-d₆) δ ppm: 8.90 (d, J=1.0 Hz, 1H), 8.50 (d, J=1.1 Hz, 1H), 8.48 (s, 1H), 8.19 (s, 1H), 8.17 (s, 0.6H), 7.95-7.89 (m, 1H), 6.98 (d, J=5.3 Hz, 1H), 6.57 (s, 2H), 5.48-5.48 (m, 1H), 4.36 (t, J=6.9 Hz, 2H), 3.05 (q, J=6.4 Hz, 2H), 2.02-1.92 (m, 2H), 1.81 (s, 3H), 1.52 (s, 6H).

LCMS (Method E): Rt=1.81 min, m/z [M+H]⁺=393

Compound 149

¹H NMR (400 MHz, DMSO-d₆) δ ppm: 8.96 (d, J=0.9 Hz, 1H), 8.68 (d, J=1.0 Hz, 1H), 8.48 (s, 1H), 8.22 (s, 0.5H), 8.11 (s, 1H), 6.16 (s, 2H), 5.32-5.32 (m, 1H), 5.05-4.94 (m, 1H), 3.90 (s, 3H), 1.57 (s, 3H), 1.55 (d, J=1.7 Hz, 6H), 1.22-1.14 (m, 1H), 0.62-0.48 (m, 2H), 0.47-0.36 (m, 2H).

LCMS (Method E): Rt=2.61 min, m/z [M+H]⁺=392

Compound 150

¹H NMR (400 MHz, DMSO-d₆) δ ppm: 9.04 (d, J=0.9 Hz, 1H), 8.64 (d, J=1.0 Hz, 1H), 8.35 (d, J=2.3 Hz, 1H), 8.27 (d, J=3.7 Hz, 1H), 6.64 (s, 2H), 6.43 (s, 1H), 5.09-5.00 (m, 1H), 3.42-3.36 (m, 3H), 2.82 (s, 2H), 2.55-2.52 (m, 1H), 2.26-2.17 (m, 1H), 1.57 (d, J=6.7 Hz, 6H).

LCMS (Method E): Rt=2.58 min, m/z [M+H]⁺=409

Compound 151

¹H NMR (400 MHz, DMSO-d₆) δ ppm: 9.12 (d, J=0.9 Hz, 1H), 8.60 (d, J=0.9 Hz, 1H), 8.45 (d, J=2.4 Hz, 1H), 8.25 (d, J=3.8 Hz, 1H), 6.64 (s, 2H), 5.48 (s, 1H), 5.43-5.36 (m, 1H), 4.65 (t, J=4.9 Hz, 1H), 4.54 (t, J=4.9 Hz, 1H), 3.23-3.16 (m, 2H), 2.95-2.74 (m, 3H), 2.56-2.53 (m, 1H), 2.47-2.38 (m, 1H), 2.03-1.93 (m, 1H), 1.52 (s, 6H).

LCMS (Method E): Rt=1.98 min, m/z [M+H]⁺=427

Compound 152

¹H NMR (400 MHz, DMSO-d₆) δ ppm: 9.10 (d, J=0.9 Hz, 1H), 8.58 (d, J=0.9 Hz, 1H), 8.42 (d, J=2.4 Hz, 1H), 8.26 (d, J=3.8 Hz, 1H), 6.63 (s, 2H), 5.43-5.38 (m, 1H), 5.34 (s, 1H), 3.23-3.18 (m, 2H), 2.81-2.67 (m, 3H), 2.62-2.52 (m, 3H), 2.38-2.29 (m, 1H), 2.03-1.92 (m, 1H), 1.55 (s, 3H), 1.22-1.14 (m, 1H), 0.62-0.49 (m, 2H), 0.48-0.36 (m, 2H).

LCMS (Method E): Rt=2.11 min, m/z [M+H]$^+$=503

Compound 153

$^1$H NMR (400 MHz, DMSO-d$_6$) δ ppm: 9.12 (d, J=0.9 Hz, 1H), 8.58 (d, J=0.9 Hz, 1H), 8.45 (d, J=2.4 Hz, 1H), 8.26 (d, J=3.8 Hz, 1H), 6.63 (s, 2H), 5.43-5.36 (m, 1H), 5.34 (s, 1H), 4.66 (t, J=4.9 Hz, 1H), 4.54 (t, J=4.9 Hz, 1H), 3.24-3.16 (m, 2H), 2.93-2.76 (m, 3H), 2.60-2.52 (m, 1H), 2.43 (q, J=8.5 Hz, 1H), 2.03-1.93 (m, 1H), 1.55 (s, 3H), 1.22-1.14 (m, 1H), 0.62-0.49 (m, 2H), 0.48-0.36 (m, 2H).

LCMS (Method E): Rt=2.24 min, m/z [M+H]$^+$=453

Compound 154

$^1$H NMR (400 MHz, DMSO-d$_6$) δ ppm: 8.94 (d, J=1.0 Hz, 1H), 8.59 (d, J=1.2 Hz, 1H), 8.54 (d, J=2.2 Hz, 1H), 8.30 (d, J=3.7 Hz, 1H), 6.68 (s, 2H), 5.73-5.64 (m, 1H), 5.35 (s, 1H), 4.70 (t, J=8.8 Hz, 1H), 4.64-4.59 (m, 1H), 4.44 (t, J=9.4 Hz, 1H), 4.28-4.22 (m, 1H), 1.88 (s, 3H), 1.55 (s, 3H), 1.22-1.14 (m, 1H), 0.61-0.48 (m, 2H), 0.48-0.37 (m, 2H).

LCMS (Method E): Rt=2.53 min, m/z [M+H]$^+$=435

Compound 155

$^1$H NMR (400 MHz, DMSO-d$_6$) δ ppm: 9.03 (d, J=1.0 Hz, 1H), 8.56 (d, J=1.0 Hz, 1H), 8.46 (d, J=2.2 Hz, 1H), 8.29 (d, J=3.7 Hz, 1H), 6.66 (s, 2H), 5.39-5.33 (m, 2H), 3.83 (t, J=7.7 Hz, 2H), 3.55-3.49 (m, 2H), 3.38 (t, J=5.7 Hz, 2H), 3.26 (s, 3H), 2.72 (t, J=5.7 Hz, 2H), 1.55 (s, 3H), 1.22-1.14 (m, 1H), 0.61-0.48 (m, 2H), 0.48-0.36 (m, 2H).

LCMS (Method E): Rt=2.27 min, m/z [M+H]$^+$=451

Compound 156

$^1$H NMR (400 MHz, DMSO-d$_6$) δ ppm: 9.04 (d, J=0.9 Hz, 1H), 8.57 (d, J=1.0 Hz, 1H), 8.47 (d, J=2.3 Hz, 1H), 8.29 (d, J=3.7 Hz, 1H), 6.66 (s, 2H), 5.37-5.34 (m, 2H), 3.77 (t, J=7.3 Hz, 2H), 3.48-3.42 (m, 2H), 3.38 (t, J=6.4 Hz, 2H), 3.24 (s, 3H), 2.60-2.54 (m, 2H), 1.61-1.54 (m, 5H), 1.22-1.14 (m, 1H), 0.62-0.49 (m, 2H), 0.48-0.36 (m, 2H).

LCMS (Method E): Rt=2.32 min, m/z [M+H]$^+$=465

Compound 157

$^1$H NMR (400 MHz, DMSO-d$_6$) δ ppm: 9.01 (d, J=0.9 Hz, 1H), 8.56 (d, J=0.9 Hz, 1H), 8.45 (d, J=2.2 Hz, 1H), 8.28 (d, J=3.6 Hz, 1H), 6.66 (s, 2H), 5.37-5.29 (m, 2H), 3.87 (t, J=7.6 Hz, 2H), 3.62-3.57 (m, 2H), 2.13-2.06 (m, 1H), 1.54 (s, 3H), 1.21-1.13 (m, 1H), 0.61-0.48 (m, 2H), 0.47-0.34 (m, 4H), 0.34-0.28 (m, 2H).

LCMS (Method E): Rt=2.28 min, m/z [M+H]$^+$=433

Compound 158

$^1$H NMR (400 MHz, DMSO-d$_6$) δ ppm: 9.03 (d, J=1.0 Hz, 1H), 8.57 (d, J=1.0 Hz, 1H), 8.47 (d, J=2.2 Hz, 1H), 8.29 (d, J=3.7 Hz, 1H), 6.66 (s, 2H), 5.41-5.32 (m, 2H), 3.83 (t, J=7.6 Hz, 2H), 3.54-3.50 (m, 2H), 3.47-3.38 (m, 4H), 2.71 (t, J=5.7 Hz, 2H), 1.55 (s, 3H), 1.22-1.14 (m, 1H), 1.11 (t, J=7.0 Hz, 3H), 0.61-0.48 (m, 2H), 0.48-0.36 (m, 2H).

LCMS (Method E): Rt=2.42 min, m/z [M+H]$^+$=465

Compound 159

$^1$H NMR (400 MHz, DMSO-d$_6$) δ ppm: 9.04 (d, J=0.9 Hz, 1H), 8.57 (d, J=0.9 Hz, 1H), 8.44 (d, J=2.2 Hz, 1H), 8.28 (d, J=3.7 Hz, 1H), 6.66 (s, 2H), 5.34 (s, 1H), 5.32-5.24 (m, 1H), 3.78 (t, J=7.6 Hz, 2H), 3.44-3.39 (m, 2H), 2.48-2.43 (m, 1H), 1.55 (s, 3H), 1.22-1.13 (m, 1H), 0.93 (d, J=6.3 Hz, 6H), 0.55 (d, J=50.2 Hz, 2H), 0.42 (d, J=39.5 Hz, 2H).

LCMS (Method E): Rt=2.25 min, m/z [M+H]$^+$=435

Compound 160

$^1$H NMR (400 MHz, DMSO-d$_6$) δ ppm: 9.01 (d, J=1.0 Hz, 1H), 8.59 (d, J=1.0 Hz, 1H), 8.45 (d, J=2.3 Hz, 1H), 8.28 (d, J=3.7 Hz, 1H), 6.67 (s, 2H), 5.47 (s, 1H), 5.38-5.29 (m, 1H), 3.87 (t, J=7.7 Hz, 2H), 3.62-3.57 (m, 2H), 2.13-2.07 (m, 1H), 0.44-0.38 (m, 2H), 0.34-0.30 (m, 2H).

LCMS (Method E): Rt=2.05 min, m/z [M+H]$^+$=413

Compound 161

$^1$H NMR (400 MHz, DMSO-d$_6$) δ ppm: 9.03 (d, J=1.0 Hz, 1H), 8.64 (d, J=1.0 Hz, 1H), 8.47 (d, J=2.2 Hz, 1H), 8.29 (d, J=3.7 Hz, 1H), 6.68 (s, 2H), 5.95 (s, 1H), 5.38-5.30 (m, 1H), 4.48-4.42 (m, 1H), 4.36-4.30 (m, 1H), 3.90-3.85 (m, 2H), 3.63-3.58 (m, 2H), 2.14-2.08 (m, 1H), 1.52 (d, J=1.9 Hz, 3H), 0.44-0.38 (m, 2H), 0.34-0.30 (m, 2H).

LCMS (Method E): Rt=2.04 min, m/z [M+H]$^+$=425

Compound 162

$^1$H NMR (400 MHz, DMSO-d$_6$) δ ppm: 9.03 (d, J=1.0 Hz, 1H), 8.56 (d, J=1.0 Hz, 1H), 8.45 (d, J=2.2 Hz, 1H), 8.29 (d, J=3.7 Hz, 1H), 6.66 (s, 2H), 5.35 (s, 1H), 5.34-5.27 (m, 1H), 3.84 (t, J=7.5 Hz, 2H), 3.52-3.46 (m, 2H), 3.30-3.28 (m, 1H), 3.26 (s, 3H), 3.15 (dd, J=5.4, 9.6 Hz, 1H), 2.66-2.59 (m, 1H), 1.55 (s, 3H), 1.22-1.14 (m, 1H), 0.91 (d, J=6.3 Hz, 3H), 0.62-0.48 (m, 2H), 0.48-0.37 (m, 2H).

LCMS (Method E): Rt=2.35 min, m/z [M+H]$^+$=465

Compound 163

$^1$H NMR (400 MHz, DMSO-d$_6$) δ ppm: 9.04 (d, J=1.0 Hz, 1H), 8.57 (d, J=1.0 Hz, 1H), 8.32 (d, J=2.0 Hz, 1H), 8.27 (d, J=3.7 Hz, 1H), 6.63 (s, 2H), 5.34 (s, 1H), 4.70-4.62 (m, 1H), 4.52 (t, J=4.8 Hz, 1H), 3.10-3.03 (m, 2H), 2.76 (t, J=4.8 Hz, 1H), 2.68 (t, J=5.0 Hz, 1H), 2.40-2.30 (m, 2H), 2.14-2.01 (m, 4H), 1.55 (s, 3H), 1.22-1.14 (m, 1H), 0.61-0.49 (m, 2H), 0.48-0.36 (m, 2H).

LCMS (Method E): Rt=2.19 min, m/z [M+H]$^+$=467

Compound 164

$^1$H NMR (400 MHz, DMSO-d$_6$) δ ppm: 8.98 (s, 1H), 8.64 (s, 1H), 8.52 (s, 1H), 8.15 (d, J=5.4 Hz, 1H), 7.08 (d, J=5.3 Hz, 1H), 6.54 (s, 2H), 5.34 (s, 1H), 4.70-4.60 (m, 1H), 3.09 (d, J=11.4 Hz, 2H), 2.48-2.43 (m, 1H), 2.06-1.97 (m, 4H), 1.76-1.69 (m, 1H), 1.54 (s, 3H), 1.22-1.13 (m, 1H), 0.61-0.37 (m, 7H), 0.36-0.32 (m, 2H).

LCMS (Method E): Rt=1.89 min, m/z [M+H]$^+$=443

Compound 165

$^1$H NMR (400 MHz, DMSO-d$_6$) δ ppm: 9.03 (d, J=0.9 Hz, 1H), 8.57 (d, J=0.9 Hz, 1H), 8.32 (d, J=2.1 Hz, 1H), 8.27 (d, J=3.7 Hz, 1H), 6.63 (s, 2H), 5.34 (s, 1H), 4.70-4.60 (m, 1H), 3.18-3.11 (m, 2H), 2.29-2.19 (m, 4H), 2.13-2.06 (m, 4H), 1.55 (s, 3H), 1.22-1.14 (m, 1H), 0.92-0.84 (m, 1H), 0.59-0.38 (m, 6H), 0.14-0.08 (m, 2H).

LCMS (Method E): Rt=2.32 min, m/z [M+H]$^+$=475

Compound 166

$^1$H NMR (400 MHz, DMSO-d$_6$) δ ppm: 9.01 (d, J=1.0 Hz, 1H), 8.59 (d, J=1.1 Hz, 1H), 8.45 (d, J=2.2 Hz, 1H), 8.28 (d, J=3.7 Hz, 1H), 6.67 (s, 2H), 5.49 (s, 1H), 5.37-5.29 (m, 1H), 3.87 (t, J=7.7 Hz, 2H), 3.62-3.57 (m, 2H), 2.13-2.07 (m, 1H), 1.52 (s, 6H), 0.44-0.38 (m, 2H), 0.34-0.30 (m, 2H).

LCMS (Method E): Rt=2.00 min, m/z [M+H]$^+$=407

Compound 167

$^1$H NMR (400 MHz, DMSO-d$_6$) δ ppm: 9.03 (d, J=0.9 Hz, 1H), 8.57 (d, J=0.9 Hz, 1H), 8.31 (d, J=2.1 Hz, 1H), 8.27 (d, J=3.7 Hz, 1H), 6.64 (s, 2H), 5.34 (s, 1H), 4.73-4.63 (m, 1H), 3.06 (d, J=11.5 Hz, 2H), 2.68-2.54 (m, 4H), 2.34-2.23 (m, 2H), 2.11-2.03 (m, 4H), 1.55 (s, 3H), 1.22-1.14 (m, 1H), 0.61-0.48 (m, 2H), 0.48-0.37 (m, 2H).

LCMS (Method E): Rt=2.42 min, m/z [M+H]$^+$=517

Compound 168

$^1$H NMR (400 MHz, DMSO-d$_6$) δ ppm: 8.95 (d, J=0.9 Hz, 1H), 8.71-8.69 (m, 2H), 8.12 (s, 1H), 6.22 (s, 2H), 5.33 (s, 1H), 5.04-4.96 (m, 1H), 4.20-4.17 (m, 2H), 3.78-3.74 (m, 2H), 3.39 (s, 3H), 1.55 (s, 6H), 1.53 (s, 3H), 1.22-1.14 (m, 1H), 0.62-0.49 (m, 2H), 0.47-0.36 (m, 2H).

LCMS (Method E): Rt=2.73 min, m/z [M+H]$^+$=436

Pharmacological Part
Biological Assay A
Inhibition of Recombinant Human NF-kappaB-Inducing Kinase (NIK/MAP3K14) Activity Assay buffer was 50 mM Tris pH 7.5 containing 1 mM EGTA (ethylene glycol tetraacetic acid), 1 mM DTT (dithiothreitol), 0.1 mM $Na_3VO_4$, 5 mM $MgCl_2$, 0.01% Tween 20. Assays were carried out in 384 well Mesoscale high binding plates which had been coated with myelin basic protein (MBP) and blocked with bovine serum albumin to prevent non-specific protein binding. All compounds tested were dissolved in dimethyl sulfoxide (DMSO) and further dilutions were made in assay buffer. Final DMSO concentration was 1% (v/v) in assays. Incubations consisted of compound (1% DMSO in control and blank wells), 25 µM Adenosine-5'-triphosphate (ATP), and 10 nM NIK/MAP3K14 substituting enzyme with buffer in the blank wells. Incubations were carried out for 1 h at 25° C. and were followed by washing and sequential incubation with rabbit anti-phospho-MBP and anti-rabbit Ig Sulfotag antibody before reading bound Sulfotag on a Mesoscale Discovery. Signal obtained in the wells containing blank samples was subtracted from all other wells and $IC_{50}$'s were determined by fitting a sigmoidal curve to % inhibition of control versus $Log_{10}$ compound concentration.

Biological Assay A2
Inhibition of Auto-Phosphorylation of Recombinant Human NF-kappaB-Inducing Kinase (NIK/MAP3K14) Activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM $Na_3VO_4$, 5 mM $MgCl_2$, 0.01% Tween 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and $IC_{50}$'s were determined by fitting a sigmoidal curve to % inhibition of control versus $Log_{10}$ compound concentration.

Biological Assay B
Effect of Compounds on P-IKKα Levels in L363 Cells

All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of $0.2 \times 10^6$ cells per ml-$1 \times 10^6$ cells per ml at 37° C. in a humidified 5% $CO_2$ atmosphere. Cells were passaged twice a week splitting back to obtain the low density. Cells were seeded in 96 well plates (Nunc 167008) at $2 \times 10^6$ per ml media in a volume of 75 µl per well plus 25 µl 1 µg/ml recombinant human B-cell activating factor BAFF/B1YS/TNFSF13B. Seeded cells were incubated at 37° C. in a humidified 5% $CO_2$ atmosphere for 24 hr. Drugs and/or solvents were added (20 µl) to a final volume of 120 µl. Following 2 hr treatment plates were removed from the incubator and cell lysis was achieved by the addition of 30 µl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 µM ADS125117, a test concentration known to give full inhibition) were run in parallel. The blank incubation value was subtracted from all control and sample values. To determine the $IC_{50}$ a sigmoidal curve was fitted to the plot of % inhibition of control P-IKKα levels versus $Log_{10}$ compound concentration.

Biological Assay C
Determination of Antiproliferative Activity on LP-1, L-363 and JJN-3 Cells All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human LP-1, L-363 and JJN-3 cells (DSMZ) were cultured in RPMI 1640 medium supplemented with 2 mM L-glutamine, and 10% fetal calf serum (PAA). Cells were routinely kept as suspension cells at 37° C. in a humidified 5% $CO_2$ atmosphere. Cells were passaged at a seeding density of $0.2 \times 10^6$/ml twice a week. Cells were seeded in black tissue culture treated 96-well plates (Perkin Elmer). Densities used for plating ranged from 2,000 to 6,000 cells per well in a total volume of 75 µl medium. After twenty four hours, drugs and/or solvents were added (25 µl) to a final volume of 100 µl. Following 72 hr of treatment plates were removed from the incubator and allowed to equilibrate to room temperature for approx 10 min. 100 µl CellTiter-Glo reagent was added to each well that was then covered (Perkin Elmer Topseal) and shaken on plate shaker for 10 min. Luminescence was measured on a HTS Topcount (Perkin Elmer). Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds (Co.) of the invention in the above assays are provided in Table 25 (the values in Table 25 are averaged values over all measurements on all batches of a compound).

TABLE 25

| Co. | Biochemical (MSD MBP) $IC_{50}$ (nM) | αscreen $IC_{50}$ (nM) | IKKα Cellular $IC_{50}$ (nM) | JJN-3 $EC_{50}$ (nM) | L-363 $EC_{50}$ (nM) | LP-1 $EC_{50}$ (nM) |
|---|---|---|---|---|---|---|
| 1 | 6.9 | 4.0 | 93 | 200 | 180 | 3200 |
| 2 | 9.7 | 48 | 82 | 220 | 210 | 1900 |
| 3 | 15 | 34 | 75 | 500 | 230 | 11000 |
| 4 | 46 | 21 | 130 | 420 | 400 | 5300 |
| 5 | 1.6 | 8.0 | 30 | 160 | 94 | 320 |

TABLE 25-continued

| Co. | Biochemical (MSD MBP) IC$_{50}$ (nM) | IKKα αscreen IC$_{50}$ (nM) | Cellular IC$_{50}$ (nM) | JJN-3 EC$_{50}$ (nM) | L-363 EC$_{50}$ (nM) | LP-1 EC$_{50}$ (nM) |
|---|---|---|---|---|---|---|
| 6 | 2.3 | 11 | 68 | 860 | 790 | 3000 |
| 7 | 15 | 210 | 540 | 1900 | 1900 | 3200 |
| 8 | 3.3 | 1.0 | 8 | 94 | 250 | 2700 |
| 9 | 1.1 | 2.0 | 37 | 74 | 120 | 1200 |
| 10 | 9.2 | 29 | 100 | 80 | 46 | 230 |
| 11 | 8.0 | 27 | 300 | 41 | 130 | 600 |
| 12 | 7.4 | 3.0 | 150 | 1300 | 1200 | 12000 |
| 13 | 30 | 150 | n.c. | 150 | 36 | 710 |
| 14 | 0.9 | 0.4 | 11 | 75 | 75 | 390 |
| 15 | 4.8 | 12 | 16 | 120 | 44 | 370 |
| 16 | 4.3 | 2.0 | 7.3 | 35 | 57 | 92 |
| 17 | 4.9 | 6.0 | 17 | 460 | 810 | 8000 |
| 18 | 3.7 | 8.0 | 47 | 340 | 450 | 1500 |
| 19 | 5.3 | 16 | 18 | 160 | 430 | 1200 |
| 20 | 9.4 | 15 | 30 | 1000 | 5000 | 11000 |
| 21 | 18 | 3.0 | 13 | 66 | 74 | 2800 |
| 22 | 20 | 9.0 | 75 | 280 | 190 | 1600 |
| 23 | 30 | 9.0 | 89 | 2500 | 9900 | 7700 |
| 24 | 8.7 | 15 | 13 | 140 | 96 | 760 |
| 25 | 9.9 | 20 | 11 | 110 | 63 | 190 |
| 26 | 49 | 19 | 120 | 5600 | 11000 | 15000 |
| 27 | 25 | 70 | 360 | 9700 | >10000 | >10000 |
| 28 | 17 | 49 | 84 | 1200 | 810 | 5800 |
| 29 | 140 | 110 | 6300 | >10000 | >10000 | >10000 |
| 30 | 120 | 930 | 1700 | 12000 | 24000 | >10000 |
| 31 | 36 | 79 | 110 | 1900 | 6400 | >10000 |
| 32 | 59 | 40 | 89 | 460 | 740 | 1500 |
| 33 | 4.2 | 16 | 53 | 150 | 1100 | 4100 |
| 34 | 76 | 42 | 160 | 330 | 240 | 4100 |
| 35 | 120 | 150 | 470 | 2000 | 3000 | 3800 |
| 36 | 17 | 86 | 900 | 1700 | 7900 | 12000 |
| 37 | 45 | 100 | 330 | 3600 | 16000 | >10000 |
| 38 | 21 | 56 | 370 | 1900 | 15000 | >10000 |
| 39 | 930 | 1600 | n.c. | n.c. | n.c. | n.c. |
| 40 | 43 | 110 | 530 | 2300 | 4500 | 25000 |
| 41 | 3.5 | 9.0 | 43 | 240 | 290 | 2200 |
| 42 | 5.7 | 24 | 84 | 330 | 1500 | 16000 |
| 43 | 29 | 38 | 280 | 650 | 4100 | >10000 |
| 44 | 25 | 21 | 36 | 250 | 400 | 1700 |
| 45 | 3.9 | 2.0 | 12 | 22 | 90 | 590 |
| 46 | 60 | 55 | 180 | 1100 | 1500 | >10000 |
| 47 | 2900 | 9200 | n.c. | >10000 | >10000 | >10000 |
| 48 | 65 | 16 | 260 | 380 | 650 | 3900 |
| 49 | 150 | 360 | 5900 | 32000 | >10000 | >10000 |
| 50 | 140 | 230 | 650 | 2700 | 7500 | >10000 |
| 51 | 48 | 23 | 83 | 990 | 2400 | >10000 |
| 52 | 29 | 33 | 99 | 1200 | 3200 | 30000 |
| 53 | 45 | 57 | 370 | 450 | >10000 | >10000 |
| 54 | 27 | 17 | 21 | 89 | 59 | 330 |
| 55 | 84 | 180 | 140 | 380 | 980 | 11000 |
| 56 | 25 | 18 | 140 | 840 | 840 | 14000 |
| 57 | 17 | 23 | 180 | 1300 | 910 | 31000 |
| 58 | 430 | 700 | 110 | 550 | 570 | 2000 |
| 59 | 71 | 230 | 5000 | 17000 | >10000 | >10000 |
| 60 | 8.4 | 11 | 19 | 170 | 150 | 14000 |
| 61 | 3.8 | 5.0 | 23 | 260 | 340 | 4600 |
| 62 | 250 | 680 | n.c. | 970 | 880 | 18000 |
| 63 | 600 | 780 | n.c. | n.c. | n.c. | n.c. |
| 64 | 5.2 | 29 | 20 | 81 | 51 | 2000 |
| 65 | 15 | 54 | 140 | 470 | 400 | 7000 |
| 66 | 5.8 | 52 | 240 | 250 | 270 | 7600 |
| 67 | 57 | 30 | 880 | 2400 | 2400 | >10000 |
| 68 | 130 | 47 | 360 | 1500 | 960 | 16000 |
| 69 | 250 | 89 | 600 | 1800 | 870 | 16000 |
| 70 | 28 | 130 | 51 | 210 | 120 | 3000 |
| 71 | 26 | 61 | n.c. | 550 | 520 | 2600 |
| 72 | 6.3 | 38 | n.c. | 320 | 190 | 7200 |
| 73 | 56 | 71 | n.c. | 190 | 140 | 1600 |
| 74 | 17 | 43 | n.c. | 76 | 45 | 1100 |
| 75 | n.c. | 35 | n.c. | 540 | 670 | >10000 |
| 76 | n.c. | 16 | 12 | 140 | 110 | 300 |
| 77 | n.c. | 88 | n.c. | 570 | 320 | 4000 |
| 78 | n.c. | 130 | n.c. | 580 | 410 | 2000 |
| 79 | n.c. | 47 | n.c. | 160 | 61 | 2000 |
| 80 | n.c. | 76 | n.c. | 310 | 160 | 2500 |
| 81 | n.c. | 100 | n.c. | 5700 | 5900 | 28000 |
| 82 | n.c. | 35 | n.c. | 1100 | 890 | 13000 |
| 83 | n.c. | 86 | n.c. | 670 | 550 | 4700 |
| 84 | n.c. | 68 | n.c. | 67 | 22 | 250 |
| 85 | n.c. | 33 | n.c. | 44 | 15 | 190 |
| 86 | n.c. | 11 | n.c. | 9.2 | 5.9 | 16 |
| 87 | n.c. | 9.0 | n.c. | 530 | 450 | 1200 |
| 88 | n.c. | 15 | n.c. | 130 | 110 | 220 |
| 89 | n.c. | 130 | n.c. | 3700 | 4200 | 7600 |
| 90 | n.c. | 44 | n.c. | 720 | 510 | 740 |
| 91 | n.c. | 12 | n.c. | 1100 | 470 | 4900 |
| 92 | n.c. | 47 | n.c. | 54 | 32 | 86 |
| 93 | n.c. | 10 | n.c. | 310 | 250 | 860 |
| 94 | n.c. | 31 | n.c. | 300 | 200 | 2700 |
| 95 | n.c. | 7.0 | n.c. | 150 | 95 | 470 |
| 96 | n.c. | 170 | n.c. | >10000 | 6600 | >10000 |
| 97 | n.c. | 21 | 70 | 170 | 100 | 1200 |
| 98 | n.c. | 220 | 110 | 78 | 42 | 210 |
| 99 | n.c. | 110 | n.c. | 1100 | 1100 | 2000 |
| 100 | n.c. | 61 | n.c. | 1400 | 1500 | 3000 |
| 101 | n.c. | 38 | n.c. | 160 | 160 | 220 |
| 102 | n.c. | 900 | 32 | 35 | 21 | 65 |
| 103 | n.c. | 13 | 49 | 91 | 48 | 680 |
| 104 | n.c. | 53 | n.c. | 260 | 180 | 470 |
| 105 | n.c. | 190 | n.c. | 200 | 140 | 530 |
| 106 | n.c. | 95 | n.c. | 120 | 90 | 340 |
| 107 | n.c. | 88 | n.c. | 78 | 57 | 150 |
| 108 | n.c. | 140 | n.c. | 270 | 280 | 640 |
| 109 | n.c. | 120 | n.c. | 460 | 360 | 1200 |
| 110 | n.c. | 17 | n.c. | 170 | 140 | 580 |
| 111 | 220 | 190 | 290 | 640 | 1300 | 7500 |
| 112 | 6.3 | 17 | 140 | 440 | 1300 | 14000 |
| 113 | 52 | 38 | 660 | 1400 | 4600 | 24000 |
| 114 | 160 | 190 | 3800 | 1600 | 1500 | 5500 |
| 115 | n.c. | 4900 | n.c. | >10000 | >10000 | >10000 |
| 116 | 120 | 170 | 5300 | 5600 | 11000 | >10000 |
| 117 | 100 | 14 | 3400 | 3300 | 9000 | >10000 |
| 118 | 240 | 740 | 1700 | 330 | 1600 | 3800 |
| 119 | n.c. | 230 | n.c. | 700 | 900 | 2100 |
| 120 | n.c. | 17 | 20 | 95 | 74 | 200 |
| 121 | n.c. | 680 | n.c. | 1400 | 1300 | 3400 |
| 122 | n.c. | 26 | 36 | 100 | 69 | 310 |
| 123 | 23%$^a$ | 27%$^a$ | n.c. | n.c. | n.c. | n.c. |
| 124 | 40%$^a$ | 33%$^a$ | n.c. | n.c. | n.c. | n.c. |
| 125 | 18%$^a$ | 24%$^a$ | n.c. | n.c. | n.c. | n.c. |
| 126 | n.c. | 140 | n.c. | 270 | 280 | 640 |
| 127 | n.c. | 180 | n.c. | 240 | 190 | 420 |
| 128 | n.c. | 76 | n.c. | 130 | 120 | 310 |
| 129 | n.c. | 23 | n.c. | 210 | 150 | 920 |
| 130 | n.c. | 28 | n.c. | 300 | 190 | 640 |
| 131 | n.c. | 21 | n.c. | 150 | 89 | 440 |
| 132 | n.c. | 6.5 | n.c. | 77 | 30 | 410 |
| 133 | n.c. | 50 | n.c. | 140 | 66 | 330 |
| 134 | n.c. | 110 | n.c. | 4100 | 3000 | 24000 |
| 135 | n.c. | 68 | n.c. | 180 | 64 | 410 |
| 136 | n.c. | 120 | n.c. | 240 | 140 | 450 |
| 137 | n.c. | 53 | n.c. | 550 | 380 | 1990 |
| 138 | n.c. | 110 | n.c. | 94 | 80 | 250 |
| 139 | n.c. | 98 | n.c. | 220 | 160 | 340 |
| 140 | n.c. | 100 | n.c. | 170 | 140 | 320 |
| 141 | n.c. | 66 | n.c. | 96 | 56 | 320 |
| 142 | n.c. | 210 | n.c. | 150 | 190 | 410 |
| 143 | n.c. | 74 | n.c. | 270 | 170 | n.c. |
| 144 | n.c. | 37 | n.c. | 35 | 16 | n.c. |
| 145 | n.c. | 140 | n.c. | 260 | 340 | n.c. |
| 146 | n.c. | 200 | n.c. | 450 | 580 | n.c. |
| 147 | n.c. | 130 | n.c. | 1400 | 530 | n.c. |
| 148 | n.c. | 64 | n.c. | 9100 | 7600 | n.c. |
| 149 | n.c. | 22 | n.c. | 38 | 22 | n.c. |
| 150 | n.c. | 210 | n.c. | 1600 | 1500 | n.c. |
| 151 | n.c. | 54 | n.c. | 46 | 45 | n.c. |
| 152 | n.c. | 47 | n.c. | 48 | 75 | n.c. |
| 153 | n.c. | 74 | n.c. | 130 | 150 | n.c. |
| 154 | n.c. | 190 | n.c. | 4700 | 2800 | n.c. |
| 155 | n.c. | 140 | n.c. | 400 | 380 | n.c. |

TABLE 25-continued

| Co. | Biochemical (MSD MBP) IC$_{50}$ (nM) | IKKα αscreen IC$_{50}$ (nM) | IKKα Cellular IC$_{50}$ (nM) | JJN-3 EC$_{50}$ (nM) | L-363 EC$_{50}$ (nM) | LP-1 EC$_{50}$ (nM) |
|---|---|---|---|---|---|---|
| 156 | n.c. | 190 | n.c. | 320 | 360 | n.c. |
| 157 | n.c. | 46 | n.c. | 180 | 140 | n.c. |
| 158 | n.c. | 180 | n.c | 440 | 390 | 740 |
| 159 | n.c. | 270 | n.c | 230 | 180 | 320 |
| 160 | n.c. | 82 | n.c | 110 | 93 | 210 |
| 161 | n.c. | 40 | n.c | 150 | 110 | 340 |
| 162 | n.c. | 340 | n.c | 370 | 350 | 790 |
| 163 | n.c. | 73 | n.c | 110 | 59 | 110 |
| 164 | n.c. | 89 | n.c | 390 | 270 | 680 |
| 165 | n.c. | 46 | n.c | 220 | 200 | 460 |
| 166 | n.c. | 76 | n.c | 96 | 60 | 180 |
| 167 | n.c. | 58 | n.c | 390 | 390 | 1000 |
| 168 | n.c. | 36 | n.c | 27 | 23 | 93 | n.c.: not calculated
$^a$Max % Inhib @ 10 μM (Average)

Prophetic Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of formula (I):

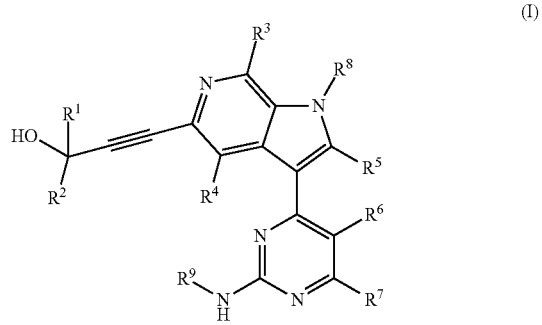

or a tautomer or a stereoisomeric form thereof, wherein

R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, C$_{3-6}$cycloalkyl, Het$^1$, Het$^2$ and phenyl; —C(=O)—NR$^{2c}$R$^{2d}$; C$_{3-6}$cycloalkyl; Het$^1$; Het$^2$; and phenyl; wherein the phenyl groups are optionally substituted with one or two substituents independently selected from the group of halogen, cyano, C$_{1-4}$alkyl, C$_{1-4}$alkoxy, C$_{1-4}$alkyl substituted with one or more fluoro substituents, and C$_{1-4}$alkyloxy substituted with one or more fluoro substituents;

R$^{1a}$, R$^{1b}$, R$^{2a}$, R$^{2b}$, R$^{2c}$ and R$^{2d}$ are each independently selected from hydrogen and C$_{1-4}$alkyl;

Het$^1$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C$_{1-4}$alkyl;

Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, C$_{1-4}$alkyl, C$_{1-4}$alkoxy, C$_{1-4}$alkyl substituted with one or more fluoro substituents, and C$_{1-4}$alkyloxy substituted with one or more fluoro substituents;

or R$^1$ and R$^2$ together with the carbon atom to which they are attached form a C$_{3-6}$cycloalkyl or a Het$^3$ group; wherein Het$^3$ is a heterocyclyl selected from the group of piperidinyl, tetrahydropyranyl, pyrrolidinyl, tetrahydrofuranyl, azetidinyl and oxetanyl, each of which may be optionally substituted with one C$_{1-4}$alkyl;

or Het$^3$ is 2-oxo-3-pyrrolidinyl optionally substituted with one C$_{1-4}$alkyl;

R$^3$ is selected from the group of hydrogen; halo; C$_{3-6}$cycloalkyl; C$_{1-4}$alkyl; C$_{1-4}$alkyl substituted with one or more fluoro substituents; and C$_{1-4}$alkyloxy substituted with one or more fluoro substituents;

R⁴ is selected from the group of hydrogen; halogen; $C_{1-4}$alkyl; $C_{1-4}$alkyl substituted with one or more fluoro substituents; and cyano;

R⁵ is selected from the group of hydrogen; $C_{1-6}$alkyl; $C_{1-6}$alkyl substituted with one or more fluoro substituents; cyano; $C_{1-6}$alkyl substituted with one substituent selected from the group of —NR⁵ᵃR⁵ᵇ, —OH, —OC$_{1-4}$alkyl, $C_{3-6}$cycloalkyl, and Het⁴; $C_{3-6}$cycloalkyl; and —C(=O)—NR⁵ᶜR⁵ᵈ; wherein R⁵ᵃ and R⁵ᵇ are each independently selected from the group of hydrogen and $C_{1-4}$alkyl; and R⁵ᶜ and R⁵ᵈ are each independently selected from the group of hydrogen; $C_{1-6}$alkyl optionally substituted with Het⁵; and $C_{2-6}$alkyl substituted with one substituent selected from —NR⁵ˣR⁵ʸ, —OH and —OC$_{1-4}$alkyl;

Het⁴ is a heterocyclyl selected from the group of piperidinyl, morpholinyl, piperazinyl, tetrahydropyranyl, pyrrolidinyl, tetrahydrofuranyl, azetidinyl and oxetanyl, each of which may be optionally substituted with one $C_{1-4}$alkyl;

Het⁵ is a heterocyclyl selected from the group of piperidinyl, morpholinyl, piperazinyl, tetrahydropyranyl, pyrrolidinyl, tetrahydrofuranyl, azetidinyl and oxetanyl, each of which may be optionally substituted with one $C_{1-4}$alkyl;

R⁵ˣ and R⁵ʸ are each independently selected from the group of hydrogen and $C_{1-4}$alkyl; or R⁵ᶜ and R⁵ᵈ together with the nitrogen atom to which they are attached form a Het⁶ group; wherein Het⁶ is a heterocyclyl selected from the group of piperidinyl, pyrrolidinyl, azetidinyl, piperazinyl and morpholinyl, each of which may be optionally substituted with one substituent selected from $C_{1-4}$alkyl; —OC$_{1-4}$alkyl; and $C_{1-4}$alkyl substituted with one —OH;

R⁶ is selected from the group of hydrogen; halogen; cyano; $C_{1-6}$alkyl; $C_{1-6}$alkyl substituted with one or more fluoro substituents; $C_{1-6}$alkyl substituted with one —OH; $C_{1-6}$alkyl substituted with one NH₂; —C$_{1-6}$alkyloxyC$_{1-4}$alkyl; —C$_{1-6}$alkyl-C(=O)—NR⁶ᵃR⁶ᵇ; —OC$_{1-6}$alkyl; —OC$_{1-6}$alkyl substituted with one or more fluoro substituents; —OC$_{1-6}$alkyl substituted with one Het⁷ substituent; —OC$_{2-6}$alkyl substituted with one substituent selected from the group of —NR⁶ᶜR⁶ᵈ, —OH, and —OC$_{1-4}$alkyl; and —C(=O)—NR⁶ᵃR⁶ᵇ; wherein R⁶ᵃ, R⁶ᶜ and R⁶ᵈ are each independently selected from hydrogen and $C_{1-4}$alkyl; and R⁶ᵇ is selected from hydrogen, $C_{1-4}$alkyl, $C_{2-4}$alkyloxyC$_{1-4}$alkyl and $C_{2-4}$alkylNR⁶ˣR⁶ʸ; or R⁶ᵃ and R⁶ᵇ, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;

R⁶ˣ is hydrogen or $C_{1-4}$alkyl and R⁶ʸ is $C_{1-4}$alkyl; and Het⁷ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;

R⁷ is selected from the group of hydrogen, $C_{1-4}$alkyl, cyano, —OC$_{1-4}$alkyl, —NHC$_{1-4}$alkyl, —NH—C(=O)—C$_{1-4}$alkyl and —C(=O)—NR⁷ᵃR⁷ᵇ; wherein R⁷ᵃ and R⁷ᵇ are each independently selected from hydrogen and $C_{1-4}$alkyl;

R⁸ is selected from the group of hydrogen; —C(=O)—NR⁸ᵍR⁸ʰ; Het⁸; $C_{1-6}$alkyl optionally substituted with Het⁹; —C(=O)—Het¹²; $C_{3-6}$cycloalkyl optionally substituted with one —OC$_{1-4}$alkyl; $C_{1-6}$alkyl substituted with one cyano; —CH₂—C(=O)NR⁸ᵃR⁸ᵇ; and $C_{2-6}$alkyl substituted with one or more substituents independently selected from the group of (i) fluoro,
(ii) —NR⁸ᵃR⁸ᵇ,
(iii) —NR⁸ᶜC(=O)R⁸ᵈ,
(iv) —NR⁸ᶜC(=O)NR⁸ᵃR⁸ᵇ,
(v) —NR⁸ᶜC(=O)OR⁸ᵉ,
(vi) —NR⁸ᶜS(=O)₂NR⁸ᵃR⁸ᵇ,
(vii) —NR⁸ᶜS(=O)₂R⁸ᵈ,
(viii) —OR⁸ᶠ,
(ix) —OC(=O)NR⁸ᵃR⁸ᵇ,
(x) —C(=O)NR⁸ᵃR⁸ᵇ,
(xi) —SR⁸ᵉ,
(xii) —S(O)₂R⁸ᵈ, and
(xiii) —S(O)₂NR⁸ᵃR⁸ᵇ; wherein R⁸ᵃ, R⁸ᵇ, R⁸ᶜ and R⁸ᶠ are each independently selected from the group of hydrogen; $C_{1-6}$alkyl, which may be optionally substituted with one substituent selected from Het¹⁰ and Het¹¹; $C_{3-6}$cycloalkyl; and $C_{2-6}$alkyl substituted with one substituent selected from —NR⁸ˣR⁸ʸ, —OH, and —OC$_{1-4}$alkyl;

R⁸ᵈ is selected from the group of $C_{1-6}$alkyl, which may be optionally substituted with one substituent selected from —NR⁸ˣR⁸ʸ, —OH, —OC$_{1-4}$alkyl, Het¹⁰ and Het¹¹; and $C_{3-6}$cycloalkyl;

R⁸ᵉ is selected from the group of $C_{1-6}$alkyl, which may be optionally substituted with one substituent selected from Het¹⁰ and Het¹¹; $C_{3-6}$cycloalkyl; and $C_{2-6}$alkyl substituted with one substituent selected from —NR⁸ˣR⁸ʸ, —OH, and —OC$_{1-4}$alkyl;

wherein R⁸ˣ and R⁸ʸ are each independently selected from hydrogen and $C_{1-4}$alkyl;

R⁸ᵍ and R⁸ʰ are each independently selected from the group of hydrogen, $C_{1-4}$alkyl and $C_{2-4}$alkyl substituted with one —OC$_{1-4}$alkyl;

and

Het⁸ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—C$_{1-4}$alkyl, $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —OC$_{1-4}$alkyl;

Het⁹ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —OC$_{1-4}$alkyl; or Het⁹ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one $C_{1-4}$alkyl; or Het⁹ is selected from the group of (a)

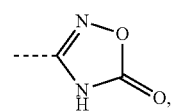

-continued

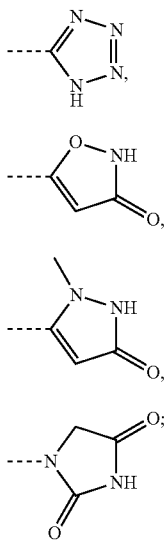

(b), (c), (d), and (e)

Het$^{10}$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one C$_{1-4}$alkyl;

Het$^{11}$ is selected from the group of

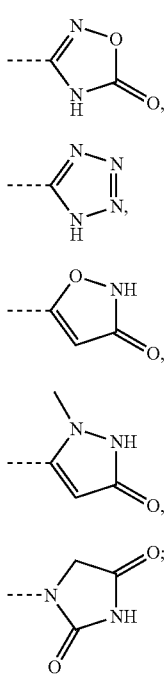

(a), (b), (c), (d), and (e)

Het$^{12}$ is a heterocyclyl selected from the group of 1-piperidinyl, 1-piperazinyl, 1-pyrrolidinyl and 1-azetidinyl, each of which may be optionally substituted with one substituent selected from C$_{1-4}$alkyl and —OC$_{1-4}$alkyl;

R$^9$ is hydrogen or C$_{1-4}$alkyl;

or a pharmaceutically acceptable salt or a solvate thereof.

2. The compound according to claim 1 wherein

R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, C$_{3-6}$cycloalkyl, Het$^1$, Het$^2$ and phenyl; C$_{3-6}$cycloalkyl; Het$^1$; Het$^2$; and phenyl; wherein the phenyl groups are optionally substituted with one or two substituents independently selected from the group of halogen, cyano, C$_{1-4}$alkyl, C$_{1-4}$alkoxy, C$_{1-4}$alkyl substituted with one or more fluoro substituents, and C$_{1-4}$alkyloxy substituted with one or more fluoro substituents;

R$^{1a}$, R$^{1b}$, R$^{2a}$, and R$^{2b}$ are each independently selected from hydrogen and C$_{1-4}$alkyl;

Het$^1$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C$_{1-4}$alkyl;

Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, C$_{1-4}$alkyl, C$_{1-4}$alkoxy, C$_{1-4}$alkyl substituted with one or more fluoro substituents, and C$_{1-4}$alkyloxy substituted with one or more fluoro substituents;

or R$^1$ and R$^2$ together with the carbon atom to which they are attached form a C$_{3-6}$cycloalkyl or a Het$^3$ group; wherein Het$^3$ is a heterocyclyl selected from the group of piperidinyl, tetrahydropyranyl, pyrrolidinyl, tetrahydrofuranyl, azetidinyl and oxetanyl, each of which may be optionally substituted with one C$_{1-4}$alkyl;

R$^3$ is selected from the group of hydrogen; C$_{1-4}$alkyl; and C$_{1-4}$alkyl substituted with one or more fluoro substituents;

R$^4$ is selected from the group of hydrogen; halogen; C$_{1-4}$alkyl; C$_{1-4}$alkyl substituted with one or more fluoro substituents; and cyano;

R$^5$ is selected from the group of hydrogen; C$_{1-6}$alkyl; C$_{1-6}$alkyl substituted with one or more fluoro substituents; cyano; C$_{1-6}$alkyl substituted with one substituent selected from the group of —NR$^{5a}$R$^{5b}$, —OH, —OC$_{1-4}$alkyl, C$_{3-6}$cycloalkyl, and Het$^4$; C$_{3-6}$cycloalkyl; and —C(=O)—NR$^{5c}$R$^{5d}$; wherein R$^{5a}$ and R$^{5b}$ are each independently selected from the group of hydrogen and C$_{1-4}$alkyl; and R$^{5c}$ and R$^{5d}$ are each independently selected from the group of hydrogen; C$_{1-6}$alkyl optionally substituted with Het$^5$; and C$_{2-6}$alkyl substituted with one substituent selected from —NR$^{5x}$R$^{5y}$, —OH and —OC$_{1-4}$alkyl;

Het$^4$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C$_{1-4}$alkyl;

Het$^5$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one C$_{1-4}$alkyl;

R$^{5x}$ and R$^{5y}$ are each independently selected from the group of hydrogen and C$_{1-4}$alkyl; or R$^{5c}$ and R$^{5d}$ together with the nitrogen atom to which they are attached form a Het$^6$ group; wherein Het$^6$ is a heterocyclyl selected from the group of piperidinyl, pyrrolidinyl, azetidinyl, piperazinyl and morpholinyl, each of which may be optionally substituted with one substituent selected from $C_{1-4}$alkyl and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-C(=O)—$NR^{6a}R^{6b}$; —$OC_{1-6}$alkyl; —$OC_{1-6}$alkyl substituted with one or more fluoro substituents; —$OC_{1-6}$alkyl substituted with one $Het^7$ substituent; —$OC_{2-6}$alkyl substituted with one substituent selected from the group of —$NR^{6c}R^{6d}$, —OH, and —$OC_{1-4}$alkyl; and —C(=O)—$NR^{6a}R^{6b}$; wherein $R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkyl$NR^{6x}R^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl;

$R^{6x}$ is hydrogen or $C_{1-4}$alkyl and $R^{6y}$ is $C_{1-4}$alkyl; and $Het^7$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one $C_{1-4}$alkyl;

$R^7$ is selected from the group of hydrogen, $C_{1-4}$alkyl, cyano, —$OC_{1-4}$alkyl, —$NHC_{1-4}$alkyl, —NH—C(=O)—$C_{1-4}$alkyl and —C(=O)—$NR^{7a}R^{7b}$; wherein $R^{7a}$ and $R^{7b}$ are each independently selected from hydrogen and $C_{1-4}$alkyl;

$R^8$ is selected from the group of hydrogen; $Het^8$; $C_{1-6}$alkyl optionally substituted with $Het^9$; and $C_{2-6}$alkyl substituted with one or more substituents independently selected from the group of (i) fluoro,
(ii) —$NR^{8a}R^{8b}$,
(iii) —$NR^{8c}C(=O)R^{8d}$,
(iv) —$NR^{8c}C(=O)NR^{8a}R^{8b}$,
(v) —$NR^{8c}C(=O)OR^{8e}$,
(vi) —$NR^{8c}S(=O)_2NR^{8a}R^{8b}$,
(vii) —$NR^{8c}S(=O)_2R^{8d}$,
(viii) —$OR^{8f}$,
(ix) —$OC(=O)NR^{8a}R^{8b}$,
(x) —$C(=O)NR^{8a}R^{8b}$,
(xi) —$SR^{8e}$,
(xii) —$S(O)_2R^{8d}$, and
(xiii) —$S(O)_2NR^{8a}R^{8b}$; wherein $R^{8a}$, $R^{8b}$, $R^{8c}$ and $R^{8f}$ are each independently selected from the group of hydrogen; $C_{1-6}$alkyl, which may be optionally substituted with one substituent selected from $Het^{10}$ and $Het^{11}$; $C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH, —$OC_{1-4}$alkyl, $Het^{10}$ and $Het^{11}$; and $C_{3-6}$cycloalkyl;

$R^{8e}$ is selected from the group of $C_{1-6}$alkyl, which may be optionally substituted with one substituent selected from $Het^{10}$ and $Het^{11}$; $C_{3-6}$cycloalkyl; and $C_{2-6}$alkyl substituted with one substituent selected from —$NR^{8x}R^{8y}$, —OH, and —$OC_{1-4}$alkyl;

wherein $R^{8x}$ and $R^{8y}$ are each independently selected from hydrogen and $C_{1-4}$alkyl;

and $Het^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one $C_{1-4}$alkyl;

$Het^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one $C_{1-4}$alkyl;

$Het^{10}$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one $C_{1-4}$alkyl;

$Het^{11}$ is selected from the group of

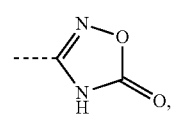

(a)

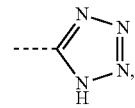

(b)

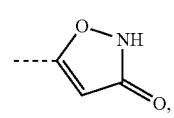

(c)

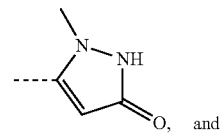

(d)

and

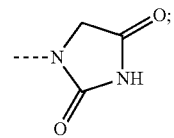

(e)

$R^9$ is hydrogen or $C_{1-4}$alkyl.

3. The compound according to claim 1, wherein $R^1$ is selected from the group of hydrogen; $C_{1-6}$alkyl; $C_{1-6}$alkyl substituted with one or more fluoro substituents; and $C_{1-6}$alkyl substituted with one substituent selected from the group of —$NR^{1a}R^{1b}$, —OH and —$OC_{1-4}$alkyl;

$R^2$ is selected from the group of hydrogen; $C_{1-6}$alkyl; $C_{1-6}$alkyl substituted with one or more fluoro substituents; $C_{1-6}$alkyl substituted with one substituent selected from the group of —$NR^{2a}R^{2b}$, —OH, —$OC_{1-4}$alkyl, $C_{3-6}$cycloalkyl, $Het^2$ and phenyl; —C(=O)—$NR^{2c}R^{2d}$; $C_{3-6}$cycloalkyl; $Het^2$; and phenyl; wherein the phenyl groups are optionally substituted with one or two substituents independently selected from the group of halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

$R^{1a}$, $R^{1b}$, $R^{2a}$, $R^{2b}$, $R^{2c}$ and $R^{2d}$ are each independently selected from hydrogen and $C_{1-4}$alkyl;

Het$^2$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is selected from the group of hydrogen; halo; $C_{3-6}$cycloalkyl; $C_{1-4}$alkyl; $C_{1-4}$alkyl substituted with one or more fluoro substituents; and $C_{1-4}$alkyloxy substituted with one or more fluoro substituents;

$R^4$ is hydrogen;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —NR$^{5a}$R$^{5b}$, —OH, —OC$_{1-4}$alkyl; $C_{3-6}$cycloalkyl; and —C(=O)—NR$^{5c}$R$^{5d}$; wherein $R^{5a}$ and $R^{5b}$ are each independently selected from the group of hydrogen and $C_{1-4}$alkyl; and $R^{5c}$ and $R^{5d}$ are each independently selected from the group of hydrogen; and $C_{2-6}$alkyl substituted with one substituent selected from —NR$^{5x}$R$^{5y}$, —OH and —OC$_{1-4}$alkyl;

$R^{5x}$ and $R^{5y}$ are each independently selected from the group of hydrogen and $C_{1-4}$alkyl;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; $C_{1-6}$alkyl substituted with one NH$_2$; —$C_{1-6}$alkyloxyC$_{1-4}$alkyl; —OC$_{1-6}$alkyl; —OC$_{1-6}$alkyl substituted with one or more fluoro substituents; and —OC$_{2-6}$alkyl substituted with one —OC$_{1-4}$alkyl;

$R^7$ is selected from the group of hydrogen, $C_{1-4}$alkyl, —OC$_{1-4}$alkyl, and —NHC$_{1-4}$alkyl;

$R^8$ is selected from the group of hydrogen; —C(=O)—NR$^{8g}$R$^{8h}$; Het$^8$; $C_{1-6}$alkyl optionally substituted with one Het$^9$; —C(=O)—Het$^{12}$; $C_{3-6}$cycloalkyl optionally substituted with one —OC$_{1-4}$alkyl; $C_{1-6}$alkyl substituted with one cyano; —CH$_2$—C(=O)NR$^{8a}$R$^{8b}$; and $C_{2-6}$alkyl substituted with one or more substituents independently selected from the group of (i), (ii), (iii), (viii), (ix), (x), and (xii); wherein $R^{8a}$, $R^{8b}$, $R^{8c}$ and $R^{8f}$ are each independently selected from the group of hydrogen; $C_{1-6}$alkyl; $C_{3-6}$cycloalkyl; and $C_{2-6}$alkyl substituted with one substituent selected from —OH, and —OC$_{1-4}$alkyl;

$R^{8d}$ is $C_{1-6}$alkyl;

$R^{8g}$ and $R^{8h}$ are each independently selected from the group of hydrogen, $C_{1-4}$alkyl and $C_{2-4}$alkyl substituted with one —OC$_{1-4}$alkyl;
and Het$^8$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one substituent selected from halo, —C(=O)—C$_{1-4}$alkyl, $C_{1-4}$alkyl, $C_{3-6}$cycloalkyl, $C_{1-4}$alkyl substituted with one $C_{3-6}$cycloalkyl, $C_{1-4}$alkyl substituted with one or more fluoro substituents, and $C_{1-4}$alkyl substituted with one —OC$_{1-4}$alkyl;

Het$^9$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one substituent selected from halo, $C_{1-4}$alkyl, $C_{1-4}$alkyl substituted with one or more fluoro substituents, and —OC$_{1-4}$alkyl; or Het$^9$ is a heteroaryl selected from the group of oxazolyl, pyrrolyl, pyrazolyl, imidazolyl, pyridinyl, pyrimidinyl, pyridazinyl and pyrazinyl, each of which may be optionally substituted with one $C_{1-4}$alkyl; or Het$^9$ is selected from the group of

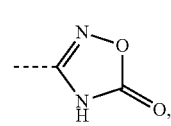

(a)

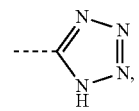

(b)

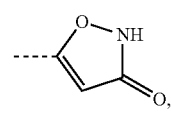

(c)

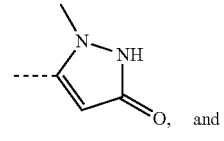

(d)

and

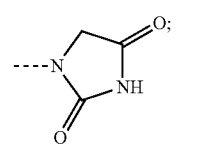

(e)

Het$^{12}$ is a heterocyclyl selected from the group of 1-piperidinyl, 1-piperazinyl, 1-pyrrolidinyl and 1-azetidinyl, each of which may be optionally substituted with one substituent selected from $C_{1-4}$alkyl and —OC$_{1-4}$alkyl;

$R^9$ is hydrogen or $C_{1-4}$alkyl.

4. The compound according to claim 1, wherein $R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; $C_{1-6}$alkyl substituted with one substituent selected from the group of —OC$_{1-4}$alkyl and $C_{3-6}$cycloalkyl; —C(=O)—NR$^{2c}$R$^{2d}$; $C_{3-6}$cycloalkyl; Het$^1$; Het$^2$; and phenyl;

$R^{2c}$ and $R^{2d}$ are each independently selected from $C_{1-4}$alkyl;

Het$^1$ is a heterocyclyl selected from the group of piperidinyl, azetidinyl and oxetanyl, each of which may be optionally substituted with one $C_{1-4}$alkyl;

Het$^2$ is a heteroaryl selected from the group of thiazolyl, oxazolyl, isoxazolyl and pyridinyl;

or $R^1$ and $R^2$ together with the carbon atom to which they are attached form a $C_{3-6}$cycloalkyl or a Het$^3$ group; wherein Het$^3$ is a heterocyclyl selected from the group of piperidinyl, tetrahydrofuranyl and azetidinyl, each of which may be optionally substituted with one $C_{1-4}$alkyl;

or Het$^3$ is 2-oxo-3-pyrrolidinyl substituted with one C$_{1-4}$alkyl on the nitrogen atom;

R$^3$ is selected from the group of hydrogen; halo; C$_{3-6}$cycloalkyl; C$_{1-4}$alkyl; and C$_{1-4}$alkyl substituted with one or more fluoro substituents;

R$^4$ is hydrogen;

R$^5$ is selected from the group of hydrogen; C$_{1-6}$alkyl; and —C(=O)—NR$^{5c}$R$^{5d}$; wherein R$^{5c}$ and R$^{5d}$ are each independently selected from the group of hydrogen; and C$_{2-6}$alkyl substituted with one —OC$_{1-4}$alkyl;

R$^6$ is selected from the group of hydrogen; halogen; cyano; C$_{1-6}$alkyl; C$_{1-6}$alkyl substituted with one or more fluoro substituents; C$_{1-6}$alkyl substituted with one NH$_2$; —C$_{1-6}$alkyloxyC$_{1-4}$alkyl; —O—C$_{1-6}$alkyl; and —OC$_{2-6}$alkyl substituted with one —OC$_{1-4}$alkyl;

R$^7$ is selected from the group of hydrogen, and C$_{1-4}$alkyl;

R$^8$ is selected from the group of hydrogen; —C(=O)—NR$^{8g}$R$^{8h}$; Het$^8$; C$_{1-6}$alkyl optionally substituted with one Het$^9$; —C(=O)—Het$^{12}$; C$_{1-4}$alkyl substituted with one cyano; —CH$_2$—C(=O)NR$^{8a}$R$^{8b}$; and C$_{2-6}$alkyl substituted with one or more substituents independently selected from the group of (ii), (iii), (viii), (x), (xii); wherein R$^{8a}$, R$^{8b}$, R$^{8c}$, and R$^{8f}$ are each independently selected from the group of hydrogen; C$_{1-6}$alkyl; and C$_{2-6}$alkyl substituted with one substituent selected from —OH, and —OC$_{1-4}$alkyl;

R$^{8d}$ is C$_{1-6}$alkyl;

R$^{8g}$ and R$^{8h}$ are each independently selected from C$_{1-4}$alkyl;

Het$^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from C$_{1-4}$alkyl, C$_{3-6}$cycloalkyl, —C(=O)—C$_{1-4}$alkyl, C$_{1-4}$alkyl substituted with one C$_{3-6}$cycloalkyl, C$_{1-4}$alkyl substituted with one or more fluoro substituents, and C$_{1-4}$alkyl substituted with one —OC$_{1-4}$alkyl;

Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl;

or Het$^9$ is pyrazolyl which may be optionally substituted with one C$_{1-4}$alkyl; or Het$^9$ is

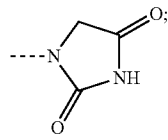

Het$^{12}$ is 1-piperazinyl which may be optionally substituted with one C$_{1-4}$alkyl substituent; R$^9$ is hydrogen or C$_{1-4}$alkyl.

5. The compound according to claim 1, wherein

R$^1$ is selected from the group of hydrogen; C$_{1-6}$alkyl; C$_{1-6}$alkyl substituted with one or more fluoro substituents; and C$_{1-6}$alkyl substituted with one substituent selected from the group of —NR$^{1a}$R$^{1b}$, —OH and —OC$_{1-4}$alkyl;

R$^2$ is selected from the group of hydrogen; C$_{1-6}$alkyl; C$_{1-6}$alkyl substituted with one or more fluoro substituents; C$_{1-6}$alkyl substituted with one substituent selected from the group of —NR$^{2a}$R$^{2b}$, —OH, —OC$_{1-4}$alkyl, C$_{3-6}$cycloalkyl, Het$^2$ and phenyl;

C$_{3-6}$cycloalkyl; Het$^2$; and phenyl; wherein the phenyl groups are optionally substituted with one or two substituents independently selected from the group of halogen, cyano, C$_{1-4}$alkyl, C$_{1-4}$alkoxy, C$_{1-4}$alkyl substituted with one or more fluoro substituents, and C$_{1-4}$alkyloxy substituted with one or more fluoro substituents;

or R$^1$ and R$^2$ together with the carbon atom to which they are attached form a C$_{3-6}$cycloalkyl.

6. The compound according to claim 1, wherein

R$^1$ is selected from the group of C$_{1-6}$alkyl; and C$_{1-6}$alkyl substituted with one or more fluoro substituents;

R$^2$ is selected from the group of C$_{1-6}$alkyl and C$_{3-6}$cycloalkyl;

or R$^1$ and R$^2$ together with the carbon atom to which they are attached form a C$_{3-6}$cycloalkyl;

R$^3$ is selected from the group of hydrogen; C$_{3-6}$cycloalkyl; and C$_{1-4}$alkyl;

R$^4$ is hydrogen;

R$^5$ is hydrogen;

R$^6$ is selected from the group of hydrogen; halogen; C$_{1-6}$alkyl; and —OC$_{1-6}$alkyl;

R$^7$ is hydrogen;

R$^8$ is selected from the group of hydrogen; Het$^8$; C$_{1-6}$alkyl optionally substituted with one Het$^9$; and C$_{2-6}$alkyl substituted with one or more —OR$^{8f}$ substituents;

R$^{8f}$ is C$_{1-4}$alkyl;

Het$^8$ is a heterocyclyl, bound through any available carbon atom, selected from the group of piperidinyl, pyrrolidinyl, tetrahydrofuranyl, azetidinyl and oxetanyl, each of which may be optionally substituted with one substituent selected from C$_{1-4}$alkyl, C$_{3-6}$cycloalkyl, C$_{1-4}$alkyl substituted with one C$_{3-6}$cycloalkyl, C$_{1-4}$alkyl substituted with one or more fluoro substituents, and C$_{1-4}$alkyl substituted with one —OC$_{1-4}$alkyl;

Het$^9$ is a heterocyclyl selected from the group of morpholinyl, piperidinyl, tetrahydropyranyl, tetrahydrofuranyl, and oxetanyl, each of which may be optionally substituted with one C$_{1-4}$alkyl;

R$^9$ is hydrogen.

7. The compound according to claim 1, wherein

R$^1$ is C$_{1-4}$alkyl;

R$^2$ is C$_{1-4}$alkyl;

or R$^1$ and R$^2$ together with the carbon atom to which they are attached form a C$_{3-6}$cycloalkyl;

R$^6$ is chloro, fluoro, methyl, or methoxy.

8. The compound according to claim 1, wherein R$^8$ is selected from hydrogen, —CH(CH$_3$)$_2$,

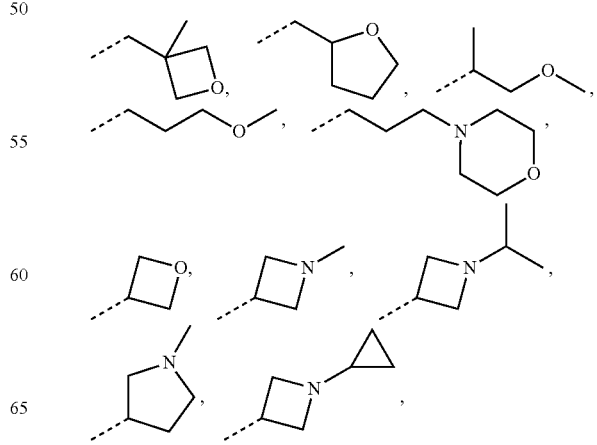

-continued
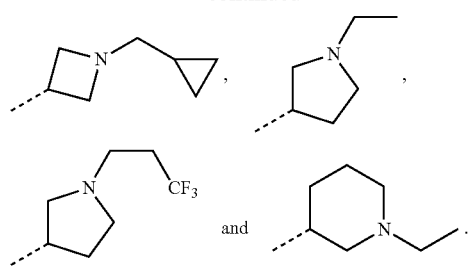
9. The compound according to claim 1 wherein $R^6$ is fluoro.
10. The compound according to claim 1, wherein the compound is selected from
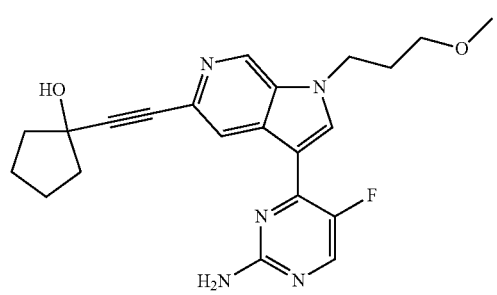
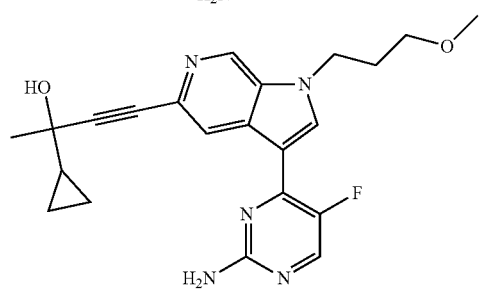
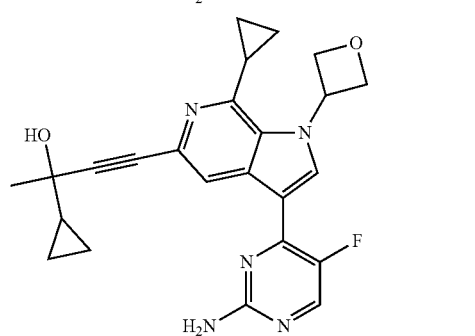
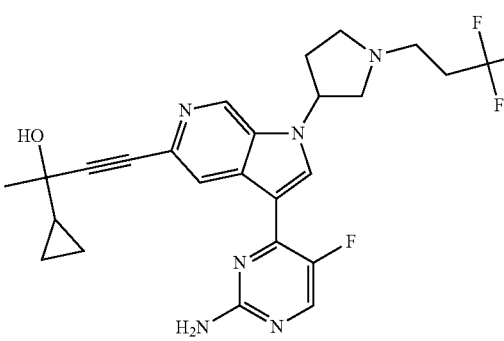
-continued
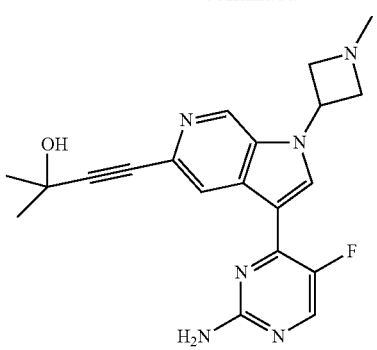
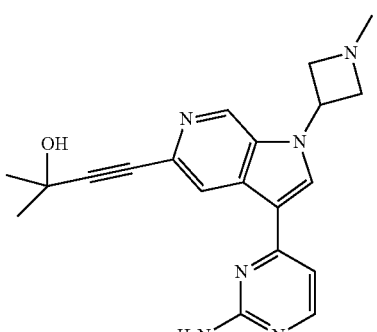
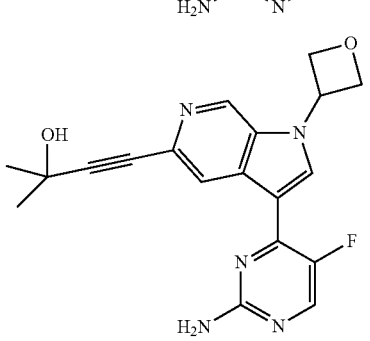
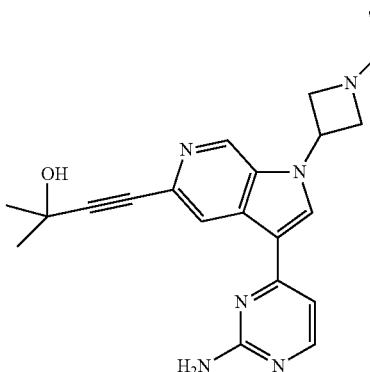
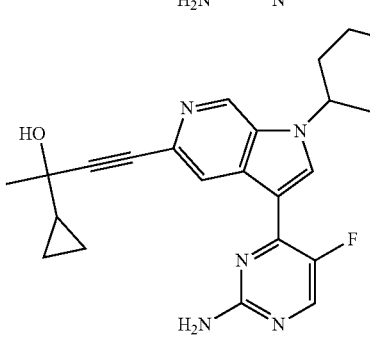

333
-continued
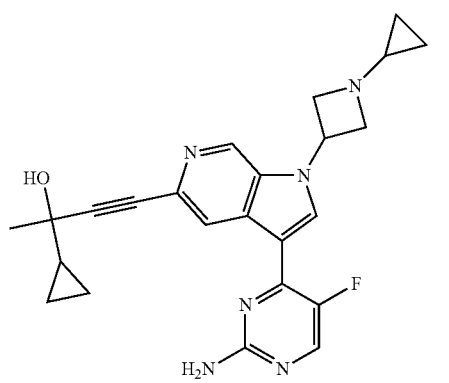
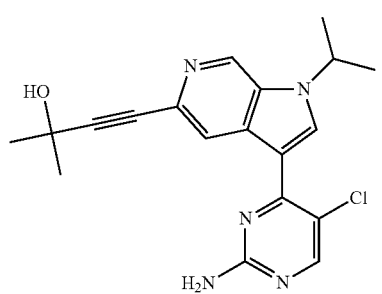
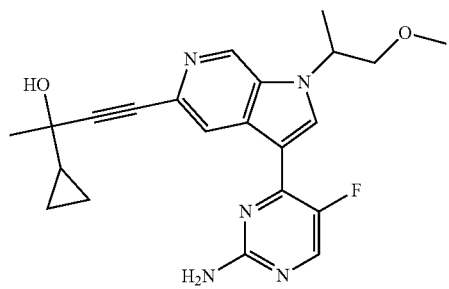
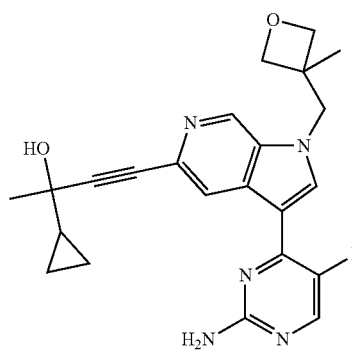
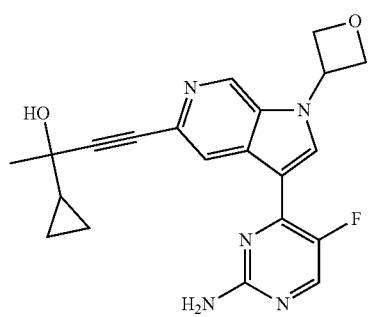
334
-continued
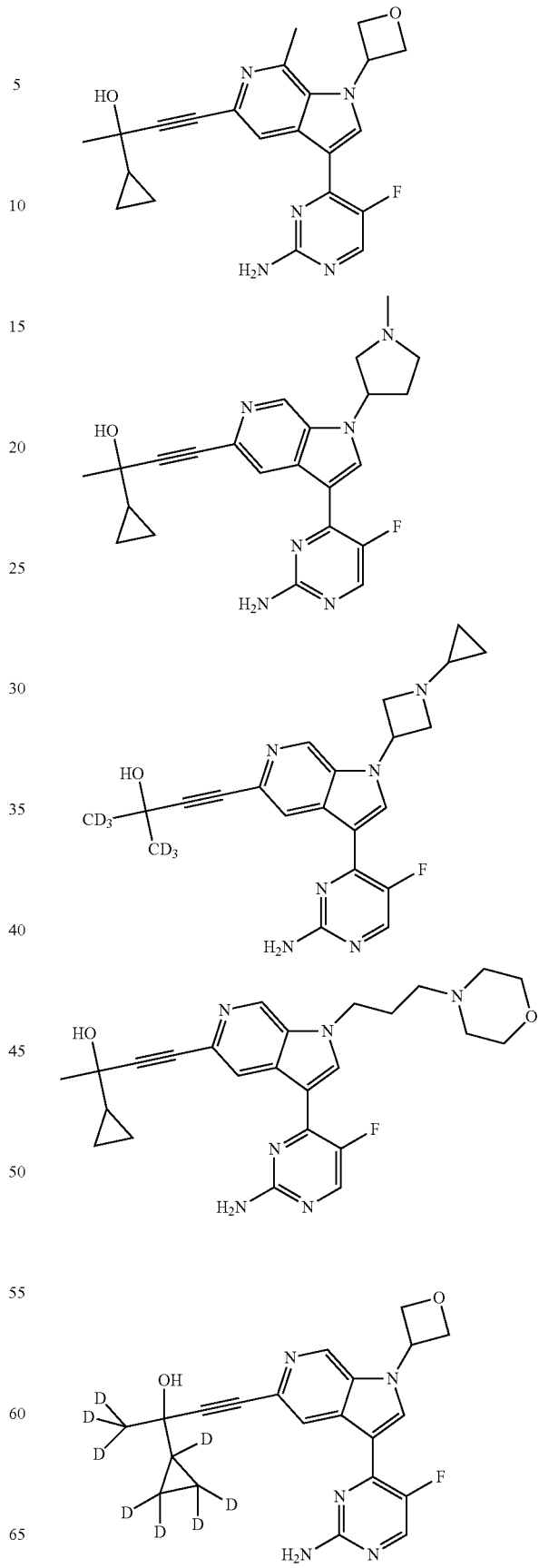

335
-continued

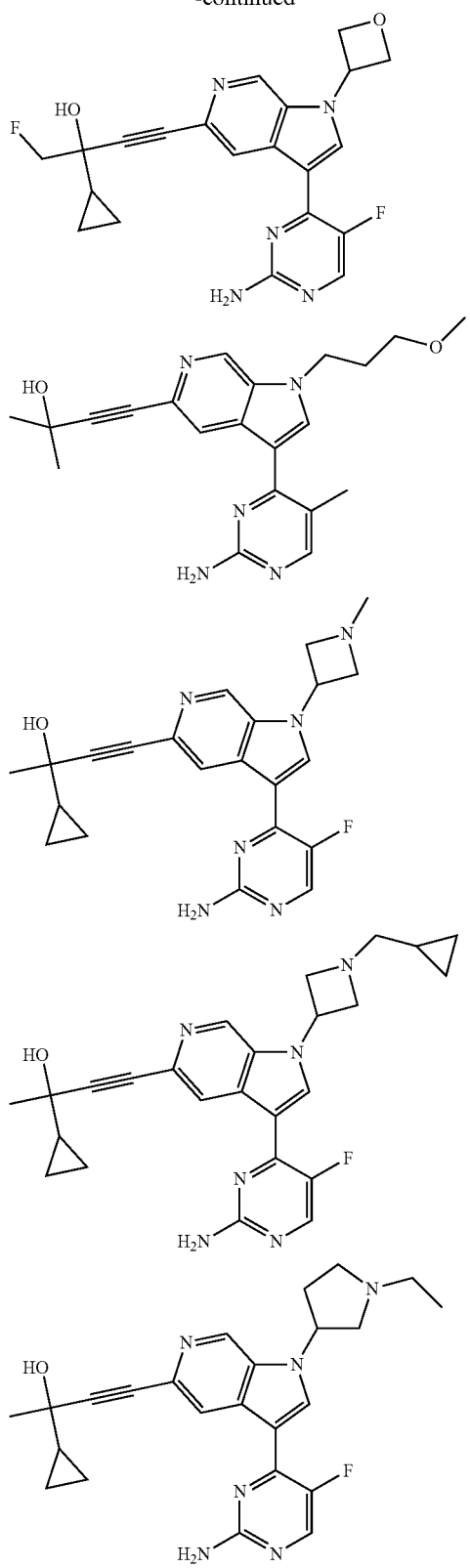

336
-continued

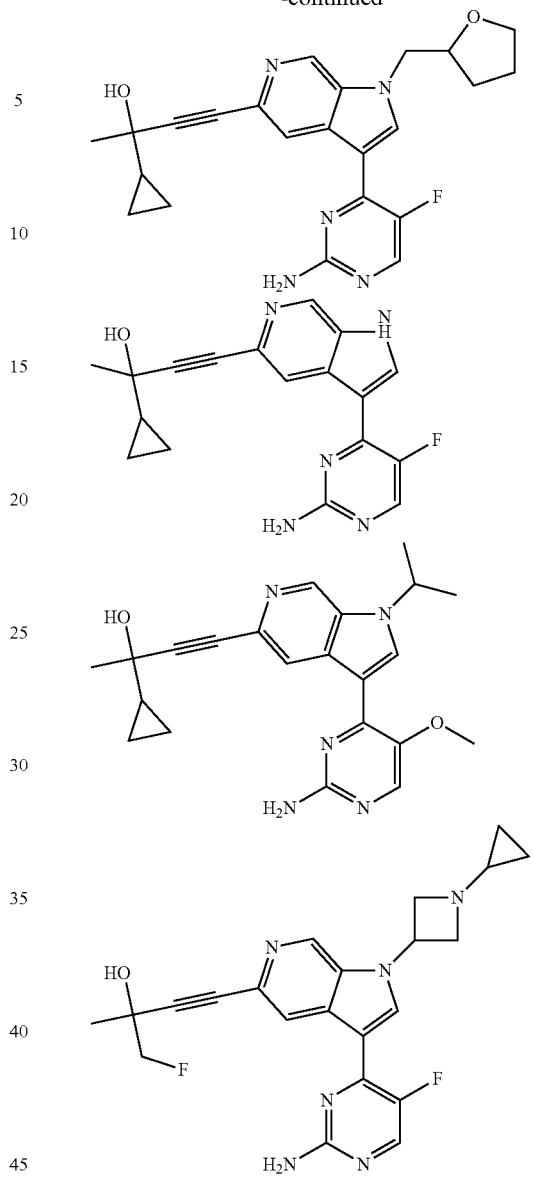

tautomers and stereoisomeric forms thereof, and the pharmaceutically acceptable salts and the solvates thereof.

11. A pharmaceutical composition comprising a compound as claimed in any of claims 1-10 and a pharmaceutically acceptable carrier or diluent.

12. A compound as claimed in any of claims 1-10 use in the treatment of cancer.

13. A pharmaceutical composition as claimed in claim 11 for use in the treatment of cancer.

14. A method of treating cancer in a human which comprises administering to said human an effective amount of a compound as claimed in any of claims 1-10.

15. A method of treating cancer in a human which comprises administering to said human an effective amount of a compound as claimed in claim 11.

* * * * *